US007700852B2

(12) United States Patent
Demmer et al.

(10) Patent No.: US 7,700,852 B2
(45) Date of Patent: Apr. 20, 2010

(54) COMPOSITIONS ISOLATED FROM FORAGE GRASSES AND METHODS FOR THEIR USE

(76) Inventors: Jeroen Demmer, 33B Glenvar Rd, Torbay, Auckland (NZ); Michael Andrew Shenk, 83A Te Aweawe St., Hokowhitu, Palmerston (NZ); Matthew Glenn, 14 Waimarie Road, Whenuapai, Auckland (NZ); Michael Geoffrey Norriss, 16 Ilan Road, Riccarton, Christchurch (NZ); Keith Martin Saulsbury, 8 Samuel Street, Christchurch (NZ); Claire Hall, 3/253 Kepa Road, Mission Bay, Auckland (NZ); Richard L. S. Forster, 263 Ostrich Rd, Pukekohe, Auckland (NZ)

( * ) Notice: Subject to any disclaimer, the term of this patent is extended or adjusted under 35 U.S.C. 154(b) by 0 days.

(21) Appl. No.: 11/756,516

(22) Filed: May 31, 2007

(65) Prior Publication Data
US 2008/0010701 A1 Jan. 10, 2008

Related U.S. Application Data

(63) Continuation of application No. 10/431,273, filed on May 6, 2003, now abandoned.

(51) Int. Cl.
*C12N 15/09* (2006.01)
*C12N 15/29* (2006.01)
*C12N 15/82* (2006.01)
*A01H 5/00* (2006.01)
*A01H 5/08* (2006.01)
*A01H 5/10* (2006.01)

(52) U.S. Cl. .............. 800/320; 800/284; 536/23.1; 536/23.6; 435/320.1; 435/419

(58) Field of Classification Search .................. None
See application file for complete search history.

(56) References Cited

U.S. PATENT DOCUMENTS

| 5,569,832 | A | 10/1996 | Holton et al. |
| 6,054,636 | A | 4/2000 | Fader |
| 6,080,920 | A | 6/2000 | Holton |
| 6,465,630 | B1 | 10/2002 | Choi et al. |
| 6,476,212 | B1 | 11/2002 | Lalgudi et al. |
| 2001/0051335 | A1 | 12/2001 | Lalgudi et al. |
| 2002/0042930 | A1 | 4/2002 | Botha et al. |

FOREIGN PATENT DOCUMENTS

| EP | 1 033 405 A2 | 9/2000 |
| WO | 99/53068 | 10/1999 |
| WO | 99/57285 | 11/1999 |
| WO | 01/64890 A2 | 9/2001 |
| WO | 01/95691 A2 | 12/2001 |
| WO | 01/95691 A3 | 12/2001 |
| WO | WO 01/95691 | * 12/2001 |
| WO | 02/16655 A2 | 2/2002 |
| WO | 02/20548 A1 | 3/2002 |
| WO | 02/086146 A2 | 10/2002 |
| WO | 03/000905 A2 | 1/2003 |
| WO | 03/031622 A1 | 4/2003 |

OTHER PUBLICATIONS

Ritsema et al, 2004 Plant Molecular Biology vol. 54: pp. 853-863.*
Cairns, 2003 Journal of Experimental Botany, Review; January, vol. 54, No. 382, pp. 549-567.*
Lüscher, Marcel, et al., "Cloning and Functional Analysis of Sucrose:Sucrose 1-Fructosyltransferase from Tall Fescue", Plant Physiology, 2000, pp. 1217-1227, vol. 124.
Carlisle, Sara M., et al., "Pyrophosphate-dependent Phosphofructokinase Conservation of Protein Sequence Between the Subuunits and With the ATP-Dependent Phosphofructokinase*", The Journal of Biological Chemistry, 1990, pp. 18366-18371, vol. 265, No. 30.
Bernhardt, J., et al., "Molecular analysis of a second functional A1 gene (dihydroflavonol 4-reductase) in Zea mays", The Plant Journal, 1998, pp. 483-488, vol. 14(4).
Carlisle, S.M., et al., "Pyrophosphate-dependent Phosphofructokinase. Conservation of protein sequence between the alpha- and beta-subunits and with the ATP-dependent phosphofructokinase", NCBI Database, (1990), Accession No. AAA63451.
Carlisle, S.M., et al., "Pyrophosphate-dependent phosphofructkinase. Conservation of protein sequence between the alpha- and beta-subunits and with the ATP-dependent phosphofructokinase", NCBI Database, (1990), Accession No. M55190.
Carlisle, S.M., et al., "Pyrophosphate-dependent phosphofructokinase. Conservation of protein sequence between the alpha- and beta-subunits and with the ATP-dependent phosphofructokinase", NCBI Database, (1990), Accession No. M55191.
Carlisle, S.M., et al., "Pyrophosphate-dependent phosphofructokinase. Conservation of protein sequence between the alpha- and beta-subunits and with the ATP-dependent phosphofructokinase", NCBI Database, (1990), Accession No. AAA63452.
Luscher, M., et al., "Cloning and functional analysis of sucrose:sucrose 1-fructosyltransferase from tall fescue", NCBI Database, (2000), Accession No. AJ297369.
Luscher, M., et al., "Cloning and functional analysis of sucrose:sucrose 1-fructosyltransferase from tall fescue", NCBI Database, (2000), Accession No. CAC05261.
Lasseur, B., et al., "Lolium perenne fructosyltransferase (putative 1-SST) mRNA, complete cds", NCBI Database, (2002), Accession No. AF492836.

(Continued)

Primary Examiner—Russell Kallis
(74) Attorney, Agent, or Firm—Janet Sleath; Speckman Law Group PLLC

(57) ABSTRACT

Isolated polynucleotides encoding polypeptides active in the fructan, cellulose, starch and/or tannin biosynthetic pathways are provided, together with expression vectors and host cells comprising such isolated polynucleotides. Methods for the use of such polynucleotides and polypeptides are also provided.

15 Claims, 12 Drawing Sheets

OTHER PUBLICATIONS

Lasseur, B., et al., "Lolium perenne fructosyltransferase (putative 1-SST) mRNA, complete cds", NCBI Database, (2002), Accession No. AAM13671.

Kapri, R., and Sadka, A., "PPi-dependent phosphofruktokinase in citrus fruit", NCBI Database, (1998), Accession No. AF095521.

Kapri, R., and Sadka, A., "PPi-dependent phosphofruktokinase in citrus fruit", NCBI Database, (1998), Accession No. AAC67587.

Kapri, R., and Sadka, A., "PPi-dependent phosphofructukinase in citrus fruit", NCBI Database, (1998), Accession No. AF095520.

Kapri, R., and Sadka, A., "PPi-dependent phosphofructukinase in citrus fruit", NCBI Database, (1998), Accession No. AAC67586.

Lunn, J.E., et al., "Cloning and sequencing of a partial cDNA encoding sucrose-phosphate synthase from barley (*Hordeum vulgare* cv. Himalya) endosperm", NCBI Database, (2000), Accession No. AF261107.

Lunn, J.E., et al., "Cloning and sequencing of a partial cDNA encoding sucrose-phosphate synthase from barley (*Hordeum vulgare* cv. Himalya) endosperm", NCBI Database, (2000), Accession No. AAF75266.

Weschke, W., et al., "Sucrose transport into Barley Seeds: Molecular Characterisation of two Transporters and Implications for Seed Development and Starch Accumulation", NCBI Database, (2000), Accession No. AJ272309.

Weschke, W., et al., "Sucrose transport into Barley Seeds: Molecular Characterisation of two Transporters and Implications for Seed Development and Starch Accumulation", NCBI Database, (2000), Accession No. CAB75882.

Aoki, N., et al., "Three sucrose transporter genes are expressed in the developing grain of wheat", NCBI Database, (2002), Accession No. AF408842.

Aoki, N., et al., "Three sucrose transporter genes are expressed in the developing grain of wheat", NCBI Database, (2002), Accession No. AF408843.

Aoki, N., et al., "Three sucrose transporter genes are expressed in the developing grain of wheat", NCBI Database, (2002), Accession No. AAM13408.

Aoki, N., et al., "Three sucrose transporter genes are expressed in the developing grain of wheat", NCBI Database, (2002), Accession No. AAM13409.

Aoki, N., et al., "Three sucrose transporter genes are expressed in the developing grain of wheat", NCBI Database, (2002), Accession No. AAM13410.

Haussuehl, K.K., et al., "Expression of chalcone synthase genes in coleoptiles and primary leaves of *Secale cereale* L. after induction by UV radiation: evidence for a UV-protective role of the coleoptile", NCBI Database, (2002), Accession No. X92547.

Haussuehl, K.K., et al., "Expression of chalcone synthase genes in coleoptiles and primary leaves of *Secale cereale* L. after induction by UV radiation: evidence for a UV-protective role of the coleoptile", NCBI Database, (1996), Accession No. CAA63305.

Rohde, W., et al., "Structure of a chalcone Synthase gene from *Hordeum vulgare*", NCBI Database, (1991), Accession No. X58339.

Rohde, W., et al., "Structure of a chalcone Synthase gene from *Hordeum vulgare*", NCBI Database, (1991), Accession No. CAA41250.

Ichikawa, H., et al., "Characterization of a full length chalcone Synthase cDNA from *Oryza sativa* L", NCBI Database, (1997), Accession No. AB000801.

Ichikawa, H., et al., "Characterization of a full length chalcone Synthase cDNA from *Oryza sativa* L", NCBI Database, (1997), Accession No. BAA19186.

Devic, M., et al., "The BANYULS gene encodes a DFR-like protein and is a marker of early seed coat development", NCBI Database, (1999), Accession No. AAF23859.

Devic, M., et al., "The BANYULS gene encodes a DFR-like protein and is a marker of early seed coat development", NCBI Database, (1999), Accession No. AF092912.

Bernhardt, J., et al., "Molecular analysis of a second functional A1 gene (dihydroflavonol 4-reductase) in Zea mays", NCBI Database, (1997), Accession No. CAA75998.

Bernhardt, J., et al., "Molecular analysis of a second functional A1 gene (dihydroflavonol 4-reductase) in Zea mays" NCBI Database, (1997), Accession No. Y16042.

Tanaka, Y., et al., "Molecular cloning and characterization of Rosa hybrida dihydroflavonol 4-reductase gene", NCBI Database, (1996), Accession No. BAA12723.

Tanaka, Y., et al., "Molecular cloning and characterization of Rosa hybrida dihydroflavonol 4-reductace gene", NCBI Database, (1995), Accession No. D85102.

Fox, T.W., et al., "Zea Mays dihydro-flavanoid reductase-like protein (ms*-bs7) mRNA, complete cds", NCBI Database, (2001), Accession No. AF366295.

Zhuang, C.X., "Differential expression of a putative dihydroflavonol reductase gene in rice (Accession No. AF134807) (PGR 99-074)", NCBI Database, (1999), Accession No. AF134807.

Hillier, L., et al., "The WashU-Merck EST Project", NCBI Database, (1995), Accession No. AA022571.

Bernhardt, J., et al., "Molecular analysis of a second functional A1 gene", NCBI Database, (1997), Accession No. CAA75998.

Bernhardt, J., et al., "Molecular analysis of a second functional A1 gene", NCBI Database, (1997), Accession No. CAA75996.

Bentley, S.D., et al., "Complete genome sequence of the model actinomycete Streptomyces coelicolor A3 (2)", NCBI Database, (2002), Accession No. NP_624490.

Marra, M., et al., "The WashU-HHMI Mouse EST Project", NCBI Database, (1996), Accession No. AA060212.

Marra, M., et al., "The WashU-HHMI Mouse EST Project", NCBI Database, (1996), Accession No. AA050084.

Marra, M., et al., "The WashU-HHMI Mouse EST Project", NCBI Database, (1996), Accession No. AA060214.

Marra, M., et al., "The WashU-HHMI Mouse EST Project", NCBI Database, (1996), Accession No. AA060213.

Hillier, L., et al., "Generation and analysis of 280,000 human expressed sequence tags", NCBI Database, (1996), Accession No. AA053552.

Li, W. and Gill, B.S., "The colinearity of the sh2/a1 orthologous region in rice, sorghum and maize is interrupted and accompanied by genome expansion in the triticeae", NCBI Database, (2002), Accession No. AF4343703.

Sasaki, T., et al., "*Oryza sativa* nipponbare (GA3) genomic DNA, chromosome 8, PAC clone:P0686C03", EMBL/GenBank/DDBJ Database, (2003), Accession No. Q84Z61.

Kaneko, T., et al., "Structural analysis of *Arabidopsis thaliana* chromosome 5. XI.", EMBL/GenBank/DDBJ database, (2003), Accession No. Q9FGH3.

Zhuang, C.X., et al., "Differential expression of a putative dihudroflavonol reductase gene in rice (Accession No. AF134807) (PGR 99-074)", EMBL/GenBank/DDBJ Database, (2002), Accession No. Q9XHC8.

Fox, T.W., et al., "Dihydro-flavanoid reductase-like protein", EMBL/GenBank/DDBJ databases, (2001), Accession No. Q94KE6.

Li, W. and Gill, B.S., "Colinearity of the Sh2/A1 region among rice, sorghum and maize Is interrupted and accompanied by genome expansion in the Triticeae", EMBL/GenBank/DDBJ Database, (2002), Accession No. Q8W564.

Kristiansen, K.N. and Rohde, W., "Structure of the *Hordeum vulgare* gene encoding dihydroflavonol-4- reductase and molecular analysis of ant18 mutants blocked in flavonoid synthesis", EMBL/GenBank/DDBJ Database, (2003), Accession No. DFRA_HORVU.

Kristiansen, K.N. and Rohde, W., "Structure of the *Hordeum vulgare* gene encoding dihydroflavonol-4-reductase and molecular analysis of ant18 mutants blocked in flavonoid synthesis", EMBL/GenBank/DDBJ Database, (1991), Accession No. S69616.

Fox, T.W., et al., "Zea mays dihydro-flavanoid reductase-like protein (ms*-bs7) mRNA, complete cds", NCBI Database, (2001), Accession No. AF366295.

Zhuang, C.X., et al., Differential expression of a putative dihydroflavonol reductase gene in rice (Accession No. AF134807) (PGR 99-074), Accession No. AF134807, Sep. 3, 2004.

Bernhardt, J., et al., "Molecular analysis of a second functional A1 gene", NCBI Database, (1997), Accession No. Y16042.

Hillier, L., et al., "The WashU-Merck EST Project", NCBI Database, (1995), Accession No. AA022571.

Bernhardt, J., et al., "Molecular analysis of a second functional A1 gene (dihydroflavonol4-reductase) in Zea mays", NCBI Database, (1997), Accession No. CAA75998.

Bernhardt, J., et al., "Molecular analysis of a second functional A1 gene (dihydroflavonol4-reductase) in Zea mays" NCBI Database, (1997), Accession No. CAA75996.

Bentley, S.D., et al., "Complete genome sequence of the model actinomycete Streptomyces coelicolor A3(2)", NCBI Database, (2002), Accession No. NP_624490.

Li, W. and Gill, B.S., "The colinearity of the sh2/a1 orthologous region in rice, sorghum and maize is interrupted and accompanied by genome expansion in the triticae", NCBI Database, (2001), Accession No. AF434703.

* cited by examiner

Fig. 3

MAAAAVAPDAKIEKFRDAVAKLGEISENEKAGCISLVSRYLSGEAEQIEWSKIQTPTDEVVVPYDTLAPAP
EDLDAMKALLDKLVVLKLNGGLGTTMGCTGPKSVIEVRNGFTFLDLIVIQIESLNKKYGCDVPLLLMNSFN
THDDTQKIVEKYSNSNININHTFNQSQYPRIVTEDFLPLPSKGQSGKDGWYPPGHGDVFPSLNNSGKLDTLL
SQGKEYVFVANSDNLGAIVDIKILNHLINNKNEYCMEVTPKTLADVKGGTLISYEGRVQLLEIAQVPDEHV
NEFKSIEKFKIFNTNNLWVNLKAIKRLVEADALKMEIIPNPKEVDGVKVLQLETAAGAAIRFFDNAIGING
PRSRFLPVKATSDLLLVQSDLYTLVDGYVIRNPARVKPSNPSIELGPEFKKVASFLARFKSIPSIVELDSL
KVSGDVSFGSGIVLKGNVTIAAKSGVKLEIPDGAVLENKDINGPEDL

Fig. 4

MAAVAADAKIEKFRDAVAKLDEISENEKAGCISLVSRYLSGEAEQIEWSKIQTPTDEVVVPYDTLAPAPQD
LDAMKALLDKLVVLKLNGGLGTTMGCTGPKSVIEVRNGFTFLDLIVIQIESLNKKYGCDVPLLLMNSFNTH
DDTQKIVEKYSNSNININHTFNQSQYPRIVTEDFLPLPSKGKSGKDGWYPPGHGDVFPSLNNSGKLDTLLSQ
GKEYVFVANSDNLGAIVDIKILNHLINNQNEYCMEVTPKTLADVKGGTLISYEGRVQLLEIAQVPDEHVNE
FKSIEKFKIFNTNNLWVNLKAIKRLVEADALKMEIIPNPKEVDGVKVLQLETAAGAAIRFFEKAIGINGPR
SRFLPVKATSDLLLVQSDLYTLVDGYVIRNPARVKPSNPSIELGPEFKKVASFLARFKSIPSIVELDSLKV
SGDVTFGSGVVLKGNVTIAAKSGVKLEIPDGAVLENKDINGPEDL

Fig. 5

CLRRRTYSNSGDTHADPNGPVYYGGWYHLFYQHNPYGDSWGNVSWGHAVSKDLVNWRHLPVALVPDQWYDI
NGVLTGSITVLPDGRVILLYTGNTDTFSQVQCLAVPADPSDPLLRSWIKHPANPILFPPPGIGLKDFRDPL
TAWFEHSDNTWRTIIGSKDDDGHAGIVLSYKTTDFVNYELMPGNMHRGPDGTGMYECLDIYPVGGNSSEML
GGDSSPEVLFVLKESANDEWHDYYALGWFDATANTWTPQDPEADLGIGLRYDWGKYYASKSFYDPIKNRRV
VWAFVGETDSEQADKAKGWASLMSIPRMVELDKKTRTNLIQWPVEEIETLRRNVTDLGGITVEAGSVIHLP
LQQGGQLDIEASFRLNSSDIDALNEADVGFNCSSSAGAAVRGALGPFGLLVFADGRHEQTAAYFYVSKGLD
GSLLTHYCHDESRSTRAKDVVSRVVGGTVPVLDGETFSVRVLVDHSIVQSFVMGGRTTVTSRAYPTEAIYA
AAGVYLFNNATSATITAEGLVVYEMASAESQAFLADDM

Fig. 6

MESSAVVVPGTTAPLLPYDSRENQSSGGGVWWRACAASAVVLLVVVGFFAGGRVDLGQAGEVSATSSVPAA
MMEIPRSRGKNFGVSEKADGGFPWSNAMLQWQHTGFHFQPLKHYMNDPNGPVYYGGWYHLFYQHNPYGDSW
GNVSWGHAVSKDLVNWRHLPVALVPDQWYDINGVLTGSITVLPDGRVILLYTGNTDTFSQVQCLAVPADPS
DPLLRSWIKHPANPILFPPPGIGLKDFRDPLTAWFEHSDNTWRTIIGSKDDDGHAGIVLSYKTTDFVNYEL
MPGNMHRGPDGTGMYECLDIYPVGGNSSEMLGGDSSPEVLFVLKESANDEWHDYYALGWFDATANTWTPQD
PEADLGIGLRYDWGKYYASKSFYDPIKNRRVVWAFVGETDSEQADKAKGWASLMSIPRMVELDKKTRTNLI
QWPVEEIETLRRNVTDLGGITVEAGSVIHLPLQQGGQLDIEASFRLNSSDIDALNEADVGFNCSSSAGAAV
RGALGPFGLLVFADGRHEQTAAYFYVSKGLDGSLLTHYCHDESRSTRAKDVVSRVVGGTVPVLDGETFSVR
VLVDHSIVQSFVMGGRTTVTSRAYPTEAIYAAAGVYLFNNATSATITAEGLVVYEMASAESQAFLADDM

Fig. 7

MAIAAAAALLPLHLGCSDAAPRRPGNSLRAHLRKGGIRGRRRSPPCAVNSLHPSGNPKTPGGGDVGGAWGL
NGGATAKPDHAPPSQRRRAPRDVEEEAWALLRESVVSYCGSPVGTIAACDPNDASPLNYDQVFIRDFVPSG
VAFLLKGEHEIVRNFILHTLQLQSWEKTIDCHSPGQGLMPASFKVRVVPLDGGDDGATEEVLDPDFGEAAI
GRVAPVDSGLWWIILLRAYGKCSGDLSFHERVDVQTGIKLILKLCLADGFDMFPTLLVTDGSCMMDRRMGI
HGHPLEIQALFYSALLSAREMLTPEDGSADLIRALNSRLMALSFHIREYYWLEKRKLNEIYRYKTEEYSYD
AVNKFNIYPDQIPPWLVEWIPPKGGYFIGNLQPAHMDFRFFSLGNLWSIVSSLATADQSHAILDLVEAKWS
DLVAEMPMKICYPALEDQEWKFITGSDPKNTPWSYHNGGSWPTLLWQLTVACIKMNRPEIAARAVEVAESR
ISMDKWPEYYDTKRGRFIGKQARLFQTWSIAGFLVAKLLLENPEKSRILWNNEDEEILNALSLMTGPSSPK
RKRGRKTYIV

Fig. 8

MNGQTTMGLAAAAAAAVRPCRRRLLSSAS<u>AAAAAKASA</u>TPLFPRCSHPQHQQHSRRIPFLVSAASHTSQSD
PSTTPTPVTSDPRSAVAGNLPFFDRVLFPGSFPLETPPVEEPAPAPPADEAQASASPVREESDTEREAWRL
LRRAVVSYCGDPVGTVAAEDPECTEMLNYDQVFIRDFVPSALAFLMRGETEIVRNFLLHTLQLQSWEKTVD
CYSPGQGLMPASFKIKTVPLDENNEAFEEVLDPDFGESAIGRVAPVDSGLWWIILLRAYCKFTGDYSLQER
VDVQTGIKLILSLCLTDGFDMFPTLLVTDGSCMIDRRMGIHGHPLEIQALFYSALRCSREMIVMNDGSKHL
LQAINNRLSALSFHIREYYWVDMKKINEIYRYKTEEYSHDATNKFNIYPEQIPSWLVDWVPEKGGYLIGNL
QPAHMDFRFFSLGNLWAISSSLTTPTQAEGILSLIEEKWDDLVANMPLKICYPAMEDDEWRIVTGSDPKNT
PWSYHNGGSWPTLLWQFTLACIKMGRPELARRAIAVAEEKLSADKWPEYYDTRSGRFVGKQSRSYQTWTIA
GFLTSKILLENPELASILTCDEDLELLEGCACCLSKRTRCSRRVTKSDIIG

Fig. 9

MAIAAAAALLPLHLGCSDAAPRRPGNSLRAHLRKGGIRGRRRSPPCAVNSLHPSGNPKTPGGGDVGGGRGV
NGGATAKPDHAPPSQRRRAPRDVEEEAWALLRESVVSYCGSPVGTIAACDPNDASPLNYDQVFIRDFVPSG
VAFLLKGEHEIVRNFILHTLQLQSWEKTIDCHSPGQGLMPASFKVRVVPLDGGDDGATEEVLDPDFGEAAI
GRVAPVDSGLWWIILLRAYGKCSGDLSFHERVDVQTGIKLILKLCLADGFDMFPTLLVTDGSCMMDRRMGI
HGHPLEIQALFYSALLSAREMLTPEDGSADLIRALNSRLMALSFHIREYYWLEKRKLNEIYRYKTEEYSYD
AVNKFNIYPDQIPPWLVEWIPPKGGYFIGNLQPAHMDFRFFSLGNLWSIVSSLATADQSHAILDLVEAKWS
DLVAEMPMKICYPALEDQEWKFITGSDPKNTPWSYHNGGSWPTLLWQLTVACIKMNRPEIAARAVEVAESR
ISTDKWPEYYDTKRGRFIGKQARLFQTWSIAGFLVAKLLLENPEKSRILWNNEDEEILNALSLMTGPSSPK
RKRGRKTYIV

Fig. 10

MKRVSSHVSIASEAEINLDLSRLLIDKPRYTLERKRSFDEQSWSELTHTHRQNDGFDSVLQSPAFRTGFDS
PFSMGTHFGEPSGPHPLVNEAWEALRKSVVYFRGQPVGTIAAVDHASEEVLNYDQVFVRDFVPSALAFLMN
NEPEIVKNFLLKTLHLQSSEKMVDRFKLGAGAMPASFKVDRNKSRNTETLVADFGESAIGRVAPVDSGFWW
IILLRAYTKYTGDASLSESPDCQKCMRLILNLCLSEGFDTFPTLLCTDGCSMIDRRMGIYGYPIEIQALFY
MALRCALQMLKPDGEGKDFIEKIGQRLHALTYHMRNYFWLDFPHLNNIYRYKTEEYSHTAVNKFNVIPDSI
PDWVFDFMPCRGGYFLGNVSPAMMD<u>FRWFALGNCIAIISSLATPEQ</u>SSAIMDLIEERWDELVGEVPLKICY
PAIENHEWRIITGCDPKNTRWSY<u>HNGGSWPVLLWLLTAACIKT</u>GRPQMAKRAIELSEARLLKDGWPEYYDG
KLGKFVGKQARKFQTWSIAGYLVARMMLEDPSTLMMISMEEDRPVKPTMRRSASWNA

Fig. 11

MEAPGGGAGPMPTTPSHASIADSDDFDLSRLLNHRPRINVERQRSFDDRSLGDLYLSAMDSRGGYMDSYDS
MYSPGGGLRSLTGTPASSTRLSFEPQLLVAEAWEALRRSLVCFRGEPLGTIAAVDSSSDEVLNYDQVFVRD
FVPSALAFLMNGEPDIVKNFLLKTLLLQGWEKRIDRFKLGEGAMPASFKVLKDPKRGVDTLAADFGESAIG
RVAPADSGFWWIILLRAYTKSTGDLTLAETPECQKGIRLIMNQCLAEGFDTFPTLLCADGCCMIDRRMGVY
GYPIEIQALFFMSLRCALLLLKPAVEGNSSSKDDDIMERIVTRLHALSYHMRSYFWLDFQQLNVIYRFKTE
EYSHTAVNKFNVIPESIPDWLFDFMPSRGGYFVGNVSPARMDFRWFALGNCVAILASLATPEQAGAIMDLI
EERWEDLIGEMPLKICYPTIEGHEWQNVTGCDPKNTRWSYHNGGSWPVLIWLLTAACIKTGRLKIARRAID
LAEARLGKDGWPEYYDGKLGRYVGKQARKHQTWSIAGYLVAKMMLEDPSHLGMIS

Fig. 12

MEFGAPGGMRRSASHNSLSGSDDFDLTHLLNKPRINVERQRSFDDRSLSDVSYSGGGHARGAGGGFDGMYS
PGGGLRSLVGTPASSALHSFEPHPIVGDAWEALRRSLVFFRGQPLGTIAAYDHASEEVLNYDQVFVRDFVP
SAMAFLMNGEPEIVKNFLLKTVLLQGWEKKVDRFKLGEGAMPASFKVLHDDKKGVDTLHADFGESAIGRVA
PVDSGFWWIILLRAYTKSTGDLTLAEKPECQKAMRLILSLCLSEGFDTFPTLLCADGCCMIDRRMGVYGYP
IEIQSLFFMALRCALLMLKHDNEGKDFVERIATRLHALSYHMRSYFWLDFQQLNDIYRYKTEEYSHTAVNK
FNVIPDSIPDWLFDFMPCEGGFFVGNVSPARMDFRWFALGNMIAIVSSLATPEQSTAIMDLIEERWEELIG
EMPLKICYPAIENHEWRIVTGCDPKNTRWSYHNGGSWPVLLWLLTAASIKTGRPQIARRAIDLAERRLLKD
GWPEYYDGKLGKYVGKQARKFQTWSIAGYLVAKMLLEDPSHLGMIALEEDKAMKPVLRRSASWTN

Fig. 13

MDSDYGVPRELSEVQKKRTLYQPDLPPCLQGTTVRVEYGDVAIAADPAGAHVISHAFPHTYGQPLAHFLRK
AANVADAKVISEHPAVRVGIVFCGRQSPGGHNVIWGLHDAIKAHNPNSKLIGFLGGSDGLLAQKTLEITDE
VLSSYKNQGGYDMLGRTKDQIRTTEQVNGAMASCQALKLDALIIIGGVTSNTDAAQLAETFAEAKCATKVV
GVPVTLNGDLKNQFVETTVGFDTICKVNSQLISNMCTDALSAEKYYYFIRMMGRKASHVALECALQSHPNM
VILGEEVAASKLTIFDITKQICDAVQARAEKDKNHGVILIPEGLVESIPELYALLQEINGLHGKGVSIENI
SSQLSPWASALFEFLPQFIRQQLLLRPESDDSAQLSQIETEKLLAQLVETEMNKRLKEGTYKGKKFNAICH
FFGYQARGAMPSKFDCDYAYVLGHVSYHILAAGLNGYMATVTNLKSPLNKWRCGAAPISSMMTVKRWSRGP
STTQIGKPAVHMASVDLRGKAYELLRQNSSSCLLEDIYRNPGPLQFEGPGSDSKPISLCVEDQDYMGRIKK
LQEYLEKVKSIVKPGCSQDVLKAALSAMSSVTDTLAIMTSSSTGQAPL

Fig. 14

MDSDYGVPRELSEVQKKRTLYQPELPPCLQGTTVRVEYGDVAIAADPAGAHVISHAFPHTYGQPLAHFLRK
AANVADAKVISEHPAVRVGIVFCGRQSPGGHNVIWGLHDAIKAHNSNSKLIGFLGGSDGLLAQKTLEITDE
VLSSYKNQGGYDMLGRTKDQIRTTEQVNGAMASCQDLKLDALIIIGGVTSNTDAAQLAETFAEAKCATKVV
GVPVTLNGDLKNQFVETTVGFDTICKVNSQLISNMCTDALSAEKYYYFIRMMGRKASHVALECALQSHPNM
VILGEEVAASKLTIFDITKQICDAVQARAEKDKNHGVILIPEGLVESIPELYALLQEINGLHGKGVSIENI
SSQLSPWASALFEFLPQFIRHQLLLRPESDDSAQLSQIETEKLLAQLVETEMNKRLKEGTYKGKKFNAICH
FFGYQARGAMPSKFDCDYAYVLGHVSYHILAAGLNGYMATVTNLKSPLNKWRCGAAPISSMMTVKRWSRGP
STTQIGKPAMHMATVDLRGKAYELLRQNSSSYLLEDIYRNPGPLQFEGPGADSKPISLCVEDQDYMGRIKK
LQEYLEKVKSIVKPGCSQDVLKAALSAMSSVTETLAIMTSSSTGQAPL

Fig. 15

MAAAAVATSNGASANGPTPGRLASVYSEVQTSRIAHALPLPSVLRSHFTLADGAASSATGNPEEIAKLFPN
LYGQPSAAVVPSAQPVATKPLKIGVVLSGGQAPGGHNVICGIFDYLQERAKGSTMYGFKGGPAGVMKGKYV
ELNADFVYPYRNQGGFDMICSGRDKIETPEQFKQAEDTVTKLDLDGLVVIGGDDSNTNACLLGEYFRGRNL
KTRVIGCPKTIDGDLKCKEVPTSFGFDTACKIYSEMIGNVMTDARSTGKYYHFVRLMGRAASHITLECALQ
THPNVSLIGEEVAEKKETLKQVTDYITDVICKRAELGYNYGVILIPEGLIDFIPEVQKLIAELNEILAHDV
VDEAGAWKSKLQPESRQLFDFLPNTIQEQLLLERDPHGNVQVAKIETEKMLIAMVETELEKRRSAGKYSAH
FRGQSHFFGYEGRCGLPTNFDSSYCYALGYGAGALLQFGKTGLISSVGNLAAPVEEWTVGGTPLTALMDVE
RRHGKFKPVIKKAMVELDAAPFKKFASMRDEWAIKNRYISPGPIQFSGPGSDASNHTLMLELGAQT

Fig. 16

MAAAAVATSNGASANGPTPGRLASVYSEVQTSRIAHALPLPSVLRSHFTLADGAASSATGNPEEIAKLFPN
LYGQPSAAVVPSAQPVATKPLKIGVVLSGGQAPGGHNVICGIFDYLQERAKGSTMYGFKGGPAGVMKGKYV
ELNADFVYPYRNQGGFDMICSGRDKIETPEQFKQAEDTVTKLDLDGLVVIGGDDSNTNACLLGEYFRGRNL
KTRVIGCPKTIDGDLKCKEVPTSFGFDTACKIYSEMIGNVMTDARSTGKYYHFVRLMGRAASHITLECALQ
THPNVSLIGEEVAEKKETLKQVTDYITDVICKRAELGYNYGVILIPEGLIDFIPEVQKLIAELNEILAHDV
VDEAGAWKSKLQPESRQLFDFLPNTIQEQLLLERDPHGNVQVAKIETEKMLIAMVETELEKRRSAGKYSAH
FRGQSHFFGYEGRCGLPTNFDSSYCYALGYGAGALLQFGKTGLISSVGNLAAPVEEWTVGGTPLTALMDVE
RRHGKFKPVIKKAMVELDAAPFKKFASMRDEWAIKNRYISPGPIQFSGPGSDASNHTLMLELGAQT

Fig. 17

MAAAAVATSNGASANGPTPGRLASVYSEVQTSRIAHALPLPSVLRSNFTLADGPASSATGNPEEIAKLFPN
LYGQPSAAVVPSAEPVPTKPLKIGVVLSGGQAPGGHNVICGIFDYLQERAKGSTMYGFKGGPAGIMKGKYI
ELNADFVYPYRNQGGFDMICSGRDKIETPEQFKQAEDTVNKLDLDGLVVIGGDDSNTNACLLGEYFRGRNL
KTRVIGCPKTIDGDLKCKEVPISFGFDTACKIYSEMIGNVMTDARSTGKYYHFVRLMGRAASHITLECALQ
THPNVSLIGEEVAEKKETLKQVTDYITDVICKRAELGYNYGVILIPEGLIDFIPEVQKLIAELNEILAHDV
VDEAGAWKSKLQPESRQLFDFLPNTIQEQLLLERDPHGNVQVAKIETEKMLIAMVETELEKRRAAGKYSAH
FRGQSHFFGYEGRCGLPTNFDSSYCYALGYGAGALLQFGKTGLISSVGNLAAPVEEWTVGGTPLTALMDVE
RRHGKFKPVIKKAMVELDAAPFKKFASMRDEWAIKNRYISPGPIQFSGPGSDASNHTLMLELGAQI

Fig. 18

MVGNDNWINSYLDAILDAGKSSIGGDRPSLLLRERGHFSPARYFVEEVITGYDETDLYKTWLRANAMRSPQ
ERNTRLENMTWRIWNLARKKKELEKEEACRLLKRHPETEKTRTDATADMSEDLFDGEKGEDAGDPSVAYGD
STTGSSPKTSSVDKLYIVLISLHGLVRGENMELGRDSDTGGQVKYVVEFAKALSSSPGVYRVDLLTRQIVA
PNFDRSYGEPEEMLVSTTFKNSKHERGVNSGGYIIRIPFGPKDKYLAKEHMWPFIQDFVDGALSHILRMSK
TIGEEIGCCHPVWPAVIHGHYASAGVAAALLSGALNLPMAFTGHFLGKDKLEGLLKQGRQSREQINMTYKI
MRRIEAEELSLDASEIVIASTRQEIEEQWNLYDGFEVILARKLRARVKRGANCYGRYMPRMVIIPPGVEFG
HVVHDFDMDGEEENHGPASEDPPIWSQIMRFFTNPRKPMILAVARPYPEKNITSLVKAFGECRPLRELANL
TLIMGNREAISKMHNTSASVLTSVLTLIDEYDLGQVAYPKHHKHSEVPDIYRLATRTKGAFVNVAYFEQF
GVTLIEAAMNGLPVIATKNGAPVEINQVLNNGLLVDPHDQNAIADALYKLLSEKQLWSRCRENGLKNIHQF
SWPEHCKNHLSRILTLGARSPAIGSKEERSNAPISGRKHIIVISVDSVNKEDLVRIIRNAIEAAHTQNTPA
STGFVLSTSLTLSEICSLLVSGMHPAGFDAFICNSGSSIYYPSYSGNTPSSSKVTHVIDQNHQSHIEYRW
GGEGLRKYLVKWATSVVERKGRIERQMIFEDSEHSSTYCLAFKVVNPNHLPPLKELRKLMRIQSLRCNALY
NHSATRLSVTPIHASRSQAIRYLFIRWGIELPNIVVLVGESGDSDYEELLGGLHRTIILKGDFNIAANRIH
TVRRYPLQDVVALDSSNIIEVEGCTTDVIKSALRQIGVPTQ

Fig. 19

MVGGMCGNDNWINSYLDAILDAGKGAPGGGAGPGGGRGGGGGAGDRPSLLLRERGHFSPARYFVEEVITG
YDETDLYKTWSRANAMRSPQERNTRLENMTWRIWNLARKKKEXEAEEANRLLKRRLETEKPRTDAAAEMSE
DLFEGQKGEDAGDASVAYGDSSASNTPRISSIDKLYIVLISLHGLVRGENMELGRDSDTSGQVKYVVELAK
ALSSCPGVYRVDLLTRQILAPNYDRGYGEPSETLLPTNLKNFKHERGENSGAYITRIPFGPKDKYLAKEQL
WPYVQEFVDGALSHIVRMSKTIGEEIGCGHPMWPAAIHGHYAS<u>AGVAAALLSGALNVHMIFTG</u>HFLGRDKL
EGLLKQGKQTREEINMTYKIMRRIEAEELSLDASEIVIASTRQEIEEQWNLYDGFEVMLARKLRARVKRGA
NCYGRYMPRMVIIPPGVEFGHMIQDFDMDGEEDSPSPASEDP<u>PIWSEIMRFFTNPRKPLILAVARPYPEKN</u>
<u>ITTLVRAFGECRPLRELANLTLIMGNREAISKMSNMSAAVLTSVLTLIDEYDLYGQVAYPKHHKHSEVLDI</u>
<u>YRLAARTKGAFVNVAYFEQFGVTLIEAAMHGLPVIATKNGAPVEIHQVLNNGLLVDPHDQNAIADALYKLL</u>
<u>SEKQLWSRCRENGLKNIHQFSWPEHCKNYLSRILTLSPRYPAFASNDDQIKAPIKGRKYIIVIAVDSASKK</u>
DLAFIIRNSIEATRTE<u>TSSGSTGFVLSTSLTISEIH</u>SLLISAGMVPTDFDAFICNSGSDLFYPSQTGDSPS
TSRVTFALDRNYQSRVEYHWGGEGLRKYLVKWASSVVERRGRMEKQVIFDDSEHSSTCCLAFRVVNPNYLP
PLKELQKLMRVQSLRCHALYNHSATRLSVIPIHASRSQAIRYLSVRWGIELPNVVILVGESGDSDYEELFG
GLHKTVVLNGEFNTPANRIHTVRRYPLQDVIALDCSNIVGVQGCSTDCMRSTLEKLGIPTK

Fig. 20

MVRGGGNG<u>EVELSVGAGGGGGGAGGLVEP</u>PVPISLGRLVLAGMVAGGVQYGWALQLSLLTPYVQT<u>LGLSHA</u>
<u>LTSFMWLCGPIAGL</u>VVQPCVGLYSDKCTSRWGRRRP<u>FIMTGCVLICIAVVIVGFS</u>ADIGAALGDSKEECSL
YHGPRWHAAIVYVLGFWLLDFSNNTVQGPARALMADLSGKYGP<u>SAANSIFCSWMALGNILGYS</u>SGSTDKWH
KWFPFLRTRACCEACANLK<u>GAFLVAVLFLCMCLVITLIF</u>AKEVPYKRIAPLPTKANGQVEVEPSGPLAVFQ
GIRNLPS<u>GMPSVLLVTGLTWLSWFPFILY</u>DTDWMGREIYHGDPKGTPAEMSAFQDGVR<u>AGAFGLLLNSIIL</u>
<u>GFSSFLIEPMCKRLGPRVVW</u>V<u>SSNFLVCIAMAATAIISWW</u>STKEFHEYVQHAITASKDIK<u>IVCMALFAFLG</u>
<u>VPLAILYS</u>VPFAVTAQLAASKGGGQGLCT<u>GVLNISIVIPQVIIALGAG</u>PWDQLFGKGNIP<u>AFAAASAFALI</u>
<u>GGIVGIFLL</u>PKISRRSFRAVSTGGH

Fig. 21

<u>ICVAVVVVGFSADIGAALGDSKEECSL</u>YHGPRWHAAIVYVLGFWLLDFSNNTVQGPARALMADLSGKYGPS
<u>AANSIFCSWMALGNILGYSS</u>GSTDKWHKWFPFLRTRACCEACANLK<u>GAFLVAVLFLCFCLVITLIF</u>AKEVP
YKRIAPLPTKANGQVEVEPSGPLAVFQGFRNLPS<u>GMPSVLLVTGLTWLSWFPFILY</u>DTDWMGREIYHGDPK
GTPAEASAFQDGVR<u>AGAFGLLLNSIILGFSSFLIEPMCKRLGPRVVW</u>V<u>SSNLLVCIAMAATAIISWW</u>STKE
FHEYVQHAITASKDIK<u>IVCMVLFAFLGVPLAILYS</u>VPFAVTAQLAANKGGGQGLCT<u>GVLNISIVIPQVIIA</u>
<u>LGAGP</u>WDQLFGKGNIP<u>AFAAASAFALIGGIVGIFLL</u>PKISRHSFRAVSTGGH

Fig. 22

MVRGGGNSE<u>VELSVGAGGGGGGAGGLVEP</u>PVPISLGRLVFAGMVAGGVQYGWALQLSLLTPYVQT<u>LGLSHA</u>
<u>LTSFMWLCGPIAGL</u>VVQPCVGLYSDKCTSRWGRRRP<u>FIMTGCVLICIAVVIVGFSA</u>DIGAALGDSKEECSL
YHGPRWHAAIVYVLGFWLLDFSNNTVQGPARALMADLSGKYGPS<u>AANSIFCSWMALGNILGYSS</u>GSTDKWH
KWFPFLRTRACCEACANLK<u>GAFLVAVLFLCFCLVITLIF</u>AKEVPYKRIAPLPTKANGQVEVEPSGPLAVFQ
GFRNLPS<u>GMPSVLLVTGLTWLSWFPFILY</u>DTDWMGREIYHGDPKGTPAEASAFQDGVR<u>AGAFGLLLNSIIL</u>
<u>GFSSFLIEPMCKRLGPRVVW</u>V<u>SSNLLVCIAMAATAIISWW</u>STKEFHEYVQHAITASKDIK<u>IVCMVLFAFLG</u>
<u>VPLAILYS</u>VPFAVTAQLAANKGGGQGLCT<u>GVLNISIVIPQVIIALGAGP</u>WDQLFGKGNIP<u>AFAAASAFALI</u>
<u>GGIVGIFLL</u>PKISRHSFRAVSTGGH

Fig. 23

MPPPRRPTTGGTTTTSAALPPPRKVPLRSLLRAASVACGVQFGWALQLSLLTPYVQELGIPHAFASLVWLC
GPLSGLLVQPLIGHLSDRIAPADSPLGRRRPFIAAGAASIAFSVLTVGFSADLGRLFGDNVRPGSTRYGAI
IVYMIGFWLLDVGNNATQGPCRAFLADLTENDPRRTRIANAYFSLFMALGNILGYATGAYSGWYKIFPFTI
TESCGVSCANLKSAFLLDIIILAITTYVTVVTVQDNPTFGSDEAAPRPSSHEEEAFLFELFGSFKYFTMPV
WMVLIVTSLTWIGWFPFILFDTDWMGREIYRGSPEIVADTQKYHDGVRMGSFGLMLNSVLLGITSVVTEKL
CRKWGAGLVWGVSNIIMALCFVAMLVITYVAQNLDYGPSGAPPTGIVVASLTVFTILGAPLSITYSIPYAM
ATSRVENLGLGQGLAMGILNLSIVIPQIIVSLGSGPWDSLFGGGNAPSFWVAAAASFIGGLVAILGLPRAR
IAPKKRSQR

Fig. 24

MPPPRRPNAGGTTSAPLPPPRKVPLRSLLRAASVACGVQFGWALQLSLLTPYVQELGIPHAFASLVWLCGP
LSGLLVQPLIGHLSDRIAPADSPLGRRRPFIAAGAASIAFSVLTVGFSADLGRLFGDNIRPGSTRFGAIIV
YMIGFWLLDVGNNATQGPCRAFLADLTENDPRRTRIANAYFSLFMALGNILGYATGAYSGWYKIFPFTITE
SCGVSCANLKSAFLLDIIILAITTYVTVVTVQDNPTFGSDEAAPRPSSHEEEAFLFELFGSFKYFTLPVWM
VLIVTSLTWIGWFPFILFDTDWMGREIYRGSPEIVADTQKYHDGVRMGSFGLMLNSVLLGITSVVMEKLCR
KWGAGLVWGVSNIIMALCFVAMLIITYVAKNLDYGPSGAPPTGIVVASLAVFTILGAPLSITYSIPYAMAT
SRVENLGLGQGLAMGILNLSIVIPQIIVSLGSGPWDSLFGGGNAPSFWVAAAASFIGGLVAILGLPRARIA
PKKRSQR

Fig. 25

MVDQDHDGRRRQEEATAVAASSVPLLEKKPGDVPYYVEGCPGCAVDRRKATDPGIPYGSFIYIWVVILCTA
IPISSLFPFLYFMIRDLHIAERTEDIGFYAGFVGAAFMFGRCLTSTIWGIAADRIGRKPVVIFGVFSVVIF
NALFGLSVTYWMAIATRFLLGALNGLLGPMKAYAIEVCRPEHEALALSLVSTAWGIGLIIGPALGGYLALP
AEKYPNIFSPDSLFGRFPYFLPCLCTSVFAAAVLIGCIWMPETLHKHKVNENRNQSVESLEAHLIDPKEKV
EQSNSPDTKKSLFKNWPLMSSIIVYCVFSFHDMAYTEVFSLWAESDRTYGGLSLSSEDVGQTLAITGSSLL
VYQLFLYPRINRVLGPIKSSQIAAGICIPILFAYPYMTYLSEPGLSIVLNIASVIKNNLGVTIITGTFILQ
NNAVPQDQRGAANGLAMTGMSFFKAVAPAGAGIVFSWAQKRQHAFFFPGDQMVFFLLNIIELLGLLLTFKF
FLAVPDKSDSN

Fig. 26

MSSMQFSSVLPLEGKACVCPVRSANNGCERLKVGDSSSLRHEMALRRKCNGARGGGAADGAQCVLTSDASP
DTLVVRSSFRMNYADPNEVAAVILGGGTGTQLFPLTSTRATPAVPIGGCYRLIDIPMSNCFNSGINKIFVM
TQFNSASLNRHIHRTYLGGGINFTDGSVEVLAATQMPGEAAGWFRGTADAVRKFIWVLEDYYKHKSIEHIL
ILSGDQLYRMDYMELVQKHVDDNADITLSCAPVGESRASEYGLVKFDSSGRVIQFSEKPKGADLEAMKVDT
SFLNFAIDDPAKNPYIASMGVYVFKREVLLNLLKSRYTELHDFGSEILPRALHDHNVQAYVFTDYWEDIGT
IRSFFDANMALCEQPPKFEFYDPKTPFFTSPRYLPPTKSDKCRIKEAIISHGCFLRECTIEHSIIGVRSRL
NSGSVLKNAMMMGADLYETEDEISGLLSEGKVPIGVGENSKLSNCIIDMNARIGRDVVIANSEGVQEADRP
EEGYYIRSGIVVILKNATVKDGTVV

Fig. 27

MSSMQFSSVLPLEGKACVCPVRSANNGCERLKVGDSSSLRHEMALRRKCNGARGGGAADGAQCVLTSDASP
DTLVVRSSFRMNYADPN<u>EVA</u>AVILGGGTGTQLFPLTSTRATPAVPIGGCYRLIDIPMSNCFNSGINKIFVM
TQFNSASLNRHIHRTYLGGGINFTDGSVEVLAATQMPGEAAGWFRGTADAVRKFIWVLEDYYKHKSIEHIL
ILSGDQLYRMDYMELVQKHVDDNADITLSCAPVGESRASEYGLVKFDSSGRVIQFSEKPKGADLEAMKVDT
SFLNFAIDDPAKNPYIASMGVYVFKREVLLNLLKSRYTELHDFGSEILPRALHDHNVQAYVFTDYWEDIGT
IRSFFDANMALCEQPPKFEFYDPKTPFFTSPRYLPPTKSDKCRIKEAIISHGCFLRECTIEHSIIGVRSRL
NSGSVLKNAMMMGADLYETEDEISGLLSEGKVPIGVGENSKLSNCIIDMNARIGRDVVIANSEGVQEADRP
EEGYYIRSGIVVILKNATVKDGTVV

Fig. 28

*MTGAPPSTVMAMGAATSPCK*ILSATQRASTAAASASTSRESVSLRAPRGRRQRPRPRGLALSLAPARRPFV
FSPRAVSDSKSSQTCLDPDASTSVLGIILGGGAGTRLYPLTKKRAKPAVPLGANYRLIDIPVSNCLNSNIS
KIYVLTQFNSASLNRHLSRAYGSNIGGYKNEGFVEVLAAQQSPDNPNWFQGTADAVRQYLWLFEEHNVMEY
LILAGDHLYRMDYEKFIQAHRETDADITVAALPMDEERATAFGLMKIDEEGRIVEFAEKPKGEQLKAMMVD
TTILGLDDVRAKEMPYIASMGIYVISKHVMLQLLRDQFPGANDFGSEVIPGATSTGMRVQAYLYDGYWEDI
GTIEAFYNANLGITKKPIPDFSFYDRSAPIYTQPRHLPPSKVLDADVTDSVIGEGCVIKNCKIHHSVVGLR
SCISEGAIIEDTLLMGADYYETEADKKLLADKGGIPIGIGKNSHIRRAIIDKNARIGDNVKIINVDNVQEA
ARETDGYFIKSGIVTVIKDALLPSGTVI

Fig. 29

*MTRAPPSTVMAMGAATSPCK*ILSATQRASAAAPSASTSRESVCLLRAPRGRRQRPRGLALSLAPARRPFVF
SPRAVSDSKSSQTCLDPDASTSVLGIILGGGAGTRLYPLTKKRAKPAVPLGANYRLIDIPVSNCLNSNISK
IYVLTQFNSASLNRHLSRAYGSNIGGYKNEGFVEVLAAQQSPDNPNWFQGTADAVRQYLWLFEEHNVMEYL
ILAGDHLYRMDYEKFIQAHRETDADITVAALPMDEERATAFGLMKIDEEGRIVEFAEKPKGEQLKAMMVDT
TILGLDDVRAKEMPYIASMGIYVISKHVMLQLLRDQFPGANDFGSEVIPGATSTGMRVQAYLYDGYWEDIG
TIEAFYNANLGITKKPIPDFSFYDRSAPIYTQPRHLPPSKVLDADVTDSVIGEGCVIKNCKIHHSVVGLRS
CISEGAIIEDTLLMGADYYETEADKKLLADKGGIPIGIGKNSHIRRAIIDKNARIGDNVKIINVDNVQEAA
RETDGYFIKSGIVTVIKDALLPSGTVI

Fig. 30

MAATMTVEEVRKAQRAEGPATVLAIGTATPANCVYQADYPDYYFKITKSDHLADLKEKFKRMCDKSQIRKR
YMHLTEEILEENPNMCAYMAPSLDARQDIVVVEVPKLGKAAAQKAIKEWGQPRSKITHLVFCTTSGVDMPG
ADYQLTKMLGLRPSVKRLMMYQQGCFAGGTVLRLAKDLAENNRGARVLVVCSEITAVTFRGPHESHLDSLV
GQALFGDGAAAVIIGADPDVSVERPLFQLVSVSQTILPDSEGAIDGHLREVGLTFHLLKDVPGLISKNIER
ALEEAFKPLGIDDWNSVFWVAHPGGPAILDMVEAKVNLNKERMRATRHVLSEYGNMSSACVLFIMDEMRKR
SAEDGHTTTGEGMDWGVLFGFGPGLTVETVVLHSMPIAADATA

Fig. 31

MATTMTVEEVRKAQRAEGPATVLAIGTATPANCVYQADYPDYYFKITKSDHLADLKEKFKRMCDKSQIRKR
YMHLTEEILEENPNMCAYMAPSLDARQDIVVVEVPKLGKAAAQKAIKEWGQPRSKITHLVFCTTSGVDMPG
ADYQLTKMLGLRPSVKRLMMYQQGCFAGGTVLRLAKDLAENNRGARVLVVCSEITAVTFRGPHESHLDSLV
GQALFGDGAAAVIIGADPDVSVEHPLFQLVSASQTILPDSEGAIDGHLREVGLTFHLLKDVPGLISKNIER
ALEEAFKPLGIDDWNSVFWVAHPGGPAILDMVEAKVNLNKERMRATRHVLSEYGNMSSACVLFIMDEMRKR
SAEDGHTTTGEGMDWGVLFGFGPGLTVETVVLHSMPIAAGATA

Fig. 32

RADLEEEGSFDDAVAGCDYAFLVAAPVNLKAENPEKDMVEPAVGGTLNAMRSCVRAGTVKRVVLTSSVASV
SARPLLQGDGHVLDEESWSDVDFLRAKATGHWGYPVSKVLLEKAAC<u>AFAQASGISLVTVCPVVVV</u>GKAPAV
QVHTSVPDVLSPLSGDEAKIQILQHIERASGSISLVHVDDLCRAEVFLAEEEAVASGRYICCSLSTTAGVL
ARFLSVKYPQYKVRTDRFSGSPEKPRVCMSSAKLVAEGFQYKYKTLDEIYDDVVEYGRALGILP

Fig. 33

MAAAGDGSRRKTACVTGGNGYIASALVKMLLEKGYAVKTTVRNPDDMEKNSHLKDLQALGPLEVFRADLQE
EGSFDDAVAGCDYAFLVAAPVNLKAENPEKDMVEPAVGGTLNVMRSCVRAGTVKRVVLTSSVASVSARPLL
QGDGHVLDEESWSDVDFLRAKATGHWGYPVSKVLLEKAAC<u>AFAQASGISLVTVCPVVVV</u>GKAPAVQVHTSV
PDVLSPLSGDEAKIQILQHIERASGSISLVHVDDLCRAEVFLAEEEAVASGRYICCSLSTTAGVLARFLSV
KYPQYKVRTDRFSGSPEKPRVCMSSAKLVAEGFQYKYKTLDEIYDDVVEYGRALGILP

Fig. 34

FISVTVFYVVGLRQRDLVQAGVQGTLNVMRSCVKAGTVKRVILTSSDSAVCQRPLEGDGHVLDEGSWSDVP
YLRAEQPEAWGYAVSKVLMEEAAGKFAD<u>ENGLGLVSVLPTFTLGAAPV</u>SQARTSVPVVLSLLSGDEEQLNL
LEAMHLITESVSINHIDDLCRAQVFLAENEASSGRYICSSHDTTVVQLARLLADKYPQYNVKSQRFDGSPE
KPRVCLSSQKLIGEGFVYKYDDLGAILDDLVEYGRTTGILPF

Fig. 35

MASAAGGRRKTACVTGGSGYIASALIKTLLDHGYAVKTTVRNPDDLEKTSHLKDLQAFGPLEIFRGELDVE
GSFDDSVSGCDYVFLVAAPMDMGSLNPERDLVQAGVQGTLNVMRSCVKAGTVKRVILTSSDSAVCQRPLEG
DGHVLDEGSWSDVPYLRAEQPEAWGYAVSKVLMEEAAGKFAD<u>ENGLGLVSVLPTFTLGAAPV</u>SQARTSVPV
VLSLLSGDEEQLNLLEAMHLITESVSINHIDDLCRAQVFLAENEASSGRYICSSHDTTVVQLARLLADKYP
QYNVKSQRFDGSPEKPRVCLSSQKLIGEGFVYKYDDLGAILDDLVEY<u>GRTTGILPFAAASIWFLFRG</u>SSSG
KKLSKLPLPPGPRGWPVLGNLPQVGAKPHHTMAALSQQFGPLFRLRFGVAEVVVAASAKVASQFLRAHDAN
FSDRPPNSGA<u>EHVAYNY</u>QDLVFAPYGSRWRALRKLCALHLFSAKALDALRAVREAEVALMVKQLKESAPAG
VVVGQEANVCATNALARAAVGRRVFGGSAGEGAREFKDMVVELMQLAGVFNIGDFVPALRWLDPQGVVARM
KRLHRRYDAMMDGFISERDQRHNQAAADGERKDLLSVMLGYMRPDGGGEEEGISFNHTDIKALLLNLFTA
GTDTTSSTVEWALAELIRHKDVLTQAQRELDDIVGQDRLVTESDLPHLTFLTAVIKETFRLHPSTPLSLPR
VATEDCEVEGYRIPKGTTLLVNVWAIARDPASWGPDALEFRPARFLAGGLHESVDVKGSDYELIPFGAGRR
<u>ICAGLSWGLRMVTLMTATLV</u>HAFDWSLVDGLTPEKLDMEEAYGLTLQRAAPLMVRPIPRLLSSAYTV

Fig. 36

AAASIWFLFRGSSSGKKLSKLPLPPGPRGWPVLGNLPQVGAKPHHTMAALSQQFGPLFRLRFGVAEVVVAA
SAKVASQFLRAHDANFSDRPPNSGAEHVAYNYQDLVFAPYGSRWRALRKLCALHLFSAKALDALRAVREAE
VALMVKQLKESAPAGVVVGQEANVCATNALARAAVGRRVFGGSAGEGAREFKDMVVELMQLAGVFNIGDFV
PALRWLDPQGVVARMKRLHRRYDAMMDGFISERDQRHNQAAADGERKDLLSVMLGYMRPDGGGEEEGISF
NHTDIKALLLNLFTAGTDTTSSTVEWALAELIRHKDVLTQAQRELDDIVGQDRLVTESDLPHLTFLTAVIK
ETFRLHPSTPLSLPRVATEDCEVEGYRIPKGTTLLVNVWAIARDPASWGPDALEFRPARFLAGGLHESVDV
KGSDYELIP[FGAGRRICAG]LSWGLRMVTLMTATLVHAFDWSLVDGLTPEKLDMEEAYGLTLQRAAPLMVRP
IPRLLSSAYTV

Fig. 37

MDHRDVLVLLCSLAALAAASIWFLFRGSSSGKKLSKLPLPPGPRGWPVLGNLPQVGAKPHHTMAALSQQFG
PLFRLRFGVAEVVVAASAKVASQFLRAHDANFSDRPPNSGAEHVAYNYQDLVFAPYGSRWRALRKLCALHL
FSAKALDALRAVREAEVALMVKQLKESAPAGVVVGQEANVCATNALARAAVGRRVFGGSAGEGAREFKDMV
VELMQLAGVFNIGDFVPALRWLDPQGVVARMKRLHRRYDAMMDGFISERDQRHNQAAADGERKDLLSVMLG
YMRPDGGGGEEEGISFNHTDIKALLLNLFTAGTDTTSSTVEWALAELIRHKDVLTQAQRELDDIVGQDRLV
TESDLPHLTFLTAVIKETFRLHPSTPLSLPRVATEDCEVEGYRIPKGTTLLVNVWAIARDPASWGPDALEF
RPARFLAGGLHESVDVKGSDYELIP FGAGRRICAG LSWGLRMVTLMTATLVHAFDWSLVDGLTPEKLDMEE
AYGLTLQRAAPLMVRPIPRLLSSAYTV

Fig. 38

RSELAGMDIPLSLLLSTLAISATICYVFFRAGKGHRAPLPLPPGPRGWPVLGNLPQLGGKTHQTLHEMTKV
YGPVLRLRFGSSVVVVAGSAAVAEQFLRTHDAKFSSRPPNSGGEHMAYNYRDVVFAPYGPRWRAMRKVCAV
NIFSARALDDLRGFREREAALMVRSLADAAKAGVAVAVGKAANVCTTNGLSRAAVGLRVFGSDGARDFKEI
VLEVMEVGGVLNVGDFVPALRWLDPQGVVARLKKLHRRFDDMMNGIIAERRTGTKTAVVEEGKGDLLGLLL
AMVQEDKSLTGSEEDKITDTDVKALILNLFVAGTETTSSIVEWAVAELIRHPDILKQAQEELDAVVGRDRL
VSESDLPRLTFFNAIIKETFRLHPSTPLSLPRMASEECEVAGYHIPRGTELLVNVWGIARDPALWPDPLEY
QPARFLPGGSHENVDLKGGDFGLIP FGAGRRICAG LSWGLRMVTITTATLVHSFDWELPAGQTPDKLNMEE
AFSLLLQRAVPLMVHPVPRLLPSAYEIS

Fig. 39

MRSELAGMDIPLPLLLSTLAISATICYVFFRAGKGHRAPLPLPPGPRGWPVLGNLPQLGGKTHQTLHEMTK
VYGPVLRLRFGSSVVVVAGSAAVAEQFLRTHDAKFSSRPPNSGGEHMAYNYRDVVFAPYGPRWRAMRKVCA
VNIFSARALDDLRGFREREAALMVRSLADAAKAGVAVAVGKAANVCTTNGLSRAAVGLRVFGSDGARDFKE
IVLEVMEVGGVLNVGDFVPALRWLDPQGVVARLKKLHRRFDDMMNGIIAERRTGTKTAVVEEGKGDLLGLL
LAMVQEDKSLTGSEEDKITDTDVKALILNLFVAGTETTSSIVEWAVAELIRHPDILKQAQEELDAVVGRDR
LVSESDLPRLTFFNAIIKETFRLHPSTPLSLPRMASEECEVAGYHIPRGTELLVNVWGIARDPALWPDPLE
YQPARFLPGGSHENVDLKGGDFGLIP FGAGRRICAG LSWGLRMVTITTATLVHSFDWELPAGQTPDKLNME
EAFSLLLQRAVPLMVHPVPRLLPSAYEIS

Fig. 40

DIPLPLLLSTLAISATICYVFFRAGKTHQTLHEMTKVYGPVLRLRFGSSVVVVAGSAAVAEQFLRTHDAKF
SSRPPNSGGEHMAYNYQDIVFAPYGPRWRAMRKVCAVNIFSARALDDLRGFREREAALMVRSLADAAKAGA
AVAVGKAANVCTTNGLSRAAVGLRVFGSDGTRDFKEIVLEVMEVGGVLNVGDFVPALRWLDPQGVVARMKK
LHRRFDDIMNGIIAERRTGAKTAVVEEGKGDLLGLLLAMVQEDKSLTGSEEDKITDTDVKALILNLFVAGT
ETTSSIVEWAVAELIRHPDILKQAQEELDTVVGRDRIVSESDLPRLTFFNAIIKETFRLHPSTPLSLPRMA
SEDCEVAGYHIPRGTELLVNVWGIARDPSLWPDPLEYRPARFLPGGSHENVDLKGGDFGLIP FGAGRRICA
G LSWGLRMVTVTTATLVHSFDWELPAGQTLDKLNMEEAFSLLLQRAMPLMVHPVPRLLPSAYEIS

Fig. 41

MRNELAGMDIPLPLLLSTLAISATICYVFFRAGKTHQTLHEMTKVYGPVLR<u>LRFGSSVVVVAGSAAVAEQF</u>
<u>L</u>RTHDAKFSSRPPNSGGEHMAYNYQDIVFAPYGPRWRAMRKVCAVNIFSARALDDLRGFREREAALMVRSL
ADAAKAGAAVAVGKAANVCTTNGLSRAAVGLRVFGSDGTRDFKEIVLEVMEVGGVLNVGDFVPALRWLDPQ
GVVARMKKLHRRFDDIMNGIIAERRTGAKTAVVEEGKGDLLGLLLAMVQEDKSLTGSEEDKITDTDVK<u>ALI</u>
<u>LNLFVAGTETTSSIVEW</u>AVAELIRHPDILKQAQEELDTVVGRDRIVSESDLPRLTFFNAIIKETFRLHPST
PLSLPRMASEDCEVAGYHIPRGTELLVNVWGIARDPSLWPDPLEYRPARFLPGGSHENVDLKGGDFGLIP⬚F
⬚GAGRRICAG⬚LSWGLRMVTVTTATLVHSFDWELPAGQTLDKLNMEEAFSLLLQRAMPLMVHPVPRLLPSAYE
IS

Fig. 42

MAMADCMQEWPEPVVRVQAVAESGLAAIPDCYVKPPRDRPAAQHLATAASADGDVLHEPLDTSIPVIDLGE
LVAATADEGRMRQIMEAVAAACREWGFFQVVNHGVAPELMHAAREAWRGFFRLPITAKQQYANLPRTYEGY
GSRVGVQKGGPLDWGDYYFLHLAPDAGKSPDKYWPTNPAICKDVSEEYGREVIRLCELLMKVMSASLGLEA
TRFQEAFGGSECGVCLRANYYPRCPQPDLTLGLSAHSDPGVLTVLLADEHVRGLQVRRADGEWVTVQPARH
DAFIVNVGDQIQILSNSMYKSVEHRVMVNAKEERISLALFYNPRGDVPIAPAPETVTPERPALYPSMTFDE
YRAYIRKYGPRGKAQVEGAKQGQGS

SEQUENCE LISTING

<160> NUMBER OF SEQ ID NOS: 92

<210> SEQ ID NO 1
<211> LENGTH: 1737
<212> TYPE: DNA
<213> ORGANISM: Lolium perenne

<400> SEQUENCE: 1

```
gctgaaatct cctcccgtcc tctcctcctc ctcctccgct tctccaaccc tcctccaccg      60
cccggatcgc gatggccgcc gccgccgtcg cccccgacgc gaagatcgag aagttccgcg     120
acgccgtcgc caagctcggc gagatcagcg agaacgagaa ggccggctgc atcagcctcg     180
tctcgcgcta cctcagcggc gaggcggagc agatcgagtg gagcaagatc cagaccccca     240
ccgacgaggt cgtcgtgccg tacgacaccc tcgcgcccgc gcccgaagat ctcgacgcca     300
tgaaggcgct gctcgacaag ctcgtcgtgc tcaagctcaa cggaggcctc ggcaccacca     360
tgggctgcac cggccccaag tctgttattg aagttcgcaa tgggtttaca tttcttgacc     420
ttattgtgat tcagattgag tccctgaaca agaagtacgg atgtgatgtc cctttacttc     480
tcatgaactc cttcaacacg catgatgata ctcaaaagat tgttgagaag tactccaact     540
ccaacatcaa catccacact ttcaaccaga gccaatatcc caggattgtt actgaagact     600
tcttgccact tccgagcaaa gggcagtcag gaaaggatgg ctggtatccc caggccatg      660
gcgatgtttt cccctctttg aacaacagtg gaaaacttga taccttattg tcgcagggca     720
aggagtatgt ctttgttgcc aactcagaca acttgggtgc tatagttgac atcaagatat     780
tgaaccacct gatcaacaac aagaatgaat actgcatgga ggttactccg aaaacattgg     840
ctgatgttaa aggtggcacc ctcatctcat atgaaggaag ggtccagctc ttggagattg     900
cccaagtccc tgatgagcat gtgaatgaat tcaagtcaat tgagaagttc aagatattca     960
ataccaacaa cctgtgggtg aacttgaagg cgatcaagag gcttgttgaa gctgatgcac    1020
ttaagatgga gatcattccc aaccctaagg aagttgatgg cgtgaaagtc cttcagctag    1080
aaactgcagc tggggcagcg attcggttct ttgataacgc aatcggcatc aacggtcccc    1140
gctcaaggtt tctgcccgtg aaggctacat cagatttgtt gcttgtgcag tctgacctct    1200
ataccttggt cgatggctat gtcatccgca acccagctag agtgaagcct tcaaacccctt   1260
ccattgagct tggtcctgag ttcaagaagg tcgccagttt cctggcccgg ttcaagtcaa    1320
tccccagcat cgttgagctc gacagcttga aggtctctgg tgatgtctcg tttggctctg    1380
gcatcgtact caagggcaac gtgaccatcg ctgccaagtc tggagtcaag ctggagatcc    1440
cagacggagc tgtgcttgag aacaaggaca tcaacggccc agaggatctt tgagcgacgc    1500
tcactcgcca ccgccagacg catcccggaa gccttccagt tctccttccc tgagttaaca    1560
acagtcttgt aattttcgtg tgcattctgc cgtggggtcg tcctgtggga gcccgtttat    1620
acagaataat tgtaatcccc tctgtccatc tgcacttctg ttcttcctgg gtggaaccag    1680
ggacgtaaag ttcttttggt gaaatgatat gccatagttt tattttcaaa aaaaaaa       1737
```

<210> SEQ ID NO 2
<211> LENGTH: 1697
<212> TYPE: DNA
<213> ORGANISM: Festuca arundinacea

<400> SEQUENCE: 2

```
gctgaaatct cctcccgtcc tctcctcctc cgcttctcca agcctcctcc tccgcccgga      60
```

```
tcgcgatggc cgccgtcgcc gccgacgcga agatcgagaa gttccgcgac gccgtcgcca    120
agctcgacga gatcagcgag aacgagaagg ccgggtgcat cagcctcgtc tcgcgctacc    180
tcagcggtga ggcggagcag atcgagtgga gcaagatcca gaccccacc gacgaggtcg     240 tggtgcccta cgacaccctc gcgcccgcgc ccaagatct cgacgccatg aaggcgctgc     300
tcgacaagct cgtcgtgctc aagctcaacg gaggcctcgg caccaccatg ggctgcaccg    360
gtcccaagtc tgttattgaa gttcgcaatg ggtttacatt tcttgacctt attgtgattc    420
agatcgagtc cctgaacaag aagtacggat gtgatgtccc tttacttctc atgaactcct    480
tcaacacgca tgacgatact caaaagattg ttgagaagta ctccaactcc aacatcaaca    540
tccacacttt caaccagagc caatatccca ggattgttac tgaagacttc ttgccacttc    600
cgagcaaagg gaagtcagga aaggatggct ggtatccccc aggccatggt gatgttttcc    660
cctctttgaa caacagtgga aaacttgata ccttactgtc gcagggcaag gagtatgtct    720
tcgttgccaa ctcagacaac ttgggtgcta tagttgacat caagatattg aaccacctga    780
tcaacaacca gaatgaatac tgcatggagg ttactccgaa acattggct gatgttaaag     840 gtggcaccct catctcatat gaaggcaggg tccagctctt ggagattgcc caagtccctg    900
atgagcatgt gaatgaattc aagtcaattg agaagttcaa gatattcaat accaacaacc    960
tgtgggtgaa cttgaaggct atcaagaggc ttgttgaagc tgatgcactt aagatggaga    1020
tcattcccaa ccctaaggaa gttgatggcg tgaaagtcct tcagctagaa actgcagctg    1080
gggcagcgat ccggttcttc gagaaagcaa tcggcatcaa cggtccccgc tcaaggtttc    1140
tgcccgtgaa ggctacatca gatttgttgc ttgtgcagtc tgacctctat accttggtcg    1200
atggttatgt catccgcaac ccagctagag tgaagccttc aaaccctttcc attgagcttg    1260 gtcctgagtt caagaaggtc gccagtttcc tggcccggtt caagtcaatc cccagcatcg    1320
ttgagctcga cagcttgaag gtctctggtg atgtcacgtt tggctctggc gtcgtactca    1380
agggcaacgt gaccatcgct gccaagtctg gagtcaagct ggagatccca gacggagctg    1440
tgcttgagaa caaggacatc aacggcccgg aggatctttg agcgacgctc actcgccacc    1500
gccagacgca tcctggaagc cttccagttc tccttccctg agttaacaac agtcttgtaa    1560
ttttcgtgtg cattctgccg tggggtcgtc ctgtgggagc ccggttacag aataattgta    1620
atcccctctg tccatctgca cttctgttct tcctgggtgg taccagggac gtaaagttct    1680
tttggttaaa aaaaaaa                                                   1697
```

<210> SEQ ID NO 3  
<211> LENGTH: 2174  
<212> TYPE: DNA  
<213> ORGANISM: Lolium perenne

<400> SEQUENCE: 3

```
gctgtctccg gcggcgtacc tactctaact cgggcgacac gcacgcagat cccaacggtc     60
cggtctacta tggcggatgg taccacctct tctaccagca caaccccctat ggcgactcgt    120 ggggaaacgt atcttgggga catgccgtgt ccaaggacct ggtgaactgg cgtcacctcc    180
cggtcgcctt ggtgcccgat cagtggtacg acatcaacgg cgtcctgacg ggctctatca    240
cagtgctccc agacgggcgt gtcatcctgc tatacacggg gaacaccgac accttttcgc    300
aggtccagtg cctcgcagtg cccgccgacc catctgaccc gctcctccgt agctggatca    360 agcacccctgc caacccccatc ctcttcccgc cacctgggat cgggctcaag gacttccgtg    420
```

-continued

```
acccgctcac ggcctggttc gaacattccg acaacacgtg gcgcaccatc atcggatcca      480
aggatgacga cggccacgcc ggcatcgtcc ttagctacaa gaccaccgac tttgtgaatt      540
atgagctcat gccagggaac atgcatcgtg gccccgacgg caccggcatg tacgagtgcc      600
ttgacatcta ccctgtgggc ggcaactcat ccgagatgtt gggtggcgac tcctcgccgg      660
aggtgttgtt cgtgctcaag gagagcgcca acgacgagtg gcacgactac tacgcgcttg      720
ggtggttcga cgccaccgcc aacacgtgga cgccacagga ccccgaggcg gaccttggga      780
tcggcctcag gtacgactgg ggcaagtact acgcatccaa gtccttctac gacccgatca      840
agaaccggcg tgtcgtttgg gctttcgtcg gcgagaccgc tctgagcag gccgacaaag      900 ccaagggatg ggcgtccctc atgtcgattc cgaggatggt ggagcttgac aagaagaccc      960
ggacgaacct catccaatgg ccagtggagg agatcgagac ccttcgcagg aacgtcacag     1020
acctcggtgg catcaccgtt gaagccggct ccgtcattca ccttcccctc caacaaggcg     1080
ggcagcttga catcgaggcc tccttccgcc tcaactcttc ggacatcgat gcactcaacg     1140
aggccgacgt tggcttcaac tgcagtagca gcgctggggc agccgtgcgt ggtgcgctcg     1200
gccccttggg cctcctcgtc ttcgccgacg gtcgccacga acagacggca gcgtacttct     1260
acgtgtccaa gggcctcgac ggcagcctcc tgacgcacta ctgccacgac gagtcacggt     1320
cgacgcgagc aaaggacgtc gtgagccggg tggttggcgg cactgtgcca gtgcttgacg     1380
gtgaaacctt ttcagtgagg gtgctagtgg accactccat cgtgcagagc ttcgtgatgg     1440
gtgggaggac cacggtgaca tcgcgggcat acccgacgga ggccatctac gccgcggcag     1500
gggtgtacct gttcaacaac gcaacgagcg ccaccatcac cgccgaaggg ctcgtcgtgt     1560
acgagatggc ctcggccgag agtcaggcct tcttggctga cgacatgtag atgaaaacta     1620
gtgaagaaca tgtcaatggc gatcgtcaag cttgctggat ggggatcgtc aggtaaggag     1680
agcaggtcac agagatcttc attcgcaagt tcgcgggcat gttgtagcta gggtggtgcc     1740
attgcatgct gtggagggc tgacggctct ctttggactg gattgcgatc tggccaagac     1800
ggtagatcga ggaagccctc gtcgcccatg gctgggcaaa gcagtttgga ccagaaggtg     1860
ttggttcatg tcgttgcacc tgatgacacg atggtgccca acgaggcatc ctgacttcca     1920
catcgtctct gcgcatgtca tgctccttac tatctacctc tcccttctg ttagttttgt      1980 tggtctcgtt cgctgtcgtc ctacctgatg tagctccaat cttgttgcc ggtgcttttt       2040 tgtcccagtt gttcatccgt atctcgccaa ggtacggtta gctatattgt ttcaaacatg     2100
cttcgagctt gtaatgttta tattttttgc tggaaccgga gatgcctcaa cgatacagat     2160
atacaaaaaa aaaa                                                       2174
```

<210> SEQ ID NO 4
<211> LENGTH: 2478
<212> TYPE: DNA
<213> ORGANISM: Lolium perenne

<400> SEQUENCE: 4

```
atggagtcca cgccgtcgt cgtcccaggc acaacggcgc cactgctccc gtacgactcc       60
cgtgaaaacc agagtagcgg cggcggtgtg tggtggcgcg cgtgcgcggc ctcggccgtg      120
gtgctgctgg tcgtcgtcgg cttcttcgct ggtggcaggg tggatttggg tcaggccggc      180
gaggtgtctg cgacttcttc tgttccggcg gcaatgatgg agatcccgag gagcaggggc      240
aagaatttcg cgcgtgtcgga gaaggccgac ggcgggttcc cgtggagcaa cgccatgctg      300
cagtggcagc acaccgggtt ccatttccag ccactgaagc actacatgaa cgatcccaac      360
```

-continued

```
ggtccggtct actatggcgg atggtaccac ctcttctacc agcacaaccc ctatggcgac    420
tcgtggggaa acgtatcttg gggacatgcc gtgtccaagg acctggtgaa ctggcgtcac    480
ctcccggtcg ccttggtgcc cgatcagtgg tacgacatca acggcgtcct gacgggctct    540
atcacagtgc tcccagacgg gcgtgtcatc ctgctataca cggggaacac cgacaccttt    600
tcgcaggtcc agtgcctcgc agtgcccgcc gacccatctg acccgctcct ccgtagctgg    660
atcaagcacc ctgccaaccc catcctcttc ccgccacctg ggatcgggct caaggacttc    720
cgtgacccgc tcacggcctg gttcgaacat tccgacaaca cgtggcgcac catcatcgga    780
tccaaggatg acgacggcca cgccggcatc gtccttagct acaagaccac cgactttgtg    840
aattatgagc tcatgccagg gaacatgcat cgtggcccccg acggcaccgg catgtacgag    900
tgccttgaca tctaccctgt gggcggcaac tcatccgaga tgttgggtgg cgactcctcg    960
ccggaggtgt tgttcgtgct caaggagagc gccaacgacg agtggcacga ctactacgcg   1020
cttgggtggt tcgacgccac cgccaacacg tggacgccac aggaccccga ggcggacctt   1080
gggatcggcc tcaggtacga ctggggcaag tactacgcat ccaagtcctt ctacgacccg   1140
atcaagaacc ggcgtgtcgt ttgggctttc gtcggcgaga ccgactctga gcaggccgac   1200
aaagccaagg gatgggcgtc cctcatgtcg attccgagga tggtggagct tgacaagaag   1260
acccggacga acctcatcca atggccagtg gaggagatcg agacccttcg caggaacgtc   1320
acagacctcg gtggcatcac cgttgaagcc ggctccgtca ttcaccttcc cctccaacaa   1380
ggcgggcagc ttgacatcga ggcctccttc cgcctcaact cttcggacat cgatgcactc   1440
aacgaggccg acgttggctt caactgcagt agcagcgctg gggcagccgt gcgtggtgcg   1500 ctcggccccct ttggcctcct cgtcttcgcc gacggtcgcc acgaacagac ggcagcgtac   1560
ttctacgtgt ccaagggcct cgacggcagc ctcctgacgc actactgcca cgacgagtca   1620
cggtcgacgc gagcaaagga cgtcgtgagc cgggtggttg gcggcactgt gccagtgctt   1680
gacggtgaaa ccttttcagt gagggtgcta gtggaccact ccatcgtgca gagcttcgtg   1740
atgggtggga ggaccacggt gacatcgcgg gcatacccga cggaggccat ctacgccgcg   1800 gcagggtgt acctgttcaa caacgcaacg agcgccacca tcaccgccga agggctcgtc   1860
gtgtacgaga tggcctcggc cgagagtcag gccttcttgg ctgacgacat gtagatgaaa   1920
actagtgaag aacatgtcaa tggcgatcgt caagcttgct ggatggggat cgtcaggtaa   1980
ggagagcagg tcacagagat cttcattcgc aagttcgcgg gcatgttgta gctagggtgg   2040
tgccattgca tgctgtggag gggctgacgg ctctctttgg actggattgc gatctggcca   2100
agacggtaga tcgaggaagc cctcgtcgcc catggctggg caaagcagtc tggaccagaa   2160
ggtgttggtt catgtcgttg cacctgatga cacgatggtg cccaacgagg catcctgact   2220
tccacatcgt ctctgcgcat gtcatgctcc ttactatcta cctctcccct tctgttagtt   2280
ttgttggtct cgttcgctgt cgtcctacct gatgtagctc caatctttgt tgccggtgct   2340
tttttgtccc agttgttcat ccgtatctcg ccaaggtacg gttagctata ttgtttcaaa   2400
catgcttcga gcttgtaatg tttatatttt ttgctggaac cggagatgcc tcaacgatac   2460
agatatacaa aaaaaaaa                                                 2478
```

<210> SEQ ID NO 5
<211> LENGTH: 2118
<212> TYPE: DNA
<213> ORGANISM: Lolium perenne

```
<400> SEQUENCE: 5
gcggcgcggc tctcaagggg ccagcctacc cattccccgc ctctccggcc accagcgggg      60
agcgctgccc gacgaagcgt ggtgggtggg ccgccccaca ttgagttaga aacaaggcac     120
taatggggat tgcggaggtg gctctccaca ccatgccggg ggcatttgcc agccactccc     180
cggcatccag tttacccctc aggactgaca cgaggagttt gaggaagagg ggcaccaatt     240
cgttttacag gacacttgga ggtccaccaa agttccctga gttgcggccg gttgagtgcc     300
agtgccagag gattgatgac cttgcggggg tcatcgaagc tgggaacggg acatgggcca     360
ccgacatggt gaacaaggcc agccaggttc ttggtgatgt cgctgtgcct ggtcaggctt     420
taggtggcaa tgcaagtctg agtggagatc ctgagaaggt tctgcctagg aggcggaact     480
tgtcatcggt tgaggatgaa gcttgggacc ttttgaggga atctgttgtt aattattgtg     540
gtagtccagt tggaacaatt gctgccaatg atccaaatga cagtaatcca gcaaattatg     600
atcaggtgtt tattcgggac tttataccgt ctggcattgc ttttctattg aaggggggagt     660
atgaaattgt acgcaatttc attctacaca cccttcagct tcagagctgg gagaagacaa     720
tggactgcca tagtccaggt caaggcttaa tgcctgccag cttcaaggtg cggactattc     780
cacttgacgg cgatgagaat gccactgagg aggtattgga tcctgatttc ggggaagctg     840
caatagggcg tgtggcacct gttgattcag gtctatggtg gatcatattg ctcagggcat     900
atggaaaatg ttcgggtgat tgtcagttc aagagagaat tgatgtccag actggcataa     960
aaatgattct gaagctttgt ttagctacg ggtttgacat gttccctaca ttactggtaa    1020
ctgatggttc atgcatgatt gatcgtcgaa tgggaatcca cggacatcca cttgaaattc    1080
aggcactgtt ctattcagct ctcttgagtg cacgtgagat gttgactcct gaagatggat    1140
cagctgactt aatccgtgcc ctaaataaca ggcttgtcgc gctgtccttt catatcaggg    1200
agtactattg ggtcgacatg caaaaactga atgagatata tcgatataaa actgaagaat    1260
attcttatga tgctgtcaac aagttcaaca tatatcctga tcaggtttct ccttggcttg    1320
ttgaatggat acctcctaaa gggggttact ttattggaaa cctgcagcct gcacatatgg    1380
acttccggtt ctttttcttg gggaatttat ggtcaattgt aagcagcttg caacaaccc    1440
aacaatcaca tgctattttg gatctgattg aatcgaaatg gtctgattta gtggcagaga    1500
tgccactgaa gatatgttat cctgctcttg agaatctgga atggaaaatc attactggaa    1560
gtgaccctaa aaacacgcct tggtcatacc ataatggagg atcctggcca acattattgt    1620
ggcagctcac agtggcatct ctcaagatga acagaccaga gattgctgca aaagctgtgg    1680
agatagctga gcggcgcatt gctacagaca aatggcctga atactatgac acgaagcgag    1740
cacgcttcat agggaaacag tctcggcttt accagacatg gtctattgct gggtaccttg    1800
tagcgaagca actgctggac aaacctgatg ctgctcgaat actctggaac gacgaggaca    1860
cggaaattct taatgctttt agcacaaaca ggaaacgtgg caagaaagtg ttgaagaaga    1920
catacattgt gtgagttctc agcactgtta agttatagga tgtctcttct gtacatactt    1980
acaaaaggtc gtgcttttga tggaggaatg cccgtgttgg atgttgttgt aatggatgca    2040
tctggccttg caagaaatca cttgcttgag cattcctcaa ttatttactt gccatcactt    2100
tttgcactaa aaaaaaaa                                                   2118

<210> SEQ ID NO 6
<211> LENGTH: 1942
<212> TYPE: DNA
<213> ORGANISM: Festuca arundinacea
```

<400> SEQUENCE: 6

```
gaccccttcc gcgccgcgct cgcgcctgcg tcgccgccgc tcgaggcgcc ccccttgat      60
gagctcccca ccgccccgtc gcactccgag ccagcgtctg cggccgccgc ggcgcccgag    120
caggatccgg tggatttgca gcacgaggag ttggacggcc tcaaggccgg ggtggaggcg    180
gtgaggagca gggaggagtc gccgcaggag aaggaagcgt ggtggctgct caaccgtgcg    240
gttgtgaatt actgcggcag cgcggtgggg acggtggccg cgaacgaccc gtccacggcc    300
aaccacatgc tcaattacga ccaggtgttc atcaggact ttgtgccgtc tgccatcgcg     360
ttcctcctca agggtgagag cgacatcgtg aagaacttct tgctgcacac cttgcagctc    420
cagagttggg agaagacagt tgattgctat agccctggtc aggggttgat gcctgctagt    480
tttaaagtca gatctgtgcc tctagatgga acaatgaag catttgaaga ggttcttgac     540
cctgactttg gagaatcggc tattgggcgt gtagcacctg ttgactctgg gctttggtgg    600
ataattctat tgagggcata tggtaaaatt actggagact atgcactaca agaaagggtt    660
gatgtgcaga caggcatcag actaatcctg aatttgtgct tgtctgacgg atttgacatg    720
tttcctacat tgttagtcac tgatggatca tgcatgattg atcggaggat gggaatccat    780
gggcatcctc ttgagatcca ggctctgttt tattctgctt tgcgatgtgc ccgtgaaatg    840
gtcaatatag atgatgggtc taagaacttg atccgtgtta caacaacag gctcagtgct     900
ctgtcatttc acataagaga gtactattgg gtggacatga agaagataaa tgagatttat    960
cgctacaaga ctgaggagta ctcacatgat gctatcaata agttcaacat ctacccagag   1020
caaatcccat cttggcttgc agactggatt cctgagaaag gtggctatct tataggaaac   1080
ctacaaccag ctcacatgga tttcaggttc ttttctctag gaaatctctg gctattgtt    1140
tcctctttag ccactccaaa gcaagcagag ggtatcttga acctcattga gaccaaatgg   1200
gatgatatag ttgcaaatat gcctctcaag atatgctacc ctgctctgga gtatgaggaa   1260
tggcgtatta tcaccggttg tgaccccaaa aacacgccct ggtcgtatca taatggtgga   1320
tcttggccta cattgctatg gcagttcacc ctagcctgta tcaagatggg taggcctgac   1380
ctggcaagga gggctgttga ggccgtggag aagaggctct cggatgacaa gtggccagaa   1440
tattatgaca ccaggaatgg aaggtttatt ggaaaacagt cgaggctata ccaaacctgg   1500
acaattgcag ggtttcttag ctcaaaattg cttttggact gtccagagat ggcatcaata   1560
ttaatatgtg acgaagatct cgatctacta aagggtgtg cttgtggcgc gaacaagagt    1620
gctcgcgtga atgctcccg tcgtgcagcc aggtctcaag tccttgtgta gttccatact   1680
tttgcttgac agccaagacc tgcagtgctc ctttcgagtc acagaagttg gcacttgtta   1740
cctcaccagg gtgaccacct cctgtgccgg ttattttggc gagtttgtgg cccttaatc   1800
tattgatacg agagtatact ttgttgtata gatttcaaca tgtgtacacg aagccaatta   1860
actcaagttg attggcagtt ttataaacag atagcatgta aatattacca cttgtaatca   1920
atttattccg agaaaaaaaa aa                                              1942
```

<210> SEQ ID NO 7
<211> LENGTH: 2250
<212> TYPE: DNA
<213> ORGANISM: Festuca arundinacea

<400> SEQUENCE: 7

```
gaaagcggtt cgagcctgtg caaacccagc tcgaaatccc tcaattccac gaatccgatc     60
```

```
gaagccttt   cttcctccgc  aatccaaatc  tcgcgagaca  agcgggcgct  gcaatggcgg   120
ccgccgccat  ctcccacctc  cgacggggca  cgcagcggca  cgcgctcctg  tacctctcgc   180
gccgccactt  ctctaactcc  ccctcaccg   ccgccgcccc  cctcgccgcc  gccgcccgcc   240
gccttctctc  cacgacagtg  gaatccggca  cgtcgtcggc  ggcgggaagc  tacaagcccc   300 cgccctcga   tcccttccgc  gccgccctcg  ccccagcgtc  gccgccgctc  gagtcgcctc   360
cccttgatga  gctccccacc  gccccgtcgc  actccgagcc  agcgtctgcg  gccgccgcgg   420
cgcccgagca  ggatccggtg  gatttgcagc  acgaggagtt  ggacggcctc  aaggccgggg   480
tggaggcggt  gaggagcagg  gaggagtcgc  cgcaggagaa  ggaagcgtgg  tggctgctca   540
accgtgcggt  tgtgaattac  tgcggcagcg  cggtggggac  ggtggccgcg  aacgacccgt   600
ccacggccaa  ccacatgctc  aattacgacc  aggtgttcat  cagggacttt  gtgccgtctg   660
ccatcgcgtt  cctcctcaag  ggtgagagcg  acatcgtgaa  gaacttcttg  ctgcacacct   720
tgcagctcca  gagttgggag  aagacagttg  attgctatag  ccctggtcag  gggttgatgc   780
ctgctagttt  taaagtcaga  tctgtgcctc  tagatggaaa  caatgaagca  tttgaagagg   840
ttcttgaccc  tgactttgga  gaatcggcta  tgggcgtgt   agcacctgtt  gactctgggc   900
tttggtggat  aattctattg  agggcatatg  gtaaaattac  tggagactat  gcactacaag   960
aaagggttga  tgtgcagaca  ggcatcagac  taatcctgaa  tttgtgcttg  tctgacggat  1020
ttgacatgtt  tcctacattg  ttagtcactg  atggatcatg  catgattgat  cggaggatgg  1080
gaatccatgg  gcatcctctt  gagatccagg  ctctgtttta  ttctgctttg  cgatgtgccc  1140
gtgaaatggt  caatatagat  gatgggtcta  agaacttgat  ccgtgttatc  aacaacaggc  1200
tcagtgctct  gtcatttcac  ataagagagt  actattgggt  ggacatgaag  aagataaatg  1260
agatttatcg  ctacaagact  gaggagtact  cacatgatgc  tatcaataag  ttcaacatct  1320
acccagagca  aatcccatct  tggcttgcag  actggattcc  tgagaaaggt  ggctatctta  1380 taggaaaccct  acaaccagct  cacatggatt  tcaggttctt  ttctctagga  aatctctggg  1440
ctattgtttc  ctctttagcc  actccaaagc  aagcagaggg  tatcttgaac  ctcattgaga  1500
ccaaatggga  tgatatagtt  gcaaatatgc  ctctcaagat  atgctaccct  gctctggagt  1560
atgaggaatg  gcgtattatc  accggttgtg  accccaaaaa  cacgccctgg  tcgtatcata  1620
atggtggatc  ttggcctaca  ttgctatggc  agttcaccct  agcctgtatc  aagatgggta  1680
ggcctgacct  ggcaaggagg  gctgttgagg  ccgtggagaa  gaggctctcg  gatgacaagt  1740
ggccagaata  ttatgacacc  aggaatggaa  ggtttattgg  aaaacagtcg  aggctatacc  1800
aaacctggac  aattgcaggg  tttcttagct  caaaattgct  tttggactgt  ccagagatgg  1860
catcaatatt  aatatgtgac  gaagatctcg  atctactaga  agggtgtgct  tgtggcgcga  1920
acaagagtgc  tcgcgtgaaa  tgctcccgtc  gtgcagccag  gtctcaagtc  cttgtgtagt  1980
tccatacttt  tgcttgacag  ccaagacctg  cagtgctcct  ttcgagtcac  agaagttggc  2040
acttgttacc  tcaccagggt  gaccacctcc  tgtgccggtt  attttggcga  gtttgtggcc  2100
ccttaatcta  ttgatacgag  agtatacttt  gttgtataga  tttcaacatg  tgtacacgaa  2160
gccaattaac  tcaagttgat  tggcagtttt  ataaacagat  agcatgtaaa  tattaccact  2220
tgtaatcaat  ttattccgag  aaaaaaaaa                                       2250
```

<210> SEQ ID NO 8
<211> LENGTH: 973
<212> TYPE: DNA
<213> ORGANISM: Lolium perenne

<400> SEQUENCE: 8

```
atttgcttga aaagagaaag ctaaatgaaa tctatagata caaaacagaa gaatattctt      60
atgatgccgt caacaagttt aacatatatc ccgatcagat tcctccctgg ctagttgaat     120
ggatccctcc gaaagggggt tatttcatcg gaaacctgca accagctcac atggatttcc     180
gattcttttc tctagggaac ttgtggtcta tagtaagcag tttggcaaca gctgatcaat     240
ctcatgctat tctggatcta gtggaagcaa aatggtctga tctagtggca gagatgccaa     300
tgaagatatg ttatcctgct cttgaggatc aagagtggaa atttattact gggagcgacc     360
ctaaaaatac accttggtca taccataatg gaggttcctg ccaacattg ttgtggcagc      420
tcacggtggc atgcatcaag atgaaccggc ccgagatcgc cgcaagagct gtggaggtgg     480
ctgaaagccg tatttccatg gataaatggc ccgaatacta cgataccaag cgtgggcggt     540
tcatcggtaa gcaggcccgg ttattccaaa cttggtccat tgccggcttt cttgtggcca     600
aactgctgct agaaaatccc gaaaaatcta gaatactctg gaacaacgaa gatgaggaaa     660
ttcttaatgc tttgagtctg atgactggcc catccagtcc gaagaggaag cgtggtagga     720
agacctatat tgtgtaagtc caacagcagt tctaacctct agggtttcat gggtgttgca     780
tttagttatg taagaatcgt ccacatatac cgttagagat atatttggta taggtatatt     840
aggtagtcta ggatttgtaa cctctaccta ccatatctct aggagagcta tcttagcctc     900
caagtcttgt accactatat atactcgccc gagaggctca atacaacatc aatcatattc     960
cgcaaaaaaa aaa                                                        973
```

<210> SEQ ID NO 9
<211> LENGTH: 2019
<212> TYPE: DNA
<213> ORGANISM: Lolium perenne

<400> SEQUENCE: 9

```
gaaaaccgtt cgcctttcgc aactcgctcc aggcgtctgc gcgcgcatgg cgatcgcggc      60
agcggccgcg ctgctgccgc tgcacctcgg atgctccgac gcggctcccc ggcggcccgg     120
taactccctc agagcccatc tgcggaaggg cgggatcagg ggcaggcggc ggagccctcc     180
gtgcgccgtc aactcgctgc atcccagcgg caacccaaaa actcccggcg gcggcgacgt     240
tggcggagcg tggggcttga acggcggcgc caccgccaag cccgatcacg cgccgccgag     300
ccagaggagg cgcgcgccgc gcgacgtgga ggaggaggcg tggcgctcc tccgggagtc      360
ggtggtgagc tactgcggca gccccgtggg caccatcgcc gcgtgcgacc ccaatgacgc     420
cagcccgctc aactacgacc aggtgttcat ccgggacttc gtgccctccg gcgtcgcctt     480
cctcctcaag ggggaacacg aaatcgtccg caacttcatc ctccacacgc tccagctcca     540
gagctgggag aaaacaattg actgtcatag cccgggccaa gggttaatgc cggctagttt     600
caaggtgcgt gttgttccac ttgatggtgg cgacgatggt gcgactgagg aagtcttgga     660
tcctgacttt ggggaggctg ctataggccg tgtggcacca gttgattcag gtctgtggtg     720
gatcatacta ctgagggcgt atggaaaatg ttcagggac ctctcattcc acgagagagt      780
ggatgtccag actggaataa aactgatctt gaagctctgc ttagctgatg ggtttgacat     840
gttccccacg ttgctagtca ctgatggctc ctgcatgatg gatcggcgaa tgggtatcca     900
tggacacccg ctggaaattc aggctctgtt ctattcagcc ctcttgtctg cacgtgagat     960
gcttaccca gaagatggat cggctgactt gatccgtgcc ctaaatagca ggcttatggc     1020
```

-continued

```
actctctttc catattaggg agtattattg gcttgaaaag agaaagctaa atgaaatcta   1080
tagatacaaa acagaagaat attcctatga tgccgtcaac aagtttaaca tatatcccga   1140
tcagattcct ccctggctag ttgaatggat ccctccgaaa gggggttatt tcatcggaaa   1200
cctgcaacca gctcacatgg atttccgatt cttttctcta gggaacttgt ggtctatagt   1260
aagcagtttg caacagctg atcaatctca tgctattctg gatctagtgg aagcaaaatg   1320
gtctgatcta gtggcagaga tgccaatgaa gatatgttat cctgctcttg aggatcaaga   1380
gtggaaattt attactggga gcgaccctaa aaatacacct tggtcatacc ataatggagg   1440
ttcctggcca acattgttgt ggcagctcac ggtggcatgc atcaagatga accggcccga   1500
gatcgccgca agagctgtgg aggtggctga agccgtatt tccatggata atggcccga   1560 atactacgat accaagcgtg ggcggttcat cggtaagcag gcccggttat tccaaacttg   1620
gtccattgcc ggctttcttg tggccaaact gctgctagaa aatcccgaaa atctagaat   1680 actctggaac aacgaagatg aggaaattct taatgctttg agtctgatga ctggcccatc   1740
cagtccgaag aggaagcgtg gtaggaagac ctatattgtg taagtccaac agcagttcta   1800
acctctaggg tttcatgggt gttgcattta gttatgtaag aatcgtccac atataccgtt   1860
agagatatat ttggtatagg tatattaggt agtctaggat ttgtaacctc tacctaccat   1920
atctctagga gagctatctt agcctccaag tcttgtacca ctatatatac tcgcccgaga   1980
ggctcaatac aacatcaatc atattccgca aaaaaaaa                          2019

<210> SEQ ID NO 10
<211> LENGTH: 2457
<212> TYPE: DNA
<213> ORGANISM: Lolium perenne

<400> SEQUENCE: 10
gctaccgccc aacctaaaca aaaccgtacc gaaccctgca attttgccat caacccctcg     60
ccgaccacat atttgcaaaa gcttaccttc aactgtacta tccctttac gccgagcccc    120 ctacgaggtt tccgcatctc gcttctgagt ccttcgccgg agtttccata tgaatggtca    180
aaccacgatg gggctcgcag cagccgccgc cgcagccgtg aggccgtgcc gccgccgcct    240
cctctcctcc gcctcagcgg cggcggcggc gaaggcctcc gcgacgccgc tcttcccgag    300
atgctcccac ccgcagcacc agcagcacag ccgccgcatc ccattcctcg tctcggcggc    360
gtcgcacacg tcgcagtccg acccgagcac caccccacc cccgtcacct ccgatccccg    420
ctccgccgtc gccgggaacc tcccttctt cgaccgcgtg ctcttcccgg gctcgttccc    480
cctcgagacc ccgcctgtcg aggagccggc gccggcgccg ccggccgatg aagcgcaggc    540
gtccgcttcg cccgtgagag aggagtcgga tacgagagg gaggcgtgga ggctgctgag    600
gagggcggtg gtgagctact gcggtgaccc ggtgggcacg gtggcggcgg aggacccgga    660
gtgcacggag atgctcaact acgaccaggt cttcatcaga gactttgtgc cttccgccct    720
cgccttcctc atgcgcgggg agaccgagat cgtccgcaat ttcctcctcc acaccctgca    780
gctgcagagc tgggagaaaa ctgttgactg ttacagccct gggcaaggct tgatgccagc    840
tagttttaag ataaagaccg ttccacttga tgaaaacaac gaagcattcg aggaggttct    900
ggatcctgac tttggtgaat cagctattgg ccgtgtagct ccagttgatt ctggactttg    960
gtggattatc ttactaagag cgtactgcaa gtttacaggc gactattcat tgcaagaaag   1020
agtggatgtg caaaccggga ttaaactgat cttgagtttg tgtttgactg atgggttcga   1080
catgtttccc acactactgg tcacagacgg atcatgcatg atagacagga ggatgggaat   1140
```

```
acatggacat cctcttgaga ttcaagcttt gttctattct gctctaagat gctcaaggga    1200
aatgattgtt atgaacgatg gctcaaaaca cctcctccaa gccatcaaca acaggctcag    1260
tgcgttgtct tttcacatta gggaatacta ctgggtcgat atgaagaaga taaatgagat    1320
ctacagatac aagacagaag aatactcaca tgatgcgacc aacaaattca acatttatcc    1380
cgagcaaatc ccttcctggc ttgttgattg ggttcctgag aaaggggtt atcttattgg     1440 aaatctgcag ccagctcaca tggattttag gttcttctcc cttggcaacc tttgggccat    1500
atcttcatct ctaactactc caacccaagc cgaaggaata cttagcctta ttgaggagaa    1560
atgggacgat cttgtggcaa atatgccact caagatatgt taccctgcaa tggaagatga    1620 tgaatgcgc attgttactg gcagtgaccc taagaacacc ccgtggtcat atcataatgg     1680
tggatcttgg ccaaccctgt tgtggcagtt tacactggct tgcatcaaaa tgggaagacc    1740
agagttggcc cgaagggcca ttgcagtggc tgaggaaaag ctctcagctg acaagtggcc    1800
ggaatactat gacacccgat ctggaagatt cgttgggaag caatcacggt catatcagac    1860
atggactatt gctggttttc tgacctcgaa gatattgctg gaaaacccgg agctggcttc    1920
tatcctgacc tgtgatgagg atcttgagct ccttgaaggc tgtgcttgct gcctctcaaa    1980
gaggacgagg tgctctcgtc gtgtgaccaa atcagatatc atcgggtaaa acagcagagc    2040
cccttttatt cttcatgctc tgcagaccat gtatactatc gactgagaat taactgaggc    2100
ggacacactg tagctgtgta cattataggt ttaagttaga tatcaatcca ttcatttcct    2160
caatgtgcgc tcattctttt tctctgagct gccattgatg ggaacaaccc tgggtgatac    2220
cggtggtcaa cgggagcatt accaatttat gttggatctc tcatgtacac acacaaaaaa    2280
aggaattatt cttgtatttg gtaaccagtt gctcctgatt cggagtgct gtgaagccct     2340 aaccattgta tctatgtcag tatttgagtt gtatgttgca ttatttgcaa cgtaaactga    2400
gactttgtat cctatccttg ttatgaataa cgatactgtt gtcctccaaa aaaaaaa      2457
```

<210> SEQ ID NO 11
<211> LENGTH: 2143
<212> TYPE: DNA
<213> ORGANISM: Lolium perenne

<400> SEQUENCE: 11

```
gcgctcctgc acgcaagctg cacgggccgc tcctgcacgc aagctgcacg gccaatccaa     60
tcaccgcagc accgttcgcc tttcgcaact cgctccaggc gtctgcgcgc gcatggcgat    120
cgcggcagcg gccgcgctgc tgccgctgca cctcggatgc tccgacgcgg ctccccggcg    180
gcccggtaac tccctcagag cccatctgcg gaagggcggg atcaggggca ggcggcggag    240
ccctccgtgc gccgtcaact cgctgcatcc cagcggcaac cccaaaactc ccggcggcgg    300
tgacgttggc ggagggaggg gcgtgaacgg cggcgccacc gccaagcccg accacgcgcc    360
gccgagccag aggaggcgcg cgccgcgcga cgtggaggag gaggcgtggg cgctcctccg    420
ggagtcggtg gtgagctact gcggcagccc cgtgggcacc atcgcggcct gcgaccccaa    480
cgacgccagc ccgctcaact acgaccaggt gttcatccgg gacttcgtgc cctccggcgt    540
cgccttcctc ctcaaggggg agcacgaaat cgtccgcaac ttcatcctcc acacgctcca    600
gctccagagc tgggagaaaa cgattgactg tcatagccca ggccaagggt taatgccggc    660
tagtttcaag gtgcgtgttg ttccacttga tggtggcgac gatggtgcga ctgaggaagt    720
cttggatcct gactttgggg aggctgcaat aggccgtgtg gcaccagttg attcaggttt    780
```

| | |
|---|---|
| gtggtggatc atactactga gggcatatgg aaaatgttca ggggacctct cattccacga | 840 |
| gagagtggat gtccagactg aataaaact gatcttgaag ctctgcttag cggatgggtt | 900 |
| cgacatgttc cccacgttgc tagtcactga tggctcctgc atgatggatc gtcgaatggg | 960 |
| tatccatgga cacccgctgg aaattcaggc tctgttctat tcagccctct tgtctgcacg | 1020 |
| tgagatgctt accccagaag atggatcggc tgacttgatc cgggccctaa atagcaggct | 1080 |
| tatggcactc tctttccata ttagggagta ttattggctt gaaaagagaa agctaaatga | 1140 |
| aatctataga tacaaaacag aagaatattc ttatgatgcc gtcaacaagt ttaacatata | 1200 |
| tcccgatcag attcctccct ggctagttga atggatccct ccgaaagggg gttatttcat | 1260 |
| cggaaacctg caaccagctc acatggattt ccgattcttt tctctaggga acttgtggtc | 1320 |
| tatagtaagc agtttggcaa cagctgatca atctcatgct attctggatc tagtggaagc | 1380 |
| aaaatggtcc gatctagtgg cagagatgcc aatgaagata tgttatcctg ctcttgagga | 1440 |
| tcaagagtgg aaatttatta ctgggagtga ccctaaaaat acaccttggt cataccataa | 1500 |
| tggaggttcc tggccaacat tgttgtggca gctcacggtg gcatgcatca agatgaaccg | 1560 |
| gcccgagatc gccgcaagag ctgtggaggt ggctgaaagc cgtatttcca cggataaatg | 1620 |
| gcccgaatac tacgatacca agcgtgggcg gttcatcggc aagcaggccc ggttattcca | 1680 |
| aacttggtcc attgccggct tccttgtggc caaactgctg ctagaaaatc ctgaaaaatc | 1740 |
| tagaatactc tggaacaacg aagatgagga aattcttaat gctttgagtc tgatgactgg | 1800 |
| cccatccagt ccgaagagga agcgtggtag gaagacctat attgtgtaag tccaacagca | 1860 |
| gttctaacct ctagggtttc atggatgttg catttagtta tgtaagaatc gtccacatac | 1920 |
| cactagattt gtacatatta aagtggatgt tgtagaggaa atgcccattt tgagatgcta | 1980 |
| tcatgctgtt ctagtgatct actgttagca aggctcaggg gaacggattg ttggctccgg | 2040 |
| agctactccg agcttcttaa ttctagaaag ttcatttcaa gttttaaaa tgtcccacgt | 2100 |
| gttgtgggag taatctatga acttataaat gctaaaaaaa aaa | 2143 |

<210> SEQ ID NO 12
<211> LENGTH: 2033
<212> TYPE: DNA
<213> ORGANISM: Lolium perenne

<400> SEQUENCE: 12

| | |
|---|---|
| atacacccag ctctggctcc caacatgccg tctcctcccc gcgcccgcgc actccacccc | 60 |
| cactccgccg cctcctcctc cgtctgcccg atccgacgcc gcgtccattc ccccacggag | 120 |
| cttaactgaa acagttgacc aaaacgtgga atcatgaaga gagtttcatc gcatgtctcc | 180 |
| attgcgtcag aggctgagat caatctcgac ctctcacgct tactaattga caagccaagg | 240 |
| tacacgttgg agcggaagag gtcatttgat gagcagtcat ggagcgagct cacccacacc | 300 |
| catcggcaaa acgacggctt tgatagtgta ctgcagtcac ctgcattccg cactgggttt | 360 |
| gactcaccgt tctcaatggg aacgcacttt ggtgagccaa gtgggccaca ccccccttgtg | 420 |
| aatgaagcat gggaggcact caggaaatct gtagtgtatt tcggggccca accagttggt | 480 |
| acaattgctg cggtagatca tgcatctgaa gaagtgctca attatgatca ggttttcgtc | 540 |
| cgggattttg ttcctagtgc attggctttt ctaatgaata acgagcccga aatagtgaag | 600 |
| aactttctgt tgaaaactct ccacttgcaa agctcagaaa aaatggtaga ccggttcaag | 660 |
| cttggagcag gagcaatgcc tgcaagtttc aaggtggacc gtaataaaag cagaaacact | 720 |
| gaaacattag ttgcagattt tggtgagagc gcgattggca gggtggcacc agtggattct | 780 |

-continued

```
ggattttggt ggattattct gctccgggca tatacaaagt atactggaga tgctagtttg      840
tcagaatctc ctgattgtca gaagtgcatg aggctgatac tgaatctctg cttatctgag      900
ggattcgata ctttcccaac tctgctctgc acagatgggt gctcaatgat cgatcgtcga      960
atgggtatat atggttatcc tattgagatc caagctctgt tctacatggc attaagatgt     1020
gctctccaaa tgcttaagcc agatggtgaa gggaaggact tcattgagaa datgggcaa      1080 cggctgcatg cattaaccta ccacatgaga aactacttct ggctggactt cccacatcta     1140
aacaatatct atagatacaa aacagaggag tactcccaca ctgctgtgaa taaattcaat     1200
gtcatcccag attcaattcc tgattgggtg tttgatttca tgccatgccg aggaggctac     1260
tttcttggca acgtcagccc tgctatgatg gacttcaggt ggtttgctct tggaaactgt     1320
attgccatta tatcatctct ggctactcct gagcagtcat cagcaataat ggatctgatc     1380
gaggagaggt gggatgaatt agtgggcgag gtgcctctga agatttgcta tcctgcaatt     1440
gagaaccatg agtggagaat aattactggc tgcgacccca agaatacccg gtggagttat     1500
cataatgggg gatcatggcc agttcttctg tggctgctga ctgcagcctg tatcaagacc     1560
gggcggccac aaatggcgaa gcgcgccatc gagctctccg aggctaggct tctgaaggat     1620
ggctggcccg agtactatga tggcaagctg ggaaagttcg taggtaagca ggccaggaag     1680
ttccaaacat ggtccattgc aggctacctg gtagcccgga tgatgttgga ggacccgtca     1740
acgctcatga tgatctccat ggaggaagac cggcctgtga agccacaat gaggcggtcg     1800 gcgtcgtgga atgcctgaaa ggctgggtgg ttgtttctta agatatttct tttacttcaa     1860
tggtctgttc ggcagaaaaa aggtccggac ttggttgtaa ttgaactctg tcagttagga     1920
cagaagtgta tacgtcagat gatcgatcct agaagctaca ctgcatttc ttactgtcaa      1980 acctttgatt ttgctatgaa accagcaagc gaagattctg cttaaaaaaa aaa            2033
```

<210> SEQ ID NO 13
<211> LENGTH: 1866
<212> TYPE: DNA
<213> ORGANISM: Lolium perenne

<400> SEQUENCE: 13

```
agtagcaccg cccaggaacc caactccggc gagagagctc ctatatcagc cacctgcctc       60
tctccaacgt ctcttttggt cgcctcccac ttgtactcgc cgtcgtaccc acttcccgta      120
cgtttgcgcc gccgcttgtc ttttctatct cgccggggcgt gtattctcga cgcgcgtgca     180
gcagccacgg cgaccgcggc ggtgtgcgag atggaggcgc cggggggcgg agcggggccg     240
atgccgacca cgccgtcgca cgcgtccata gcggactcgg acgacttcga cctgtcgcgg     300
ctgctgaacc accgcccgcg gatcaacgtg gagcggcagc gctccttcga cgaccgctcg     360
ctcggcgacc tctacctctc cgccatggac agccgcggcg ggtacatgga cagctacgac     420
agcatgtact cgccgggcgg cgggctccgc tcgctcaccg gcacgccggc ctcctccacg     480
cgcctctcct tcgagcccca gctcctggtc gccgaggcct gggaggccct ccgccgctcg     540
ctcgtctgct tccgtgggga gcccctcggc accatcgccg ccgtcgacag ctcctccgac     600
gaagtcctca actacgacca ggtgttcgtg cgggattttg tgccgagcgc gctggcgttc     660
ctgatgaacg gggagccgga catcgtgaag aacttcctgc tgaagacgct gctgctgcag     720
gggtgggaga gcggatcga ccggttcaag ctcggggagg gcgccatgcc ggcgagcttc     780
aaggtgctca aggacccgaa gcgcgggtg gacaccctgg cggcggactt cggcgagagc     840
```

-continued

```
gccatcgggc gcgtggcgcc ggccgactcc gggttctggt ggatcatcct gctccgcgcc      900
tacaccaagt ccaccggcga cctcaccctc gccgagacgc ccgagtgcca gaagggcatc      960
cggctcatca tgaaccagtg cctcgccgag gggttcgaca ccttccccac cctcctctgc     1020
gccgacggct gctgcatgat cgaccgcagg atgggcgtgt acgggtaccc gatcgagatc     1080
caagccctct tcttcatgtc actgcggtgc gcgctgctgc tgctgaagcc ggcggtggaa     1140
gggaacagca gcagcaagga cgacgacatc atggagcgga tcgtgacgcg gctgcacgcg     1200
ctcagctacc acatgcgcag ctacttctgg ctcgacttcc agcagctcaa cgtcatctac     1260
cgcttcaaga cggaggagta ctcccacacc gccgtcaaca gttcaacgt catcccggag      1320
tccatcccgg actggctctt cgacttcatg ccctcccgcg cggatactt cgtcggcaac      1380
gtcagccccg ccaggatgga cttccggtgg ttcgcgctgg caactgcgt cgccatcctc      1440
gcgtcgctcg ccacgccaga gcaggccggc gccatcatgg acctcatcga ggagcgctgg     1500
gaggacctca tcggcgagat gccgctcaag atctgctacc cgaccatcga gggacacgag     1560
tggcagaacg tcaccggatg cgaccccaag aacaccaggt ggagctacca acggagga      1620
tcatggccag tgctgatctg gctcctgacg cggcgtgca tcaagaccgg gcggctcaag      1680
atcgcgaggc gggcgatcga cctggcagag gcgaggctgg ggaaggacgg ctggccggag     1740
tactacgacg gcaagctcgg gcggtacgtg gggaagcagg cgaggaagca ccagacgtgg     1800
tccatcgcgg ggtacctggt ggccaagatg atgctggagg acccgtccca cctgggcatg     1860
atctcg                                                                1866
```

<210> SEQ ID NO 14
<211> LENGTH: 2058
<212> TYPE: DNA
<213> ORGANISM: Lolium perenne

<400> SEQUENCE: 14

```
gccatagatc tggccgcggc gagcaggcgg aggccggccg aggattcctg agcaggggac       60
ggaagcgaag agaagggcat ggagttcggg gcgccgggcg ggatgcggcg gtcggcgtcg      120
cacaactcgc tgtccggctc ggacgacttc gacctcacgc acctgctcaa caagccgcgg      180
atcaacgtcg agcgccagcg ctccttcgac gaccgctccc tcagcgacgt gtcctactcc      240
ggcggcggac acgccagggg cgctggcggg ggattcgacg gcatgtactc gccgggcggc      300
gggctgcgct cgctcgtcgg cacgccggcc tcgtccgcgc tccactcctt cgagccgcac      360
cccatcgtcg gggacgcgtg ggaggcgcta cgacgctcgc tcgtcttctt ccgcggccag      420
ccgctcggaa ccatcgccgc ctacgaccac gcctcagagg aggtgctcaa ctacgaccag      480
gtgttcgtgc gggatttcgt gcccagcgcc atggccttcc tcatgaacgg cgagccggag      540
atcgtcaaga acttcctgct caagaccgtg ctgctgcagg gctgggagaa gaaggtcgac      600
cgcttcaagc tcggcgaggg ggccatgccc gccagcttca aggtgctaca cgacgacaag      660
aagggcgtcg acacgctgca cgccgatttc ggggagagcg ccattggccg gtcgcgcca      720
gtggactcgg gcttctggtg gatcatactg ctgcgggcct acaccaagtc cacggggac      780
ttgaccctgg ccgagaagcc ggagtgccag aaggccatga ggctcatact cagcctctgc     840
ctctccgagg ggttcgacac cttccccaca ttgctgtgtg ctgatggatg ctgcatgata     900
gatcgaagga tgggtgtgta tggctacccc attgaaattc aatccctgtt cttcatggca     960
ctgaggtgtg ctcttctaat gcttaagcat gataatgaag ggaaagattt tgtggagcgg    1020
attgcaactc gtcttcatgc tttaagttat cacatgcgga gttactttg gctggatttc     1080
```

```
cagcagctaa atgatatttta tcgttacaag acggaagaat attctcacac agctgtcaac    1140
aagttcaatg tcattccaga ttctattccg gactggctgt ttgattttat gccttgtgaa    1200
ggtggttttt ttgttggcaa tgtcagtcct gcaaggatgg acttccgttg gtttgcactt    1260
ggtaacatga ttgccatagt atcatctctt gccacacctg agcaatctac ggctataatg    1320
gatctcattg aggagcggtg ggaagagcta attggtgaaa tgcctctgaa gatatgctat    1380
cctgccattg agaaccatga gtggcgaata gtgacggggt gtgacccaaa aaatacgaga    1440
tggagttacc acaatggagg atcttggcca gtacttctct ggctgctgac ggcagcaagc    1500
atcaaaactg gacggccgca aattgcaaga gagcaatcg acctagctga gaggaggctt    1560
ttgaaggatg gctggcctga gtattatgac gggaagctcg gaaaatatgt tggcaagcag    1620
gcaaggaaat ttcaaacttg gtctattgcc gggtatttgg tcgctaagat gctgcttgag    1680 gaccttcac atcttggaat gatagccctg gaggaagaca aggctatgaa gccagttttg    1740
agaaggtccg cctcatggac aaactaagat atcgacgaaa actcttaggg gagcaaagtc    1800
tggattgaaa acacgaattc tttgggcagc acttctctct gctcatcctt tctttgactt    1860
tcctaacgga aaggtttgtt ttcctctgga ttgtacaata tctcagctca tttcttgagt    1920
tggaaaagaa gcaattgtgg aaatgggcat tttgttttgt ttttccctt caatcccgtg    1980 ttgtaagaag atacttccga ttcttgattg ggtcatcctg aagttatggg atccttttgg    2040
ttggtctcaa aaaaaaaa                                                  2058

<210> SEQ ID NO 15
<211> LENGTH: 2167
<212> TYPE: DNA
<213> ORGANISM: Lolium perenne

<400> SEQUENCE: 15
ggccaccacc aacaccaaaa acgcatcgac gcggcgcaga tacaaacgag gcagccgccc      60
ttcgccggcg aggcgatgga ttccgactac ggcgtgccgc gcgagctctc ggaggtgcag     120
aagaagcgga ccctctacca gcccgacctg ccgccctgcc tccagggcac tactgtgagg     180
gtggagtatg gtgatgtggc gatcgctgct gatcctgccg gcgctcatgt gatcagccac     240
gcgttcccac acacatacgg gcagccactg gctcattttcc tcaggaaggc ggctaatgtc     300
gctgatgcta aagtcatatc agagcaccct gccgtcaggg ttggcattgt attctgtgga     360
aggcagtccc caggaggcca caatgtcata tggggactcc atgatgctat caaagctcac     420
aacccgaata gcaaacttat tggtttcctc ggaggatccg atggtcttct tgcacagaaa     480
actttggaga tcagatgaa agttctttct tcctacaaaa accaaggtgg ttatgatatg     540
cttggtagga ccaaggatca aatcagaaca acagagcaag tcaatggtgc aatggctagt     600
tgccaggctt tgaagttgga tgctctgata taattggag tgtcacgtc aaatacagat     660 gctgctcaac ttgctgagac ttttgccgag gcaaagtgtg caacaaaggt tgtaggtgtt     720
cctgtaactt tgaatgggga tctcaagaac caatttgttg agacaactgt tggttttgat     780
accatatgca aggtcaactc acaacttata agcaatatgt gcaccgatgc tctatctgct     840
gagaagtatt actatttcat ccgtatgatg ggacggaagg cttcccatgt ggcattggag     900
tgtgctcttc aatcgcatcc aaatatggtt atccttggtg aggaggttgc tgcatcaaaa     960
ctcacaattt ttgatatcac aaagcaaata tgtgatgcag ttcaggcgag agctgaaaaa    1020
gacaagaacc atggtgtcat acttattcct gagggccttg tggagagtat tcctgaatta    1080
```

```
tatgctctcc ttcaggaaat taatggcctt cacggtaaag gtgtttccat tgagaatatc     1140
tcttctcagc tttctccttg ggcatcagcg ctatttgagt ttttgcccca gtttattagg     1200
cagcagctgc ttctccgccc tgaatctgat gattcagctc aactttctca gattgaaact     1260
gaaaagcttc tagcccaatt ggttgaaacc gaaatgaaca aacgtttgaa ggaaggcacc     1320
tacaaaggaa agaagttcaa tgcaatctgt cacttttttg gctaccaagc taggggtgca     1380
atgccttcga agtttgactg cgattatgcc tatgttctgg gtcacgtgtc ttaccacatc     1440
ttggcagctg gtttgaacgg ttacatggct actgtgacaa atcttaagag tcccctgaac     1500
aagtggcgat gtggtgctgc tcctatttcg tccatgatga ccgtgaagcg atggtcacgt     1560 ggccccttcaa ccacacaaat cgggaagcca gctgtgcata tggctagtgt tgacttgaga     1620
ggaaaagcat atgagctgtt gaggcagaat tcatccagct gcttgttgga agacatctac     1680
agaaaccctg gaccactcca attcgaagga ccgggttctg attccaagcc tatttcactg     1740
tgcgttgagg atcaagacta catgggtagg atcaagaaat tgcaggagta cttggagaag     1800
gtgaagagca tagtgaagcc tgggtgctca caggatgttc tcaaggcggc gctgagtgcc     1860
atgtcttctg tgacagatac tctggctatc atgacttctt cttccactgg ccaggcccca     1920
ctctgagagt cgagttactc tgatctacat gtttccctat cctcttttgt tccatctgac     1980
ggttgggatt agaaacagt gatcttgtga tcccgtggtt cgttcttttc ctagtttgca     2040
gagagttttt gtcattcctg gctctgatag tgtaccgagg gtttgttgtt ggcgaggttg     2100
aactggaata atcgatcaaa ctgccggttg tgatctatta ataaactaaa ttttgataaa     2160
aaaaaaa                                                              2167
```

<210> SEQ ID NO 16
<211> LENGTH: 2179
<212> TYPE: DNA
<213> ORGANISM: Festuca arundinacea

<400> SEQUENCE: 16

```
ggccaccatc ccaccaacaa caaaaaaaac gcatcgacgc ggcgcagata caaacgaggc       60
aggcgacgag tgctaggcga tggattccga ctacggcgtg ccgcgcgagc tctcggaggt      120
gcagaagaag cggaccctct accagcccga gctgccgccc tgcctccagg cactactgt       180 gagggtggag tatggtgatg tggcgatcgc tgctgatcct gctggcgctc atgtgatcag      240
ccacgctttc ccacacacgt acgggcagcc actggctcat ttcctcagga aggcggctaa      300
tgtcgctgat gctaaagtca tatcagagca ccctgccgtc agggttggca ttgtattctg      360
tggaaggcag tccccaggag gccacaatgt catatgggga ctccatgacg ctatcaaagc      420
tcacaactcg aatagcaaac ttattggttt cctcggagga tccgatggtc ttcttgcaca      480
gaaaactttg gagatcacag atgaagttct tcttcctac aaaaaccaag gtggttatga      540
tatgcttggt aggactaagg atcaaatcag aacaacagag caagtcaatg gtgcaatggc      600
tagttgccag gatttgaagt tggatgctct gataataatt ggaggtgtca cgtcgaatac      660
agatgctgct cagcttgctg agacttttgc cgaggcaaag tgtgcaacaa aggttgtagg      720
tgttcctgta actttgaatg gagatctcaa gaaccaattc gttgagacaa ctgttggttt      780
tgataccata tgcaaggtga actcacaact tataagcaat atgtgcaccg acgctctatc      840
tgctgagaag tattactatt tcatccgtat gatgggacgg aaggcttccc atgtggcatt      900
ggagtgtgct cttcaatcgc atccaaatat ggttatcctt ggtgaggagg ttgctgcatc      960
aaaactcaca attttgata tcacaaagca aatatgtgat gcagttcagg cgagagctga     1020
```

-continued

| | |
|---|---|
| aaaagacaag aatcatggtg ttatacttat tcctgagggc cttgtggaga gtattcctga | 1080 |
| attatatgct ctccttcagg aaattaatgg ccttcacggt aaaggtgttt ccattgagaa | 1140 |
| tatctcttct cagcttt ctc cttgggcatc tgcgctattt gagttttt gc cccagtttat | 1200 |
| taggcatcag ctgcttctcc gccctgaatc tgatgactca gctcaacttt ctcagattga | 1260 |
| aactgaaaag cttctagccc aattggttga aaccgaaatg aacaaacgtt tgaaggaagg | 1320 |
| cacctacaaa ggaaagaagt tcaatgcaat ctgtcacttt tttggctacc aagcgagggg | 1380 |
| tgcaatgcct tcgaagtttg actgcgatta tgcctatgtt ctgggtcatg tgtcttacca | 1440 |
| catcttggca gctggtttga acggttacat ggctactgtg acaaatctta agagtcccct | 1500 |
| gaacaagtgg cgatgtggtg ctgctcctat ttcgtccatg atgactgtga agcgatggtc | 1560 |
| acgtggccct tcaaccacac aaatcgggaa gccagctatg catatggcta ctgtcgactt | 1620 |
| gagaggaaaa gcatatgagc tgttgaggca gaattcatcc agctacttgt tggaagacat | 1680 |
| ctacagaaac cctggaccac tccaatttga aggaccgggt gctgattcca agcctatttc | 1740 |
| gctgtgcgtt gaggatcaag actacatggg caggatcaag aaattgcagg agtacttgga | 1800 |
| gaaggtgaag agcatagtga agcctgggtg ctcacaggat gttctcaagg cggcgctgag | 1860 |
| tgccatgtct tctgtgacgg agactctggc tatcatgact tcatcttcca ctggccaggc | 1920 |
| cccactctga gagtcgagtt actcaagtgg gctaaaaatc tacgtttccc tatcctcttt | 1980 |
| tgttccatct gacggttggg attagagaac agtgatcttg tgatcctgta gtttgttctt | 2040 |
| ttcctagttt gcagagtttt tgtcatttct ggctctgata gtgttcgagg gtttgttgtt | 2100 |
| ggcgaggttg acctggaata atcgatcaaa ctgccggttg tgatctatta ataaactaaa | 2160 |
| ttttgataca aaaaaaaaa | 2179 |

<210> SEQ ID NO 17
<211> LENGTH: 1961
<212> TYPE: DNA
<213> ORGANISM: Lolium perenne

<400> SEQUENCE: 17

| | |
|---|---|
| ctcacctcac ctgcctccgt ctctccgccc gaaagcgcat attcctccaa atctcacccc | 60 |
| gtcaccaccc tcgccggcgc atcgcatcgc atggcggccg ccgcggtggc cacctccaac | 120 |
| ggcgcctcgg ccaacgggcc gacgcccggg cgcctcgcgt ccgtgtacag cgaggtgcag | 180 |
| acgagccgca tcgcgcacgc gctgcccctc ccctccgtcc tccgctccca cttcacgctc | 240 |
| gccgacgggg ccgccagctc cgccacgggc aaccccgagg agatcgccaa gctcttcccc | 300 |
| aacctgtacg gccagccgtc cgcggccgtg gtgcccctcgg cccagccggt cgccaccaag | 360 |
| ccgctcaaga tcggcgtcgt gctctccggc ggccaggcgc caggcggcca caatgtgatc | 420 |
| tgcggcatct ttgactacct gcaagagcgt gcgaagggca gcaccatgta cggattcaag | 480 |
| ggaggcccag ctgggtcat gaagggcaag tacgtcgagc tcaatgctga tttcgtctac | 540 |
| ccctacagga accagggtgg atttgatatg atctgcagtg aagggacaa gattgaaaca | 600 |
| ccagagcagt tcaagcaagc tgaagacact gtcaccaaac ttgatttgga tggacttgtt | 660 |
| gtcattggtg gtgatgattc aaacactaac gcatgcctcc ttggtgaata cttcaggga | 720 |
| aggaacttga agactcgtgt tattggttgc cccaagacta ttgatggaga tctgaaatgc | 780 |
| aaggaggtcc caacaagctt tggatttgac actgcttgca agatatactc tgaaatgatt | 840 |
| ggcaatgtga tgactgatgc tcggtcaaca ggaaaatact atcactttgt gaggcttatg | 900 |

-continued

```
ggccgagctg cttctcacat tacattagag tgtgctctgc aaacacaccc taacgtttca      960
ctcattggcg aagaggttgc tgagaagaag gaaacactca agcaagtcac agactacatt     1020
actgatgtta tctgcaaacg tgcagaactt ggttacaact atggagttat ccttatcccg     1080
gagggactta ttgatttcat tccagaggtt caaaagctca ttgcagaatt gaatgaaatt     1140
ttggcacatg atgttgttga cgaggcaggt gcatggaaaa gcaagcttca accagaatct     1200
aggcaactgt tgacttctt gcccaacacc attcaggagc agcttttgct tgaaagagat      1260
ccacatggca atgttcaggt tgcgaaaatt gaaactgaga agatgctat tgccatggtt      1320
gaaactgaat tggagaagag aagatctgca gggaagtact cagcacattt cagaggccag     1380
tctcacttct ttggatatga aggaagatgt ggtcttccta caaattttga ttctagctac     1440
tgctatgcat taggctatgg tgctggggct cttctccaat tggaaagac aggacttatt      1500
tcgtcggttg gtaaccttgc tgctcctgtg aagaatgga ctgtcggagg aactccattg      1560
acggcgttga tggatgtaga gaggagacat ggcaagttca agccagtgat caagaaggct    1620
atggtggaac ttgatgctgc gccattcaag aagtttgctt ccatgcggga tgaatgggcc    1680
atcaagaaca gatacatcag ccctggcccc atccagttca gcggccctgg aagcgatgcg    1740
tcgaaccaca ccttgatgct ggagcttggt gctcagacat gagatgctgt gttatagagt    1800
gcacctcttc tgtttttttt ctccctcctt acagttttga gagtggagac caaacctccc    1860
agtgggcagt ctccacattg tggaatgatt aataagagct attggagttt cctgagtgga    1920
tttcgtagca ataataactg attttagctg caaaaaaaaa a                         1961

<210> SEQ ID NO 18
<211> LENGTH: 1959
<212> TYPE: DNA
<213> ORGANISM: Lolium perenne

<400> SEQUENCE: 18
ctcacctcac ctgcctccgt ctctccgccc gaaagcgcat attcctccaa atctcacccc       60
gtcaccaccc tcgccggcgc atcgcatcgc atggcggccg ccgcggtggc cacctccaac      120
ggcgcctcgg ccaacgggcc gacgcccggg cgcctcgcgt ccgtgtacag cgaggtgcag      180
acgagccgca tcgcgcacgc gctgcccctc ccctccgtcc tccgctccca cttcacgctc      240
gccgacgggg ccgccagctc cgccacgggc aaccccgagg agatcgccaa gctcttcccc      300
aacctgtacg gccagccgtc cgcggccgtg gtgccctcgg cccagccggt cgccaccaag      360
ccgctcaaga tcggcgtcgt gctctccggc ggccaggcgc aggcggcca caatgtgatc      420
tgcggcatct ttgactacct gcaagagcgt gcgaagggca gcaccatgta cggattcaag      480
ggaggcccag ctggggtcat gaagggcaag tacgtcgagc tcaatgctga tttcgtctac      540
ccctacagga accagggtgg atttgatatg atctgcagtg aagggacaa gattgaaaca       600
ccagagcagt tcaagcaagc tgaagacact gtcaccaaac ttgatttgga tggacttgtt      660
gtcattggtg gtgatgattc aaacactaac gcatgcctcc ttggtgaata cttcagggga     720
aggaacttga agactcgtgt tattggttgc cccaagacta ttgatggaga tctgaaatgc      780
aaggaggtcc caacaagctt tggatttgac actgcttgca agatatactc tgaaatgatt     840
ggcaatgtga tgactgatgc tcggtcaaca ggaaaatact atcactttgt gaggcttatg      900
ggccgagctg cttctcacat tacattagag tgtgctctgc aaacacaccc taacgtttca     960
ctcattggcg aagaggttgc tgagaagaag gaaacactca agcaagtcac agactacatt    1020
actgatgtta tctgcaaacg tgcagaactt ggttacaact atggagttat ccttatcccg    1080
```

```
gagggactta ttgatttcat tccagaggtt caaaagctca ttgcagaatt gaatgaaatt    1140
ttggcacatg atgttgttga cgaggcaggt gcatggaaaa gcaagcttca accagaatct    1200
aggcaactgt ttgacttctt gcccaacacc attcaggagc agcttttgct tgaaagagat    1260
ccacatggca atgttcaggt tgcgaaaatt gaaactgaga agatgcttat tgccatggtt    1320
gaaactgaat tggagaagag aagatctgca gggaagtact cagcacattt cagaggccag    1380
tctcacttct ttggatatga aggaagatgt ggtcttccta caaattttga ttctagctac    1440
tgctatgcat taggctatgg tgctgggggct cttctccaat tggaaagac aggacttatt    1500 tcgtcggttg gtaaccttgc tgctcctgtg aagaatgga ctgtcggagg aactccattg    1560
acggcgttga tggatgtaga gaggagacat ggcaagttca agccagtgat caagaaggct    1620
atggtggaac ttgatgctgc gccattcaag aagtttgctt ccatgcggga tgaatgggcc    1680
atcaagaaca gatacatcag ccctggcccc atccagttca gcggccctgg aagcgatgcg    1740
tcgaaccaca ccttgatgct ggagcttggt gctcagacat gagatgctgt gttatagagt    1800
gcacctcttc tgttttttt ctccctcctt acagttttga gagtggagac caaacctccc    1860
agtgggcagt ctccacattg tggaatgatt aataagagct attggagttt cctgagtgga    1920
tttcgtagca ataataactg attttagcta aaaaaaaaa                           1959

<210> SEQ ID NO 19
<211> LENGTH: 1954
<212> TYPE: DNA
<213> ORGANISM: Festuca arundinacea

<400> SEQUENCE: 19
gtgcctccgc ccctccgccc gaaagcatat tcctccaaat ctcgcgatac ccccgtcacc      60
acctcgccgg cgcatcgcat cgcatggcgg ccgcggcggt ggccacctcc aacggggcct     120
cggcgaacgg gccgacgccc gggcgcctcg cgtccgtgta cagcgaggtg cagacgagcc     180
gcatcgcgca cgcgctgccc ctcccctccg tcctccgctc caacttcacg ctcgccgacg     240
ggcccgccag ctccgccacg gggaaccccg aggagatcgc caagctgttc cccaacctgt     300
acggccagcc gtccgcggcc gtggtgccct cggccgagcc ggtgcccacc aagccgctca     360
agatcggcgt cgtgctctcc ggcggccagg cgccaggcgg gcacaatgtg atctgcggca     420
tcttcgatta cctgcaagag cgcgctaagg gcagcaccat gtacggattc aaaggaggcc     480
cagctgggat catgaagggc aagtacatcg agctcaatgc tgatttcgtc taccccctaca    540 ggaaccaggg tggatttgat atgatctgca gtggaaggga caagattgaa acaccagagc    600
agttcaagca agctgaagac acagtcaaca aacttgatct ggatggactt gttgttattg    660
gtggtgacga ctcaaacact aacgcatgcc tccttggtga atacttcagg ggaaggaatt    720
tgaagactcg tgttattggt tgccccaaga ccattgatgg agatctgaaa tgcaaggagg    780
tcccaataag ctttggattt gacactgctt gcaagatata ctccgaaatg attggcaatg    840
tgatgactga cgctcggtca acaggcaaat actatcactt tgtgaggctt atggggcgtg    900
ctgcttctca cattacatta gagtgtgctc tgcaaacaca ccctaacgtt tcactcattg    960
gcgaagaggt tgctgagaag aaggaaacac tcaagcaagt cacagactac attactgatg   1020
ttatctgcaa acgtgcagaa cttggttaca actatggagt tatccttatc ccggagggac   1080
ttattgattt catcccagag gttcaaaagc tcattgcaga gttgaatgaa attttggcac   1140
atgatgttgt tgacgaggca ggtgcttgga aaagcaagct tcaaccagaa tctaggcagc   1200
```

-continued

```
tgtttgactt cttgcccaac accattcagg agcagctttt gcttgaaaga gatccacatg      1260
gcaatgttca ggttgcgaaa attgaaactg agaagatgct tattgccatg gttgaaactg      1320
aattggagaa gagaagagct gcagggaagt actccgcaca tttcagaggc cagtctcact      1380
tctttggata tgaaggaaga tgtggtcttc ctaccaattt tgattctagc tactgctatg      1440
cattaggcta tggtgctggg gctcttctcc aatttggaaa gacaggactt atttcgtcgg      1500
ttggtaacct tgctgctcct gtggaagaat ggaccgtcgg aggaactcct ttgacggcat      1560
tgatggatgt tgagaggaga cacggcaagt tcaagccagt gatcaagaag gctatggtgg      1620
aacttgatgc cgcgccattc aagaagtttg cttccatgcg agatgaatgg gccatcaaga      1680
acagatacat cagccctggt cccatccagt tcagtggccc tggaagtgac gcgtcgaacc      1740
acaccttgat gttggagctt ggcgctcaga tatagagatg ctgcgttgta gagtgcacct      1800
cttcattcc ttctctcctt acagttttga gagtggagac gaaaagctct cagagcgaca       1860
gtctccacat tgtggaatgt tcaataagag cttctggtat ggatgtcgca gcaataataa      1920
ctgattttag cttttataa tctgaaaaaa aaaa                                   1954

<210> SEQ ID NO 20
<211> LENGTH: 3302
<212> TYPE: DNA
<213> ORGANISM: Lolium perenne

<400> SEQUENCE: 20
gctcacttcc cccctccatc cctccttccc tttggcttcg cctccactct tcccatcccc        60
cgatctcgcc gtcgagcggc ggcggcgccg gcgacgatgg tgggcaacga caactggatc       120
aacagctacc tcgacgccat cctcgacgcc ggcaagtcgt ccatcggcgg cgaccgcccc       180
tcgctgctcc tccgcgagcg cggccacttc tccccggccc gctacttcgt cgaggaggtc       240
atcaccggct acgacgagac cgacctctac aagacatggc tccgcgcgaa cgcgatgcgg       300
agtccccagg agaggaacac gcggctggag aacatgacat ggaggatctg gaacctcgcc       360
aggaagaaga aggagttaga gaaagaagaa gcctgtcgtt tgttgaaacg catccagaa        420
actgagaaaa cgcgaactga tgctacggcc gatatgtctg aagatctctt tgatggcgaa       480
aagggagaag atgctggtga tccatctgtt gcatatggtg acagcaccac agggagctca       540
cctaagacca gttcagttga caagctatac atagtattga tcagcttaca tggtcttgtc       600
cgtggtgaga atatggagct aggccgagat tcagatactg gtggccaggt caaatatgtg       660
gttgagtttg ctaaagcatt gagttcatct cctggcgttt accgggtcga tttgctcaca       720
agacaaattg tagcaccaaa ttttgatcgt agttatggtg aacctgaaga atgctggtt        780
tcgacaacct ttaaaaattc caagcatgaa aggggagtga acagtggtgg atacatcatt       840
cggataccat ttggtccaaa agacaagtac ttagctaaag aacatatgtg gccttcatt        900
caagattttg ttgatggtgc actcagccat atttttgcgga tgtcaaaaac cattggtgaa       960
gaaataggct gtgggcatcc agtatggcct gctgtgattc atgggcatta tgccagtgct      1020
ggagtagctg ctgccctgtt atcaggagca cttaacctgc ctatggcatt cacgggacat      1080
tttcttggga agataaatt ggaagggctt ctcaaacaag gcgacaatc aagggaacag        1140
ataaatatga catacaaaat aatgcgccga attgaggcgg aggaattatc tcttgacgca      1200
tctgaaattg ttattgctag tactaggcaa gagattgaag agcagtggaa cttgtatgat      1260
ggttttgagg tcatacttgc aaggaagctt cgagcaagag tcaagcgtgg tgctaactgc      1320
tatggccgtt atatgcctcg tatggttata attcctcctg gtgttgagtt tggccatgtc      1380
```

```
gttcatgatt ttgatatgga cggtgaagaa gaaaaccatg gcccagcatc tgaagatcca    1440
cctatctggt cgcagataat gcgcttcttt acgaatccta ggaagcctat gattctggct    1500
gttgcccgtc catatccgga aaagaatatc acatcacttg taaaagcatt tggtgaatgt    1560
cgcccactaa gagagcttgc gaatcttaca ctaatcatgg gtaaccgtga ggctatttca    1620
aagatgcaca acacaagtgc ttctgtcttg acatcagtgc tcacactaat tgatgaatac    1680
gatttgtatg gtcaagtggc ataccccaag caccataagc actctgaagt tcctgacatt    1740
tatcgtttgg ccacaagaac aaagggcgct tttgtaaatg tggcttattt tgaacaattt    1800
ggtgttacct tgatagaggc tgctatgaat ggtttgcctg ttattgctac aaaaaatgga    1860
gctcctgttg aaattaatca ggtgctcaac aatggtctcc ttgtcgatcc acatgatcag    1920
aatgccattg cagatgcact gtataaactt cttctgaga agcaactctg gtcaagatgc    1980
agagaaaatg ggcttaaaaa tatccaccaa ttttcatggc ctgaacattg caagaatcac    2040
ttgtcaagga tattgactct tggtgcaaga tctcctgcta taggtagcaa agaggaaagg    2100
agcaatgcac ctatatcagg aaggaagcat ataattgtta tttctgtaga ctctgttaac    2160
aaggaagatc tagtacggat aatcagaaat gctattgagg ctgcacatac acagaacacg    2220
ccggcttcaa ctggtttcgt gctgtcaact tcactaacat tatcagagat ttgctcactg    2280
ctagtatctg taggcatgca tcctgctggc tttgatgcat tcatctgcaa tagtgggagt    2340
agcatttatt atccttcata ttctggtaat acgccaagca gttcaaaggt tacgcatgta    2400
atagatcaga atcaccaatc acatattgag tatcgttggg gaggagaagg tctaagaaag    2460
tatctagtga atgggctac ttcagtggta gaaagaaagg gaagaattga aaggcaaatg    2520
atatttgaag attctgaaca ttcttctacc tattgtcttg catttaaagt ggtcaatcca    2580
aatcatctac ctcctctaaa ggagttgagg aagttgatga gaatccagtc actccgttgt    2640
aatgcgcttt acaaccacag tgctaccaga ctgtctgtaa ctcctattca tgcgtcccgc    2700
tctcaggcaa taaggtactt gtttatacgc tggggaatag agttgccgaa tattgtagtc    2760
cttgttggtg aaagtggtga ctcagattac gaagaactgc taggggggtct ccacaggacc    2820 ataatcctga agggtgactt caatattgcc gcaaacagaa tccacacggt caggagatac    2880
cccctacagg atgtcgtggc actggacagc tcaaatatca ttgaagtcga gggttgcact    2940
acagatgtca ttaagtctgc tctgcggcag attggggtac cgacacaata gcgttttgtg    3000
tttgcatgcg acacagagaa aagaaggggg aagaacaagc caaaccaagt actgtaccac    3060
aattcccata gttgatggga atgccgattt tgtttgtagg ttgtagagtg tgggtgtctt    3120
gagagagctg tgaataactt gcaacatcag tttgtactat tcacaaattt tgaagtgaaa    3180
cgatatgggt acgttatacg ttaaagacag gatatggatg cacttatcca taatgagaaa    3240
acatacttga agaagcctgg aaaggcagat aaaaaaaaaa aaaaaaaaa aaaaaaaaa    3300 aa                                                                    3302
```

<210> SEQ ID NO 21
<211> LENGTH: 3171
<212> TYPE: DNA
<213> ORGANISM: Festuca arundinacea
<220> FEATURE:
<221> NAME/KEY: misc_feature
<222> LOCATION: (1)...(3171)
<223> OTHER INFORMATION: n = A,T,C or G

<400> SEQUENCE: 21

```
gttggtttcc caccccccaac ccattcgccg cctcccgccc gccgcccgat tgccgccacc    60
gccggcgcgc gcggctccgg cggcgaaacc tcctcctagc atcgggggag catggtgggc   120
gggatgtgcg ggaacgacaa ctggatcaac agctacctgg acgccatcct cgacgcgggg   180
aagggcgccc cgggcggagg cgccgggccc ggcggcggac gcggaggcgg cggggtgga   240
gcggcgacc gcccctcgct cctcctccgc gagcgcggcc acttctcccc cgcccggtat   300
ttcgtcgagg aggtcatcac cggctacgac gagaccgacc tctacaagac ctggtcacgc   360
gcgaacgcga tgcggagccc gcaggagagg aacacgcggc tggagaacat gacctggagg   420
atctggaacc tcgccaggaa gaagaaggag gtngaggctg aagaagccaa ccgtttgtta   480
aaacgtcgcc tagagacaga gaagccacgg actgatgccg ctgcagaaat gtctgaagat   540
ctctttgaag acaaaaggg agaggatgct ggtgatgcat ctgttgccta cggtgacagc   600
tcggcttcaa acacacctag gatcagttcc atcgacaagc tatacatagt gttgatcagc   660
cttcatggcc tggtccgtgg tgagaacatg gaacttggcc gggattcaga cactagtggg   720
caggtcaaat atgttgtgga acttgctaaa gcattgagtt catgccctgg agtataccgg   780
gttgacctgt tgacaaggca aatattagca ccgaattatg atcgtggata tggtgaacca   840
tcagagacac tgttgccaac aaacttaaag aattttaaac atgaaagagg agagaacagt   900
ggtgcgtata tcaccagaat accatttgga ccaaaagaca gtatctagc taaagaacag   960
ctctggcctt atgttcaaga atttgttgat ggtgcactca gtcatatagt gcgcatgtcg  1020
aaaaccatag gtgaagaaat cggctgtggg catccaatgt ggcctgctgc gattcatggc  1080
cattatgcca gtgcaggagt agctgctgct ctactatctg gagcacttaa tgttcacatg  1140
atatttacag gccatttct tgggagagat aagttagaag gcttctcaa gcaagggaaa  1200
cagacaaggg aagaaataaa tatgacatac aaaataatgc gccgaattga ggcagaggaa  1260
ctgtctcttg atgcgtctga aatagtgatt gcaagtacta ggcaagagat agaagagcaa  1320
tggaacttgt atgatggttt tgaagtcatg cttgcaagga aacttcgtgc aagagtcaag  1380
cgtggtgcaa actgctatgg tcgttacatg cctcgtatgg ttataattcc tccaggtgtt  1440
gaatttggcc atatgattca agattttgat atggatggtg aggaagatag cccatcacca  1500
gcatccgaag atccacctat ttggtctgag ataatgcggt tctttacaaa tcctaggaaa  1560
ccattgattc tggctgttgc tcgtccttac ccagaaaaga atattacaac gcttgtgagg  1620
gcttttggtg aatgccgacc attgaggag cttgctaacc taactctgat tatgggtaac  1680
cgtgaggcta tttccaaaat gagtaatatg agtgcagctg ttttgacatc agtgcttaca  1740
ctgattgatg aatatgatct gtatggtcaa gtggcatacc caaagcatca caaacactct  1800
gaagttcttg atatttatcg tttagcggcg agaacaaagg gtgcttttgt aaatgtagct  1860
tactttgaac aattcggtgt caccttgata gaggcggcca tgcatggttt acctgtaatt  1920
gcaacaaaaa atggagctcc tgttgaaatt caccaggtgc tgaacaatgg tcttcttgtt  1980
gatccccatg atcagaatgc aattgctgat gcactctata aacttcttc tgaaaaacaa  2040
ctttggtcaa gatgtcgaga gaatgggctg aaaaatatac accagttttc ttggcctgaa  2100
cattgcaaga attacttgtc aaggatatta actcttagcc caagataccc tgcttttgcg  2160
agcaatgatg accaaattaa ggctcctatc aaggaagaa agtatattat tgttattgcc  2220
gtagactctg ccagtaagaa agatctggcc tttatcatca gaaattctat tgaggctaca  2280
cggacagaaa cttcgtcagg ttcaacgggt tcgtgttgt cgacttccct gacaatatca  2340
gagatacatt ctctattaat atccgcaggg atggttccca ctgattttga tgctttcata  2400
```

-continued

| | |
|---|---|
| tgcaatagtg ggagtgattt attttaccct tcacagactg gtgattcacc aagcacttcc | 2460 |
| cgcgtaacat ttgcattaga ccgtaattac cagtctcgtg tcgagtatca ttggggcgga | 2520 |
| gaaggtttaa gaaagtatct agtgaagtgg gcttcttcag tagtggaaag gaggggcaga | 2580 |
| atggaaaagc aagttatttt tgatgattca gaacactcct cgacatgttg cctagcattt | 2640 |
| agagtggtca atccaaatta tttacctcct ttaaaggagc tgcagaagtt gatgagagtc | 2700 |
| caatcactac gttgtcatgc tctttataac cacagtgcta ctaggctatc tgtaattcca | 2760 |
| attcatgcat cacggtctca ggctataagg tacttatctg ttcgttgggg catagagttg | 2820 |
| ccaaatgtag tgattcttgt tggtgaaagc ggtgactcag actacgaaga gctgtttgga | 2880 |
| ggtcttcaca agacggttgt gctgaatggc gaattcaaca ccctgcaaa cagaatccac | 2940 |
| acagtcaggc ggtacccatt acaagatgtt atcgcgcttg attgctccaa catcgtagga | 3000 |
| gtccagggat gcagcactga ttgcatgagg tctactctag aaaagctcgg tataccgaca | 3060 |
| aaatgacact agtagacgtt ttttgtttt ttttgtatac gatgaaaaga aagaacgata | 3120 |
| cacatatagc aaatgaatac catcatttcc atgcttgatg gaaaaaaaaa a | 3171 |

<210> SEQ ID NO 22
<211> LENGTH: 2092
<212> TYPE: DNA
<213> ORGANISM: Festuca arundinacea

<400> SEQUENCE: 22

| | |
|---|---|
| ccaccctct cctcactcca cgctccctcc ctcccccct ctcttccact cgcactttcc | 60 |
| gccctcgtct cctcctcttc ttcctcccgt cagccccgtt cctggcgcca ccttcttctt | 120 |
| cctcgcatgc gttgattcga tcaacgtact tttcccctct ctagatcctt ggccgaagaa | 180 |
| ttgataggcg aacgaggtga tcatcgttcg cacgacgtcc cggccatggt gcgcggcggc | 240 |
| ggcaacggcg aggtggagct ctccgtgggg gctggtggcg gcggcggcgg ggcgggaggc | 300 |
| ctggtggagc cgcccgtgcc gatcagtctc ggcaggctcg tcctcgccgg catggtcgcc | 360 |
| ggcggcgtgc agtatggatg ggccctccag ctctccctgc tcacccccta cgtccagact | 420 |
| ctgggacttt cacatgccct gacttcattc atgtggctct gcggcccaat tgctggctta | 480 |
| gtggttcaac catgtgttgg tctgtacagt gataagtgca cttccagatg gggaagacgg | 540 |
| aggccgttta ttatgacagg atgtgtgctc atatgcattg ctgttgtgat tgttggcttc | 600 |
| tcggctgaca ttggagctgc tctgggcgat agcaaggaag agtgcagtct ctaccatggt | 660 |
| cctcgctggc acgctgcaat tgtgtatgtg cttggattct ggcttcttga cttctccaac | 720 |
| aatactgtgc aaggtccagc tcgtgctctg atggctgatt tgtcaggcaa gtatggaccc | 780 |
| agtgctgcaa attcaatctt ctgttcttgg atggcgctag gaaatatcct agggtactcc | 840 |
| tctggttcca ccgataagtg gcacaagtgg tttccctttc ttcggacaag agcttgttgt | 900 |
| gaagcttgcg caaatctgaa aggcgcgttt ctggtggctg tgctgttcct gtgcatgtgt | 960 |
| ttggtgataa ctctgatctt cgccaaggag gtaccataca aacgaattgc acccctccca | 1020 |
| acaaaggcaa atggtcaggt tgaagttgaa cctagtggcc cgcttgcggt gttccaaggc | 1080 |
| atcaggaact tgccttccgg aatgccatcg gtgctccttg taactggcct cacctggctg | 1140 |
| tcctggttcc cgttcatcct ctacgacacg gactggatgg gtcgtgagat ttaccacggt | 1200 |
| gaccccaagg gcaccccagc tgagatgtcg gcgttccagg acggtgtcag ggctggcgcg | 1260 |
| ttcggactgc tactcaactc gatcatcctg gggttcagct cgttcctgat cgagccgatg | 1320 |

-continued

```
tgcaagcggc taggcccgag ggtggtgtgg gtgtccagca acttcctcgt ctgcatcgct   1380
atggctgcca ccgccatcat cagctggtgg tctaccaagg aattccatga gtacgttcag   1440
catgccatta ccgccagcaa ggacatcaaa atcgtatgca tggccctctt cgcattcctc   1500
ggagtgcctc tcgccattct gtacagcgtt ccctttgcgg tgacggcgca gttggcggca   1560
agcaaaggag cgggccaagg gctgtgcacc ggcgtgctga atatctccat cgtcatccca   1620
caggtgatca tcgcgctggg ggcggggccg tgggaccagc tgttcgggaa gggcaacatc   1680
ccggccttcg ccgcggcctc cgccttcgcg ctcatcggcg gcatcgtcgg catattcctg   1740
ctgcccaaga tctccaggcg ctcgttccgg ccgtcagca ccggcggtca ctgaccgcgt    1800
cgggcgcctg cctgagcgcg ggcgaaagct cgatcgtgca ggccgggcgg ttccagctcg   1860
catgtgccaa tttttacata ggcttaaaaa taggtggctc tcgcttcaag actccgtaga   1920
gcagaataag aatgtgagga accgtatgtt tgtgtatgtg tgctagcgtg tgtaacagaa   1980
cgggcgaggg ggatgtggtc atccattacc ggctgggtgg tctgtaaagg ctatgtggcc   2040
gtcggatttg gatcggagcg cccttaatga gggcaggttg ttaaaaaaaa aa           2092
```

<210> SEQ ID NO 23
<211> LENGTH: 1600
<212> TYPE: DNA
<213> ORGANISM: Festuca arundinacea

<400> SEQUENCE: 23

```
gcatctgcgt tgctgttgtg gtcgtcggct tctcggctga cattggagct gctctgggtg     60
atagcaagga agagtgcagt ctctaccatg gtcctcgctg gcacgctgca attgtgtatg    120
tgcttggatt ctggcttctt gacttctcca acaatactgt gcaaggtcca gctcgtgctc    180
tgatggctga tttgtcaggc aagtatggac ccagtgctgc aaattcaatc ttctgttctt    240
ggatggcgct aggaaatatc ctagggtact cctctggttc cacagataag tggcacaagt    300
ggtttccctt ccttcggaca agagcctgct gtgaagcttg cgcaaatttg aaaggcgctt    360
ttctggtggc tgtgctgttc ctgtgcttct gtttggtgat aactctgatc ttcgccaagg    420
aggtaccata caaacgaatt gcaccctcc caacaaaggc aaatggtcag gttgaagttg    480
aacctagtgg cccgcttgcg tgttccaag gcttcaggaa cttgccttcc ggaatgccat     540
cggtgctcct tgtaactggc ctcacctggc tgtcctggtt cccgttcatc ctctacgaca    600
ccgactggat gggtcgtgag atttaccacg gtgaccccaa gggcacccca gctgaggcct    660
cggcgttcca ggacggtgtc agggctggcg cgttcggact gctactcaac tcgatcatcc    720
tgggggttcag ctcgttcctg atcgagccga tgtgcaagcg gctgggcccg agggtggtgt    780
gggtgtccag caacctcctc gtctgcatcg ccatggccgc caccgccatc atcagctggt    840
ggtctaccaa ggaattccat gagtacgtcc agcatgccat accgccagc aaggacatca     900
agatcgtatg catggtcctc ttcgcattcc tcggagtgcc tctcgccatt ctgtacagcg    960
ttccctttgc ggtgacggcg cagttggcgg caaacaaagg aggcggccaa gggctgtgca   1020
ccggcgtgct gaacatctcc atcgtcatcc cacaggtgat catcgcgctg ggggcggggc   1080
cgtgggacca gctgttcggg aagggcaaca tcccggcctt cgccgcggcc tccgccttcg   1140
cgctcatcgg cggcatcgtc ggcatattcc tgctgcccaa gatctccagg cactcgttcc   1200
gggccgtcag caccggcggt cactgaccgc gccgggcgcc gacctgagta cgggcgaaag   1260
ctcgcgtgca ggccgggcgg ttccagtccg catgtgccaa tttttacata ggcttaattt   1320
aggtggctct cgcttcaaga ctccgtagag cagaataaga atgtgaggaa ccgtatgctt   1380
```

```
gtgtatgtgt gctagtgtgt gtaacagaac gggcgaggga gtgtggtcat ccattaccgg    1440
ctgggtggtc tctgaaggct atgtggccgt cggatttgga tcggagcgcc cttaatgagg    1500
ccaggtgtca tccttgtgtt gtgacttgtg tagcaaacca aggttaaccg agtaaaggga    1560
aaagactgga tggtgcattt tcagcaacac aaaaaaaaaa                          1600

<210> SEQ ID NO 24
<211> LENGTH: 2223
<212> TYPE: DNA
<213> ORGANISM: Festuca arundinacea

<400> SEQUENCE: 24
aaaagaacac aaacccacac caccaccacc acctctcctc actccacgct ccctcctcc      60 ctcgcatcac acacccctc gtctcctcct cttcttcctc ccgtcagccc cgttcctggc     120
gctaccatct tcttcctcgc atgcgttgat tcgatcaacg tacttttccc ctctctagat     180
ccttgttggc cgaagaattg ataggcgaac gaggtgatca tcgttcgcac gacgtcccgg     240
ccatggtgcg cggcggcggc aacagcgagg tggagctctc cgtgggggcc ggtggcggcg     300
gcggcggggc gggaggcctg gtggagccgc ccgtgccgat cagcctcggc aggctcgtct     360
tcgccggcat ggtcgccggc ggcgtgcagt atggatgggc cctccagctc tccctgctca     420 cccctacgt ccagactctg ggactttcac atgccctgac ttcattcatg tggctctgcg     480
gcccaatagc tggcttagtg gttcaaccat gtgttggtct gtacagtgat aagtgcactt     540
ccagatgggg aagacggagg ccgtttatta tgacaggatg tgtgctcata tgcattgctg     600
ttgtgattgt tggcttctcg gctgacattg agctgctct gggcgatagc aaggaagagt     660
gcagtctcta ccatggtcct cgctggcacg ctgcaattgt gtatgtgctt ggattctggc    720
ttcttgactt ctccaacaat actgtgcaag gtccagctcg tgctctgatg gctgatttgt     780
caggcaagta tggacccagt gctgcaaatt caatcttctg ttcttggatg gcgctaggaa    840
atatcctagg gtactcctct ggttccacag ataagtggca caagtggttt cccttccttc     900
ggacaagagc ctgctgtgaa gcttgcgcaa atttgaaagg cgcttttctg gtggctgtgc     960
tgttcctgtg cttctgtttg gtgataactc tgatcttcgc caaggaggta ccatacaaac    1020
gaattgcacc cctcccaaca aaggcaaatg gtcaggttga agttgaacct agtgccccgc    1080
ttgcggtgtt ccaaggcttc aggaacttgc cttccggaat gccatcggtg ctccttgtaa    1140
ctggcctcac ctggctgtcc tggttcccgt tcatcctcta cgacaccgac tggatgggtc    1200
gtgagattta ccacggtgac cccaagggca ccccagctga ggcctcggcg ttccaggacg    1260
gtgtcagggc tggcgcgttc ggactgctac tcaactcgat catcctgggg ttcagctcgt    1320
tcctgatcga gccgatgtgc aagcggctgg gcccgagggt ggtgtgggtg tccagcaacc    1380
tcctcgtctg catcgccatg gccgccaccg ccatcatcag ctggtggtct accaaggaat    1440
tccatgagta cgtccagcat gccatcaccg ccagcaagga catcaagatc gtatgcatgg    1500
tcctcttcgc attcctcgga gtgcctctcg ccattctgta cagcgttccc tttgcggtga    1560
cggcgcagtt ggcggcaaac aaaggaggcg gccaagggct gtgcaccggc gtgctgaaca    1620
tctccatcgt catcccacag gtgatcatcg cgctggggc ggggccgtgg gaccagctgt    1680
tcgggaaggg caacatcccg gccttcgccg cggcctccgc cttcgcgctc atcggcggca    1740
tcgtcggcat attcctgctg cccaagatct ccaggcactc gttccgggcc gtcagcaccg    1800
gcggtcactg accgcgccgg cgccgacctg agtacgggc gaaagctcgc gtgcaggccg    1860
```

```
ggcggttcca gttcgcatgt gccaattttt acataggctt aatttaggtg gctctcgctt    1920
caagactccg tagagcagaa taagaatgtg aggaaccgta tgcttgtgta tgtgtgctag    1980
tgtgtgtaac agaacgggcg agggagtgtg gtcatccatt accggctggg tggtctctga    2040
aggctatgtg gccgtcggat ttggatcgga gcgcccttaa tgaggccagg tgtcatcctt    2100
gtgttgtgac ttgtgtagca aaccaaggtt aaccgagtaa agggaaaaga ctggatggtg    2160
cattttcagc aacacaaaaa aaaaaaaaaa aaaaaaaaaa aaaaaaaaaa aaaaaaaaaa    2220
aaa                                                                 2223

<210> SEQ ID NO 25
<211> LENGTH: 2042
<212> TYPE: DNA
<213> ORGANISM: Lolium perenne

<400> SEQUENCE: 25
gatttccaac tccttccgtg gcggcaccgc cgtggcccga cgggattgga gccaccggaa      60
caagattctt tgctcgctgc tctccccctt cttcttcctc ctcactgctc ccgccggcac     120
agtcgggagc tcacaatcca gcagccacac caccggcggc gtaggcgtag gcggagcggg     180
ggtcgaaaag ttcaatccga cacaagatgc cgccccgcg gcggccgacc accggcggca     240
ccaccaccac ctccgccgcc ctccccccac cccgcaaggt cccgctgcgc tcctcctgc     300 gcgccgcctc ggtcgcctgc ggggtgcagt tcgggtgggc gctgcagctc tcgctgctca    360
cgccctacgt gcaggagctg gcatcccgc acgccttcgc gtcgtcgtc tggctctgcg      420 gcccgctctc cggcctgctg gtgcagccgc tcatcggcca cctctccgac cgcatcgcgc    480
ccgccgactc cccgctcggc cgccgccggc ccttcatcgc cgcgggcgcc gcctccatcg    540
ccttctccgt gctcaccgtc ggcttctcgg ccgatctggg gcggctgttc ggggacaacg    600
tccggcccgg gtcgaccagg tacgcgcga ttattgtgta tatgatcggc ttctggctgc     660
tggatgtcgg caacaacgcc acccaggggc cctgcagggc cttcctcgct gacctcaccg    720
agaatgaccc gaggaggact cggatcgcca acgcctattt ctcgctcttc atggccctgg    780
ggaacatcct cgggtatgcc accggagcgt acagcggctg gtacaagata tttcccttca    840
ccatcaccga gtcatgtggc gtcagctgtg ccaacctcaa gtctgcgttc ctgctagaca    900
tcatcatcct ggcaattacg acatacgtca ccgtggtaac ggtgcaagac aacccgacat    960
tcgggagcga tgaagcagcg ccacgtccga gcagccacga agaggaggct ttcctcttcg   1020
agctctttgg gtcattcaag tacttcacga tgcctgtctg gatggtcctg atcgtcactt   1080
ccctcacctg gatcgggtgg ttcccgttca tcctcttcga taccgactgg atgggccggg   1140
aaatctaccg agggagcccg gagatcgtcg ccgacaccca gaagtaccat gacggtgtga   1200
gaatgggttc ctttggcctc atgctcaatt cagtccttct cgggatcacg tcggtcgtga   1260
cggagaagct gtgcaggaag tggggggctg ggctcgtatg gggtgtttcc aatattatca   1320
tggctctctg ctttgtggcg atgctcgtta taacgtacgt ggcgcagaat ttggactatg   1380
gacctagcgg agcacctccg accggcatcg ttgttgcttc cctcacagtt ttcacgattc   1440
tgggagcacc cttgtcgatc acgtacagta taccatacgc gatggctacg agccgtgttg   1500
agaatcttgg gcttggccag ggtctagcaa tgggtattct caatttatct atcgtcatac   1560
cacagatcat cgtgtcactg gcagtgggc cgtgggactc gctatttggc ggagggaacg    1620
cgccatcgtt ttgggtggcg gctgccgcgt ccttcattgg cgggctggtg gccatcctgg   1680 gtctccccg agcccgtatt gcgccaaaga agaggagcca gcgatgatga tcagagtaca   1740
```

```
ttatttcagg ttgtctgtat atcgtggctc taagttaagt tgcaagttgc aaccattctt    1800
tgctctatca tccagtggat taggcatggg tatctgtctg tatatcagtt cgatggggaa    1860
agaaatacag ctctggaatc tggtcttctt ttctttcctc catgagctgt tgttttttc    1920 gcgtctccgt gtcaaacatg gtcggttgta tcttgttgta tgttggattt ttatggtttt    1980
gtcggagatg gtgggtgaat gaatgaataa aaagtcggca gggttttgct tgaaaaaaaa    2040
aa                                                                   2042

<210> SEQ ID NO 26
<211> LENGTH: 1930
<212> TYPE: DNA
<213> ORGANISM: Festuca arundinacea

<400> SEQUENCE: 26
gctcctagta cagtcgggag ttcagaattc tgcagacgca ccaccgcgaa ccaaggaggc     60
ggcggcggag gcgtagggga agtgggccat ccgagagaag atgccgcccc cgcggcggcc    120
caacgccggc ggcaccacct ccgcccctct acccccaccc cgcaaggtcc cgctccgctc    180
cctccttcgg gcggcctccg tcgcctgcgg ggtccagttc gggtgggcgc tgcagctctc    240
cctcctcacg ccctacgtgc aagaactcgg catcccgcac gccttcgcct ccctcgtctg    300
gctctgcggc ccgctctccg gcctcctggt ccagcccctc atcggccacc tgtccgatcg    360
catcgcgccc gccgactccc cgctcggccg ccgccggccc ttcatcgccg cggggggcggc    420 gtccatcgcc ttctctgttc tcacggtcgg cttctcggcg gatttgggga ggctgttcgg    480
ggacaacatc cggccgggat ccaccaggtt cggcgcgatt attgtttaca tgatcgggtt    540
ctggctgctg gatgtaggga acaacgccac ccaggggccc tgcagggcct tcctcgcaga    600
cctcaccgag aatgacccga ggaggactcg gatcgccaac gcctatttct cgctcttcat    660
ggccctgggg aacatcctcg ggtacgccac tggagcgtac agcggctggt acaagatatt    720 cccccttcacc atcaccgagt cctgtggcgt cagctgtgcc aacctcaagt ctgcgttcct    780
gctagacatc atcatcctgg caattacgac atacgtcacc gtggtaacgg tgcaagacaa    840
cccgacattc gggagcgatg aagcggcacc gcgtccgagc agccacgaag aggaggcttt    900
cctcttcgag ctcttcgggt cattcaagta cttcacgctg cctgtctgga tggtcctgat    960
cgtcacttcc ctcacctgga tcgggtggtt cccgttcatc ctcttcgata ctgactggat   1020
gggccgggaa atctaccgag ggagcccgga atcgtcgcc gacacccaga agtaccatga   1080
tggtgtgaga atgggttcct ttggcctcat gctcaactca gtccttctcg ggatcacatc   1140
ggtcgtgatg gagaagctgt gcaggaagtg ggggctggg ctcgtatggg gtgtttccaa   1200
tattatcatg gctctctgct ttgtggcgat gctcattata acgtacgtgg cgaagaattt   1260
ggactatgga cctagcggag cacctccgac cggcatcgtc gttgcttccc tcgcagtttt   1320
cacgattctg ggagcaccct gtcgatcac gtacagtata ccgtacgcga tggctacgag   1380
ccgtgttgag aatcttgggc ttggccaggg tctagcaatg gcattctca atttatctat   1440 cgtcatacca cagatcatcg tgtcactggg cagtgggcca tgggactcgc tttttggcgg   1500
agggaacgcg ccatcgtttt gggtggcggc cgccgcgtcc ttcattggcg gctggtggc   1560 catcctgggt ctccccgag cccgcattgc gccaaagaag agaagccagc gatgatgatc   1620
agagtacatt gtttcaggtt gtctgtatat cctggctctg agttaagttg caagttgcaa   1680
ccattctttg gtctatcatc cagttgatta ggcatgggta tctgtctgta tatcggttcg   1740
```

```
atggggaaag aaatacagct ctggaatctg gtcttgtttt ccttcctcca tgagctgttg    1800 ttttttcgc gtctccgtgt caaacatggt cggttgtatc ttgttgtatg ttggattttt    1860
atggttttgt ccgagatggt gggtgaatga atgaataaaa agtcggcagg gttttgcttc    1920
aaaaaaaaaa                                                          1930

<210> SEQ ID NO 27
<211> LENGTH: 1911
<212> TYPE: DNA
<213> ORGANISM: Lolium perenne

<400> SEQUENCE: 27
ggcccagctc ccgcaactac caacctccca tataaatccc tggtacacag agttcttcag      60
cagcagccta gtgatctccc cattaccccg cacgatcaat cctcgatatg gtggaccaag     120
atcacgatgg gcggcggcga caggaggagg cgacggcggt ggcggcgtcg tcagttccgt     180
tgctggagaa gaagcccggc gacgtgccgt actacgtgga ggggtgcccg gggtgcgcgg     240
tggaccggag gaaggcgacg gacccaggca tcccctacgg cagcttcatc tacatctggg     300
tcgtcatcct ctgcaccgct ataccaatat cgtcgctatt ccccttcttg tatttcatga     360
taagagactt gcacatcgcg gaaagaacag aagatattgg gttctatgct gggtttgtag     420
gtgccgcttt tatgtttggt agatgtttga cttcaactat ttggggcata gcagcagatc     480
gtattgggag gaagccagtt gtgatatttg gtgttttctc tgtggtaata tttaatgctt     540
tgtttgggct tagtgttacc tactggatgg caatagctac aaggtttctc cttggcgctt     600
taaatggttt acttggacca atgaaggcat atgctattga agtttgccgg cctgaacacg     660
aagctctagc actatcactt gtcagcacag catggggaat aggtctcatc attggtcctg     720
ctcttggagg ctaccttgca ctgcctgcag aaaaatatcc aaatatcttt tcgcctgact     780
cgctatttgg aaggttcccg tacttcttac catgcttatg cacatcagtg tttgctgccg     840
ctgttctgat aggctgcata tggatgccgg agacgttgca caagcataaa gtaaatgaga     900
ataggaatca aagtgtcgaa tctttggagg cccatctgat tgatccaaaa gagaaggttg     960
aacaaagtaa tagtccggat accaagaaga gcttattcaa gaattggcca ttaatgtcat    1020
ccataattgt ttattgtgtc ttctccttcc acgacatggc ttacacagag tgttctctc    1080 tgtgggctga aagtgacagg acatatggtg gactcagttt gtcatctgaa gatgtaggcc    1140
aaacacttgc aattacaggc tccagtcttc ttgtgtatca actcttcttg tacccgcgca    1200
tcaacagggt tcttggacct atcaaatcat ctcaaatcgc agctggcata tgcatacccta    1260 ttctctttgc ctaccccctat atgacgtacc tgtcagaacc tggattatca attgttctga    1320
atattgcatc agtcataaaa aataatcttg gtgttaccat cattacaggc actttcatcc    1380
ttcaaaataa tgccgtgcct caggaccaaa gaggtgcagc aaacgggtta gccatgactg    1440
gaatgtcctt tttcaaggca gttgctcctg caggcgctgg cattgtgttt tcatgggcgc    1500
agaaacgaca acatgctttc ttctttccag gtgatcagat ggtgttcttt ctgctgaaca    1560
tcattgagct ccttggactt ctcctcacat tcaaattctt cctggccgtg ccagataaat    1620
ctgatagcaa ctagctgttc agctattgtt ctagatattt tttggataat tattcagatg    1680
gcgatgactc atggatcttg catccgcgag agaagggct taaggcgccc ttataacagg    1740
attaagaggt ggccaggtac aagttgtgtt gttgtgtgta agatgtagga gcactccagt    1800
agaggagatg caacatttgt aagtagtgat gtagtaagag actgcggctc ggaataattg    1860
gcggaattgg actcagcata attgctatat ctctcgctat caaaaaaaaa a            1911
```

<210> SEQ ID NO 28
<211> LENGTH: 2039
<212> TYPE: DNA
<213> ORGANISM: Lolium perenne

<400> SEQUENCE: 28

| | | | | | |
|---|---|---|---|---|---|
| gctccctctc | gccacatcac | ccccgcccag | cccactccct | ccatcaattc | ctccccacat | 60 |
| ttgattcatc | cctgctccca | tcccatccca | ttccgttgca | ttccaccggt | ccttccccga | 120 |
| tccgccgatt | cgttccagtt | gcagggccga | tgtcatcgat | gcagttcagc | agcgtgctcc | 180 |
| cgctggaggg | caaagcgtgc | gtgtgcccgg | tgaggagcgc | caacaacggg | tgcgagaggc | 240 |
| tcaaggtcgg | ggacagcagc | agcctcaggc | acgagatggc | gctgaggagg | aagtgcaacg | 300 |
| gcgccagagg | aggaggcgcc | gccaacggcg | cgcagtgcgt | gctcacctcc | gacgccagcc | 360 |
| cggacaccct | tgttgtccga | tcgtccttcc | ggaggaacta | cgccgatccg | aacgaggttg | 420 |
| cggcggtcat | actgggcggc | ggcaccggga | ctcaactctt | ccctctcacc | agcacaaggg | 480 |
| ctacgcctgc | tgttcctatt | ggaggatgtt | acaggcttat | cgatattccc | atgagcaact | 540 |
| gcttcaacag | tggcataaac | aagatattcg | tgatgactca | gttcaactcg | gcatctctta | 600 |
| atcgtcacat | tcaccgtacg | tacctcggcg | ggggatcaa | tttcactgat | ggatctgttg | 660 |
| aggtattggc | cgcaacgcaa | atgcctgggg | aggctgctgg | atggttccgg | ggaaccgcag | 720 |
| atgcggtcag | aaaatttatc | tgggtacttg | aggactatta | taagcataaa | tctatcgagc | 780 |
| acattttgat | cttgtcgggg | gaccagcttt | atcgcatgga | ttacatggag | cttgtgcaga | 840 |
| aacatgttga | tgacaatgct | gacattactc | tatcatgtgc | ccctgttgga | gaaagccggg | 900 |
| catccgaata | tggactagtg | aagttcgaca | gttcaggtcg | cgtgatccag | ttttctgaga | 960 |
| agccaaaggg | cgcggacttg | gaagcaatga | agtggatac | cagcttctc | aattttgcca | 1020 |
| tagatgatcc | agccaaaaat | ccctacattg | cttccatggg | agtttatgtc | ttcaaaagag | 1080 |
| aagttctttt | gaaccttcta | aagtcaagat | acacagaact | acatgacttt | gggtctgaaa | 1140 |
| tcctcccgag | agctctacat | gaccacaatg | tacaggcata | tgtcttcact | gactactggg | 1200 |
| aggacattgg | aacaatcaga | tcgttcttcg | atgcaaacat | ggcactctgc | gagcagcctc | 1260 |
| caaagtttga | gttttatgac | ccaaagactc | ccttcttcac | ttcgcctcga | tacttgccac | 1320 |
| caacaaagtc | cgataagtgc | aggatcaaag | aggcgatcat | ttcacacggc | tgcttcctgc | 1380 |
| gcgaatgcac | cattgagcac | tctatcatcg | gcgtccgttc | acgcctaaac | tccggatctg | 1440 |
| tgcttaagaa | cgcgatgatg | atgggtgcgg | atctgtacga | gaccgaggac | gagatctcgg | 1500 |
| ggctgctgtc | cgagggcaag | gtccccatcg | tgttgggga | gaactccaag | ctcagcaact | 1560 |
| gcatcatcga | catgaacgct | aggatcggaa | gggacgtggt | catcgcgaac | agcgagggcg | 1620 |
| tccaggagc | tgatcggcca | gaggaagggt | actacatcag | gtccgggatc | gtggtgatac | 1680 |
| tgaagaacgc | aaccgtgaag | gacggcaccg | tggtgtagaa | cgccgcctgc | gccgcggcaa | 1740 |
| ccgcatcttt | ttcgagagtt | gttggtagcc | cagagctgcc | gacctgaagt | tcattcagac | 1800 |
| gaggaagaag | ataggatccc | tggcgggacg | gtagaagttg | ggagctggga | caggagacgg | 1860 |
| ctcatgcagc | aagcatcagt | agcaaagcaa | gtactcctag | tagtagtcgt | tcttcccctg | 1920 |
| taataataaa | gctgcgtgcg | tgcgcgtcga | gttgaagtgg | cagcagactc | ttctggggga | 1980 |
| tcgatcctgt | aaataaaact | tgaaaaatat | gggattttc | cgttgcctca | aaaaaaaaa | 2039 |

<210> SEQ ID NO 29

<211> LENGTH: 2063
<212> TYPE: DNA
<213> ORGANISM: Festuca arundinacea

<400> SEQUENCE: 29

```
gccgtggtgg cgtttcgtcg ccggccggat aaaaatactt gtgcttcttc tatctccgtc      60
tgtgcaagag agagagagag agcagcggcg tttgtcgccg gtgggctggt tcggcgcgtg     120
tcgctgaggc cagccccaac agagttcatc actattgcag cagggccgat gtcatcgatg     180
cagttcagca gcgtgctccc gctggagggc aaagcgtgcg tgtgcccggt gaggagcgcc     240
aacaacgggt gcgagaggct caaggtcggg gacagcagca gcctcaggca cgagatggcg     300
ctgaggagga agtgcaacgg cgccagaggg ggaggcgccg ccgacggcgc gcagtgcgtg     360
ctcacctccg acgccagccc ggacacccct gtcgtccggt cgtccttccg gatgaactac     420
gccgatccga acgaggttgc ggcggtcata ctgggcggcg gcaccgggac tcagctcttc     480
cctctcacca gcacaagggc tacgcctgct gttcctattg gaggatgtta caggcttatc     540
gatattccca tgagcaactg cttcaacagt ggcataaaca agatattcgt gatgactcag     600
ttcaactcgg catctcttaa tcgtcacatt caccgcacgt acctcggcgg ggggatcaat     660
ttcactgatg gatctgttga ggtattggcc gcaacgcaaa tgcctgggga ggctgctgga     720
tggttccggg gaaccgcaga tgcagtcaga aaatttatct gggtacttga ggactattat     780
aagcataaat ctatcgagca cattttgatc ttgtcggggg accagcttta tcgcatggat     840
tacatggagc ttgtgcagaa acatgttgat gacaatgctg acattactct atcatgtgcc     900
cctgttggag aaagccgggc atccgaatat ggactagtga agttcgatag ttcaggtcgc     960
gtgatccagt tttctgagaa gccaaagggc gcggacttgg aagcaatgaa agtggatacc    1020
agctttctca atttgccat agatgatcca gccaaaaatc cctacattgc ttccatggga    1080
gtttatgtct tcaaaagaga agttcttttg aaccttctaa agtcaagata cacagaacta    1140
catgactttg ggtctgaaat cctcccgaga gctctacatg accacaatgt acaggcatat    1200
gtcttcactg actactggga ggacattgga acaatcagat cgttcttcga tgcaaacatg    1260
gcactctgcg agcagcctcc aaagtttgag ttttatgacc caaagactcc cttcttcact    1320
tcgcctcgat acttgccacc aacaaagtcc gacaagtgca ggatcaaaga gcgatcatt    1380
tcacacggct gcttcctgcg cgaatgcacc attgagcact ctatcatcgg cgtccgttca    1440
cgcctaaact ccggatctgt gcttaagaac gcgatgatga tgggcgcgga tctgtacgag    1500
accgaggacg agatctcggg gctgctgtcc gagggcaagg tccccatcgg tgtcggggag    1560
aactccaagc tgagcaactg catcatcgac atgaacgcta ggatcggaag ggacgtggtc    1620
atcgcgaaca gtgagggcgt ccaggaggct gatcggccag aggaagggta ctacatcagg    1680
tccgggatcg tggtgatact gaagaacgca accgtgaagg acggcaccgt ggtgtagaac    1740
gccgcctgcg ccgcggcagc tgcatctttt tcgagagttg gcggtagccc agagctgccg    1800
acctgaagtt cattcagacg aggaagaaga tagggtccct ggcgggaccg tagaagttgg    1860
gagctgggag cctgggacga gagacggctc atgcagcaag catcagtagc aaagcaagta    1920
ctcctagtaa tagtcgttct tcccctgtaa taataagctg cgtgcgtgcg tcgagttgaa    1980
gtggcagcag actcttctgg gggatcgatc ctgtaaataa aacttgaaaa atatgggatt    2040
tttccgttgc ctcaaaaaaa aaa                                              2063
```

<210> SEQ ID NO 30
<211> LENGTH: 1815

<212> TYPE: DNA
<213> ORGANISM: Lolium perenne

<400> SEQUENCE: 30

```
gcggacgcgc catgaccgga gctccgccat ccaccgtaat ggcgatgggt gcggccacct      60
ccccttgcaa gatcttgagc gccacgcaac gtgcctccac cgcggcggct tcggcatcca     120
cctcccgcga gtccgtctcc ctccgcgcac cacggggacg gcgccagcgc ccgcgcccgc     180
gcgggttggc cttgtccctg gctccagcgc gacggccgtt tgtcttctcc ccgcgcgccg     240
tgtcagactc caagagctcc cagacctgcc tcgaccctga cgcaagcacg agtgttctcg     300
gaatcattct gggaggtggt gcagggacta gattgtatcc tctgacaaag aagcgtgcga     360
agcctgctgt gccattgggt gccaactaca ggcttattga tattcctgtc agcaattgtt     420
tgaacagcaa tatatcaaag atctatgtgc tgacacagtt caactctgct tctcttaatc     480
gtcatctctc acgagcttat gggagcaaca ttggaggata caagaatgaa ggatttgttg     540
aagtcctcgc ggcacagcag agcccagaca atcctaactg gtttcagggt actgcagatg     600
ctgtaaggca gtatttatgg ctattcgagg aacataatgt tatggaatat ctaattcttg     660
ccggagatca cttgtaccga atggactatg aaaagtttat tcaggcgcac agagaaacag     720
atgctgatat tactgttgcc gccttgccca tggatgagga acgtgcaact gcatttggcc     780
ttatgaaaat cgatgaagaa gggaggatag ttgaatttgc agagaaacca aaaggagagc     840
agttgaaagc aatgatggtt gatacaacca tacttggtct tgatgacgtg agggcaaagg     900
aaatgcctta tatcgctagc atgggtatct acgttattag caaacatgta atgctccagc     960
ttctccgtga ccaatttcct ggagctaatg actttggaag tgaggttatt cctggtgcga    1020
ctagcactgg aatgagggta caagcatact tatatgatgg ttactgggaa gatattggta    1080
caattgaggc attctataac gcaaatttgg gaattaccaa aaagccaata ccagatttca    1140
gtttctatga tcgttctgct ccaatttaca cacaacctcg acacttgcct ccttcaaagg    1200
ttcttgatgc tgacgtgaca gacagtgtta ttggcgaagg atgtgttatt aaaaactgca    1260
agatacacca ttcagtagtt ggactgcggt cctgcatatc tgaaggtgca attatagagg    1320
acacattact aatgggcgca gactactatg agactgaagc tgacaagaaa ctccttgccg    1380
acaaaggtgg gattcccatt ggtattggaa agaattcaca catcagaaga gcaatcattg    1440
acaagaatgc tcgtattgga gacaacgtga agataatcaa tgttgacaat gttcaagaag    1500
cagcccggga gactgatgga tacttcatca aaagtggcat cgtaactgtg atcaaggatg    1560
ctttactccc aagtgggaca gtcatatgaa acagatgcaa aatatgtggc aagtcacggc    1620
gcttcttgta tcattctgca atcaaccaat gaggtcgcca aagatcata agagcaataa    1680
aaaggagtgc cctgcaaggc acttcatctt ttttctccct taatgtatta gcaaccgtaa    1740
tgtacaagca acttgcatcc agatgttctg gagatcgaat atacctgctt gcatcttgtt    1800
gtttcaaaaa aaaaa                                                     1815
```

<210> SEQ ID NO 31
<211> LENGTH: 1873
<212> TYPE: DNA
<213> ORGANISM: Festuca arundinacea

<400> SEQUENCE: 31

```
gcccatgacc cgagctccgc catccaccgt aatggcgatg ggtgcggcca cctccccttg      60
caagatcttg agcgccacgc aacgtgcctc cgccgcggcg ccttcggcat ccacctcccg     120
```

| | |
|---|---|
| cgagtccgtc tgcctcctcc gcgcgccacg gggacggcgc cagcgcccgc gcgggttggc | 180 |
| cttgtccctg gctccagcgc gacggccgtt tgtcttctcc ccgcgcgccg tgtcagactc | 240 |
| caagagctcc cagacctgcc tcgaccctga cgcaagcacg agtgttctcg gaatcattct | 300 |
| gggaggtggt gcagggacta gattgtatcc tctgacaaag aagcgtgcga agcctgctgt | 360 |
| gccattgggt gccaactaca ggcttattga tattcctgtc agcaattgtt gaacagcaa | 420 |
| tatatcaaag atctatgtgc tgacacagtt caactctgct tctcttaatc gtcatctctc | 480 |
| acgagcctat gggagcaaca ttggaggata caagaatgaa ggatttgttg aagtcctcgc | 540 |
| ggcacagcag agcccagaca atcctaactg gtttcagggt actgcagatg ctgtaaggca | 600 |
| gtatttatgg ctattcgagg aacataatgt tatggaatat ctaattcttg ccggagatca | 660 |
| cttgtaccga atggactatg aaaagtttat tcaggcgcac agagaaacag atgctgatat | 720 |
| tactgttgcc gccttgccca tggatgagga acgtgcaact gcatttggcc ttatgaaaat | 780 |
| cgacgaagaa gggaggatag ttgaatttgc agagaaacca aaaggagagc agttgaaagc | 840 |
| aatgatggtt gatacgacca tacttggcct tgatgacgtg agggcaaagg aaatgccta | 900 |
| tatcgctagc atgggtatct acgttattag caaacatgta atgctccagc ttctccgtga | 960 |
| ccaatttcct ggagctaatg actttggaag tgaggttatt cctggtgcga ctagcactgg | 1020 |
| aatgagggta caagcatact tatatgtgg ttactgggaa gatattggta caattgaggc | 1080 |
| attctataac gcaaatttgg gaattaccaa aaagccaata ccagatttca gtttctatga | 1140 |
| ccgttctgct ccaatttaca cccaacctcg acacttgcct ccttcaaagg ttcttgatgc | 1200 |
| tgacgtgaca gacagtgtta ttggcgaagg atgtgttatt aaaaactgca agatacacca | 1260 |
| ttcagtagtt ggactgcggt cctgcatatc tgaaggcgca attatagagg acacattact | 1320 |
| aatgggtgca gactactatg agactgaagc tgacaagaaa ctccttgccg acaaaggtgg | 1380 |
| gattcccatt ggtattggaa agaattcaca catcagaaga gcaatcattg acaagaatgc | 1440 |
| tcgtattgga gacaacgtga agataatcaa tgttgacaat gttcaagaag cagcccggga | 1500 |
| gacggatgga tacttcatca aaagtggcat cgtaactgtg atcaaggatg ctttactccc | 1560 |
| gagtgggaca gtcatatgaa acagatgcaa aatatgtggc aagtcacggc acttcttgta | 1620 |
| tcattctgca atcaaccaat gaggtcgcca gaagatcata agagcaataa aaaggagtgc | 1680 |
| cctggaaggc acttctccat cttttttctc ccttaatgta ttaggaaccg taatgtacaa | 1740 |
| gcaacttgca tccagatgtt ctggagatcg aaaatacctg cttgcatctt gttgtttcaa | 1800 |
| atatgaagtg tactagataa agccccgcat gttttttcac gatattacaa aactttgtag | 1860 |
| ttgaaaaaaa aaa | 1873 |

<210> SEQ ID NO 32
<211> LENGTH: 1494
<212> TYPE: DNA
<213> ORGANISM: Festuca arundinacea

<400> SEQUENCE: 32

| | |
|---|---|
| gcaacaagga gcaactgtca ctcattcatc tgtcgtctcc tgcttccctc aagcttagat | 60 |
| cgattgcagc cggccgggga ctgttgagct accactgccg gtcgctggta cgagcggacg | 120 |
| taaggagaga tccagatggc cgcgacgatg accgtgagg aggtgaggaa ggcgcagcgg | 180 |
| gcggaggggc cggcgacggt gctggccatc ggcacggcga cgcccgctaa ctgtgtctac | 240 |
| caggctgact acccggacta ctacttcaag atcaccaaga gcgaccacct cgccgatctc | 300 |
| aaggagaagt tcaagaggat gtgcgacaag tctcagatca ggaagaggta catgcacctg | 360 |

| | |
|---|---|
| acggaggaga tcctggagga gaaccccaac atgtgcgcgt acatggcgcc gtcgctggac | 420 |
| gcgcgccagg acatagtcgt cgtcgaggtc ccgaagctcg ggaaggcggc ggcacagaag | 480 |
| gcgatcaagg agtggggcca gccgcggtcc aagatcaccc acctcgtctt ctgcactacc | 540 |
| tctggtgtgg acatgccagg cgccgactac cagctcacca agatgctcgg cctgcgcccg | 600 |
| tcggtgaagc gcctcatgat gtaccagcag ggctgcttcg ccggcggcac ggtgctccgc | 660 |
| ctcgccaagg acctggctga aaacaaccgc ggcgcgcgcg tgctggtggt ctgctcggag | 720 |
| atcacggccg tgaccttccg cggcccgcac gagtcacacc tcgactcgct ggtcggccag | 780 |
| gcgctcttcg gggacggcgc tgccgcggtg ataatcggcg ccgaccccga cgtgtccgtc | 840 |
| gagcgcccgc tgttccagct ggtgtcggtg agccagacca cctgccgga ctcggagggc | 900 |
| gccatcgacg gccacctcag ggaggtcggc ctcaccttcc acctcctcaa ggacgtgccc | 960 |
| gggctcatct ccaagaacat cgagcgcgcc ctggaggaag ccttcaagcc gctcggcatc | 1020 |
| gacgactgga actccgtctt tggggtggcg caccccgggcg ggccggcgat cctcgacatg | 1080 |
| gtggaggcca aggtaaaacct caacaaggag cggatgcgtg ccaccaggca cgtcctctcc | 1140 |
| gagtacggca acatgtccag cgcatgcgtc ctcttcatca tggacgagat cgcaagcgc | 1200 |
| tccgccgagg atggccacac caccaccggc gagggaatgg attggggcgt cctcttttggc | 1260 |
| ttcgggcccg gcctcaccgt cgagaccgtt gtcctccaca gcatgcccat tgccgctgat | 1320 |
| gccaccgctt gaccgatggt tccatctccg tttatctgcc acattgatga atacctacta | 1380 |
| ctactaccgc cgccgccgct gctatccaaa gtaatttgta ttgtattcat gcatacctgg | 1440 |
| tttgtatttg ttggtaggat tcgttctgct attatgtcgc ttgtgttgcg taca | 1494 |

<210> SEQ ID NO 33
<211> LENGTH: 1661
<212> TYPE: DNA
<213> ORGANISM: Festuca arundinacea

<400> SEQUENCE: 33

| | |
|---|---|
| gcaacaagca gcaactgtca ttcattcatc tgtcgtctcc tgcttccctc aaacttagat | 60 |
| cgatcgcagc cggccgggga ctggtgagct accactgtcg gtcgctggta cgagcggacg | 120 |
| caaggagaga tccagatggc cacgacgatg accgtggagg aggtgaggaa ggcgcagcgg | 180 |
| gcggaggggc cggcgacggt gctagccatc ggcacggcga cgcccgctaa ctgtgtctac | 240 |
| caggctgact acccggacta ctacttcaag atcaccaaga gcgaccacct cgccgacctc | 300 |
| aaggagaagt tcaagaggat gtgcgacaag tctcagatca ggaagaggta catgcacctg | 360 |
| acggaggaga tcctggagga gaaccccaac atgtgcgcgt acatggcgcc gtcgctggac | 420 |
| gcgcgccagg acatagtcgt cgtcgaggtc ccgaagctcg ggaaggcggc ggcgcagaag | 480 |
| gcgatcaagg agtggggcca gccgcggtcc aagatcaccc acctcgtctt ctgcaccacc | 540 |
| tccggtgtgg acatgccggg cgccgactac cagctcacca agatgctcgg cctgcgcccg | 600 |
| tcggtgaagc gcctcatgat gtaccagcag ggctgcttcg ccggcggcac ggtgctccgc | 660 |
| ctcgccaagg acctggctga aaacaaccgc ggcgcgcgcg tgctggtggt ctgctcggag | 720 |
| atcacggccg tgaccttccg cggcccgcac gagtcacacc tcgactcgct ggtcggccag | 780 |
| gcgctcttcg gggacggcgc tgccgcggtg atcatcggcg ccgaccccga cgtgtccgtc | 840 |
| gagcacccgc tgttccagct ggtgtcggcg agccagacca cctgccgga ctcggagggc | 900 |
| gccatcgacg gccacctcag ggaggtcggc ctcaccttcc acctcctcaa ggacgtgccc | 960 |

```
gggctcatct ccaagaacat cgagcgcgcc ctggaggaag ccttcaagcc gctcggcatc    1020
gacgactgga actccgtctt ctgggtggcc cacccgggcg gccggcgat  cctcgacatg    1080 gtggaggcca aggtaaacct caacaaggag cggatgcgcg ccaccaggca cgtcctgtcc    1140
gagtacggca acatgtccag cgcatgcgtc ctcttcatta tggacgagat cgcaagcgc    1200 tccgccgagg atggccacac caccaccggc gagggaatgg actggggcgt cctctttggc    1260
ttcggccccg gcctcaccgt cgagaccgtt gtcctccaca gcatgccat  tgccgctggt    1320 gccaccgctt gatcgatggt tccatctccg tttatctgcg acatcgataa aaacctacta    1380
ctactactac cgccgccgcc gccgctgcta tccaaagtac tgtaatttgt atcgtattca    1440
tgcatacctg gtttgtattt gttggtagga ttcgttctac tattatgtcg cgtgtgtcgc    1500
gtacaccgtc gtatcctagt agtagtaatc aaacggagta aggtttatat acgtgtcata    1560
atatgggttg tgaggtgcat ttacctgtgt acgagaagat tggctgttta atttcaagct    1620
tatgtggtgg ggaaaaaaaa aaaaaaaaaa aaaaaaaaa  a                        1661

<210> SEQ ID NO 34
<211> LENGTH: 992
<212> TYPE: DNA
<213> ORGANISM: Festuca arundinacea

<400> SEQUENCE: 34
gccgcgccga cctggaagaa gagggcagct tcgacgatgc cgtggctggt tgcgactacg      60
ccttcctcgt cgcagctccg gtgaacctaa aagcagagaa ccccgagaaa gacatggtgg     120
agcctgccgt cggaggaact ctgaacgcga tgaggtcgtg cgtgagagca gggacggtga     180
agcgtgttgt cctgacatcg tcggtggcgt ccgtctccgc ccgtcctctg ctgcaaggcg     240
acggccatgt cctggacgag gagtcctggt ccgacgtcga cttcctcaga gccaaagcga     300
ccggtcactg ggggtaccct gtgtcgaagg tgcttctgga gaaggcggcg tgcgcgttcg     360
cgcaggcgag cggcatcagc ctggtcaccg tgtgccccgt cgtcgtggtg ggcaaggcgc     420
cggcggtgca ggtccacacc agcgtccccg acgtcctctc cccgctatcc ggcgacgaag     480
ccaagatcca atcctgcag  cacatcgaac gggcgtccgg ctccatctcg ttggtccacg     540
tcgacgacct ctgccgcgcc gaggtgttcc tcgccgagga ggaggcggtg gcgtcggggc     600
ggtacatctg ctgcagcctc agcaccaccg ccggcgtgct cgcccgcttc ctctccgtca     660
agtacccgca gtacaaagtc aggaccgacc ggttcagtgg ttcccccgag aagccgagag     720
tgtgcatgtc gtcggcgaag ctcgtcgcgg aagggttcca gtacaagtac aagaccctcg     780
acgagatata cgatgatgtc gtcgagtatg gcagggcctt gggaatcctt ccataatgat     840
acgcgaacgc gacgaggcac tccatgtctc catctatctc tacaactcag gatcaagtga     900
tgcacttgca ataagcctat cctcttatct ctcgatatta atatattttc cttatcaaaa     960
aataaatcta acctcctcct aaaaaaaaaa aa                                   992

<210> SEQ ID NO 35
<211> LENGTH: 1279
<212> TYPE: DNA
<213> ORGANISM: Festuca arundinacea

<400> SEQUENCE: 35
gaaaagttag ctttccgaat aaaattatcc tagtgcgtgc agtgcgaacg acactttagc      60
tcgcgcgggc aggaacccac cgacgggcga tacgatggcg ccgcaggtg  atgggagcag     120 gaggaagacg gcgtgcgtca ccggagggaa cgggtacatc gcgtcggcgc tcgtgaagat     180
```

```
gctgctggag aagggatacg ccgtgaagac gaccgtcaga aacccagatg acatggagaa    240
gaactcccac ctcaaggatt tgcaagcgct gggccccttg gaggtgttcc gcgccgacct    300
gcaagaagag ggcagcttcg acgacgccgt tgccggctgc gactacgcct tcctcgtcgc    360
cgctccggtc aacctcaaag cagagaaccc cgagaaagac atggttgagc agccgttgg    420 aggaactctg aacgtgatga ggtcgtgcgt gagagcaggg acggtgaagc gtgttgtcct    480
gacatcgtcg gtggcgtccg tctccgcccg tcctctgctg caaggcgacg gccatgtcct    540
ggacgaggag tcctggtccg acgtcgactt cctcagagcc aaagcgaccg gtcactgggg    600
gtaccctgtg tcgaaggtgc ttctggagaa ggcggcgtgc gcgttcgcgc aggcgagcgg    660
catcagcctg gtcaccgtgt gccccgtcgt cgtggtgggc aaggcgccgg cggtgcaggt    720
ccacaccagc gtccccgacg tcctctcccc gctatccggc gacgaagcca agatccaaat    780
cctgcagcac atcgaacggg cgtccggctc catctcgttg gtccacgtcg acgacctctg    840
ccgcgccgag gtgttcctcg ccgaggagga ggcggtggcg tcgggcgggt acatctgctg    900
cagcctcagc accaccgccg gcgtgctcgc ccgcttcctc tccgtcaagt acccgcagta    960
caaagtcagg accgaccggt tcagtggttc ccccgagaag ccgagagtgt gcatgtcgtc   1020
ggcgaagctc gtcgcggaag ggttccagta caagtacaag accctcgacg agatatacga   1080
tgatgtcgtc gagtatggca gggccttggg aatccttcca taatgatacg cgaacgcgac   1140
gaggcactcc atgtctccat ctatctctac aactcaggat caagtgatgc acttgcaata   1200
agcctatcct cttatctctc gatattaata tatttttcctt atcaaaaaat aaatctaacc   1260
tcctcctaaa aaaaaaaaa                                                 1279

<210> SEQ ID NO 36
<211> LENGTH: 1206
<212> TYPE: DNA
<213> ORGANISM: Lolium perenne

<400> SEQUENCE: 36
ggtcgcggct ccaatggaca tgggtcact gaatcctgag gtaaacaaca atccagttca     60
tttcatgttt tgggtatgat tcatctcagt tactgtattc tatgtggtgg gactgcgaca    120
gagagatctt gtccaggcag gcgtccaagg aaccctgaac gtgatgaggt cgtgtgtgaa    180
agcggggaca gtgaagcgcg tgatcctgac gtcgtcggat tccgcggtgt gccagaggcc    240
gctggaaggc gacgggcacg tcctggacga gggctcctgg tcgacgtgc cgtacctgcg    300 agcagagcag ccggaggctt ggggtacgc ggtgtcgaag gtgcttatgg aagaggcggc    360
gggcaagttc gcggacgaga acggcctcgg cctcgtcagc gtgctgccca cctttaccct    420
aggcgcggca ccagtgtcgc aggccagaac cagcgtcccc gtcgtcctct ccttgttgtc    480
cggcgacgag gaacagctaa acctcctgga agccatgcac ttgattaccg aatccgtgtc    540
aataaaccac atcgacgacc tctgccgtgc ccaggtgttc ctcgccgaga cgaggcctc    600 atctgggagt acatctgca gtagccacga caccaccgtc gtgcagctcg cccgtctctt    660
ggcagacaag tacccacaat acaacgtgaa atcccaacgt tttgatgggt cccctgagaa    720
gccaagagtg tgcctctcgt ctcagaagct catcggagaa gggttcgtgt acaagtatga    780
tgacctaggt gccatcttgg acgacctcgt cgagtacggc aggaccacgg ggattcttcc    840
cttctgatat gctcctcctg ttctgccgat cgtatgtatg tgatcggaac gcaacagtgt    900
gtgctttctt cgtcaatggc aggaacaaca cgacagtgtg ctttcttcgt tcttagacag    960
```

```
gtctctatgg ctctgaagat tggggatctg atctcttgtt gttttttgcc ccgtagtgtg      1020
gtcttgacga caaggccaca ggcgggtttt cctaccaaat gcttcccttc ttcccagttc      1080
ccttttaatt gctgttaaag agacaaagta ctcctgtatt actacttgat tgatgactct     1140
ggtctctgga acaaagtggg aagatctaga tggaagagt aatattatca aattttaaaa      1200
aaaaaa                                                                 1206

<210> SEQ ID NO 37
<211> LENGTH: 1463
<212> TYPE: DNA
<213> ORGANISM: Lolium perenne

<400> SEQUENCE: 37
aaaaagtgcc tcgagtcaac tttccaattc ctgagcagag gtagtgactt gagtagttca       60
gttagcagcg ggcagcgatc gatggcgtcc gcagctggag gcaggaggaa gacggcctgc      120
gtcaccggag ggagcggcta catcgcctca gcgctcatca agacgctcct cgatcacggc      180
tacgccgtca agacgaccgt cagaaacccc gatgacctgg agaagacctc ccacctcaag      240
gacttacaag cgtttggccc cttggagatc ttccgtggag agctggatgt ggaaggcagc      300
ttcgacgact cggtttcagg ctgcgactat gtattcctcg tcgcggctcc gatggacatg      360
gggtcactga atcctgagag agatcttgtc caggcaggcg tccaaggaac cctgaacgtg      420
atgaggtcgt gtgtgaaagc ggggacagtg aagcgcgtga tcctgacgtc gtcggattcc      480
gcggtgtgcc agaggccgct ggaaggcgac gggcacgtcc tggacgaggg ctcctggtcg      540
gacgtgccgt acctgcgagc agagcagccg gaggcttggg ggtacgcggt gtcgaaggtg      600
cttatggaag aggcggcggg caagttcgcg gacgagaacg gcctcggcct cgtcagcgtg      660
ctgcccacct ttaccctagg cgcggcacca gtgtcgcagg ccagaaccag cgtccccgtc      720
gtcctctcct tgttgtccgg cgacgaggaa cagctaaacc tcctggaagc catgcacttg      780
attaccgaat ccgtgtcaat aaaccacatc gacgacctct gccgtgccca ggtgttcctc      840
gccgagaacg aggcctcatc tgggaggtac atctgcagta gccacgacac caccgtcgtg      900
cagctcgccc gtctcttggc agacaagtac ccacaataca acgtgaaatc ccaacgtttt      960
gatgggtccc ctgagaagcc aagagtgtgc ctctcgtctc agaagctcat cggagaaggg      1020
ttcgtgtaca agtatgatga cctaggtgcc atcttggacg acctcgtcga gtacggcagg      1080
accacgggga ttcttccctt ctgatatgct cctcctgttc tgccgatcgt atgtatgtga     1140
tcggaacgca acagtgtgtg ctttcttcgt caatggcagg aacaacacga cagtgtgctt      1200
tcttcgttct tagacaggtc tctatggctc tgaagattgg ggatctgatc tcttgttgtt      1260
ttttgccccg tagtgtggtc ttgacgacaa ggccacaggc gggttttcct accaaatgct      1320
tcccttcttc ccagttccct tttaattgct gttaaagaga caaagtactc ctgtattact      1380
acttgattga tgactctggt ctctggaaca agtgggaag atctagatgg aaagagtaat      1440
attatcaaat tttaaaaaaa aaa                                              1463

<210> SEQ ID NO 38
<211> LENGTH: 1606
<212> TYPE: DNA
<213> ORGANISM: Lolium perenne

<400> SEQUENCE: 38
gggcagccgc atccatctgg tttctcttcc gtggcagcag cagcgggaag aagttgtcga       60
agctgccgct gccgccgggg cctcgggggt ggcccgtgct gggcaacctg ccgcaggtgg      120
```

```
gcgccaagcc gcaccacacc atggccgctc tctcccaaca gttcggcccg ctcttccgcc      180
tccgcttcgg ggtcgccgag gtggtcgtcg ccgcgtccgc caaggtggcc tcccagttcc      240
tccgcgccca cgacgccaac ttcagcgacc gcccgcccaa ctccggcgcc gagcacgtcg      300
cctacaacta ccaggacctc gtcttcgccc cctacggctc ccgctggcgc gccctccgca      360
agctctgcgc gctccacctc ttctccgcta aggcctcga cgccctccgc gccgtccgcg      420
aggctgaggt tgcgctgatg gtgaagcagc tcaaggagtc ggcgcccgcg ggagtggtgg      480
tggggcagga ggcaaacgtg tgtgccacca cgcccctggc gagggcggcc gtggggaggc      540
gcgtgttcgg gggcagcgcc ggagagggcg cacgggagtt caaggacatg gtggtggagc      600
tcatgcagct gccgggggtg ttcaacatcg cgacttcgt tccggcgctc cgctggctcg      660
acccgcaggg cgttgtggcc aggatgaagc gcctgcaccg ccgctacgac gccatgatgg      720
acggcttcat cagcgagagg gaccagcgtc ataatcaggc tgctgctgac ggggaaagga      780
aggacctgct cagcgtcatg ctggggtaca tgcggccgga cggcggaggc ggcgaggagg      840 agggggatcag cttcaaccac accgacatca aagctcttct cctgaatctg ttcacagctg      900
ggaccgacac gacttctagc acggttgagt gggccctagc tgagctgata cgacacaagg      960
acgtcctcac ccaggcccaa cgcgagctcg atgacatcgt gggccaggat cgcctggtaa     1020
cggaatccga cctaccacac ctcaccttcc tcactgccgt catcaaggag acgttccggc     1080
tgcacccgtc gacgccgctc tcccttcctc gggtggccac tgaggattgt gaggtcgagg     1140
gctaccgcat ccccaagggt accaccttac ttgtcaatgt gtgggccatc gcacgtgacc     1200
cagcctcatg gggccccgat gcgttggagt tcaggcccgc ccgcttcctc gccggcgggc     1260
tgcacgagag tgtggacgtc aaggggagtg actacgagct tataccgttc ggggctggac     1320
gaaggatatg tgcaggcctc agttgggct tgaggatggt cactctcatg accgccacgc     1380
tggtgcatgc atttgactgg tccttagtcg atggccttac cccagaaaaa ctcgacatgg     1440
aggaggcata tggtctcacc cttcagcggg ccgctccgtt aatggttcgg cccattccta     1500
ggttgttatc gtcagcgtac accgtgtgac agatgatgat taatcacttt tgtcgaatgt     1560
atgcaatttg tgcaagtgag ctttacatat gttacaaaaa aaaaaa                    1606

<210> SEQ ID NO 39
<211> LENGTH: 1708
<212> TYPE: DNA
<213> ORGANISM: Lolium perenne

<400> SEQUENCE: 39
gaaagactgg agcacgagga cactgacatg gactgaagga gtagaaaaat tacacatatg       60
gatcatcggg acgtgcttgt gctgctctgc tccttggctg ccctggcagc cgcatccatc      120
tggtttctct tccgtggcag cagcagcgga aagaagttgt cgaagctgcc gctgccgccg      180
gggcctcggg ggtggcccgt gctgggcaac ctgccgcagg tgggcgccaa gccgcaccac      240
accatggccg ctctctccca acagttcggc ccgctcttcc gctccgcttc ggggtcgcc      300 gaggtggtcg tcgccgcgtc cgccaaggtg gcctcccagt tcctccgcgc ccacgacgcc      360
aacttcagcg accgcccgcc caactccggc gccgagcacg tcgcctacaa ctaccaggac      420
ctcgtcttcg ccccctacgg ctcccgctgg cgcgccctcc gcaagctctg cgcgctccac      480
ctcttctccg ctaaggccct cgacgccctc cgcgccgtcc gcgaggctga ggttgcgctg      540
atggtgaagc agctcaagga gtcggcgccc gcggagtgg tggtggggca ggaggcaaac      600
```

| | |
|---|---:|
| gtgtgtgcca ccaacgccct ggcgagggcg ccgtgggga ggcgcgtgtt cggggggcagc | 660 |
| gccggagagg gcgcacggga gttcaaggac atggtggtgg agctcatgca gcttgccggg | 720 |
| gtgttcaaca tcggcgactt cgttccggcg ctccgctggc tcgacccgca gggcgttgtg | 780 |
| gccaggatga agcgcctgca ccgccgctac gacgccatga tggacggctt catcagcgag | 840 |
| agggaccagc gtcataatca ggctgctgct gacgggaaa ggaaggacct gctcagcgtc | 900 |
| atgctggggt acatgcggcc ggacggcgga ggcggcgagg aggagggat cagcttcaac | 960 |
| cacaccgaca tcaaagctct tctcctgaat ctgttcacag ctgggaccga cacgacttct | 1020 |
| agcacggttg agtgggccct agctgagctg atacgacaca aggacgtcct cacccaggcc | 1080 |
| caacgcgagc tcgatgacat cgtgggccag gatcgcctgg taacggaatc cgacctacca | 1140 |
| cacctcacct tcctcactgc cgtcatcaag gagacgttcc ggctgcaccc gtcgacgccg | 1200 |
| ctctcccttc ctcgggtggc cactgaggat tgtgaggtcg agggctaccg catccccaag | 1260 |
| ggtaccacct tacttgtcaa tgtgtgggcc atcgcacgtg acccagcctc atggggcccc | 1320 |
| gatgcgttgg agttcaggcc cgcccgcttc ctcgccggcg ggctgcacga gagtgtggac | 1380 |
| gtcaagggga gtgactacga gcttataccg ttcggggctg gacgaaggat atgtgcaggc | 1440 |
| ctcagttggg gcttgaggat ggtcactctc atgaccgcca cgctggtgca tgcatttgac | 1500 |
| tggtccttag tcgatggcct tacccccagaa aaactcgaca tggaggaggc atatggtctc | 1560 |
| acccttcagc gggccgctcc gttaatggtt cggcccattc ctaggttgtt atcgtcagcg | 1620 |
| tacaccgtgt gacagatgat gattaatcac ttttgtcgaa tgtatgcaat ttgtgcaagt | 1680 |
| gagctttaca tatgttacaa aaaaaaaa | 1708 |

<210> SEQ ID NO 40
<211> LENGTH: 1747
<212> TYPE: DNA
<213> ORGANISM: Festuca arundinacea

<400> SEQUENCE: 40

| | |
|---|---:|
| ggcgtagcga actggccggc atggacatcc cactctcact gctgctctcc actctggcca | 60 |
| tctctgcgac catatgctat gtcttcttcc gagccggcaa ggggcaccgt gcgccgctgc | 120 |
| cgctgccgcc tggcccgagg ggctggccag tgctggggaa cctcccgcag ctgggcggca | 180 |
| agacacacca gaccctgcat gagatgacca aggtgtacgg gcccgtgctc cggctccggt | 240 |
| tcggcagctc cgtcgtggtg gtcgccgggt cagccgccgt ggccgagcag ttcctccgca | 300 |
| cccacgacgc caagttcagc agccggccgc ccaactccgg cggcgaacac atggcgtaca | 360 |
| actacaggga cgtggttttc gcgccctacg gcccccggtg gcgcgcgatg cgcaaggtgt | 420 |
| gcgccgtcaa catcttctcg gcccgcgcgc tcgacgatct ccgcggtttc agggagcggg | 480 |
| aggccgcgct catggtgcgg tccctcgcgg atgctgccaa agccggggtg gcggtggcgg | 540 |
| tcggcaaggc ggcgaacgtg tgcacgacca acggcctgtc tcgggcagcg gtggggctcc | 600 |
| gggtgttcgg aagcgatggc gccagagact tcaaggagat cgtgctggag gtgatggagg | 660 |
| tgggcggggt tcttaacgtc ggggactttg tgccggcgct ccgtggctc gacccgcagg | 720 |
| gtgtcgtcgc gaggttgaag aagctgcacc gccggttcga cgacatgatg aatgggataa | 780 |
| tcgccgagag gaggaccgga accaagacgc ccgtggtgga ggaaggtaag ggagacctgc | 840 |
| tgggcttgct gcttgcgatg gtgcaggaag acaagtcgct caccggcagc gaggaggaca | 900 |
| agatcaccga cactgacgtc aaggcgctta tactgaactt gtttgtggcg ggaacagaga | 960 |
| caacgtcgag tatagtggag tgggcagtag cggagctgat caggcaccct gacatcctga | 1020 |

```
agcaggccca ggaggagcta gatgccgtcg tgggccgtga caggcttgtc tcggagtctg    1080
acctgccacg actcacgttt ttcaatgcca tcatcaagga gacgttccgg ctgcatccgt    1140
cgacgccgct ctcgcttccc cggatggcct ccgaggagtg cgaggtcgcc ggctaccaca    1200
tcccaagggg cactgagcta ctggtcaatg tgtggggcat cgcccgcgat ccggccctat    1260
ggcccgaccc gctggagtac cagcctgccc ggttcctccc aggagggtcg catgagaatg    1320
tcgacctcaa gggaggtgac tttgggctga taccgtttgg ggcgggccgg aggatatgtg    1380
cgggcctaag ctgggcttg cggatggtta ccattacaac cgctaccctg gtgcactcgt    1440
tcgactggga gctgccggcg ggccagacgc cggataagtt gaacatggag gaggccttta    1500
gtctgctgct gcagcgagcc gtgccattga tggtccaccc agtgcccagg ttgcttccat    1560
ccgcatacga aatttcgtag aaaatcgctg cgccagtgat tgtcctgatt gatgatgtat    1620
ggagggcaaa gctccaatta taccatgcac tactatcgat gggttatctc accgtttgaa    1680
ctaaagtagt ttacaatgca tattgttccg agaagttcaa taagaagaa taacatgaaa     1740 aaaaaaa                                                              1747

<210> SEQ ID NO 41
<211> LENGTH: 1763
<212> TYPE: DNA
<213> ORGANISM: Festuca arundinacea

<400> SEQUENCE: 41
gaacagttgc cgtgcatgcg tagcgagctg gctggcatgg acatcccact cccactgctg     60
ctctccactc tggccatctc tgcgaccata tgctatgtct tcttccgagc cggcaagggg    120
caccgtgcgc cgctgccgct gccgcctggc ccgaggggct ggccagtgct ggggaacctc    180
ccgcagctgg gcggcaagac acaccagacc ctgcatgaga tgaccaaggt gtacgggccc    240
gtgctccggt tccggttcgg cagctccgtc gtggtggtcg ccgggtcagc cgccgtggcc    300
gagcagttcc tccgcaccca cgacgccaag ttcagcagcc ggccgcccaa ctccggcggc    360
gaacacatgc cgtacaacta cagggacgtg gttttcgcgc cctacggccc ccggtggcgc    420
gcgatgcgca aggtgtgcgc cgtcaacatc ttctcggccc gcgcgctcga cgatctccgc    480
ggtttcaggg agcgggaggc cgcgctcatg gtgcggtccc tcgcggatgc tgccaaagcc    540
ggggtggcgg tggcggtcgg caaggcggcg aacgtgtgca cgaccaacgg cctgtctcgg    600
gcagcggtgg ggctccgggt gttcggaagc gatggcgcca gagacttcaa ggagatcgtg    660
ctggaggtga tggaggtggg cggggttctt aacgtcgggg actttgtgcc ggcgctccgg    720
tggctcgacc cgcagggtgt cgtcgcgagg ttgaagaagc tgcaccgccg gttcgacgac    780
atgatgaatg ggataatcgc cgagaggagg accggaacca agacggccgt ggtggaggaa    840
ggtaagggag acctgctggg cttgctgctt cgcgatggtg caggaagacaa gtcgctcacc    900 ggcagcgagg aggacaagat caccgacact gacgtcaagg cgcttatact gaacttgttt    960
gtggcgggaa cagagacaac gtcgagtata tggagtgggg cagtagcgga gctgatcagg   1020
caccctgaca tcctgaagca ggcccaggag gagctagatg ccgtcgtggg ccgtgacagg   1080
cttgtctcgg agtctgacct gccacgactc acgtttttca atgccatcat caaggagacg   1140
ttccggctgc atccgtcgac gccgctctcg cttccccgga tggcctccga ggagtgcgag   1200 gtcgccgget accacatccc aaggggcact gagctactgg tcaatgtgtg gggcatcgcc   1260
cgcgatccgg ccctatggcc cgacccgctg gagtaccagc ctgccggtt cctcccagga   1320
```

-continued

```
gggtcgcatg agaatgtcga cctcaaggga ggtgactttg ggctgatacc gtttggggcg   1380
ggccggagga tatgtgcggg cctaagctgg ggcttgcgga tggttaccat tacaaccgct   1440
accctggtgc actcgttcga ctgggagctg ccggcgggcc agacgccgga taagttgaac   1500
atggaggagg cctttagtct gctgctgcag cgagccgtgc cattgatggt ccacccagtg   1560
cccaggttgc ttccatccgc atacgaaatt tcgtagaaaa tcgctgcgcc agtgattgtc   1620
ctgattgatg atgtatggag ggcaaagctc caattatacc atgcactact atcgatgggt   1680
tatctcaccg tttgaactaa agtagtttac aatgcatatt gttccgagaa gttcaataag   1740
aaagaataac atgaaaaaaa aaa                                            1763
```

<210> SEQ ID NO 42
<211> LENGTH: 1673
<212> TYPE: DNA
<213> ORGANISM: Festuca arundinacea

<400> SEQUENCE: 42

```
gggacatccc actcccactg ctgctctcca ctctggccat ctctgcgacc atatgctatg     60
tcttcttccg agccggcaag acacaccaga ccctgcatga gatgaccaag gtgtacgggc    120
ccgtgctccg gctccggttc ggcagctccg tggtggtagt ggccggatca gccgccgtgg    180
ccgagcagtt cctgcgcacc cacgacgcca agttcagcag ccggccgccc aactctggcg    240
gcgagcacat ggcttacaac taccaggaca tcgtgttcgc gccctacggg ccccggtggc    300
gcgccatgcg caaggtgtgc gccgtcaaca tcttctcggc ccgcgcgctc gacgatctcc    360
gcgggttcag ggagcgggag gccgcactca tggtgcggtc cctcgcagac gctgccaaag    420
ccggggcggc ggtggcggtc ggcaaggcgg caaacgtgtg cacgaccaac ggcctgtctc    480
gggcggcggt ggggctccgg gtgttcggaa gcgatggcac cagagacttc aaggagatcg    540
tgctggaggt gatggaggtg ggtgggttc ttaatgtcgg ggattttgtg ccggcgctcc    600
ggtggctcga cccacagggg gtcgtcgcga ggatgaagaa gctgcaccgc cggttcgacg    660
acataatgaa cgggataata gccgagagga ggaccggagc caagacgcc gtcgtggagg    720 aaggtaaggg agacctgctg ggcttgctac ttgcgatggt gcaggaagac aagtcgctca    780
ccggcagcga ggaggacaaa atcaccgaca ctgacgtcaa ggcgcttata ctgaacttgt    840
ttgtggcggg aacagagaca acgtcgagca tagtggagtg ggcagtagcg gagctgatca    900
ggcaccctga catcctgaag caggcccagg aggagctaga taccgtcgtg ggccgtgaca    960
ggatcgtctc ggagtcggac ctgccacgac tcaccttttt taatgccatc atcaaggaga   1020
cgttccggct gcatccgtcg acgccgctct cgcttccccg gatggcctcc gaggactgtg   1080
aggtcgctgg ctaccacatc ccaagggca ccgagctact ggtcaatgtg tggggcatcg    1140
cccgtgaccc atccctatgg cctgacccgc tggagtaccg gccgcccgg ttcctcccag    1200 gagggtcgca tgagaatgtc gacctcaagg gaggtgactt gggctgata ccgtttgggg    1260 cgggccggag gatatgtgcg ggcctaagct ggggcttgcg gatggtcacc gttacaaccg    1320
ctaccctggt gcactcgttc gactgggagc tgccggcggg ccagacgctg ataagttga   1380 acatggagga ggcctttagc ctgctgctgc agcgagccat gccattgatg gtccacccgg    1440
tgcccaggtt gcttccatcg gcatacgaaa tttcgtagaa aattgctgcg ccagtgcttg    1500
tcatgattga tgatgtatgg agggcaagct ccaattatac catgcactac tatcgatggg    1560
ttgtctcccc gtttgaacta agtagtttta caatgcatat tgttccgaga agttcaataa    1620
gaaagaataa catgaaaaaa tacaatctgt tggacggcca aaaaaaaaa aaa            1673
```

<210> SEQ ID NO 43
<211> LENGTH: 1714
<212> TYPE: DNA
<213> ORGANISM: Festuca arundinacea

<400> SEQUENCE: 43

| | | | | | |
|---|---|---|---|---|---|
| gaaagaacag | ttgccgtgca | tgcgtaacga | gctggctggc | atggacatcc | cactcccact | 60 |
| gctgctctcc | actctggcca | tctctgcgac | catatgctat | gtcttcttcc | gagccggcaa | 120 |
| gacacaccag | accctgcatg | agatgaccaa | ggtgtacggg | cccgtgctcc | ggctccggtt | 180 |
| cggcagctcc | gtggtggtag | tggccggatc | agccgccgtg | gccgagcagt | tcctgcgcac | 240 |
| ccacgacgcc | aagttcagca | gccggccgcc | caactctggc | ggcgagcaca | tggcttacaa | 300 |
| ctaccaggac | atcgtgttcg | cgccctacgg | gccccgtgg | cgcgccatgc | gcaaggtgtg | 360 |
| cgccgtcaac | atcttctcgg | cccgcgcgct | cgacgatctc | cgcgggttca | gggagcggga | 420 |
| ggccgcactc | atggtgcggt | ccctcgcaga | cgctgccaaa | gccggggcgg | cggtggcggt | 480 |
| cggcaaggcg | gcaaacgtgt | gcacgaccaa | cggcctgtct | cgggcggcgg | tggggctccg | 540 |
| ggtgttcgga | agcgatggca | ccagagactt | caaggagatc | gtgctggagg | tgatggaggt | 600 |
| gggtgggggtt | cttaatgtcg | gggattttgt | gccggcgctc | cggtggctcg | acccacaggg | 660 |
| ggtcgtcgcg | aggatgaaga | agctgcaccg | ccggttcgac | gacataatga | acgggataat | 720 |
| agccgagagg | aggaccggag | ccaagacggc | cgtcgtggag | gaaggtaagg | gagacctgct | 780 |
| gggcttgcta | cttgcgatgg | tgcaggaaga | caagtcgctc | accggcagcg | aggaggacaa | 840 |
| aatcaccgac | actgacgtca | aggcgcttat | actgaacttg | tttgtggcgg | gaacagagac | 900 |
| aacgtcgagc | atagtggagt | gggcagtagc | ggagctgatc | aggcaccctg | acatcctgaa | 960 |
| gcaggcccag | gaggagctag | ataccgtcgt | gggccgtgac | aggatcgtct | cggagtcgga | 1020 |
| cctgccacga | ctcacctttt | ttaatgccat | catcaaggag | acgttccggc | tgcatccgtc | 1080 |
| gacgccgctc | tcgcttcccc | ggatggcctc | cgaggactgt | gaggtcgctg | gctaccacat | 1140 |
| cccaagggc | accgagctac | tggtcaatgt | gtggggcatc | gcccgtgacc | catccctatg | 1200 |
| gcctgacccg | ctggagtacc | ggccgcccg | gttcctccca | ggagggtcgc | atgagaatgt | 1260 |
| cgacctcaag | ggaggtgact | ttgggctgat | accgtttggg | gcgggccgga | ggatatgtgc | 1320 |
| gggcctaagc | tggggcttgc | ggatggtcac | cgttacaacc | gctaccctgg | tgcactcgtt | 1380 |
| cgactgggag | ctgccggcgg | gccagacgct | ggataagttg | aacatggagg | aggcctttag | 1440 |
| cctgctgctg | cagcgagcca | tgccattgat | ggtccacccg | gtgcccaggt | tgcttccatc | 1500 |
| ggcatacgaa | atttcgtaga | aaattgctgc | gccagtgctt | gtcatgattg | atgatgtatg | 1560 |
| gagggcaagc | tccaattata | ccatgcacta | ctatcgatgg | gttgtctccc | cgtttgaact | 1620 |
| aaagtagttt | acaatgcata | ttgttccgag | aagttcaata | agaaagaata | acatggaaaa | 1680 |
| atacaatctg | ttggacggcc | aaaaaaaaaa | aaaa | | | 1714 |

<210> SEQ ID NO 44
<211> LENGTH: 1449
<212> TYPE: DNA
<213> ORGANISM: Lolium perenne

<400> SEQUENCE: 44

| | | | | | |
|---|---|---|---|---|---|
| gacaaacacc | ttaactagat | cagctcgatc | agcttccagc | ttcctctcct | agctagctcg | 60 |
| ctcgctctta | tcgccggtga | actgtccccc | ggccccggta | ctaagctgcg | cagggcatgg | 120 |

-continued

```
caatggcgga ctgcatgcag gagtggccgg agcccgtggt gcgcgtgcag gcggtggccg    180
agagcggtct ggccgccatc cccgactgct acgtcaagcc gccgcgcgac cgcccagcgg    240
cgcagcacct ggctaccgcc gcttctgcag atggcgacgt cctccatgag cctctggaca    300
ccagcattcc ggtgatcgac cttggcgagc tcgtcgcggc gacagccgac gagggccgca    360
tgcgccagat catggaggcc gtggcggcg cgtgccggga gtggggttc ttccaggtgg      420 tgaaccacgg ggtggcgccg gagctgatgc acgcggcgcg ggaggcgtgg cgcggattct    480
tccggctgcc gatcacggcg aagcagcagt acgccaacct gccgcggacg tacgaggggt    540
acggcagccg agtcggcgtc cagaagggcg gccccctcga ctggggcgac tactatttcc    600
tccacctcgc gccggacgcc ggcaagagcc cggacaagta ctggcccacc aatcccgcca    660
tctgcaagga tgtgtcggag gagtacggtc gtgaggtgat ccggttgtgc gagctgctga    720
tgaaggtgat gtcggcgagc ctgggcctag aggcgacgag gttccaggag gcgttcggcg    780
gatcagagtg cggcgtgtgc cttcgcgcca actactaccc gcggtgcccg cagccggatc    840
tgacgctggg cctgtcggcg cactctgacc cgggcgtcct caccgtgctc ctcgctgacg    900
agcacgtccg cggcctccag gtccgccgcg ccgatggcga gtgggtcacc gtgcagcccg    960
cacggcacga cgccttcatc gtcaacgtcg gcgaccagat ccagatactg agcaactcca   1020
tgtacaagag cgtggagcac cgggtgatgg tgaacgccaa ggaggagcgc atctccctgg   1080
cgctcttcta caacccgcga ggcgacgtcc cgatcgcgcc ggcgccggag acggtgacgc   1140
cggagcggcc ggcgctctac ccgtccatga ccttcgacga gtacagggcc tacatcagga   1200
agtacggccc caggggcaag gcgcaggtcg agggtgccaa gcagggacaa ggtagctagt   1260
tagctggatc cttggagcta gtatctgatc catgggaata attaagccgt ccaggttgta   1320
ccggccaatc tatggattcc tgcatgcatg tacgtgtggc taatgtagca caagctcgcc   1380
cttgtacccg aactgcatat atgctaattg tattggcatc tcgcttagcc gtgccgtcca   1440
aaaaaaaaa                                                          1449
```

<210> SEQ ID NO 45
<211> LENGTH: 473
<212> TYPE: PRT
<213> ORGANISM: Lolium perenne

<400> SEQUENCE: 45

```
Met Ala Ala Ala Val Ala Pro Asp Ala Lys Ile Glu Lys Phe Arg
 1               5                  10                  15

Asp Ala Val Ala Lys Leu Gly Glu Ile Ser Glu Asn Glu Lys Ala Gly
             20                  25                  30

Cys Ile Ser Leu Val Ser Arg Tyr Leu Ser Gly Glu Ala Glu Gln Ile
         35                  40                  45

Glu Trp Ser Lys Ile Gln Thr Pro Thr Asp Glu Val Val Pro Tyr
     50                  55                  60

Asp Thr Leu Ala Pro Ala Pro Glu Asp Leu Asp Ala Met Lys Ala Leu
 65                  70                  75                  80

Leu Asp Lys Leu Val Leu Lys Leu Asn Gly Gly Leu Gly Thr Thr
                 85                  90                  95

Met Gly Cys Thr Gly Pro Lys Ser Val Ile Glu Val Arg Asn Gly Phe
            100                 105                 110

Thr Phe Leu Asp Leu Ile Val Ile Gln Ile Glu Ser Leu Asn Lys Lys
        115                 120                 125

Tyr Gly Cys Asp Val Pro Leu Leu Leu Met Asn Ser Phe Asn Thr His
```

```
                    130                 135                 140
Asp Asp Thr Gln Lys Ile Val Glu Lys Tyr Ser Asn Ser Asn Ile Asn
145                 150                 155                 160

Ile His Thr Phe Asn Gln Ser Gln Tyr Pro Arg Ile Val Thr Glu Asp
                165                 170                 175

Phe Leu Pro Leu Pro Ser Lys Gly Gln Ser Gly Lys Asp Gly Trp Tyr
                180                 185                 190

Pro Pro Gly His Gly Asp Val Phe Pro Ser Leu Asn Asn Ser Gly Lys
                195                 200                 205

Leu Asp Thr Leu Leu Ser Gln Gly Lys Glu Tyr Val Phe Val Ala Asn
210                 215                 220

Ser Asp Asn Leu Gly Ala Ile Val Asp Ile Lys Ile Leu Asn His Leu
225                 230                 235                 240

Ile Asn Asn Lys Asn Glu Tyr Cys Met Glu Val Thr Pro Lys Thr Leu
                245                 250                 255

Ala Asp Val Lys Gly Gly Thr Leu Ile Ser Tyr Glu Gly Arg Val Gln
                260                 265                 270

Leu Leu Glu Ile Ala Gln Val Pro Asp Glu His Val Asn Glu Phe Lys
                275                 280                 285

Ser Ile Glu Lys Phe Lys Ile Phe Asn Thr Asn Asn Leu Trp Val Asn
290                 295                 300

Leu Lys Ala Ile Lys Arg Leu Val Glu Ala Asp Ala Leu Lys Met Glu
305                 310                 315                 320

Ile Ile Pro Asn Pro Lys Glu Val Asp Gly Val Lys Val Leu Gln Leu
                325                 330                 335

Glu Thr Ala Ala Gly Ala Ala Ile Arg Phe Phe Asp Asn Ala Ile Gly
                340                 345                 350

Ile Asn Gly Pro Arg Ser Arg Phe Leu Pro Val Lys Ala Thr Ser Asp
                355                 360                 365

Leu Leu Leu Val Gln Ser Asp Leu Tyr Thr Leu Val Asp Gly Tyr Val
                370                 375                 380

Ile Arg Asn Pro Ala Arg Val Lys Pro Ser Asn Pro Ser Ile Glu Leu
385                 390                 395                 400

Gly Pro Glu Phe Lys Lys Val Ala Ser Phe Leu Ala Arg Phe Lys Ser
                405                 410                 415

Ile Pro Ser Ile Val Glu Leu Asp Ser Leu Lys Val Ser Gly Asp Val
                420                 425                 430

Ser Phe Gly Ser Gly Ile Val Leu Lys Gly Asn Val Thr Ile Ala Ala
                435                 440                 445

Lys Ser Gly Val Lys Leu Glu Ile Pro Asp Gly Ala Val Leu Glu Asn
450                 455                 460

Lys Asp Ile Asn Gly Pro Glu Asp Leu
465                 470

<210> SEQ ID NO 46
<211> LENGTH: 471
<212> TYPE: PRT
<213> ORGANISM: Festuca arundinacea

<400> SEQUENCE: 46

Met Ala Ala Val Ala Asp Ala Lys Ile Glu Lys Phe Arg Asp Ala
  1               5                  10                  15

Val Ala Lys Leu Asp Glu Ile Ser Glu Asn Glu Lys Ala Gly Cys Ile
                 20                  25                  30
```

```
Ser Leu Val Ser Arg Tyr Leu Ser Gly Glu Ala Glu Gln Ile Glu Trp
            35                  40                  45

Ser Lys Ile Gln Thr Pro Thr Asp Glu Val Val Pro Tyr Asp Thr
 50                  55                  60

Leu Ala Pro Ala Pro Gln Asp Leu Asp Ala Met Lys Ala Leu Leu Asp
 65                  70                  75                  80

Lys Leu Val Val Leu Lys Leu Asn Gly Leu Gly Thr Thr Met Gly
                85                  90                  95

Cys Thr Gly Pro Lys Ser Val Ile Glu Val Arg Asn Gly Phe Thr Phe
                100                 105                 110

Leu Asp Leu Ile Val Ile Gln Ile Glu Ser Leu Asn Lys Lys Tyr Gly
            115                 120                 125

Cys Asp Val Pro Leu Leu Met Asn Ser Phe Asn Thr His Asp Asp
            130                 135                 140

Thr Gln Lys Ile Val Glu Lys Tyr Ser Asn Ser Asn Ile Asn Ile His
145                 150                 155                 160

Thr Phe Asn Gln Ser Gln Tyr Pro Arg Ile Val Thr Glu Asp Phe Leu
                165                 170                 175

Pro Leu Pro Ser Lys Gly Lys Ser Gly Lys Asp Gly Trp Tyr Pro Pro
            180                 185                 190

Gly His Gly Asp Val Phe Pro Ser Leu Asn Asn Ser Gly Lys Leu Asp
            195                 200                 205

Thr Leu Leu Ser Gln Gly Lys Glu Tyr Val Phe Val Ala Asn Ser Asp
        210                 215                 220

Asn Leu Gly Ala Ile Val Asp Ile Lys Ile Leu Asn His Leu Ile Asn
225                 230                 235                 240

Asn Gln Asn Glu Tyr Cys Met Glu Val Thr Pro Lys Thr Leu Ala Asp
                245                 250                 255

Val Lys Gly Gly Thr Leu Ile Ser Tyr Glu Gly Arg Val Gln Leu Leu
            260                 265                 270

Glu Ile Ala Gln Val Pro Asp Glu His Val Asn Glu Phe Lys Ser Ile
        275                 280                 285

Glu Lys Phe Lys Ile Phe Asn Thr Asn Asn Leu Trp Val Asn Leu Lys
        290                 295                 300

Ala Ile Lys Arg Leu Val Glu Ala Asp Ala Leu Lys Met Glu Ile Ile
305                 310                 315                 320

Pro Asn Pro Lys Glu Val Asp Gly Val Lys Val Leu Gln Leu Glu Thr
                325                 330                 335

Ala Ala Gly Ala Ala Ile Arg Phe Phe Glu Lys Ala Ile Gly Ile Asn
            340                 345                 350

Gly Pro Arg Ser Arg Phe Leu Pro Val Lys Ala Thr Ser Asp Leu Leu
        355                 360                 365

Leu Val Gln Ser Asp Leu Tyr Thr Leu Val Asp Gly Tyr Val Ile Arg
    370                 375                 380

Asn Pro Ala Arg Val Lys Pro Ser Asn Pro Ser Ile Glu Leu Gly Pro
385                 390                 395                 400

Glu Phe Lys Lys Val Ala Ser Phe Leu Ala Arg Phe Lys Ser Ile Pro
                405                 410                 415

Ser Ile Val Glu Leu Asp Ser Leu Lys Val Ser Gly Asp Val Thr Phe
            420                 425                 430

Gly Ser Gly Val Val Leu Lys Gly Asn Val Thr Ile Ala Ala Lys Ser
        435                 440                 445

Gly Val Lys Leu Glu Ile Pro Asp Gly Ala Val Leu Glu Asn Lys Asp
```

```
                    450                 455                 460
Ile Asn Gly Pro Glu Asp Leu
465                 470

<210> SEQ ID NO 47
<211> LENGTH: 535
<212> TYPE: PRT
<213> ORGANISM: Lolium perenne

<400> SEQUENCE: 47

Cys Leu Arg Arg Arg Thr Tyr Ser Asn Ser Gly Asp Thr His Ala Asp
 1               5                  10                  15

Pro Asn Gly Pro Val Tyr Tyr Gly Gly Trp Tyr His Leu Phe Tyr Gln
                20                  25                  30

His Asn Pro Tyr Gly Asp Ser Trp Gly Asn Val Ser Trp Gly His Ala
            35                  40                  45

Val Ser Lys Asp Leu Val Asn Trp Arg His Leu Pro Val Ala Leu Val
 50                  55                  60

Pro Asp Gln Trp Tyr Asp Ile Asn Gly Val Leu Thr Gly Ser Ile Thr
 65                  70                  75                  80

Val Leu Pro Asp Gly Arg Val Ile Leu Leu Tyr Thr Gly Asn Thr Asp
                85                  90                  95

Thr Phe Ser Gln Val Gln Cys Leu Ala Val Pro Ala Asp Pro Ser Asp
            100                 105                 110

Pro Leu Leu Arg Ser Trp Ile Lys His Pro Ala Asn Pro Ile Leu Phe
        115                 120                 125

Pro Pro Pro Gly Ile Gly Leu Lys Asp Phe Arg Asp Pro Leu Thr Ala
    130                 135                 140

Trp Phe Glu His Ser Asp Asn Thr Trp Arg Thr Ile Ile Gly Ser Lys
145                 150                 155                 160

Asp Asp Asp Gly His Ala Gly Ile Val Leu Ser Tyr Lys Thr Thr Asp
                165                 170                 175

Phe Val Asn Tyr Glu Leu Met Pro Gly Asn Met His Arg Gly Pro Asp
            180                 185                 190

Gly Thr Gly Met Tyr Glu Cys Leu Asp Ile Tyr Pro Val Gly Gly Asn
        195                 200                 205

Ser Ser Glu Met Leu Gly Gly Asp Ser Ser Pro Glu Val Leu Phe Val
    210                 215                 220

Leu Lys Glu Ser Ala Asn Asp Glu Trp His Asp Tyr Tyr Ala Leu Gly
225                 230                 235                 240

Trp Phe Asp Ala Thr Ala Asn Thr Trp Thr Pro Gln Asp Pro Glu Ala
                245                 250                 255

Asp Leu Gly Ile Gly Leu Arg Tyr Asp Trp Gly Lys Tyr Tyr Ala Ser
            260                 265                 270

Lys Ser Phe Tyr Asp Pro Ile Lys Asn Arg Arg Val Val Trp Ala Phe
        275                 280                 285

Val Gly Glu Thr Asp Ser Glu Gln Ala Asp Lys Ala Lys Gly Trp Ala
    290                 295                 300

Ser Leu Met Ser Ile Pro Arg Met Val Glu Leu Asp Lys Lys Thr Arg
305                 310                 315                 320

Thr Asn Leu Ile Gln Trp Pro Val Glu Glu Ile Glu Thr Leu Arg Arg
                325                 330                 335

Asn Val Thr Asp Leu Gly Gly Ile Thr Val Glu Ala Gly Ser Val Ile
            340                 345                 350
```

-continued

```
His Leu Pro Leu Gln Gln Gly Gly Gln Leu Asp Ile Glu Ala Ser Phe
        355                 360                 365

Arg Leu Asn Ser Ser Asp Ile Asp Ala Leu Asn Glu Ala Asp Val Gly
    370                 375                 380

Phe Asn Cys Ser Ser Ala Gly Ala Val Arg Gly Ala Leu Gly
385                 390                 395                 400

Pro Phe Gly Leu Leu Val Phe Ala Asp Gly Arg His Glu Gln Thr Ala
                405                 410                 415

Ala Tyr Phe Tyr Val Ser Lys Gly Leu Asp Gly Ser Leu Leu Thr His
            420                 425                 430

Tyr Cys His Asp Glu Ser Arg Ser Thr Arg Ala Lys Asp Val Val Ser
        435                 440                 445

Arg Val Val Gly Gly Thr Val Pro Val Leu Asp Gly Glu Thr Phe Ser
    450                 455                 460

Val Arg Val Leu Val Asp His Ser Ile Val Gln Ser Phe Val Met Gly
465                 470                 475                 480

Gly Arg Thr Thr Val Thr Ser Arg Ala Tyr Pro Thr Glu Ala Ile Tyr
                485                 490                 495

Ala Ala Ala Gly Val Tyr Leu Phe Asn Asn Ala Thr Ser Ala Thr Ile
            500                 505                 510

Thr Ala Glu Gly Leu Val Val Tyr Glu Met Ala Ser Ala Glu Ser Gln
        515                 520                 525

Ala Phe Leu Ala Asp Asp Met
    530                 535

<210> SEQ ID NO 48
<211> LENGTH: 637
<212> TYPE: PRT
<213> ORGANISM: Lolium perenne

<400> SEQUENCE: 48

Met Glu Ser Ser Ala Val Val Pro Gly Thr Thr Ala Pro Leu Leu
  1               5                  10                  15

Pro Tyr Asp Ser Arg Glu Asn Gln Ser Ser Gly Gly Gly Val Trp Trp
                20                  25                  30

Arg Ala Cys Ala Ala Ser Ala Val Leu Leu Val Val Gly Phe
            35                  40                  45

Phe Ala Gly Gly Arg Val Asp Leu Gly Gln Ala Gly Glu Val Ser Ala
     50                  55                  60

Thr Ser Ser Val Pro Ala Ala Met Met Glu Ile Pro Arg Ser Arg Gly
 65                  70                  75                  80

Lys Asn Phe Gly Val Ser Glu Lys Ala Asp Gly Gly Phe Pro Trp Ser
                 85                  90                  95

Asn Ala Met Leu Gln Trp Gln His Thr Gly Phe His Phe Gln Pro Leu
                100                 105                 110

Lys His Tyr Met Asn Asp Pro Asn Gly Pro Val Tyr Gly Gly Trp
            115                 120                 125

Tyr His Leu Phe Tyr Gln His Asn Pro Tyr Gly Asp Ser Trp Gly Asn
        130                 135                 140

Val Ser Trp Gly His Ala Val Ser Lys Asp Leu Val Asn Trp Arg His
145                 150                 155                 160

Leu Pro Val Ala Leu Val Pro Asp Gln Trp Tyr Asp Ile Asn Gly Val
                165                 170                 175

Leu Thr Gly Ser Ile Thr Val Leu Pro Asp Gly Arg Val Ile Leu Leu
            180                 185                 190
```

```
Tyr Thr Gly Asn Thr Asp Thr Phe Ser Gln Val Gln Cys Leu Ala Val
            195                 200                 205

Pro Ala Asp Pro Ser Asp Pro Leu Leu Arg Ser Trp Ile Lys His Pro
210                 215                 220

Ala Asn Pro Ile Leu Phe Pro Pro Gly Ile Gly Leu Lys Asp Phe
225                 230                 235                 240

Arg Asp Pro Leu Thr Ala Trp Phe Glu His Ser Asp Asn Thr Trp Arg
            245                 250                 255

Thr Ile Ile Gly Ser Lys Asp Asp Gly His Ala Gly Ile Val Leu
            260                 265                 270

Ser Tyr Lys Thr Thr Asp Phe Val Asn Tyr Glu Leu Met Pro Gly Asn
            275                 280                 285

Met His Arg Gly Pro Asp Gly Thr Gly Met Tyr Glu Cys Leu Asp Ile
            290                 295                 300

Tyr Pro Val Gly Gly Asn Ser Ser Glu Met Leu Gly Gly Asp Ser Ser
305                 310                 315                 320

Pro Glu Val Leu Phe Val Leu Lys Glu Ser Ala Asn Asp Glu Trp His
            325                 330                 335

Asp Tyr Tyr Ala Leu Gly Trp Phe Asp Ala Thr Ala Asn Thr Trp Thr
            340                 345                 350

Pro Gln Asp Pro Glu Ala Asp Leu Gly Ile Gly Leu Arg Tyr Asp Trp
            355                 360                 365

Gly Lys Tyr Tyr Ala Ser Lys Ser Phe Tyr Asp Pro Ile Lys Asn Arg
            370                 375                 380

Arg Val Val Trp Ala Phe Val Gly Glu Thr Asp Ser Glu Gln Ala Asp
385                 390                 395                 400

Lys Ala Lys Gly Trp Ala Ser Leu Met Ser Ile Pro Arg Met Val Glu
            405                 410                 415

Leu Asp Lys Lys Thr Arg Thr Asn Leu Ile Gln Trp Pro Val Glu Glu
            420                 425                 430

Ile Glu Thr Leu Arg Arg Asn Val Thr Asp Leu Gly Gly Ile Thr Val
            435                 440                 445

Glu Ala Gly Ser Val Ile His Leu Pro Leu Gln Gln Gly Gly Gln Leu
450                 455                 460

Asp Ile Glu Ala Ser Phe Arg Leu Asn Ser Ser Asp Ile Asp Ala Leu
465                 470                 475                 480

Asn Glu Ala Asp Val Gly Phe Asn Cys Ser Ser Ser Ala Gly Ala Ala
            485                 490                 495

Val Arg Gly Ala Leu Gly Pro Phe Gly Leu Leu Val Phe Ala Asp Gly
            500                 505                 510

Arg His Glu Gln Thr Ala Ala Tyr Phe Tyr Val Ser Lys Gly Leu Asp
            515                 520                 525

Gly Ser Leu Leu Thr His Tyr Cys His Asp Glu Ser Arg Ser Thr Arg
            530                 535                 540

Ala Lys Asp Val Val Ser Arg Val Val Gly Gly Thr Val Pro Val Leu
545                 550                 555                 560

Asp Gly Glu Thr Phe Ser Val Arg Val Leu Val Asp His Ser Ile Val
            565                 570                 575

Gln Ser Phe Val Met Gly Gly Arg Thr Thr Val Thr Ser Arg Ala Tyr
            580                 585                 590

Pro Thr Glu Ala Ile Tyr Ala Ala Ala Gly Val Tyr Leu Phe Asn Asn
            595                 600                 605
```

Ala Thr Ser Ala Thr Ile Thr Ala Glu Gly Leu Val Val Tyr Glu Met
            610                 615                 620

Ala Ser Ala Glu Ser Gln Ala Phe Leu Ala Asp Asp Met
625                 630                 635

<210> SEQ ID NO 49
<211> LENGTH: 603
<212> TYPE: PRT
<213> ORGANISM: Lolium perenne

<400> SEQUENCE: 49

Met Gly Ile Ala Glu Val Ala Leu His Thr Met Pro Gly Ala Phe Ala
  1               5                  10                  15

Ser His Ser Pro Ala Ser Ser Leu Pro Leu Arg Thr Asp Thr Arg Ser
                 20                  25                  30

Leu Arg Lys Arg Gly Thr Asn Ser Phe Tyr Arg Thr Leu Gly Gly Pro
             35                  40                  45

Pro Lys Phe Pro Glu Leu Arg Pro Val Glu Cys Gln Cys Gln Arg Ile
         50                  55                  60

Asp Asp Leu Ala Gly Val Ile Glu Ala Gly Asn Gly Thr Trp Ala Thr
 65                  70                  75                  80

Asp Met Val Asn Lys Ala Ser Gln Val Leu Gly Asp Val Ala Val Pro
                 85                  90                  95

Gly Gln Ala Leu Gly Gly Asn Ala Ser Leu Ser Gly Asp Pro Glu Lys
            100                 105                 110

Val Leu Pro Arg Arg Asn Leu Ser Val Glu Asp Glu Ala Trp
        115                 120                 125

Asp Leu Leu Arg Glu Ser Val Val Asn Tyr Cys Gly Ser Pro Val Gly
130                 135                 140

Thr Ile Ala Ala Asn Asp Pro Asn Asp Ser Asn Pro Ala Asn Tyr Asp
145                 150                 155                 160

Gln Val Phe Ile Arg Asp Phe Ile Pro Ser Gly Ile Ala Phe Leu Leu
                165                 170                 175

Lys Gly Glu Tyr Glu Ile Val Arg Asn Phe Ile Leu His Thr Leu Gln
            180                 185                 190

Leu Gln Ser Trp Glu Lys Thr Met Asp Cys His Ser Pro Gly Gln Gly
        195                 200                 205

Leu Met Pro Ala Ser Phe Lys Val Arg Thr Ile Pro Leu Asp Gly Asp
    210                 215                 220

Glu Asn Ala Thr Glu Glu Val Leu Asp Pro Asp Phe Gly Glu Ala Ala
225                 230                 235                 240

Ile Gly Arg Val Ala Pro Val Asp Ser Gly Leu Trp Trp Ile Ile Leu
                245                 250                 255

Leu Arg Ala Tyr Gly Lys Cys Ser Gly Asp Leu Ser Val Gln Glu Arg
            260                 265                 270

Ile Asp Val Gln Thr Gly Ile Lys Met Ile Leu Lys Leu Cys Leu Ala
        275                 280                 285

Asp Gly Phe Asp Met Phe Pro Thr Leu Leu Val Thr Asp Gly Ser Cys
    290                 295                 300

Met Ile Asp Arg Arg Met Gly Ile His Gly His Pro Leu Glu Ile Gln
305                 310                 315                 320

Ala Leu Phe Tyr Ser Ala Leu Leu Ser Ala Arg Glu Met Leu Thr Pro
                325                 330                 335

Glu Asp Gly Ser Ala Asp Leu Ile Arg Ala Leu Asn Asn Arg Leu Val
            340                 345                 350

```
Ala Leu Ser Phe His Ile Arg Glu Tyr Tyr Trp Val Asp Met Gln Lys
            355                 360                 365

Leu Asn Glu Ile Tyr Arg Tyr Lys Thr Glu Glu Tyr Ser Tyr Asp Ala
        370                 375                 380

Val Asn Lys Phe Asn Ile Tyr Pro Asp Gln Val Ser Pro Trp Leu Val
385                 390                 395                 400

Glu Trp Ile Pro Pro Lys Gly Gly Tyr Phe Ile Gly Asn Leu Gln Pro
                405                 410                 415

Ala His Met Asp Phe Arg Phe Phe Ser Leu Gly Asn Leu Trp Ser Ile
            420                 425                 430

Val Ser Ser Leu Ala Thr Thr Gln Gln Ser His Ala Ile Leu Asp Leu
        435                 440                 445

Ile Glu Ser Lys Trp Ser Asp Leu Val Ala Glu Met Pro Leu Lys Ile
    450                 455                 460

Cys Tyr Pro Ala Leu Glu Asn Leu Glu Trp Lys Ile Ile Thr Gly Ser
465                 470                 475                 480

Asp Pro Lys Asn Thr Pro Trp Ser Tyr His Asn Gly Gly Ser Trp Pro
                485                 490                 495

Thr Leu Leu Trp Gln Leu Thr Val Ala Ser Leu Lys Met Asn Arg Pro
            500                 505                 510

Glu Ile Ala Ala Lys Ala Val Glu Ile Ala Glu Arg Arg Ile Ala Thr
        515                 520                 525

Asp Lys Trp Pro Glu Tyr Tyr Asp Thr Lys Arg Ala Arg Phe Ile Gly
    530                 535                 540

Lys Gln Ser Arg Leu Tyr Gln Thr Trp Ser Ile Ala Gly Tyr Leu Val
545                 550                 555                 560

Ala Lys Gln Leu Leu Asp Lys Pro Asp Ala Ala Arg Ile Leu Trp Asn
                565                 570                 575

Asp Glu Asp Thr Glu Ile Leu Asn Ala Phe Ser Thr Asn Arg Lys Arg
            580                 585                 590

Gly Lys Lys Val Leu Lys Lys Thr Tyr Ile Val
        595                 600

<210> SEQ ID NO 50
<211> LENGTH: 556
<212> TYPE: PRT
<213> ORGANISM: Festuca arundinacea

<400> SEQUENCE: 50

Asp Pro Phe Arg Ala Ala Leu Ala Pro Ala Ser Pro Pro Leu Glu Ala
1               5                   10                  15

Pro Pro Leu Asp Glu Leu Pro Thr Ala Pro Ser His Ser Glu Pro Ala
            20                  25                  30

Ser Ala Ala Ala Ala Pro Glu Gln Asp Pro Val Asp Leu Gln His
        35                  40                  45

Glu Glu Leu Asp Gly Leu Lys Ala Gly Val Glu Ala Val Arg Ser Arg
    50                  55                  60

Glu Glu Ser Pro Gln Glu Lys Glu Ala Trp Trp Leu Leu Asn Arg Ala
65                  70                  75                  80

Val Val Asn Tyr Cys Gly Ser Ala Val Gly Thr Val Ala Ala Asn Asp
                85                  90                  95

Pro Ser Thr Ala Asn His Met Leu Asn Tyr Asp Gln Val Phe Ile Arg
            100                 105                 110

Asp Phe Val Pro Ser Ala Ile Ala Phe Leu Leu Lys Gly Glu Ser Asp
```

-continued

```
            115                 120                 125
Ile Val Lys Asn Phe Leu Leu His Thr Leu Gln Leu Gln Ser Trp Glu
    130                 135                 140

Lys Thr Val Asp Cys Tyr Ser Pro Gly Gln Gly Leu Met Pro Ala Ser
145                 150                 155                 160

Phe Lys Val Arg Ser Val Pro Leu Asp Gly Asn Asn Glu Ala Phe Glu
                165                 170                 175

Glu Val Leu Asp Pro Asp Phe Gly Glu Ser Ala Ile Gly Arg Val Ala
            180                 185                 190

Pro Val Asp Ser Gly Leu Trp Trp Ile Ile Leu Leu Arg Ala Tyr Gly
        195                 200                 205

Lys Ile Thr Gly Asp Tyr Ala Leu Gln Glu Arg Val Asp Val Gln Thr
    210                 215                 220

Gly Ile Arg Leu Ile Leu Asn Leu Cys Leu Ser Asp Gly Phe Asp Met
225                 230                 235                 240

Phe Pro Thr Leu Leu Val Thr Asp Gly Ser Cys Met Ile Asp Arg Arg
                245                 250                 255

Met Gly Ile His Gly His Pro Leu Glu Ile Gln Ala Leu Phe Tyr Ser
            260                 265                 270

Ala Leu Arg Cys Ala Arg Glu Met Val Asn Ile Asp Asp Gly Ser Lys
        275                 280                 285

Asn Leu Ile Arg Val Ile Asn Asn Arg Leu Ser Ala Leu Ser Phe His
    290                 295                 300

Ile Arg Glu Tyr Tyr Trp Val Asp Met Lys Lys Ile Asn Glu Ile Tyr
305                 310                 315                 320

Arg Tyr Lys Thr Glu Glu Tyr Ser His Asp Ala Ile Asn Lys Phe Asn
                325                 330                 335

Ile Tyr Pro Glu Gln Ile Pro Ser Trp Leu Ala Asp Trp Ile Pro Glu
            340                 345                 350

Lys Gly Gly Tyr Leu Ile Gly Asn Leu Gln Pro Ala His Met Asp Phe
        355                 360                 365

Arg Phe Phe Ser Leu Gly Asn Leu Trp Ala Ile Val Ser Ser Leu Ala
    370                 375                 380

Thr Pro Lys Gln Ala Glu Gly Ile Leu Asn Leu Ile Glu Thr Lys Trp
385                 390                 395                 400

Asp Asp Ile Val Ala Asn Met Pro Leu Lys Ile Cys Tyr Pro Ala Leu
                405                 410                 415

Glu Tyr Glu Glu Trp Arg Ile Ile Thr Gly Cys Asp Pro Lys Asn Thr
            420                 425                 430

Pro Trp Ser Tyr His Asn Gly Gly Ser Trp Pro Thr Leu Leu Trp Gln
        435                 440                 445

Phe Thr Leu Ala Cys Ile Lys Met Gly Arg Pro Asp Leu Ala Arg Arg
    450                 455                 460

Ala Val Glu Ala Val Glu Lys Arg Leu Ser Asp Lys Trp Pro Glu
465                 470                 475                 480

Tyr Tyr Asp Thr Arg Asn Gly Arg Phe Ile Gly Lys Gln Ser Arg Leu
                485                 490                 495

Tyr Gln Thr Trp Thr Ile Ala Gly Phe Leu Ser Ser Lys Leu Leu Leu
            500                 505                 510

Asp Cys Pro Glu Met Ala Ser Ile Leu Ile Cys Asp Glu Asp Leu Asp
        515                 520                 525

Leu Leu Glu Gly Cys Ala Cys Gly Ala Asn Lys Ser Ala Arg Val Lys
    530                 535                 540
```

```
Cys Ser Arg Arg Ala Ala Arg Ser Gln Val Leu Val
545                 550                 555
```

<210> SEQ ID NO 51
<211> LENGTH: 621
<212> TYPE: PRT
<213> ORGANISM: Festuca arundinacea

<400> SEQUENCE: 51

```
Met Ala Ala Ala Ile Ser His Leu Arg Arg Gly Thr Gln Arg His
 1               5                  10                  15

Ala Leu Leu Tyr Leu Ser Arg Arg His Phe Ser Asn Ser Pro Leu Thr
                20                  25                  30

Ala Ala Ala Pro Leu Ala Ala Ala Arg Arg Leu Leu Ser Thr Thr
         35                  40                  45

Val Glu Ser Gly Thr Ser Ser Ala Ala Gly Ser Tyr Lys Pro Pro Pro
 50                  55                  60

Leu Asp Pro Phe Arg Ala Ala Leu Ala Pro Ala Ser Pro Pro Leu Glu
65                  70                  75                  80

Ser Pro Pro Leu Asp Glu Leu Pro Thr Ala Pro Ser His Ser Glu Pro
                 85                  90                  95

Ala Ser Ala Ala Ala Ala Pro Glu Gln Asp Pro Val Asp Leu Gln
                100                 105                 110

His Glu Glu Leu Asp Gly Leu Lys Ala Gly Val Glu Ala Val Arg Ser
                115                 120                 125

Arg Glu Glu Ser Pro Gln Glu Lys Glu Ala Trp Trp Leu Leu Asn Arg
    130                 135                 140

Ala Val Val Asn Tyr Cys Gly Ser Ala Val Gly Thr Val Ala Ala Asn
145                 150                 155                 160

Asp Pro Ser Thr Ala Asn His Met Leu Asn Tyr Asp Gln Val Phe Ile
                165                 170                 175

Arg Asp Phe Val Pro Ser Ala Ile Ala Phe Leu Leu Lys Gly Glu Ser
                180                 185                 190

Asp Ile Val Lys Asn Phe Leu Leu His Thr Leu Gln Leu Gln Ser Trp
                195                 200                 205

Glu Lys Thr Val Asp Cys Tyr Ser Pro Gly Gln Gly Leu Met Pro Ala
    210                 215                 220

Ser Phe Lys Val Arg Ser Val Pro Leu Asp Gly Asn Asn Glu Ala Phe
225                 230                 235                 240

Glu Glu Val Leu Asp Pro Asp Phe Gly Glu Ser Ala Ile Gly Arg Val
                245                 250                 255

Ala Pro Val Asp Ser Gly Leu Trp Trp Ile Ile Leu Leu Arg Ala Tyr
                260                 265                 270

Gly Lys Ile Thr Gly Asp Tyr Ala Leu Gln Glu Arg Val Asp Val Gln
    275                 280                 285

Thr Gly Ile Arg Leu Ile Leu Asn Leu Cys Leu Ser Asp Gly Phe Asp
    290                 295                 300

Met Phe Pro Thr Leu Leu Val Thr Asp Gly Ser Cys Met Ile Asp Arg
305                 310                 315                 320

Arg Met Gly Ile His Gly His Pro Leu Glu Ile Gln Ala Leu Phe Tyr
                325                 330                 335

Ser Ala Leu Arg Cys Ala Arg Glu Met Val Asn Ile Asp Asp Gly Ser
                340                 345                 350

Lys Asn Leu Ile Arg Val Ile Asn Asn Arg Leu Ser Ala Leu Ser Phe
```

```
                  355                 360                 365
His Ile Arg Glu Tyr Tyr Trp Val Asp Met Lys Lys Ile Asn Glu Ile
370                 375                 380

Tyr Arg Tyr Lys Thr Glu Glu Tyr Ser His Asp Ala Ile Asn Lys Phe
385                 390                 395                 400

Asn Ile Tyr Pro Glu Gln Ile Pro Ser Trp Leu Ala Asp Trp Ile Pro
                405                 410                 415

Glu Lys Gly Gly Tyr Leu Ile Gly Asn Leu Gln Pro Ala His Met Asp
                420                 425                 430

Phe Arg Phe Phe Ser Leu Gly Asn Leu Trp Ala Ile Val Ser Ser Leu
            435                 440                 445

Ala Thr Pro Lys Gln Ala Glu Gly Ile Leu Asn Leu Ile Glu Thr Lys
        450                 455                 460

Trp Asp Asp Ile Val Ala Asn Met Pro Leu Lys Ile Cys Tyr Pro Ala
465                 470                 475                 480

Leu Glu Tyr Glu Glu Trp Arg Ile Ile Thr Gly Cys Asp Pro Lys Asn
                485                 490                 495

Thr Pro Trp Ser Tyr His Asn Gly Gly Ser Trp Pro Thr Leu Leu Trp
            500                 505                 510

Gln Phe Thr Leu Ala Cys Ile Lys Met Gly Arg Pro Asp Leu Ala Arg
        515                 520                 525

Arg Ala Val Glu Ala Val Glu Lys Arg Leu Ser Asp Asp Lys Trp Pro
530                 535                 540

Glu Tyr Tyr Asp Thr Arg Asn Gly Arg Phe Ile Gly Lys Gln Ser Arg
545                 550                 555                 560

Leu Tyr Gln Thr Trp Thr Ile Ala Gly Phe Leu Ser Ser Lys Leu Leu
                565                 570                 575

Leu Asp Cys Pro Glu Met Ala Ser Ile Leu Ile Cys Asp Glu Asp Leu
            580                 585                 590

Asp Leu Leu Glu Gly Cys Ala Cys Gly Ala Asn Lys Ser Ala Arg Val
        595                 600                 605

Lys Cys Ser Arg Arg Ala Ala Arg Ser Gln Val Leu Val
610                 615                 620

<210> SEQ ID NO 52
<211> LENGTH: 244
<212> TYPE: PRT
<213> ORGANISM: Lolium perenne

<400> SEQUENCE: 52

Leu Leu Glu Lys Arg Lys Leu Asn Glu Ile Tyr Arg Tyr Lys Thr Glu
1               5                   10                  15

Glu Tyr Ser Tyr Asp Ala Val Asn Lys Phe Asn Ile Tyr Pro Asp Gln
            20                  25                  30

Ile Pro Pro Trp Leu Val Glu Trp Ile Pro Pro Lys Gly Gly Tyr Phe
        35                  40                  45

Ile Gly Asn Leu Gln Pro Ala His Met Asp Phe Arg Phe Phe Ser Leu
    50                  55                  60

Gly Asn Leu Trp Ser Ile Val Ser Ser Leu Ala Thr Ala Asp Gln Ser
65                  70                  75                  80

His Ala Ile Leu Asp Leu Val Glu Ala Lys Trp Ser Asp Leu Val Ala
                85                  90                  95

Glu Met Pro Met Lys Ile Cys Tyr Pro Ala Leu Glu Asp Gln Glu Trp
            100                 105                 110
```

-continued

```
Lys Phe Ile Thr Gly Ser Asp Pro Lys Asn Thr Pro Trp Ser Tyr His
        115                 120                 125

Asn Gly Gly Ser Trp Pro Thr Leu Leu Trp Gln Leu Thr Val Ala Cys
130                 135                 140

Ile Lys Met Asn Arg Pro Glu Ile Ala Ala Arg Ala Val Glu Val Ala
145                 150                 155                 160

Glu Ser Arg Ile Ser Met Asp Lys Trp Pro Glu Tyr Tyr Asp Thr Lys
                165                 170                 175

Arg Gly Arg Phe Ile Gly Lys Gln Ala Arg Leu Phe Gln Thr Trp Ser
            180                 185                 190

Ile Ala Gly Phe Leu Val Ala Lys Leu Leu Leu Glu Asn Pro Glu Lys
                195                 200                 205

Ser Arg Ile Leu Trp Asn Asn Glu Asp Glu Glu Ile Leu Asn Ala Leu
210                 215                 220

Ser Leu Met Thr Gly Pro Ser Ser Pro Lys Arg Lys Arg Gly Arg Lys
225                 230                 235                 240

Thr Tyr Ile Val

<210> SEQ ID NO 53
<211> LENGTH: 578
<212> TYPE: PRT
<213> ORGANISM: Lolium perenne

<400> SEQUENCE: 53

Met Ala Ile Ala Ala Ala Ala Leu Leu Pro Leu His Leu Gly Cys
1               5                   10                  15

Ser Asp Ala Ala Pro Arg Arg Pro Gly Asn Ser Leu Arg Ala His Leu
                20                  25                  30

Arg Lys Gly Gly Ile Arg Gly Arg Arg Ser Pro Pro Cys Ala Val
            35                  40                  45

Asn Ser Leu His Pro Ser Gly Asn Pro Lys Thr Pro Gly Gly Asp
50                  55                  60

Val Gly Gly Ala Trp Gly Leu Asn Gly Gly Ala Thr Ala Lys Pro Asp
65                  70                  75                  80

His Ala Pro Pro Ser Gln Arg Arg Ala Pro Arg Asp Val Glu Glu
                85                  90                  95

Glu Ala Trp Ala Leu Leu Arg Glu Ser Val Val Ser Tyr Cys Gly Ser
            100                 105                 110

Pro Val Gly Thr Ile Ala Ala Cys Asp Pro Asn Asp Ala Ser Pro Leu
        115                 120                 125

Asn Tyr Asp Gln Val Phe Ile Arg Asp Phe Val Pro Ser Gly Val Ala
130                 135                 140

Phe Leu Leu Lys Gly Glu His Glu Ile Val Arg Asn Phe Ile Leu His
145                 150                 155                 160

Thr Leu Gln Leu Gln Ser Trp Glu Lys Thr Ile Asp Cys His Ser Pro
                165                 170                 175

Gly Gln Gly Leu Met Pro Ala Ser Phe Lys Val Arg Val Pro Leu
            180                 185                 190

Asp Gly Gly Asp Asp Gly Ala Thr Glu Glu Val Leu Asp Pro Asp Phe
                195                 200                 205

Gly Glu Ala Ala Ile Gly Arg Val Ala Pro Val Asp Ser Gly Leu Trp
            210                 215                 220

Trp Ile Ile Leu Leu Arg Ala Tyr Gly Lys Cys Ser Gly Asp Leu Ser
225                 230                 235                 240
```

```
Phe His Glu Arg Val Asp Val Gln Thr Gly Ile Lys Leu Ile Leu Lys
                245                 250                 255

Leu Cys Leu Ala Asp Gly Phe Asp Met Phe Pro Thr Leu Leu Val Thr
            260                 265                 270

Asp Gly Ser Cys Met Met Asp Arg Arg Met Gly Ile His Gly His Pro
        275                 280                 285

Leu Glu Ile Gln Ala Leu Phe Tyr Ser Ala Leu Leu Ser Ala Arg Glu
    290                 295                 300

Met Leu Thr Pro Glu Asp Gly Ser Ala Asp Leu Ile Arg Ala Leu Asn
305                 310                 315                 320

Ser Arg Leu Met Ala Leu Ser Phe His Ile Arg Glu Tyr Tyr Trp Leu
                325                 330                 335

Glu Lys Arg Lys Leu Asn Glu Ile Tyr Arg Tyr Lys Thr Glu Glu Tyr
            340                 345                 350

Ser Tyr Asp Ala Val Asn Lys Phe Asn Ile Tyr Pro Asp Gln Ile Pro
        355                 360                 365

Pro Trp Leu Val Glu Trp Ile Pro Lys Gly Gly Tyr Phe Ile Gly
    370                 375                 380

Asn Leu Gln Pro Ala His Met Asp Phe Arg Phe Ser Leu Gly Asn
385                 390                 395                 400

Leu Trp Ser Ile Val Ser Ser Leu Ala Thr Ala Asp Gln Ser His Ala
                405                 410                 415

Ile Leu Asp Leu Val Glu Ala Lys Trp Ser Asp Leu Val Ala Glu Met
            420                 425                 430

Pro Met Lys Ile Cys Tyr Pro Ala Leu Glu Asp Gln Glu Trp Lys Phe
        435                 440                 445

Ile Thr Gly Ser Asp Pro Lys Asn Thr Pro Trp Ser Tyr His Asn Gly
    450                 455                 460

Gly Ser Trp Pro Thr Leu Leu Trp Gln Leu Thr Val Ala Cys Ile Lys
465                 470                 475                 480

Met Asn Arg Pro Glu Ile Ala Ala Arg Ala Val Glu Val Ala Glu Ser
                485                 490                 495

Arg Ile Ser Met Asp Lys Trp Pro Glu Tyr Tyr Asp Thr Lys Arg Gly
            500                 505                 510

Arg Phe Ile Gly Lys Gln Ala Arg Leu Phe Gln Thr Trp Ser Ile Ala
        515                 520                 525

Gly Phe Leu Val Ala Lys Leu Leu Glu Asn Pro Glu Lys Ser Arg
    530                 535                 540

Ile Leu Trp Asn Asn Glu Asp Glu Glu Ile Leu Asn Ala Leu Ser Leu
545                 550                 555                 560

Met Thr Gly Pro Ser Ser Pro Lys Arg Lys Arg Gly Lys Thr Tyr
                565                 570                 575

Ile Val

<210> SEQ ID NO 54
<211> LENGTH: 619
<212> TYPE: PRT
<213> ORGANISM: Lolium perenne

<400> SEQUENCE: 54

Met Asn Gly Gln Thr Thr Met Gly Leu Ala Ala Ala Ala Ala Ala
  1               5                  10                  15

Val Arg Pro Cys Arg Arg Arg Leu Leu Ser Ser Ala Ser Ala Ala
            20                  25                  30
```

```
Ala Ala Lys Ala Ser Ala Thr Pro Leu Phe Pro Arg Cys Ser His Pro
        35                  40                  45

Gln His Gln Gln His Ser Arg Arg Ile Pro Phe Leu Val Ser Ala Ala
        50                  55                  60

Ser His Thr Ser Gln Ser Asp Pro Ser Thr Thr Pro Thr Pro Val Thr
65                  70                  75                  80

Ser Asp Pro Arg Ser Ala Val Ala Gly Asn Leu Pro Phe Phe Asp Arg
                85                  90                  95

Val Leu Phe Pro Gly Ser Phe Pro Leu Glu Thr Pro Pro Val Glu Glu
            100                 105                 110

Pro Ala Pro Ala Pro Ala Asp Glu Ala Gln Ala Ser Ala Ser Pro
            115                 120                 125

Val Arg Glu Glu Ser Asp Thr Glu Arg Glu Ala Trp Arg Leu Leu Arg
        130                 135                 140

Arg Ala Val Val Ser Tyr Cys Gly Asp Pro Val Gly Thr Val Ala Ala
145                 150                 155                 160

Glu Asp Pro Glu Cys Thr Glu Met Leu Asn Tyr Asp Gln Val Phe Ile
                165                 170                 175

Arg Asp Phe Val Pro Ser Ala Leu Ala Phe Leu Met Arg Gly Glu Thr
            180                 185                 190

Glu Ile Val Arg Asn Phe Leu Leu His Thr Leu Gln Leu Gln Ser Trp
        195                 200                 205

Glu Lys Thr Val Asp Cys Tyr Ser Pro Gly Gln Gly Leu Met Pro Ala
        210                 215                 220

Ser Phe Lys Ile Lys Thr Val Pro Leu Asp Glu Asn Asn Glu Ala Phe
225                 230                 235                 240

Glu Glu Val Leu Asp Pro Asp Phe Gly Glu Ser Ala Ile Gly Arg Val
                245                 250                 255

Ala Pro Val Asp Ser Gly Leu Trp Trp Ile Ile Leu Leu Arg Ala Tyr
            260                 265                 270

Cys Lys Phe Thr Gly Asp Tyr Ser Leu Gln Glu Arg Val Asp Val Gln
        275                 280                 285

Thr Gly Ile Lys Leu Ile Leu Ser Leu Cys Leu Thr Asp Gly Phe Asp
        290                 295                 300

Met Phe Pro Thr Leu Leu Val Thr Asp Gly Ser Cys Met Ile Asp Arg
305                 310                 315                 320

Arg Met Gly Ile His Gly His Pro Leu Glu Ile Gln Ala Leu Phe Tyr
                325                 330                 335

Ser Ala Leu Arg Cys Ser Arg Glu Met Ile Val Met Asn Asp Gly Ser
            340                 345                 350

Lys His Leu Leu Gln Ala Ile Asn Asn Arg Leu Ser Ala Leu Ser Phe
        355                 360                 365

His Ile Arg Glu Tyr Tyr Trp Val Asp Met Lys Lys Ile Asn Glu Ile
        370                 375                 380

Tyr Arg Tyr Lys Thr Glu Glu Tyr Ser His Asp Ala Thr Asn Lys Phe
385                 390                 395                 400

Asn Ile Tyr Pro Glu Gln Ile Pro Ser Trp Leu Val Asp Trp Val Pro
                405                 410                 415

Glu Lys Gly Gly Tyr Leu Ile Gly Asn Leu Gln Pro Ala His Met Asp
            420                 425                 430

Phe Arg Phe Phe Ser Leu Gly Asn Leu Trp Ala Ile Ser Ser Ser Leu
        435                 440                 445

Thr Thr Pro Thr Gln Ala Glu Gly Ile Leu Ser Leu Ile Glu Glu Lys
```

```
               450                 455                 460
Trp Asp Asp Leu Val Ala Asn Met Pro Leu Lys Ile Cys Tyr Pro Ala
465                 470                 475                 480

Met Glu Asp Asp Glu Trp Arg Ile Val Thr Gly Ser Asp Pro Lys Asn
            485                 490                 495

Thr Pro Trp Ser Tyr His Asn Gly Gly Ser Trp Pro Thr Leu Leu Trp
            500                 505                 510

Gln Phe Thr Leu Ala Cys Ile Lys Met Gly Arg Pro Glu Leu Ala Arg
            515                 520                 525

Arg Ala Ile Ala Val Ala Glu Glu Lys Leu Ser Ala Asp Lys Trp Pro
            530                 535                 540

Glu Tyr Tyr Asp Thr Arg Ser Gly Arg Phe Val Gly Lys Gln Ser Arg
545                 550                 555                 560

Ser Tyr Gln Thr Trp Thr Ile Ala Gly Phe Leu Thr Ser Lys Ile Leu
            565                 570                 575

Leu Glu Asn Pro Glu Leu Ala Ser Ile Leu Thr Cys Asp Glu Asp Leu
            580                 585                 590

Glu Leu Leu Glu Gly Cys Ala Cys Cys Leu Ser Lys Arg Thr Arg Cys
            595                 600                 605

Ser Arg Arg Val Thr Lys Ser Asp Ile Ile Gly
            610                 615

<210> SEQ ID NO 55
<211> LENGTH: 578
<212> TYPE: PRT
<213> ORGANISM: Lolium perenne

<400> SEQUENCE: 55

Met Ala Ile Ala Ala Ala Ala Leu Leu Pro Leu His Leu Gly Cys
  1               5                  10                  15

Ser Asp Ala Ala Pro Arg Arg Pro Gly Asn Ser Leu Arg Ala His Leu
            20                  25                  30

Arg Lys Gly Gly Ile Arg Gly Arg Arg Ser Pro Pro Cys Ala Val
        35                  40                  45

Asn Ser Leu His Pro Ser Gly Asn Pro Lys Thr Pro Gly Gly Gly Asp
 50                  55                  60

Val Gly Gly Gly Arg Gly Val Asn Gly Gly Ala Thr Ala Lys Pro Asp
65                  70                  75                  80

His Ala Pro Pro Ser Gln Arg Arg Arg Ala Pro Arg Asp Val Glu Glu
                85                  90                  95

Glu Ala Trp Ala Leu Leu Arg Glu Ser Val Val Ser Tyr Cys Gly Ser
            100                 105                 110

Pro Val Gly Thr Ile Ala Ala Cys Asp Pro Asn Asp Ala Ser Pro Leu
        115                 120                 125

Asn Tyr Asp Gln Val Phe Ile Arg Asp Phe Val Pro Ser Gly Val Ala
130                 135                 140

Phe Leu Leu Lys Gly Glu His Glu Ile Val Arg Asn Phe Ile Leu His
145                 150                 155                 160

Thr Leu Gln Leu Gln Ser Trp Glu Lys Thr Ile Asp Cys His Ser Pro
                165                 170                 175

Gly Gln Gly Leu Met Pro Ala Ser Phe Lys Val Arg Val Val Pro Leu
            180                 185                 190

Asp Gly Gly Asp Asp Gly Ala Thr Glu Glu Val Leu Asp Pro Asp Phe
        195                 200                 205
```

Gly Glu Ala Ala Ile Gly Arg Val Ala Pro Val Asp Ser Gly Leu Trp
210                 215                 220

Trp Ile Ile Leu Leu Arg Ala Tyr Gly Lys Cys Ser Gly Asp Leu Ser
225                 230                 235                 240

Phe His Glu Arg Val Asp Val Gln Thr Gly Ile Lys Leu Ile Leu Lys
            245                 250                 255

Leu Cys Leu Ala Asp Gly Phe Asp Met Phe Pro Thr Leu Leu Val Thr
            260                 265                 270

Asp Gly Ser Cys Met Met Asp Arg Arg Met Gly Ile His Gly His Pro
        275                 280                 285

Leu Glu Ile Gln Ala Leu Phe Tyr Ser Ala Leu Leu Ser Ala Arg Glu
290                 295                 300

Met Leu Thr Pro Glu Asp Gly Ser Ala Asp Leu Ile Arg Ala Leu Asn
305                 310                 315                 320

Ser Arg Leu Met Ala Leu Ser Phe His Ile Arg Glu Tyr Tyr Trp Leu
                325                 330                 335

Glu Lys Arg Lys Leu Asn Glu Ile Tyr Arg Tyr Lys Thr Glu Glu Tyr
                340                 345                 350

Ser Tyr Asp Ala Val Asn Lys Phe Asn Ile Tyr Pro Asp Gln Ile Pro
            355                 360                 365

Pro Trp Leu Val Glu Trp Ile Pro Pro Lys Gly Gly Tyr Phe Ile Gly
370                 375                 380

Asn Leu Gln Pro Ala His Met Asp Phe Arg Phe Phe Ser Leu Gly Asn
385                 390                 395                 400

Leu Trp Ser Ile Val Ser Ser Leu Ala Thr Ala Asp Gln Ser His Ala
                405                 410                 415

Ile Leu Asp Leu Val Glu Ala Lys Trp Ser Asp Leu Val Ala Glu Met
                420                 425                 430

Pro Met Lys Ile Cys Tyr Pro Ala Leu Glu Asp Gln Glu Trp Lys Phe
            435                 440                 445

Ile Thr Gly Ser Asp Pro Lys Asn Thr Pro Trp Ser Tyr His Asn Gly
            450                 455                 460

Gly Ser Trp Pro Thr Leu Leu Trp Gln Leu Thr Val Ala Cys Ile Lys
465                 470                 475                 480

Met Asn Arg Pro Glu Ile Ala Ala Arg Ala Val Glu Val Ala Glu Ser
                485                 490                 495

Arg Ile Ser Thr Asp Lys Trp Pro Glu Tyr Tyr Asp Thr Lys Arg Gly
                500                 505                 510

Arg Phe Ile Gly Lys Gln Ala Arg Leu Phe Gln Thr Trp Ser Ile Ala
            515                 520                 525

Gly Phe Leu Val Ala Lys Leu Leu Leu Glu Asn Pro Glu Lys Ser Arg
            530                 535                 540

Ile Leu Trp Asn Asn Glu Asp Glu Glu Ile Leu Asn Ala Leu Ser Leu
545                 550                 555                 560

Met Thr Gly Pro Ser Ser Pro Lys Arg Lys Gly Arg Lys Thr Tyr
                565                 570                 575

Ile Val

<210> SEQ ID NO 56
<211> LENGTH: 554
<212> TYPE: PRT
<213> ORGANISM: Lolium perenne

<400> SEQUENCE: 56

-continued

```
Met Lys Arg Val Ser Ser His Val Ser Ile Ala Ser Glu Ala Glu Ile
 1               5                  10                  15

Asn Leu Asp Leu Ser Arg Leu Leu Ile Asp Lys Pro Arg Tyr Thr Leu
            20                  25                  30

Glu Arg Lys Arg Ser Phe Asp Glu Gln Ser Trp Ser Glu Leu Thr His
        35                  40                  45

Thr His Arg Gln Asn Asp Gly Phe Asp Ser Val Leu Gln Ser Pro Ala
50                      55                  60

Phe Arg Thr Gly Phe Asp Ser Pro Phe Ser Met Gly Thr His Phe Gly
65                  70                  75                  80

Glu Pro Ser Gly Pro His Pro Leu Val Asn Glu Ala Trp Glu Ala Leu
                85                  90                  95

Arg Lys Ser Val Val Tyr Phe Arg Gly Gln Pro Val Gly Thr Ile Ala
                100                 105                 110

Ala Val Asp His Ala Ser Glu Glu Val Leu Asn Tyr Asp Gln Val Phe
            115                 120                 125

Val Arg Asp Phe Val Pro Ser Ala Leu Ala Phe Leu Met Asn Asn Glu
        130                 135                 140

Pro Glu Ile Val Lys Asn Phe Leu Leu Lys Thr Leu His Leu Gln Ser
145                 150                 155                 160

Ser Glu Lys Met Val Asp Arg Phe Lys Leu Gly Ala Gly Ala Met Pro
                165                 170                 175

Ala Ser Phe Lys Val Asp Arg Asn Lys Ser Arg Asn Thr Glu Thr Leu
            180                 185                 190

Val Ala Asp Phe Gly Glu Ser Ala Ile Gly Arg Val Ala Pro Val Asp
        195                 200                 205

Ser Gly Phe Trp Trp Ile Ile Leu Leu Arg Ala Tyr Thr Lys Tyr Thr
210                 215                 220

Gly Asp Ala Ser Leu Ser Glu Ser Pro Asp Cys Gln Lys Cys Met Arg
225                 230                 235                 240

Leu Ile Leu Asn Leu Cys Leu Ser Glu Gly Phe Asp Thr Phe Pro Thr
                245                 250                 255

Leu Leu Cys Thr Asp Gly Cys Ser Met Ile Asp Arg Arg Met Gly Ile
            260                 265                 270

Tyr Gly Tyr Pro Ile Glu Ile Gln Ala Leu Phe Tyr Met Ala Leu Arg
        275                 280                 285

Cys Ala Leu Gln Met Leu Lys Pro Asp Gly Glu Gly Lys Asp Phe Ile
290                 295                 300

Glu Lys Ile Gly Gln Arg Leu His Ala Leu Thr Tyr His Met Arg Asn
305                 310                 315                 320

Tyr Phe Trp Leu Asp Phe Pro His Leu Asn Asn Ile Tyr Arg Tyr Lys
                325                 330                 335

Thr Glu Glu Tyr Ser His Thr Ala Val Asn Lys Phe Asn Val Ile Pro
            340                 345                 350

Asp Ser Ile Pro Asp Trp Val Phe Asp Phe Met Pro Cys Arg Gly Gly
        355                 360                 365

Tyr Phe Leu Gly Asn Val Ser Pro Ala Met Met Asp Phe Arg Trp Phe
370                 375                 380

Ala Leu Gly Asn Cys Ile Ala Ile Ser Ser Leu Ala Thr Pro Glu
385                 390                 395                 400

Gln Ser Ser Ala Ile Met Asp Leu Ile Glu Glu Arg Trp Asp Glu Leu
                405                 410                 415

Val Gly Glu Val Pro Leu Lys Ile Cys Tyr Pro Ala Ile Glu Asn His
```

-continued

```
                    420                 425                 430
Glu Trp Arg Ile Ile Thr Gly Cys Asp Pro Lys Asn Thr Arg Trp Ser
            435                 440                 445
Tyr His Asn Gly Gly Ser Trp Pro Val Leu Leu Trp Leu Leu Thr Ala
        450                 455                 460
Ala Cys Ile Lys Thr Gly Arg Pro Gln Met Ala Lys Arg Ala Ile Glu
465                 470                 475                 480
Leu Ser Glu Ala Arg Leu Leu Lys Asp Gly Trp Pro Glu Tyr Tyr Asp
                485                 490                 495
Gly Lys Leu Gly Lys Phe Val Gly Lys Gln Ala Arg Lys Phe Gln Thr
            500                 505                 510
Trp Ser Ile Ala Gly Tyr Leu Val Ala Arg Met Met Leu Glu Asp Pro
        515                 520                 525
Ser Thr Leu Met Met Ile Ser Met Glu Glu Asp Arg Pro Val Lys Pro
    530                 535                 540
Thr Met Arg Arg Ser Ala Ser Trp Asn Ala
545                 550
```

<210> SEQ ID NO 57
<211> LENGTH: 552
<212> TYPE: PRT
<213> ORGANISM: Lolium perenne

<400> SEQUENCE: 57

```
Met Glu Ala Pro Gly Gly Gly Ala Gly Pro Met Pro Thr Thr Pro Ser
1               5                   10                  15
His Ala Ser Ile Ala Asp Ser Asp Asp Phe Asp Leu Ser Arg Leu Leu
                20                  25                  30
Asn His Arg Pro Arg Ile Asn Val Glu Arg Gln Arg Ser Phe Asp Asp
            35                  40                  45
Arg Ser Leu Gly Asp Leu Tyr Leu Ser Ala Met Asp Ser Arg Gly Gly
        50                  55                  60
Tyr Met Asp Ser Tyr Asp Ser Met Tyr Ser Pro Gly Gly Gly Leu Arg
65                  70                  75                  80
Ser Leu Thr Gly Thr Pro Ala Ser Ser Thr Arg Leu Ser Phe Glu Pro
                85                  90                  95
Gln Leu Leu Val Ala Glu Ala Trp Glu Ala Leu Arg Arg Ser Leu Val
            100                 105                 110
Cys Phe Arg Gly Glu Pro Leu Gly Thr Ile Ala Ala Val Asp Ser Ser
        115                 120                 125
Ser Asp Glu Val Leu Asn Tyr Asp Gln Val Phe Val Arg Asp Phe Val
130                 135                 140
Pro Ser Ala Leu Ala Phe Leu Met Asn Gly Glu Pro Asp Ile Val Lys
145                 150                 155                 160
Asn Phe Leu Leu Lys Thr Leu Leu Gln Gly Trp Glu Lys Arg Ile
                165                 170                 175
Asp Arg Phe Lys Leu Gly Glu Gly Ala Met Pro Ala Ser Phe Lys Val
            180                 185                 190
Leu Lys Asp Pro Lys Arg Gly Val Asp Thr Leu Ala Ala Asp Phe Gly
        195                 200                 205
Glu Ser Ala Ile Gly Arg Val Ala Pro Ala Asp Ser Gly Phe Trp Trp
    210                 215                 220
Ile Ile Leu Leu Arg Ala Tyr Thr Lys Ser Thr Gly Asp Leu Thr Leu
225                 230                 235                 240
```

```
Ala Glu Thr Pro Glu Cys Gln Lys Gly Ile Arg Leu Ile Met Asn Gln
            245                 250                 255

Cys Leu Ala Glu Gly Phe Asp Thr Phe Pro Thr Leu Leu Cys Ala Asp
            260                 265                 270

Gly Cys Cys Met Ile Asp Arg Arg Met Gly Val Tyr Gly Tyr Pro Ile
            275                 280                 285

Glu Ile Gln Ala Leu Phe Phe Met Ser Leu Arg Cys Ala Leu Leu Leu
290                 295                 300

Leu Lys Pro Ala Val Glu Gly Asn Ser Ser Lys Asp Asp Ile
305                 310                 315                 320

Met Glu Arg Ile Val Thr Arg Leu His Ala Leu Ser Tyr His Met Arg
                325                 330                 335

Ser Tyr Phe Trp Leu Asp Phe Gln Gln Leu Asn Val Ile Tyr Arg Phe
            340                 345                 350

Lys Thr Glu Glu Tyr Ser His Thr Ala Val Asn Lys Phe Asn Val Ile
            355                 360                 365

Pro Glu Ser Ile Pro Asp Trp Leu Phe Asp Phe Met Pro Ser Arg Gly
            370                 375                 380

Gly Tyr Phe Val Gly Asn Val Ser Pro Ala Arg Met Asp Phe Arg Trp
385                 390                 395                 400

Phe Ala Leu Gly Asn Cys Val Ala Ile Leu Ala Ser Leu Ala Thr Pro
                405                 410                 415

Glu Gln Ala Gly Ala Ile Met Asp Leu Ile Glu Glu Arg Trp Glu Asp
            420                 425                 430

Leu Ile Gly Glu Met Pro Leu Lys Ile Cys Tyr Pro Thr Ile Glu Gly
            435                 440                 445

His Glu Trp Gln Asn Val Thr Gly Cys Asp Pro Lys Asn Thr Arg Trp
450                 455                 460

Ser Tyr His Asn Gly Ser Trp Pro Val Leu Ile Trp Leu Leu Thr
465                 470                 475                 480

Ala Ala Cys Ile Lys Thr Gly Arg Leu Lys Ile Ala Arg Arg Ala Ile
                485                 490                 495

Asp Leu Ala Glu Ala Arg Leu Gly Lys Asp Gly Trp Pro Glu Tyr Tyr
            500                 505                 510

Asp Gly Lys Leu Gly Arg Tyr Val Gly Lys Gln Ala Arg Lys His Gln
            515                 520                 525

Thr Trp Ser Ile Ala Gly Tyr Leu Val Ala Lys Met Met Leu Glu Asp
            530                 535                 540

Pro Ser His Leu Gly Met Ile Ser
545                 550

<210> SEQ ID NO 58
<211> LENGTH: 562
<212> TYPE: PRT
<213> ORGANISM: Lolium perenne

<400> SEQUENCE: 58

Met Glu Phe Gly Ala Pro Gly Gly Met Arg Arg Ser Ala Ser His Asn
1               5                   10                  15

Ser Leu Ser Gly Ser Asp Asp Phe Asp Leu Thr His Leu Leu Asn Lys
            20                  25                  30

Pro Arg Ile Asn Val Glu Arg Gln Ser Phe Asp Asp Arg Ser Leu
            35                  40                  45

Ser Asp Val Ser Tyr Ser Gly Gly His Ala Arg Gly Ala Gly Gly
50                  55                  60
```

```
Gly Phe Asp Gly Met Tyr Ser Pro Gly Gly Leu Arg Ser Leu Val
65                  70                  75                  80

Gly Thr Pro Ala Ser Ser Ala Leu His Ser Phe Glu Pro His Pro Ile
                85                  90                  95

Val Gly Asp Ala Trp Glu Ala Leu Arg Arg Ser Leu Val Phe Phe Arg
                100                 105                 110

Gly Gln Pro Leu Gly Thr Ile Ala Ala Tyr Asp His Ala Ser Glu Glu
            115                 120                 125

Val Leu Asn Tyr Asp Gln Val Phe Val Arg Asp Phe Val Pro Ser Ala
            130                 135                 140

Met Ala Phe Leu Met Asn Gly Glu Pro Glu Ile Val Lys Asn Phe Leu
145                 150                 155                 160

Leu Lys Thr Val Leu Leu Gln Gly Trp Glu Lys Lys Val Asp Arg Phe
                165                 170                 175

Lys Leu Gly Glu Gly Ala Met Pro Ala Ser Phe Lys Val Leu His Asp
                180                 185                 190

Asp Lys Lys Gly Val Asp Thr Leu His Ala Asp Phe Gly Glu Ser Ala
            195                 200                 205

Ile Gly Arg Val Ala Pro Val Asp Ser Gly Phe Trp Trp Ile Ile Leu
            210                 215                 220

Leu Arg Ala Tyr Thr Lys Ser Thr Gly Asp Leu Thr Leu Ala Glu Lys
225                 230                 235                 240

Pro Glu Cys Gln Lys Ala Met Arg Leu Ile Leu Ser Leu Cys Leu Ser
                245                 250                 255

Glu Gly Phe Asp Thr Phe Pro Thr Leu Leu Cys Ala Asp Gly Cys Cys
                260                 265                 270

Met Ile Asp Arg Arg Met Gly Val Tyr Gly Tyr Pro Ile Glu Ile Gln
            275                 280                 285

Ser Leu Phe Phe Met Ala Leu Arg Cys Ala Leu Leu Met Leu Lys His
            290                 295                 300

Asp Asn Glu Gly Lys Asp Phe Val Glu Arg Ile Ala Thr Arg Leu His
305                 310                 315                 320

Ala Leu Ser Tyr His Met Arg Ser Tyr Phe Trp Leu Asp Phe Gln Gln
                325                 330                 335

Leu Asn Asp Ile Tyr Arg Tyr Lys Thr Glu Glu Tyr Ser His Thr Ala
            340                 345                 350

Val Asn Lys Phe Asn Val Ile Pro Asp Ser Ile Pro Asp Trp Leu Phe
            355                 360                 365

Asp Phe Met Pro Cys Glu Gly Phe Phe Val Gly Asn Val Ser Pro
            370                 375                 380

Ala Arg Met Asp Phe Arg Trp Phe Ala Leu Gly Asn Met Ile Ala Ile
385                 390                 395                 400

Val Ser Ser Leu Ala Thr Pro Glu Gln Ser Thr Ala Ile Met Asp Leu
                405                 410                 415

Ile Glu Glu Arg Trp Glu Glu Leu Ile Gly Glu Met Pro Leu Lys Ile
                420                 425                 430

Cys Tyr Pro Ala Ile Glu Asn His Glu Trp Arg Ile Val Thr Gly Cys
                435                 440                 445

Asp Pro Lys Asn Thr Arg Trp Ser Tyr His Asn Gly Gly Ser Trp Pro
            450                 455                 460

Val Leu Leu Trp Leu Leu Thr Ala Ala Ser Ile Lys Thr Gly Arg Pro
465                 470                 475                 480
```

```
Gln Ile Ala Arg Arg Ala Ile Asp Leu Ala Glu Arg Arg Leu Leu Lys
                485                 490                 495

Asp Gly Trp Pro Glu Tyr Tyr Asp Gly Lys Leu Gly Lys Tyr Val Gly
            500                 505                 510

Lys Gln Ala Arg Lys Phe Gln Thr Trp Ser Ile Ala Gly Tyr Leu Val
                515                 520                 525

Ala Lys Met Leu Leu Glu Asp Pro Ser His Leu Gly Met Ile Ala Leu
            530                 535                 540

Glu Glu Asp Lys Ala Met Lys Pro Val Leu Arg Arg Ser Ala Ser Trp
545                 550                 555                 560

Thr Asn

<210> SEQ ID NO 59
<211> LENGTH: 616
<212> TYPE: PRT
<213> ORGANISM: Lolium perenne

<400> SEQUENCE: 59

Met Asp Ser Asp Tyr Gly Val Pro Arg Glu Leu Ser Glu Val Gln Lys
1               5                   10                  15

Lys Arg Thr Leu Tyr Gln Pro Asp Leu Pro Pro Cys Leu Gln Gly Thr
                20                  25                  30

Thr Val Arg Val Glu Tyr Gly Asp Val Ala Ile Ala Ala Asp Pro Ala
            35                  40                  45

Gly Ala His Val Ile Ser His Ala Phe Pro His Thr Tyr Gly Gln Pro
        50                  55                  60

Leu Ala His Phe Leu Arg Lys Ala Ala Asn Val Ala Asp Ala Lys Val
65                  70                  75                  80

Ile Ser Glu His Pro Ala Val Arg Val Gly Ile Val Phe Cys Gly Arg
                85                  90                  95

Gln Ser Pro Gly Gly His Asn Val Ile Trp Gly Leu His Asp Ala Ile
            100                 105                 110

Lys Ala His Asn Pro Asn Ser Lys Leu Ile Gly Phe Leu Gly Gly Ser
        115                 120                 125

Asp Gly Leu Leu Ala Gln Lys Thr Leu Glu Ile Thr Asp Glu Val Leu
130                 135                 140

Ser Ser Tyr Lys Asn Gln Gly Gly Tyr Asp Met Leu Gly Arg Thr Lys
145                 150                 155                 160

Asp Gln Ile Arg Thr Thr Glu Gln Val Asn Gly Ala Met Ala Ser Cys
                165                 170                 175

Gln Ala Leu Lys Leu Asp Ala Leu Ile Ile Ile Gly Gly Val Thr Ser
            180                 185                 190

Asn Thr Asp Ala Ala Gln Leu Ala Glu Thr Phe Ala Glu Ala Lys Cys
        195                 200                 205

Ala Thr Lys Val Val Gly Val Pro Val Thr Leu Asn Gly Asp Leu Lys
    210                 215                 220

Asn Gln Phe Val Glu Thr Thr Val Gly Phe Asp Thr Ile Cys Lys Val
225                 230                 235                 240

Asn Ser Gln Leu Ile Ser Asn Met Cys Thr Asp Ala Leu Ser Ala Glu
                245                 250                 255

Lys Tyr Tyr Tyr Phe Ile Arg Met Met Gly Arg Lys Ala Ser His Val
            260                 265                 270

Ala Leu Glu Cys Ala Leu Gln Ser His Pro Asn Met Val Ile Leu Gly
        275                 280                 285
```

-continued

Glu Glu Val Ala Ala Ser Lys Leu Thr Ile Phe Asp Ile Thr Lys Gln
            290                 295                 300

Ile Cys Asp Ala Val Gln Ala Arg Ala Glu Lys Asp Lys Asn His Gly
305                 310                 315                 320

Val Ile Leu Ile Pro Glu Gly Leu Val Glu Ser Ile Pro Glu Leu Tyr
                325                 330                 335

Ala Leu Leu Gln Glu Ile Asn Gly Leu His Gly Lys Gly Val Ser Ile
            340                 345                 350

Glu Asn Ile Ser Ser Gln Leu Ser Pro Trp Ala Ser Ala Leu Phe Glu
        355                 360                 365

Phe Leu Pro Gln Phe Ile Arg Gln Gln Leu Leu Arg Pro Glu Ser
    370                 375                 380

Asp Asp Ser Ala Gln Leu Ser Gln Ile Glu Thr Glu Lys Leu Leu Ala
385                 390                 395                 400

Gln Leu Val Glu Thr Glu Met Asn Lys Arg Leu Lys Glu Gly Thr Tyr
                405                 410                 415

Lys Gly Lys Lys Phe Asn Ala Ile Cys His Phe Gly Tyr Gln Ala
            420                 425                 430

Arg Gly Ala Met Pro Ser Lys Phe Asp Cys Asp Tyr Ala Tyr Val Leu
            435                 440                 445

Gly His Val Ser Tyr His Ile Leu Ala Ala Gly Leu Asn Gly Tyr Met
    450                 455                 460

Ala Thr Val Thr Asn Leu Lys Ser Pro Leu Asn Lys Trp Arg Cys Gly
465                 470                 475                 480

Ala Ala Pro Ile Ser Ser Met Met Thr Val Lys Arg Trp Ser Arg Gly
                485                 490                 495

Pro Ser Thr Thr Gln Ile Gly Lys Pro Ala Val His Met Ala Ser Val
            500                 505                 510

Asp Leu Arg Gly Lys Ala Tyr Glu Leu Leu Arg Gln Asn Ser Ser Ser
        515                 520                 525

Cys Leu Leu Glu Asp Ile Tyr Arg Asn Pro Gly Pro Leu Gln Phe Glu
    530                 535                 540

Gly Pro Gly Ser Asp Ser Lys Pro Ile Ser Leu Cys Val Glu Asp Gln
545                 550                 555                 560

Asp Tyr Met Gly Arg Ile Lys Lys Leu Gln Glu Tyr Leu Glu Lys Val
                565                 570                 575

Lys Ser Ile Val Lys Pro Gly Cys Ser Gln Asp Val Leu Lys Ala Ala
            580                 585                 590

Leu Ser Ala Met Ser Ser Val Thr Asp Thr Leu Ala Ile Met Thr Ser
        595                 600                 605

Ser Ser Thr Gly Gln Ala Pro Leu
    610                 615

<210> SEQ ID NO 60
<211> LENGTH: 616
<212> TYPE: PRT
<213> ORGANISM: Festuca arundinacea

<400> SEQUENCE: 60

Met Asp Ser Asp Tyr Gly Val Pro Arg Glu Leu Ser Glu Val Gln Lys
1               5                   10                  15

Lys Arg Thr Leu Tyr Gln Pro Glu Leu Pro Pro Cys Leu Gln Gly Thr
            20                  25                  30

Thr Val Arg Val Glu Tyr Gly Asp Val Ala Ile Ala Ala Asp Pro Ala
        35                  40                  45

```
Gly Ala His Val Ile Ser His Ala Phe Pro His Thr Tyr Gly Gln Pro
     50                  55                  60

Leu Ala His Phe Leu Arg Lys Ala Ala Asn Val Ala Asp Ala Lys Val
 65                  70                  75                  80

Ile Ser Glu His Pro Ala Val Arg Val Gly Ile Val Phe Cys Gly Arg
                 85                  90                  95

Gln Ser Pro Gly Gly His Asn Val Ile Trp Gly Leu His Asp Ala Ile
            100                 105                 110

Lys Ala His Asn Ser Asn Ser Lys Leu Ile Gly Phe Leu Gly Gly Ser
            115                 120                 125

Asp Gly Leu Leu Ala Gln Lys Thr Leu Glu Ile Thr Asp Glu Val Leu
130                 135                 140

Ser Ser Tyr Lys Asn Gln Gly Gly Tyr Asp Met Leu Gly Arg Thr Lys
145                 150                 155                 160

Asp Gln Ile Arg Thr Thr Glu Gln Val Asn Gly Ala Met Ala Ser Cys
                165                 170                 175

Gln Asp Leu Lys Leu Asp Ala Leu Ile Ile Ile Gly Gly Val Thr Ser
            180                 185                 190

Asn Thr Asp Ala Ala Gln Leu Ala Glu Thr Phe Ala Glu Ala Lys Cys
            195                 200                 205

Ala Thr Lys Val Val Gly Val Pro Val Thr Leu Asn Gly Asp Leu Lys
            210                 215                 220

Asn Gln Phe Val Glu Thr Thr Val Gly Phe Asp Thr Ile Cys Lys Val
225                 230                 235                 240

Asn Ser Gln Leu Ile Ser Asn Met Cys Thr Asp Ala Leu Ser Ala Glu
                245                 250                 255

Lys Tyr Tyr Tyr Phe Ile Arg Met Met Gly Arg Lys Ala Ser His Val
            260                 265                 270

Ala Leu Glu Cys Ala Leu Gln Ser His Pro Asn Met Val Ile Leu Gly
            275                 280                 285

Glu Glu Val Ala Ala Ser Lys Leu Thr Ile Phe Asp Ile Thr Lys Gln
290                 295                 300

Ile Cys Asp Ala Val Gln Ala Arg Ala Glu Lys Asp Lys Asn His Gly
305                 310                 315                 320

Val Ile Leu Ile Pro Glu Gly Leu Val Glu Ser Ile Pro Glu Leu Tyr
                325                 330                 335

Ala Leu Leu Gln Glu Ile Asn Gly Leu His Gly Lys Gly Val Ser Ile
            340                 345                 350

Glu Asn Ile Ser Ser Gln Leu Ser Pro Trp Ala Ser Ala Leu Phe Glu
            355                 360                 365

Phe Leu Pro Gln Phe Ile Arg His Gln Leu Leu Arg Pro Glu Ser
370                 375                 380

Asp Asp Ser Ala Gln Leu Ser Gln Ile Glu Thr Glu Lys Leu Leu Ala
385                 390                 395                 400

Gln Leu Val Glu Thr Glu Met Asn Lys Arg Leu Lys Glu Gly Thr Tyr
                405                 410                 415

Lys Gly Lys Lys Phe Asn Ala Ile Cys His Phe Phe Gly Tyr Gln Ala
            420                 425                 430

Arg Gly Ala Met Pro Ser Lys Phe Asp Cys Asp Tyr Ala Tyr Val Leu
            435                 440                 445

Gly His Val Ser Tyr His Ile Leu Ala Ala Gly Leu Asn Gly Tyr Met
450                 455                 460
```

-continued

```
Ala Thr Val Thr Asn Leu Lys Ser Pro Leu Asn Lys Trp Arg Cys Gly
465                 470                 475                 480

Ala Ala Pro Ile Ser Ser Met Met Thr Val Lys Arg Trp Ser Arg Gly
            485                 490                 495

Pro Ser Thr Thr Gln Ile Gly Lys Pro Ala Met His Met Ala Thr Val
            500                 505                 510

Asp Leu Arg Gly Lys Ala Tyr Glu Leu Leu Arg Gln Asn Ser Ser Ser
        515                 520                 525

Tyr Leu Leu Glu Asp Ile Tyr Arg Asn Pro Gly Pro Leu Gln Phe Glu
    530                 535                 540

Gly Pro Gly Ala Asp Ser Lys Pro Ile Ser Leu Cys Val Glu Asp Gln
545                 550                 555                 560

Asp Tyr Met Gly Arg Ile Lys Lys Leu Gln Glu Tyr Leu Glu Lys Val
                565                 570                 575

Lys Ser Ile Val Lys Pro Gly Cys Ser Gln Asp Val Leu Lys Ala Ala
            580                 585                 590

Leu Ser Ala Met Ser Ser Val Thr Glu Thr Leu Ala Ile Met Thr Ser
        595                 600                 605

Ser Ser Thr Gly Gln Ala Pro Leu
    610                 615

<210> SEQ ID NO 61
<211> LENGTH: 563
<212> TYPE: PRT
<213> ORGANISM: Lolium perenne

<400> SEQUENCE: 61

Met Ala Ala Ala Ala Val Ala Thr Ser Asn Gly Ala Ser Ala Asn Gly
1               5                   10                  15

Pro Thr Pro Gly Arg Leu Ala Ser Val Tyr Ser Glu Val Gln Thr Ser
            20                  25                  30

Arg Ile Ala His Ala Leu Pro Leu Pro Ser Val Leu Arg Ser His Phe
        35                  40                  45

Thr Leu Ala Asp Gly Ala Ala Ser Ser Ala Thr Gly Asn Pro Glu Glu
    50                  55                  60

Ile Ala Lys Leu Phe Pro Asn Leu Tyr Gly Gln Pro Ser Ala Ala Val
65                  70                  75                  80

Val Pro Ser Ala Gln Pro Val Ala Thr Lys Pro Leu Lys Ile Gly Val
                85                  90                  95

Val Leu Ser Gly Gly Gln Ala Pro Gly Gly His Asn Val Ile Cys Gly
            100                 105                 110

Ile Phe Asp Tyr Leu Gln Glu Arg Ala Lys Gly Ser Thr Met Tyr Gly
        115                 120                 125

Phe Lys Gly Gly Pro Ala Gly Val Met Lys Gly Lys Tyr Val Glu Leu
    130                 135                 140

Asn Ala Asp Phe Val Tyr Pro Tyr Arg Asn Gln Gly Gly Phe Asp Met
145                 150                 155                 160

Ile Cys Ser Gly Arg Asp Lys Ile Glu Thr Pro Glu Gln Phe Lys Gln
                165                 170                 175

Ala Glu Asp Thr Val Thr Lys Leu Asp Leu Asp Gly Leu Val Val Ile
            180                 185                 190

Gly Gly Asp Asp Ser Asn Thr Asn Ala Cys Leu Leu Gly Glu Tyr Phe
        195                 200                 205

Arg Gly Arg Asn Leu Lys Thr Arg Val Ile Gly Cys Pro Lys Thr Ile
    210                 215                 220
```

-continued

```
Asp Gly Asp Leu Lys Cys Lys Glu Val Pro Thr Ser Phe Gly Phe Asp
225                 230                 235                 240

Thr Ala Cys Lys Ile Tyr Ser Glu Met Ile Gly Asn Val Met Thr Asp
            245                 250                 255

Ala Arg Ser Thr Gly Lys Tyr Tyr His Phe Val Arg Leu Met Gly Arg
        260                 265                 270

Ala Ala Ser His Ile Thr Leu Glu Cys Ala Leu Gln Thr His Pro Asn
    275                 280                 285

Val Ser Leu Ile Gly Glu Glu Val Ala Glu Lys Lys Glu Thr Leu Lys
290                 295                 300

Gln Val Thr Asp Tyr Ile Thr Asp Val Ile Cys Lys Arg Ala Glu Leu
305                 310                 315                 320

Gly Tyr Asn Tyr Gly Val Ile Leu Ile Pro Glu Gly Leu Ile Asp Phe
                325                 330                 335

Ile Pro Glu Val Gln Lys Leu Ile Ala Glu Leu Asn Glu Ile Leu Ala
            340                 345                 350

His Asp Val Val Asp Glu Ala Gly Ala Trp Lys Ser Lys Leu Gln Pro
        355                 360                 365

Glu Ser Arg Gln Leu Phe Asp Phe Leu Pro Asn Thr Ile Gln Glu Gln
    370                 375                 380

Leu Leu Leu Glu Arg Asp Pro His Gly Asn Val Gln Val Ala Lys Ile
385                 390                 395                 400

Glu Thr Glu Lys Met Leu Ile Ala Met Val Glu Thr Glu Leu Glu Lys
                405                 410                 415

Arg Arg Ser Ala Gly Lys Tyr Ser Ala His Phe Arg Gly Gln Ser His
            420                 425                 430

Phe Phe Gly Tyr Glu Gly Arg Cys Gly Leu Pro Thr Asn Phe Asp Ser
        435                 440                 445

Ser Tyr Cys Tyr Ala Leu Gly Tyr Gly Ala Gly Ala Leu Leu Gln Phe
    450                 455                 460

Gly Lys Thr Gly Leu Ile Ser Ser Val Gly Asn Leu Ala Ala Pro Val
465                 470                 475                 480

Glu Glu Trp Thr Val Gly Gly Thr Pro Leu Thr Ala Leu Met Asp Val
                485                 490                 495

Glu Arg Arg His Gly Lys Phe Lys Pro Val Ile Lys Lys Ala Met Val
            500                 505                 510

Glu Leu Asp Ala Ala Pro Phe Lys Lys Phe Ala Ser Met Arg Asp Glu
        515                 520                 525

Trp Ala Ile Lys Asn Arg Tyr Ile Ser Pro Gly Pro Ile Gln Phe Ser
    530                 535                 540

Gly Pro Gly Ser Asp Ala Ser Asn His Thr Leu Met Leu Glu Leu Gly
545                 550                 555                 560

Ala Gln Thr
```

<210> SEQ ID NO 62
<211> LENGTH: 563
<212> TYPE: PRT
<213> ORGANISM: Lolium perenne

<400> SEQUENCE: 62

```
Met Ala Ala Ala Ala Val Ala Thr Ser Asn Gly Ala Ser Ala Asn Gly
1               5                   10                  15

Pro Thr Pro Gly Arg Leu Ala Ser Val Tyr Ser Glu Val Gln Thr Ser
            20                  25                  30
```

```
-continued

Arg Ile Ala His Ala Leu Pro Leu Pro Ser Val Leu Arg Ser His Phe
         35                  40                  45

Thr Leu Ala Asp Gly Ala Ala Ser Ser Ala Thr Gly Asn Pro Glu Glu
     50                  55                  60

Ile Ala Lys Leu Phe Pro Asn Leu Tyr Gly Gln Pro Ser Ala Ala Val
 65              70                  75                      80

Val Pro Ser Ala Gln Pro Val Ala Thr Lys Pro Leu Lys Ile Gly Val
                 85                  90                  95

Val Leu Ser Gly Gly Gln Ala Pro Gly Gly His Asn Val Ile Cys Gly
             100                 105                 110

Ile Phe Asp Tyr Leu Gln Glu Arg Ala Lys Gly Ser Thr Met Tyr Gly
             115                 120                 125

Phe Lys Gly Gly Pro Ala Gly Val Met Lys Gly Lys Tyr Val Glu Leu
         130                 135                 140

Asn Ala Asp Phe Val Tyr Pro Tyr Arg Asn Gln Gly Gly Phe Asp Met
145                 150                 155                 160

Ile Cys Ser Gly Arg Asp Lys Ile Glu Thr Pro Glu Gln Phe Lys Gln
                 165                 170                 175

Ala Glu Asp Thr Val Thr Lys Leu Asp Leu Asp Gly Leu Val Val Ile
             180                 185                 190

Gly Gly Asp Asp Ser Asn Thr Asn Ala Cys Leu Leu Gly Glu Tyr Phe
         195                 200                 205

Arg Gly Arg Asn Leu Lys Thr Arg Val Ile Gly Cys Pro Lys Thr Ile
     210                 215                 220

Asp Gly Asp Leu Lys Cys Lys Glu Val Pro Thr Ser Phe Gly Phe Asp
225                 230                 235                 240

Thr Ala Cys Lys Ile Tyr Ser Glu Met Ile Gly Asn Val Met Thr Asp
                 245                 250                 255

Ala Arg Ser Thr Gly Lys Tyr Tyr His Phe Val Arg Leu Met Gly Arg
             260                 265                 270

Ala Ala Ser His Ile Thr Leu Glu Cys Ala Leu Gln Thr His Pro Asn
         275                 280                 285

Val Ser Leu Ile Gly Glu Glu Val Ala Glu Lys Lys Glu Thr Leu Lys
     290                 295                 300

Gln Val Thr Asp Tyr Ile Thr Asp Val Ile Cys Lys Arg Ala Glu Leu
305                 310                 315                 320

Gly Tyr Asn Tyr Gly Val Ile Leu Ile Pro Glu Gly Leu Ile Asp Phe
                 325                 330                 335

Ile Pro Glu Val Gln Lys Leu Ile Ala Glu Leu Asn Glu Ile Leu Ala
             340                 345                 350

His Asp Val Val Asp Glu Ala Gly Ala Trp Lys Ser Lys Leu Gln Pro
         355                 360                 365

Glu Ser Arg Gln Leu Phe Asp Phe Leu Pro Asn Thr Ile Gln Glu Gln
     370                 375                 380

Leu Leu Leu Glu Arg Asp Pro His Gly Asn Val Gln Val Ala Lys Ile
385                 390                 395                 400

Glu Thr Glu Lys Met Leu Ile Ala Met Val Glu Thr Glu Leu Glu Lys
                 405                 410                 415

Arg Arg Ser Ala Gly Lys Tyr Ser Ala His Phe Arg Gly Gln Ser His
             420                 425                 430

Phe Phe Gly Tyr Glu Gly Arg Cys Gly Leu Pro Thr Asn Phe Asp Ser
         435                 440                 445
```

```
Ser Tyr Cys Tyr Ala Leu Gly Tyr Gly Ala Gly Ala Leu Leu Gln Phe
    450                 455                 460

Gly Lys Thr Gly Leu Ile Ser Ser Val Gly Asn Leu Ala Ala Pro Val
465                 470                 475                 480

Glu Glu Trp Thr Val Gly Gly Thr Pro Leu Thr Ala Leu Met Asp Val
                485                 490                 495

Glu Arg Arg His Gly Lys Phe Lys Pro Val Ile Lys Lys Ala Met Val
            500                 505                 510

Glu Leu Asp Ala Ala Pro Phe Lys Lys Phe Ala Ser Met Arg Asp Glu
        515                 520                 525

Trp Ala Ile Lys Asn Arg Tyr Ile Ser Pro Gly Pro Ile Gln Phe Ser
530                 535                 540

Gly Pro Gly Ser Asp Ala Ser Asn His Thr Leu Met Leu Glu Leu Gly
545                 550                 555                 560

Ala Gln Thr

<210> SEQ ID NO 63
<211> LENGTH: 563
<212> TYPE: PRT
<213> ORGANISM: Festuca arundinacea

<400> SEQUENCE: 63

Met Ala Ala Ala Val Ala Thr Ser Asn Gly Ala Ser Ala Asn Gly
  1               5                  10                  15

Pro Thr Pro Gly Arg Leu Ala Ser Val Tyr Ser Glu Val Gln Thr Ser
                 20                  25                  30

Arg Ile Ala His Ala Leu Pro Leu Pro Ser Val Leu Arg Ser Asn Phe
             35                  40                  45

Thr Leu Ala Asp Gly Pro Ala Ser Ser Ala Thr Gly Asn Pro Glu Glu
         50                  55                  60

Ile Ala Lys Leu Phe Pro Asn Leu Tyr Gly Gln Pro Ser Ala Ala Val
 65                  70                  75                  80

Val Pro Ser Ala Glu Pro Val Pro Thr Lys Pro Leu Lys Ile Gly Val
                 85                  90                  95

Val Leu Ser Gly Gly Gln Ala Pro Gly Gly His Asn Val Ile Cys Gly
            100                 105                 110

Ile Phe Asp Tyr Leu Gln Glu Arg Ala Lys Gly Ser Thr Met Tyr Gly
        115                 120                 125

Phe Lys Gly Gly Pro Ala Gly Ile Met Lys Gly Lys Tyr Ile Glu Leu
130                 135                 140

Asn Ala Asp Phe Val Tyr Pro Tyr Arg Asn Gln Gly Gly Phe Asp Met
145                 150                 155                 160

Ile Cys Ser Gly Arg Asp Lys Ile Glu Thr Pro Glu Gln Phe Lys Gln
                165                 170                 175

Ala Glu Asp Thr Val Asn Lys Leu Asp Leu Asp Gly Leu Val Val Ile
            180                 185                 190

Gly Gly Asp Asp Ser Asn Thr Asn Ala Cys Leu Leu Gly Glu Tyr Phe
        195                 200                 205

Arg Gly Arg Asn Leu Lys Thr Arg Val Ile Gly Cys Pro Lys Thr Ile
210                 215                 220

Asp Gly Asp Leu Lys Cys Lys Glu Val Pro Ile Ser Phe Gly Phe Asp
225                 230                 235                 240

Thr Ala Cys Lys Ile Tyr Ser Glu Met Ile Gly Asn Val Met Thr Asp
                245                 250                 255
```

```
Ala Arg Ser Thr Gly Lys Tyr Tyr His Phe Val Arg Leu Met Gly Arg
            260                 265                 270

Ala Ala Ser His Ile Thr Leu Glu Cys Ala Leu Gln Thr His Pro Asn
        275                 280                 285

Val Ser Leu Ile Gly Glu Glu Val Ala Glu Lys Lys Glu Thr Leu Lys
    290                 295                 300

Gln Val Thr Asp Tyr Ile Thr Asp Val Ile Cys Lys Arg Ala Glu Leu
305                 310                 315                 320

Gly Tyr Asn Tyr Gly Val Ile Leu Ile Pro Glu Gly Leu Ile Asp Phe
                325                 330                 335

Ile Pro Glu Val Gln Lys Leu Ile Ala Glu Leu Asn Glu Ile Leu Ala
            340                 345                 350

His Asp Val Val Asp Glu Ala Gly Ala Trp Lys Ser Lys Leu Gln Pro
        355                 360                 365

Glu Ser Arg Gln Leu Phe Asp Phe Leu Pro Asn Thr Ile Gln Glu Gln
    370                 375                 380

Leu Leu Leu Glu Arg Asp Pro His Gly Asn Val Gln Val Ala Lys Ile
385                 390                 395                 400

Glu Thr Glu Lys Met Leu Ile Ala Met Val Glu Thr Glu Leu Glu Lys
                405                 410                 415

Arg Arg Ala Ala Gly Lys Tyr Ser Ala His Phe Arg Gly Gln Ser His
            420                 425                 430

Phe Phe Gly Tyr Glu Gly Arg Cys Gly Leu Pro Thr Asn Phe Asp Ser
        435                 440                 445

Ser Tyr Cys Tyr Ala Leu Gly Tyr Gly Ala Gly Leu Leu Gln Phe
    450                 455                 460

Gly Lys Thr Gly Leu Ile Ser Ser Val Gly Asn Leu Ala Ala Pro Val
465                 470                 475                 480

Glu Glu Trp Thr Val Gly Gly Thr Pro Leu Thr Ala Leu Met Asp Val
                485                 490                 495

Glu Arg Arg His Gly Lys Phe Lys Pro Val Ile Lys Lys Ala Met Val
            500                 505                 510

Glu Leu Asp Ala Ala Pro Phe Lys Lys Phe Ala Ser Met Arg Asp Glu
        515                 520                 525

Trp Ala Ile Lys Asn Arg Tyr Ile Ser Pro Gly Pro Ile Gln Phe Ser
    530                 535                 540

Gly Pro Gly Ser Asp Ala Ser Asn His Thr Leu Met Leu Glu Leu Gly
545                 550                 555                 560

Ala Gln Ile

<210> SEQ ID NO 64
<211> LENGTH: 964
<212> TYPE: PRT
<213> ORGANISM: Lolium perenne

<400> SEQUENCE: 64

Met Val Gly Asn Asp Asn Trp Ile Asn Ser Tyr Leu Asp Ala Ile Leu
1               5                   10                  15

Asp Ala Gly Lys Ser Ser Ile Gly Gly Asp Arg Pro Ser Leu Leu Leu
            20                  25                  30

Arg Glu Arg Gly His Phe Ser Pro Ala Arg Tyr Phe Val Glu Glu Val
        35                  40                  45

Ile Thr Gly Tyr Asp Glu Thr Asp Leu Tyr Lys Thr Trp Leu Arg Ala
    50                  55                  60
```

-continued

```
Asn Ala Met Arg Ser Pro Gln Glu Arg Asn Thr Arg Leu Glu Asn Met
 65                  70                  75                  80

Thr Trp Arg Ile Trp Asn Leu Ala Arg Lys Lys Glu Leu Glu Lys
                 85                  90                  95

Glu Glu Ala Cys Arg Leu Leu Lys Arg His Pro Glu Thr Glu Lys Thr
                100                 105                 110

Arg Thr Asp Ala Thr Ala Asp Met Ser Glu Asp Leu Phe Asp Gly Glu
                115                 120                 125

Lys Gly Glu Asp Ala Gly Asp Pro Ser Val Ala Tyr Gly Asp Ser Thr
130                 135                 140

Thr Gly Ser Ser Pro Lys Thr Ser Ser Val Asp Lys Leu Tyr Ile Val
145                 150                 155                 160

Leu Ile Ser Leu His Gly Leu Val Arg Gly Glu Asn Met Glu Leu Gly
                165                 170                 175

Arg Asp Ser Asp Thr Gly Gly Gln Val Lys Tyr Val Glu Phe Ala
                180                 185                 190

Lys Ala Leu Ser Ser Ser Pro Gly Val Tyr Arg Val Asp Leu Leu Thr
                195                 200                 205

Arg Gln Ile Val Ala Pro Asn Phe Asp Arg Ser Tyr Gly Glu Pro Glu
210                 215                 220

Glu Met Leu Val Ser Thr Thr Phe Lys Asn Ser Lys His Glu Arg Gly
225                 230                 235                 240

Val Asn Ser Gly Gly Tyr Ile Ile Arg Ile Pro Phe Gly Pro Lys Asp
                245                 250                 255

Lys Tyr Leu Ala Lys Glu His Met Trp Pro Phe Ile Gln Asp Phe Val
                260                 265                 270

Asp Gly Ala Leu Ser His Ile Leu Arg Met Ser Lys Thr Ile Gly Glu
                275                 280                 285

Glu Ile Gly Cys Gly His Pro Val Trp Pro Ala Val Ile His Gly His
                290                 295                 300

Tyr Ala Ser Ala Gly Val Ala Ala Leu Leu Ser Gly Ala Leu Asn
305                 310                 315                 320

Leu Pro Met Ala Phe Thr Gly His Phe Leu Gly Lys Asp Lys Leu Glu
                325                 330                 335

Gly Leu Leu Lys Gln Gly Arg Gln Ser Arg Glu Gln Ile Asn Met Thr
                340                 345                 350

Tyr Lys Ile Met Arg Arg Ile Glu Ala Glu Glu Leu Ser Leu Asp Ala
                355                 360                 365

Ser Glu Ile Val Ile Ala Ser Thr Arg Gln Glu Ile Glu Glu Gln Trp
370                 375                 380

Asn Leu Tyr Asp Gly Phe Glu Val Ile Leu Ala Arg Lys Leu Arg Ala
385                 390                 395                 400

Arg Val Lys Arg Gly Ala Asn Cys Tyr Gly Arg Tyr Met Pro Arg Met
                405                 410                 415

Val Ile Ile Pro Pro Gly Val Glu Phe Gly His Val His Asp Phe
                420                 425                 430

Asp Met Asp Gly Glu Glu Asn His Gly Pro Ala Ser Glu Asp Pro
                435                 440                 445

Pro Ile Trp Ser Gln Ile Met Arg Phe Thr Asn Pro Arg Lys Pro
                450                 455                 460

Met Ile Leu Ala Val Ala Arg Pro Tyr Pro Glu Lys Asn Ile Thr Ser
465                 470                 475                 480

Leu Val Lys Ala Phe Gly Glu Cys Arg Pro Leu Arg Glu Leu Ala Asn
```

-continued

```
                485                 490                 495
Leu Thr Leu Ile Met Gly Asn Arg Glu Ala Ile Ser Lys Met His Asn
            500                 505                 510
Thr Ser Ala Ser Val Leu Thr Ser Val Leu Thr Leu Ile Asp Glu Tyr
            515                 520                 525
Asp Leu Tyr Gly Gln Val Ala Tyr Pro Lys His His Lys His Ser Glu
            530                 535                 540
Val Pro Asp Ile Tyr Arg Leu Ala Thr Arg Thr Lys Gly Ala Phe Val
545                 550                 555                 560
Asn Val Ala Tyr Phe Glu Gln Phe Gly Val Thr Leu Ile Glu Ala Ala
                565                 570                 575
Met Asn Gly Leu Pro Val Ile Ala Thr Lys Asn Gly Ala Pro Val Glu
            580                 585                 590
Ile Asn Gln Val Leu Asn Asn Gly Leu Leu Val Asp Pro His Asp Gln
            595                 600                 605
Asn Ala Ile Ala Asp Ala Leu Tyr Lys Leu Leu Ser Glu Lys Gln Leu
            610                 615                 620
Trp Ser Arg Cys Arg Glu Asn Gly Leu Lys Asn Ile His Gln Phe Ser
625                 630                 635                 640
Trp Pro Glu His Cys Lys Asn His Leu Ser Arg Ile Leu Thr Leu Gly
                645                 650                 655
Ala Arg Ser Pro Ala Ile Gly Ser Lys Glu Glu Arg Ser Asn Ala Pro
            660                 665                 670
Ile Ser Gly Arg Lys His Ile Ile Val Ile Ser Val Asp Ser Val Asn
            675                 680                 685
Lys Glu Asp Leu Val Arg Ile Ile Arg Asn Ala Ile Glu Ala Ala His
690                 695                 700
Thr Gln Asn Thr Pro Ala Ser Thr Gly Phe Val Leu Ser Thr Ser Leu
705                 710                 715                 720
Thr Leu Ser Glu Ile Cys Ser Leu Leu Val Ser Val Gly Met His Pro
                725                 730                 735
Ala Gly Phe Asp Ala Phe Ile Cys Asn Ser Gly Ser Ser Ile Tyr Tyr
            740                 745                 750
Pro Ser Tyr Ser Gly Asn Thr Pro Ser Ser Ser Lys Val Thr His Val
            755                 760                 765
Ile Asp Gln Asn His Gln Ser His Ile Glu Tyr Arg Trp Gly Gly Glu
770                 775                 780
Gly Leu Arg Lys Tyr Leu Val Lys Trp Ala Thr Ser Val Val Glu Arg
785                 790                 795                 800
Lys Gly Arg Ile Glu Arg Gln Met Ile Phe Glu Asp Ser Glu His Ser
                805                 810                 815
Ser Thr Tyr Cys Leu Ala Phe Lys Val Val Asn Pro Asn His Leu Pro
            820                 825                 830
Pro Leu Lys Glu Leu Arg Lys Leu Met Arg Ile Gln Ser Leu Arg Cys
            835                 840                 845
Asn Ala Leu Tyr Asn His Ser Ala Thr Arg Leu Ser Val Thr Pro Ile
850                 855                 860
His Ala Ser Arg Ser Gln Ala Ile Arg Tyr Leu Phe Ile Arg Trp Gly
865                 870                 875                 880
Ile Glu Leu Pro Asn Ile Val Val Leu Val Gly Ser Gly Asp Ser
            885                 890                 895
Asp Tyr Glu Glu Leu Leu Gly Gly Leu His Arg Thr Ile Ile Leu Lys
            900                 905                 910
```

-continued

```
Gly Asp Phe Asn Ile Ala Ala Asn Arg Ile His Thr Val Arg Arg Tyr
            915                 920                 925

Pro Leu Gln Asp Val Val Ala Leu Asp Ser Ser Asn Ile Ile Glu Val
            930                 935                 940

Glu Gly Cys Thr Thr Asp Val Ile Lys Ser Ala Leu Arg Gln Ile Gly
945                 950                 955                 960

Val Pro Thr Gln

<210> SEQ ID NO 65
<211> LENGTH: 984
<212> TYPE: PRT
<213> ORGANISM: Festuca arundinacea
<220> FEATURE:
<221> NAME/KEY: VARIANT
<222> LOCATION: (1)...(984)
<223> OTHER INFORMATION: Xaa = Any Amino Acid

<400> SEQUENCE: 65

Met Val Gly Gly Met Cys Gly Asn Asp Asn Trp Ile Asn Ser Tyr Leu
1               5                   10                  15

Asp Ala Ile Leu Asp Ala Gly Lys Gly Ala Pro Gly Gly Gly Ala Gly
            20                  25                  30

Pro Gly Gly Gly Arg Gly Gly Gly Gly Ala Gly Asp Arg Pro
        35                  40                  45

Ser Leu Leu Leu Arg Glu Arg Gly His Phe Ser Pro Ala Arg Tyr Phe
    50                  55                  60

Val Glu Glu Val Ile Thr Gly Tyr Asp Glu Thr Asp Leu Tyr Lys Thr
65                  70                  75                  80

Trp Ser Arg Ala Asn Ala Met Arg Ser Pro Gln Glu Arg Asn Thr Arg
                85                  90                  95

Leu Glu Asn Met Thr Trp Arg Ile Trp Asn Leu Ala Arg Lys Lys Lys
            100                 105                 110

Glu Xaa Glu Ala Glu Glu Ala Asn Arg Leu Leu Lys Arg Arg Leu Glu
        115                 120                 125

Thr Glu Lys Pro Arg Thr Asp Ala Ala Ala Glu Met Ser Glu Asp Leu
    130                 135                 140

Phe Glu Gly Gln Lys Gly Glu Asp Ala Gly Asp Ala Ser Val Ala Tyr
145                 150                 155                 160

Gly Asp Ser Ser Ala Ser Asn Thr Pro Arg Ile Ser Ser Ile Asp Lys
                165                 170                 175

Leu Tyr Ile Val Leu Ile Ser Leu His Gly Leu Val Arg Gly Glu Asn
            180                 185                 190

Met Glu Leu Gly Arg Asp Ser Asp Thr Ser Gly Gln Val Lys Tyr Val
        195                 200                 205

Val Glu Leu Ala Lys Ala Leu Ser Ser Cys Pro Gly Val Tyr Arg Val
    210                 215                 220

Asp Leu Leu Thr Arg Gln Ile Leu Ala Pro Asn Tyr Asp Arg Gly Tyr
225                 230                 235                 240

Gly Glu Pro Ser Glu Thr Leu Leu Pro Thr Asn Leu Lys Asn Phe Lys
                245                 250                 255

His Glu Arg Gly Glu Asn Ser Gly Ala Tyr Ile Thr Arg Ile Pro Phe
            260                 265                 270

Gly Pro Lys Asp Lys Tyr Leu Ala Lys Glu Gln Leu Trp Pro Tyr Val
        275                 280                 285

Gln Glu Phe Val Asp Gly Ala Leu Ser His Ile Val Arg Met Ser Lys
```

```
            290                 295                 300
Thr Ile Gly Glu Glu Ile Gly Cys Gly His Pro Met Trp Pro Ala Ala
305                 310                 315                 320

Ile His Gly His Tyr Ala Ser Ala Gly Val Ala Ala Ala Leu Leu Ser
                325                 330                 335

Gly Ala Leu Asn Val His Met Ile Phe Thr Gly His Phe Leu Gly Arg
                340                 345                 350

Asp Lys Leu Glu Gly Leu Leu Lys Gln Gly Lys Gln Thr Arg Glu Glu
                355                 360                 365

Ile Asn Met Thr Tyr Lys Ile Met Arg Arg Ile Glu Ala Glu Glu Leu
                370                 375                 380

Ser Leu Asp Ala Ser Glu Ile Val Ile Ala Ser Thr Arg Gln Glu Ile
385                 390                 395                 400

Glu Glu Gln Trp Asn Leu Tyr Asp Gly Phe Glu Val Met Leu Ala Arg
                405                 410                 415

Lys Leu Arg Ala Arg Val Lys Arg Gly Ala Asn Cys Tyr Gly Arg Tyr
                420                 425                 430

Met Pro Arg Met Val Ile Ile Pro Pro Gly Val Glu Phe Gly His Met
                435                 440                 445

Ile Gln Asp Phe Asp Met Asp Gly Glu Glu Asp Ser Pro Ser Pro Ala
                450                 455                 460

Ser Glu Asp Pro Pro Ile Trp Ser Glu Ile Met Arg Phe Phe Thr Asn
465                 470                 475                 480

Pro Arg Lys Pro Leu Ile Leu Ala Val Ala Arg Pro Tyr Pro Glu Lys
                485                 490                 495

Asn Ile Thr Thr Leu Val Arg Ala Phe Gly Glu Cys Arg Pro Leu Arg
                500                 505                 510

Glu Leu Ala Asn Leu Thr Leu Ile Met Gly Asn Arg Glu Ala Ile Ser
                515                 520                 525

Lys Met Ser Asn Met Ser Ala Ala Val Leu Thr Ser Val Leu Thr Leu
                530                 535                 540

Ile Asp Glu Tyr Asp Leu Tyr Gly Gln Val Ala Tyr Pro Lys His His
545                 550                 555                 560

Lys His Ser Glu Val Leu Asp Ile Tyr Arg Leu Ala Ala Arg Thr Lys
                565                 570                 575

Gly Ala Phe Val Asn Val Ala Tyr Phe Glu Gln Phe Gly Val Thr Leu
                580                 585                 590

Ile Glu Ala Ala Met His Gly Leu Pro Val Ile Ala Thr Lys Asn Gly
                595                 600                 605

Ala Pro Val Glu Ile His Gln Val Leu Asn Asn Gly Leu Leu Val Asp
                610                 615                 620

Pro His Asp Gln Asn Ala Ile Ala Asp Ala Leu Tyr Lys Leu Leu Ser
625                 630                 635                 640

Glu Lys Gln Leu Trp Ser Arg Cys Arg Glu Asn Gly Leu Lys Asn Ile
                645                 650                 655

His Gln Phe Ser Trp Pro Glu His Cys Lys Asn Tyr Leu Ser Arg Ile
                660                 665                 670

Leu Thr Leu Ser Pro Arg Tyr Pro Ala Phe Ala Ser Asn Asp Asp Gln
                675                 680                 685

Ile Lys Ala Pro Ile Lys Gly Arg Lys Tyr Ile Ile Val Ile Ala Val
                690                 695                 700

Asp Ser Ala Ser Lys Lys Asp Leu Ala Phe Ile Ile Arg Asn Ser Ile
705                 710                 715                 720
```

```
Glu Ala Thr Arg Thr Glu Thr Ser Ser Gly Ser Thr Gly Phe Val Leu
            725                 730                 735

Ser Thr Ser Leu Thr Ile Ser Glu Ile His Ser Leu Leu Ile Ser Ala
            740                 745                 750

Gly Met Val Pro Thr Asp Phe Asp Ala Phe Ile Cys Asn Ser Gly Ser
            755                 760                 765

Asp Leu Phe Tyr Pro Ser Gln Thr Gly Asp Ser Pro Ser Thr Ser Arg
            770                 775                 780

Val Thr Phe Ala Leu Asp Arg Asn Tyr Gln Ser Arg Val Glu Tyr His
785                 790                 795                 800

Trp Gly Gly Glu Gly Leu Arg Lys Tyr Leu Val Lys Trp Ala Ser Ser
            805                 810                 815

Val Val Glu Arg Arg Gly Arg Met Glu Lys Gln Val Ile Phe Asp Asp
            820                 825                 830

Ser Glu His Ser Ser Thr Cys Cys Leu Ala Phe Arg Val Val Asn Pro
            835                 840                 845

Asn Tyr Leu Pro Pro Leu Lys Glu Leu Gln Lys Leu Met Arg Val Gln
            850                 855                 860

Ser Leu Arg Cys His Ala Leu Tyr Asn His Ser Ala Thr Arg Leu Ser
865                 870                 875                 880

Val Ile Pro Ile His Ala Ser Arg Ser Gln Ala Ile Arg Tyr Leu Ser
            885                 890                 895

Val Arg Trp Gly Ile Glu Leu Pro Asn Val Val Ile Leu Val Gly Glu
            900                 905                 910

Ser Gly Asp Ser Asp Tyr Glu Glu Leu Phe Gly Gly Leu His Lys Thr
            915                 920                 925

Val Val Leu Asn Gly Glu Phe Asn Thr Pro Ala Asn Arg Ile His Thr
            930                 935                 940

Val Arg Arg Tyr Pro Leu Gln Asp Val Ile Ala Leu Asp Cys Ser Asn
945                 950                 955                 960

Ile Val Gly Val Gln Gly Cys Ser Thr Asp Cys Met Arg Ser Thr Leu
            965                 970                 975

Glu Lys Leu Gly Ile Pro Thr Lys
            980

<210> SEQ ID NO 66
<211> LENGTH: 522
<212> TYPE: PRT
<213> ORGANISM: Festuca arundinacea

<400> SEQUENCE: 66

Met Val Arg Gly Gly Gly Asn Gly Glu Val Glu Leu Ser Val Gly Ala
1               5                   10                  15

Gly Gly Gly Gly Gly Gly Ala Gly Gly Leu Val Glu Pro Val Pro
            20                  25                  30

Ile Ser Leu Gly Arg Leu Val Leu Ala Gly Met Val Ala Gly Gly Val
            35                  40                  45

Gln Tyr Gly Trp Ala Leu Gln Leu Ser Leu Leu Thr Pro Tyr Val Gln
            50                  55                  60

Thr Leu Gly Leu Ser His Ala Leu Thr Ser Phe Met Trp Leu Cys Gly
65                  70                  75                  80

Pro Ile Ala Gly Leu Val Val Gln Pro Cys Val Gly Leu Tyr Ser Asp
            85                  90                  95

Lys Cys Thr Ser Arg Trp Gly Arg Arg Arg Pro Phe Ile Met Thr Gly
```

```
                    100                 105                 110
Cys Val Leu Ile Cys Ile Ala Val Val Ile Val Gly Phe Ser Ala Asp
            115                 120                 125
Ile Gly Ala Ala Leu Gly Asp Ser Lys Glu Cys Ser Leu Tyr His
    130                 135                 140
Gly Pro Arg Trp His Ala Ala Ile Val Tyr Val Leu Gly Phe Trp Leu
145                 150                 155                 160
Leu Asp Phe Ser Asn Asn Thr Val Gln Gly Pro Ala Arg Ala Leu Met
            165                 170                 175
Ala Asp Leu Ser Gly Lys Tyr Gly Pro Ser Ala Ala Asn Ser Ile Phe
            180                 185                 190
Cys Ser Trp Met Ala Leu Gly Asn Ile Leu Gly Tyr Ser Ser Gly Ser
            195                 200                 205
Thr Asp Lys Trp His Lys Trp Phe Pro Phe Leu Arg Thr Arg Ala Cys
    210                 215                 220
Cys Glu Ala Cys Ala Asn Leu Lys Gly Ala Phe Leu Val Ala Val Leu
225                 230                 235                 240
Phe Leu Cys Met Cys Leu Val Ile Thr Leu Ile Phe Ala Lys Glu Val
            245                 250                 255
Pro Tyr Lys Arg Ile Ala Pro Leu Pro Thr Lys Ala Asn Gly Gln Val
            260                 265                 270
Glu Val Glu Pro Ser Gly Pro Leu Ala Val Phe Gln Gly Ile Arg Asn
            275                 280                 285
Leu Pro Ser Gly Met Pro Ser Val Leu Val Thr Gly Leu Thr Trp
    290                 295                 300
Leu Ser Trp Phe Pro Phe Ile Leu Tyr Asp Thr Asp Trp Met Gly Arg
305                 310                 315                 320
Glu Ile Tyr His Gly Asp Pro Lys Gly Thr Pro Ala Glu Met Ser Ala
            325                 330                 335
Phe Gln Asp Gly Val Arg Ala Gly Ala Phe Gly Leu Leu Leu Asn Ser
            340                 345                 350
Ile Ile Leu Gly Phe Ser Ser Phe Leu Ile Glu Pro Met Cys Lys Arg
            355                 360                 365
Leu Gly Pro Arg Val Val Trp Val Ser Ser Asn Phe Leu Val Cys Ile
    370                 375                 380
Ala Met Ala Ala Thr Ala Ile Ile Ser Trp Trp Ser Thr Lys Glu Phe
385                 390                 395                 400
His Glu Tyr Val Gln His Ala Ile Thr Ala Ser Lys Asp Ile Lys Ile
            405                 410                 415
Val Cys Met Ala Leu Phe Ala Phe Leu Gly Val Pro Leu Ala Ile Leu
            420                 425                 430
Tyr Ser Val Pro Phe Ala Val Thr Ala Gln Leu Ala Ala Ser Lys Gly
            435                 440                 445
Gly Gly Gln Gly Leu Cys Thr Gly Val Leu Asn Ile Ser Ile Val Ile
            450                 455                 460
Pro Gln Val Ile Ile Ala Leu Gly Ala Gly Pro Trp Asp Gln Leu Phe
465                 470                 475                 480
Gly Lys Gly Asn Ile Pro Ala Phe Ala Ala Ser Ala Phe Ala Leu
            485                 490                 495
Ile Gly Gly Ile Val Gly Ile Phe Leu Leu Pro Lys Ile Ser Arg Arg
            500                 505                 510
Ser Phe Arg Ala Val Ser Thr Gly Gly His
            515                 520
```

<210> SEQ ID NO 67
<211> LENGTH: 407
<212> TYPE: PRT
<213> ORGANISM: Festuca arundinacea

<400> SEQUENCE: 67

```
Ile Cys Val Ala Val Val Val Gly Phe Ser Ala Asp Ile Gly Ala
 1               5                  10                  15

Ala Leu Gly Asp Ser Lys Glu Glu Cys Ser Leu Tyr His Gly Pro Arg
            20                  25                  30

Trp His Ala Ile Val Tyr Val Leu Gly Phe Trp Leu Leu Asp Phe
            35                  40                  45

Ser Asn Asn Thr Val Gln Gly Pro Ala Arg Ala Leu Met Ala Asp Leu
        50                  55                  60

Ser Gly Lys Tyr Gly Pro Ser Ala Ala Asn Ser Ile Phe Cys Ser Trp
 65                  70                  75                  80

Met Ala Leu Gly Asn Ile Leu Gly Tyr Ser Ser Gly Ser Thr Asp Lys
                85                  90                  95

Trp His Lys Trp Phe Pro Phe Leu Arg Thr Arg Ala Cys Cys Glu Ala
            100                 105                 110

Cys Ala Asn Leu Lys Gly Ala Phe Leu Val Ala Val Leu Phe Leu Cys
            115                 120                 125

Phe Cys Leu Val Ile Thr Leu Ile Phe Ala Lys Glu Val Pro Tyr Lys
        130                 135                 140

Arg Ile Ala Pro Leu Pro Thr Lys Ala Asn Gly Gln Val Glu Val Glu
145                 150                 155                 160

Pro Ser Gly Pro Leu Ala Val Phe Gln Gly Phe Arg Asn Leu Pro Ser
                165                 170                 175

Gly Met Pro Ser Val Leu Leu Val Thr Gly Leu Thr Trp Leu Ser Trp
            180                 185                 190

Phe Pro Phe Ile Leu Tyr Asp Thr Asp Trp Met Gly Arg Glu Ile Tyr
            195                 200                 205

His Gly Asp Pro Lys Gly Thr Pro Ala Glu Ala Ser Ala Phe Gln Asp
        210                 215                 220

Gly Val Arg Ala Gly Ala Phe Gly Leu Leu Asn Ser Ile Ile Leu
225                 230                 235                 240

Gly Phe Ser Ser Phe Leu Ile Glu Pro Met Cys Lys Arg Leu Gly Pro
                245                 250                 255

Arg Val Val Trp Val Ser Ser Asn Leu Leu Val Cys Ile Ala Met Ala
            260                 265                 270

Ala Thr Ala Ile Ile Ser Trp Trp Ser Thr Lys Glu Phe His Glu Tyr
            275                 280                 285

Val Gln His Ala Ile Thr Ala Ser Lys Asp Ile Lys Ile Val Cys Met
        290                 295                 300

Val Leu Phe Ala Phe Leu Gly Val Pro Leu Ala Ile Leu Tyr Ser Val
305                 310                 315                 320

Pro Phe Ala Val Thr Ala Gln Leu Ala Ala Asn Lys Gly Gly Gly Gln
                325                 330                 335

Gly Leu Cys Thr Gly Val Leu Asn Ile Ser Val Ile Pro Gln Val
            340                 345                 350

Ile Ile Ala Leu Gly Ala Gly Pro Trp Asp Gln Leu Phe Gly Lys Gly
        355                 360                 365

Asn Ile Pro Ala Phe Ala Ala Ala Ser Ala Phe Ala Leu Ile Gly Gly
```

-continued

```
                370                 375                 380
Ile Val Gly Ile Phe Leu Leu Pro Lys Ile Ser Arg His Ser Phe Arg
385                 390                 395                 400

Ala Val Ser Thr Gly Gly His
            405

<210> SEQ ID NO 68
<211> LENGTH: 522
<212> TYPE: PRT
<213> ORGANISM: Festuca arundinacea

<400> SEQUENCE: 68

Met Val Arg Gly Gly Asn Ser Glu Val Glu Leu Ser Val Gly Ala
1               5                   10                  15

Gly Gly Gly Gly Gly Ala Gly Gly Leu Val Glu Pro Val Pro
                20                  25                  30

Ile Ser Leu Gly Arg Leu Val Phe Ala Gly Met Val Ala Gly Gly Val
                35                  40                  45

Gln Tyr Gly Trp Ala Leu Gln Leu Ser Leu Leu Thr Pro Tyr Val Gln
    50                  55                  60

Thr Leu Gly Leu Ser His Ala Leu Thr Ser Phe Met Trp Leu Cys Gly
65                  70                  75                  80

Pro Ile Ala Gly Leu Val Val Gln Pro Cys Val Gly Leu Tyr Ser Asp
                85                  90                  95

Lys Cys Thr Ser Arg Trp Gly Arg Arg Pro Phe Ile Met Thr Gly
                100                 105                 110

Cys Val Leu Ile Cys Ile Ala Val Val Ile Val Gly Phe Ser Ala Asp
            115                 120                 125

Ile Gly Ala Ala Leu Gly Asp Ser Lys Glu Glu Cys Ser Leu Tyr His
    130                 135                 140

Gly Pro Arg Trp His Ala Ala Ile Val Tyr Val Leu Gly Phe Trp Leu
145                 150                 155                 160

Leu Asp Phe Ser Asn Asn Thr Val Gln Gly Pro Ala Arg Ala Leu Met
                165                 170                 175

Ala Asp Leu Ser Gly Lys Tyr Gly Pro Ser Ala Ala Asn Ser Ile Phe
            180                 185                 190

Cys Ser Trp Met Ala Leu Gly Asn Ile Leu Gly Tyr Ser Ser Gly Ser
    195                 200                 205

Thr Asp Lys Trp His Lys Trp Phe Pro Phe Leu Arg Thr Arg Ala Cys
210                 215                 220

Cys Glu Ala Cys Ala Asn Leu Lys Gly Ala Phe Leu Val Ala Val Leu
225                 230                 235                 240

Phe Leu Cys Phe Cys Leu Val Ile Thr Leu Ile Phe Ala Lys Glu Val
                245                 250                 255

Pro Tyr Lys Arg Ile Ala Pro Leu Pro Thr Lys Ala Asn Gly Gln Val
            260                 265                 270

Glu Val Glu Pro Ser Gly Pro Leu Ala Val Phe Gln Gly Phe Arg Asn
    275                 280                 285

Leu Pro Ser Gly Met Pro Ser Val Leu Leu Val Thr Gly Leu Thr Trp
290                 295                 300

Leu Ser Trp Phe Pro Phe Ile Leu Tyr Asp Thr Asp Trp Met Gly Arg
305                 310                 315                 320

Glu Ile Tyr His Gly Asp Pro Lys Gly Thr Pro Ala Glu Ala Ser Ala
                325                 330                 335
```

```
Phe Gln Asp Gly Val Arg Ala Gly Ala Phe Gly Leu Leu Asn Ser
            340                 345                 350

Ile Ile Leu Gly Phe Ser Ser Phe Leu Ile Glu Pro Met Cys Lys Arg
        355                 360                 365

Leu Gly Pro Arg Val Val Trp Val Ser Ser Asn Leu Leu Val Cys Ile
    370                 375                 380

Ala Met Ala Ala Thr Ala Ile Ile Ser Trp Trp Ser Thr Lys Glu Phe
385                 390                 395                 400

His Glu Tyr Val Gln His Ala Ile Thr Ala Ser Lys Asp Ile Lys Ile
            405                 410                 415

Val Cys Met Val Leu Phe Ala Phe Leu Gly Val Pro Leu Ala Ile Leu
        420                 425                 430

Tyr Ser Val Pro Phe Ala Val Thr Ala Gln Leu Ala Ala Asn Lys Gly
    435                 440                 445

Gly Gly Gln Gly Leu Cys Thr Gly Val Leu Asn Ile Ser Ile Val Ile
        450                 455                 460

Pro Gln Val Ile Ile Ala Leu Gly Ala Gly Pro Trp Asp Gln Leu Phe
465                 470                 475                 480

Gly Lys Gly Asn Ile Pro Ala Phe Ala Ala Ala Ser Ala Phe Ala Leu
            485                 490                 495

Ile Gly Gly Ile Val Gly Ile Phe Leu Leu Pro Lys Ile Ser Arg His
        500                 505                 510

Ser Phe Arg Ala Val Ser Thr Gly Gly His
        515                 520

<210> SEQ ID NO 69
<211> LENGTH: 506
<212> TYPE: PRT
<213> ORGANISM: Lolium perenne

<400> SEQUENCE: 69

Met Pro Pro Pro Arg Arg Pro Thr Thr Gly Gly Thr Thr Thr Thr Ser
1               5                   10                  15

Ala Ala Leu Pro Pro Arg Lys Val Pro Leu Arg Ser Leu Leu Arg
            20                  25                  30

Ala Ala Ser Val Ala Cys Gly Val Gln Phe Gly Trp Ala Leu Gln Leu
        35                  40                  45

Ser Leu Leu Thr Pro Tyr Val Gln Glu Leu Gly Ile Pro His Ala Phe
    50                  55                  60

Ala Ser Leu Val Trp Leu Cys Gly Pro Leu Ser Gly Leu Leu Val Gln
65                  70                  75                  80

Pro Leu Ile Gly His Leu Ser Asp Arg Ile Ala Pro Ala Asp Ser Pro
            85                  90                  95

Leu Gly Arg Arg Arg Pro Phe Ile Ala Ala Gly Ala Ala Ser Ile Ala
        100                 105                 110

Phe Ser Val Leu Thr Val Gly Phe Ser Ala Asp Leu Gly Arg Leu Phe
    115                 120                 125

Gly Asp Asn Val Arg Pro Gly Ser Thr Arg Tyr Gly Ala Ile Ile Val
130                 135                 140

Tyr Met Ile Gly Phe Trp Leu Leu Asp Val Gly Asn Asn Ala Thr Gln
145                 150                 155                 160

Gly Pro Cys Arg Ala Phe Leu Ala Asp Leu Thr Glu Asn Asp Pro Arg
            165                 170                 175

Arg Thr Arg Ile Ala Asn Ala Tyr Phe Ser Leu Phe Met Ala Leu Gly
        180                 185                 190
```

```
Asn Ile Leu Gly Tyr Ala Thr Gly Ala Tyr Ser Gly Trp Tyr Lys Ile
            195                 200                 205

Phe Pro Phe Thr Ile Thr Glu Ser Cys Gly Val Ser Cys Ala Asn Leu
        210                 215                 220

Lys Ser Ala Phe Leu Leu Asp Ile Ile Leu Ala Ile Thr Thr Tyr
225                 230                 235                 240

Val Thr Val Val Thr Val Gln Asp Asn Pro Thr Phe Gly Ser Asp Glu
                245                 250                 255

Ala Ala Pro Arg Pro Ser Ser His Glu Glu Ala Phe Leu Phe Glu
            260                 265                 270

Leu Phe Gly Ser Phe Lys Tyr Phe Thr Met Pro Val Trp Met Val Leu
        275                 280                 285

Ile Val Thr Ser Leu Thr Trp Ile Gly Trp Phe Pro Phe Ile Leu Phe
        290                 295                 300

Asp Thr Asp Trp Met Gly Arg Glu Ile Tyr Arg Gly Ser Pro Glu Ile
305                 310                 315                 320

Val Ala Asp Thr Gln Lys Tyr His Asp Gly Val Arg Met Gly Ser Phe
                325                 330                 335

Gly Leu Met Leu Asn Ser Val Leu Leu Gly Ile Thr Ser Val Val Thr
            340                 345                 350

Glu Lys Leu Cys Arg Lys Trp Gly Ala Gly Leu Val Trp Gly Val Ser
        355                 360                 365

Asn Ile Ile Met Ala Leu Cys Phe Val Ala Met Leu Val Ile Thr Tyr
        370                 375                 380

Val Ala Gln Asn Leu Asp Tyr Gly Pro Ser Gly Ala Pro Pro Thr Gly
385                 390                 395                 400

Ile Val Val Ala Ser Leu Thr Val Phe Thr Ile Leu Gly Ala Pro Leu
                405                 410                 415

Ser Ile Thr Tyr Ser Ile Pro Tyr Ala Met Ala Thr Ser Arg Val Glu
            420                 425                 430

Asn Leu Gly Leu Gly Gln Gly Leu Ala Met Gly Ile Leu Asn Leu Ser
        435                 440                 445

Ile Val Ile Pro Gln Ile Ile Val Ser Leu Gly Ser Gly Pro Trp Asp
        450                 455                 460

Ser Leu Phe Gly Gly Asn Ala Pro Ser Phe Trp Val Ala Ala Ala
465                 470                 475                 480

Ala Ser Phe Ile Gly Gly Leu Val Ala Ile Leu Gly Leu Pro Arg Ala
                485                 490                 495

Arg Ile Ala Pro Lys Lys Arg Ser Gln Arg
            500                 505

<210> SEQ ID NO 70
<211> LENGTH: 504
<212> TYPE: PRT
<213> ORGANISM: Festuca arundinacea

<400> SEQUENCE: 70

Met Pro Pro Pro Arg Arg Pro Asn Ala Gly Gly Thr Thr Ser Ala Pro
  1               5                  10                  15

Leu Pro Pro Pro Arg Lys Val Pro Leu Arg Ser Leu Leu Arg Ala Ala
             20                  25                  30

Ser Val Ala Cys Gly Val Gln Phe Gly Trp Ala Leu Gln Leu Ser Leu
         35                  40                  45

Leu Thr Pro Tyr Val Gln Glu Leu Gly Ile Pro His Ala Phe Ala Ser
```

-continued

```
        50                  55                  60
Leu Val Trp Leu Cys Gly Pro Leu Ser Gly Leu Val Gln Pro Leu
65                  70                  75                  80

Ile Gly His Leu Ser Asp Arg Ile Ala Pro Ala Asp Ser Pro Leu Gly
                    85                  90                  95

Arg Arg Arg Pro Phe Ile Ala Gly Ala Ala Ser Ile Ala Phe Ser
                100                 105                 110

Val Leu Thr Val Gly Phe Ser Ala Asp Leu Gly Arg Leu Phe Gly Asp
                115                 120                 125

Asn Ile Arg Pro Gly Ser Thr Arg Phe Gly Ala Ile Ile Val Tyr Met
130                 135                 140

Ile Gly Phe Trp Leu Leu Asp Val Gly Asn Asn Ala Thr Gln Gly Pro
145                 150                 155                 160

Cys Arg Ala Phe Leu Ala Asp Leu Thr Glu Asn Asp Pro Arg Arg Thr
                165                 170                 175

Arg Ile Ala Asn Ala Tyr Phe Ser Leu Phe Met Ala Leu Gly Asn Ile
                180                 185                 190

Leu Gly Tyr Ala Thr Gly Ala Tyr Ser Gly Trp Tyr Lys Ile Phe Pro
                195                 200                 205

Phe Thr Ile Thr Glu Ser Cys Gly Val Ser Cys Ala Asn Leu Lys Ser
                210                 215                 220

Ala Phe Leu Leu Asp Ile Ile Leu Ala Ile Thr Thr Tyr Val Thr
225                 230                 235                 240

Val Val Thr Val Gln Asp Asn Pro Thr Phe Gly Ser Asp Glu Ala Ala
                245                 250                 255

Pro Arg Pro Ser Ser His Glu Glu Ala Phe Leu Phe Glu Leu Phe
                260                 265                 270

Gly Ser Phe Lys Tyr Phe Thr Leu Pro Val Trp Met Val Leu Ile Val
                275                 280                 285

Thr Ser Leu Thr Trp Ile Gly Trp Phe Pro Phe Ile Leu Phe Asp Thr
                290                 295                 300

Asp Trp Met Gly Arg Glu Ile Tyr Arg Gly Ser Pro Glu Ile Val Ala
305                 310                 315                 320

Asp Thr Gln Lys Tyr His Asp Gly Val Arg Met Gly Ser Phe Gly Leu
                325                 330                 335

Met Leu Asn Ser Val Leu Gly Ile Thr Ser Val Val Met Glu Lys
                340                 345                 350

Leu Cys Arg Lys Trp Gly Ala Gly Leu Val Trp Gly Val Ser Asn Ile
                355                 360                 365

Ile Met Ala Leu Cys Phe Val Ala Met Leu Ile Ile Thr Tyr Val Ala
370                 375                 380

Lys Asn Leu Asp Tyr Gly Pro Ser Gly Ala Pro Pro Thr Gly Ile Val
385                 390                 395                 400

Val Ala Ser Leu Ala Val Phe Thr Ile Leu Gly Ala Pro Leu Ser Ile
                405                 410                 415

Thr Tyr Ser Ile Pro Tyr Ala Met Ala Thr Ser Arg Val Glu Asn Leu
                420                 425                 430

Gly Leu Gly Gln Gly Leu Ala Met Gly Ile Leu Asn Leu Ser Ile Val
                435                 440                 445

Ile Pro Gln Ile Ile Val Ser Leu Gly Ser Gly Pro Trp Asp Ser Leu
                450                 455                 460

Phe Gly Gly Gly Asn Ala Pro Ser Phe Trp Val Ala Ala Ala Ala Ser
465                 470                 475                 480
```

```
Phe Ile Gly Gly Leu Val Ala Ile Leu Gly Leu Pro Arg Ala Arg Ile
                485                 490                 495
Ala Pro Lys Lys Arg Ser Gln Arg
            500

<210> SEQ ID NO 71
<211> LENGTH: 508
<212> TYPE: PRT
<213> ORGANISM: Lolium perenne

<400> SEQUENCE: 71

Met Val Asp Gln Asp His Asp Gly Arg Arg Gln Glu Glu Ala Thr
  1               5                  10                  15

Ala Val Ala Ala Ser Ser Val Pro Leu Leu Glu Lys Lys Pro Gly Asp
                 20                  25                  30

Val Pro Tyr Tyr Val Glu Gly Cys Pro Gly Cys Ala Val Asp Arg Arg
             35                  40                  45

Lys Ala Thr Asp Pro Gly Ile Pro Tyr Gly Ser Phe Ile Tyr Ile Trp
         50                  55                  60

Val Val Ile Leu Cys Thr Ala Ile Pro Ile Ser Ser Leu Phe Pro Phe
 65                  70                  75                  80

Leu Tyr Phe Met Ile Arg Asp Leu His Ile Ala Glu Arg Thr Glu Asp
                 85                  90                  95

Ile Gly Phe Tyr Ala Gly Phe Val Gly Ala Ala Phe Met Phe Gly Arg
            100                 105                 110

Cys Leu Thr Ser Thr Ile Trp Gly Ile Ala Ala Asp Arg Ile Gly Arg
            115                 120                 125

Lys Pro Val Val Ile Phe Gly Val Phe Ser Val Ile Phe Asn Ala
130                 135                 140

Leu Phe Gly Leu Ser Val Thr Tyr Trp Met Ala Ile Ala Thr Arg Phe
145                 150                 155                 160

Leu Leu Gly Ala Leu Asn Gly Leu Leu Gly Pro Met Lys Ala Tyr Ala
                165                 170                 175

Ile Glu Val Cys Arg Pro Glu His Glu Ala Leu Ala Leu Ser Leu Val
            180                 185                 190

Ser Thr Ala Trp Gly Ile Gly Leu Ile Ile Gly Pro Ala Leu Gly Gly
            195                 200                 205

Tyr Leu Ala Leu Pro Ala Glu Lys Tyr Pro Asn Ile Phe Ser Pro Asp
210                 215                 220

Ser Leu Phe Gly Arg Phe Pro Tyr Phe Leu Pro Cys Leu Cys Thr Ser
225                 230                 235                 240

Val Phe Ala Ala Val Leu Ile Gly Cys Ile Trp Met Pro Glu Thr
                245                 250                 255

Leu His Lys His Lys Val Asn Glu Asn Arg Asn Gln Ser Val Glu Ser
                260                 265                 270

Leu Glu Ala His Leu Ile Asp Pro Lys Glu Lys Val Glu Gln Ser Asn
            275                 280                 285

Ser Pro Asp Thr Lys Lys Ser Leu Phe Lys Asn Trp Pro Leu Met Ser
        290                 295                 300

Ser Ile Ile Val Tyr Cys Val Phe Ser Phe His Asp Met Ala Tyr Thr
305                 310                 315                 320

Glu Val Phe Ser Leu Trp Ala Glu Ser Asp Arg Thr Tyr Gly Gly Leu
                325                 330                 335

Ser Leu Ser Ser Glu Asp Val Gly Gln Thr Leu Ala Ile Thr Gly Ser
```

-continued

```
                340                 345                 350
Ser Leu Leu Val Tyr Gln Leu Phe Leu Tyr Pro Arg Ile Asn Arg Val
            355                 360                 365
Leu Gly Pro Ile Lys Ser Ser Gln Ile Ala Ala Gly Ile Cys Ile Pro
        370                 375                 380
Ile Leu Phe Ala Tyr Pro Tyr Met Thr Tyr Leu Ser Glu Pro Gly Leu
385                 390                 395                 400
Ser Ile Val Leu Asn Ile Ala Ser Val Ile Lys Asn Asn Leu Gly Val
                405                 410                 415
Thr Ile Ile Thr Gly Thr Phe Ile Leu Gln Asn Asn Ala Val Pro Gln
            420                 425                 430
Asp Gln Arg Gly Ala Ala Asn Gly Leu Ala Met Thr Gly Met Ser Phe
        435                 440                 445
Phe Lys Ala Val Ala Pro Ala Gly Ala Gly Ile Val Phe Ser Trp Ala
    450                 455                 460
Gln Lys Arg Gln His Ala Phe Phe Pro Gly Asp Gln Met Val Phe
465                 470                 475                 480
Phe Leu Leu Asn Ile Ile Glu Leu Leu Gly Leu Leu Leu Thr Phe Lys
                485                 490                 495
Phe Phe Leu Ala Val Pro Asp Lys Ser Asp Ser Asn
            500                 505

<210> SEQ ID NO 72
<211> LENGTH: 522
<212> TYPE: PRT
<213> ORGANISM: Lolium perenne

<400> SEQUENCE: 72

Met Ser Ser Met Gln Phe Ser Ser Val Leu Pro Leu Glu Gly Lys Ala
 1               5                  10                  15
Cys Val Cys Pro Val Arg Ser Ala Asn Asn Gly Cys Glu Arg Leu Lys
            20                  25                  30
Val Gly Asp Ser Ser Ser Leu Arg His Glu Met Ala Leu Arg Arg Lys
        35                  40                  45
Cys Asn Gly Ala Arg Gly Gly Gly Ala Ala Asn Gly Ala Gln Cys Val
    50                  55                  60
Leu Thr Ser Asp Ala Ser Pro Asp Thr Leu Val Val Arg Ser Ser Phe
65                  70                  75                  80
Arg Arg Asn Tyr Ala Asp Pro Asn Glu Val Ala Ala Val Ile Leu Gly
                85                  90                  95
Gly Gly Thr Gly Thr Gln Leu Phe Pro Leu Thr Ser Thr Arg Ala Thr
            100                 105                 110
Pro Ala Val Pro Ile Gly Gly Cys Tyr Arg Leu Ile Asp Ile Pro Met
        115                 120                 125
Ser Asn Cys Phe Asn Ser Gly Ile Asn Lys Ile Phe Val Met Thr Gln
    130                 135                 140
Phe Asn Ser Ala Ser Leu Asn Arg His Ile His Arg Thr Tyr Leu Gly
145                 150                 155                 160
Gly Gly Ile Asn Phe Thr Asp Gly Ser Val Glu Val Leu Ala Ala Thr
                165                 170                 175
Gln Met Pro Gly Glu Ala Ala Gly Trp Phe Arg Gly Thr Ala Asp Ala
            180                 185                 190
Val Arg Lys Phe Ile Trp Val Leu Glu Asp Tyr Tyr Lys His Lys Ser
        195                 200                 205
```

```
Ile Glu His Ile Leu Ile Leu Ser Gly Asp Gln Leu Tyr Arg Met Asp
    210                 215                 220

Tyr Met Glu Leu Val Gln Lys His Val Asp Asp Asn Ala Asp Ile Thr
225                 230                 235                 240

Leu Ser Cys Ala Pro Val Gly Glu Ser Arg Ala Ser Glu Tyr Gly Leu
                245                 250                 255

Val Lys Phe Asp Ser Ser Gly Arg Val Ile Gln Phe Ser Glu Lys Pro
                260                 265                 270

Lys Gly Ala Asp Leu Glu Ala Met Lys Val Asp Thr Ser Phe Leu Asn
            275                 280                 285

Phe Ala Ile Asp Asp Pro Ala Lys Asn Pro Tyr Ile Ala Ser Met Gly
    290                 295                 300

Val Tyr Val Phe Lys Arg Glu Val Leu Leu Asn Leu Leu Lys Ser Arg
305                 310                 315                 320

Tyr Thr Glu Leu His Asp Phe Gly Ser Glu Ile Leu Pro Arg Ala Leu
                325                 330                 335

His Asp His Asn Val Gln Ala Tyr Val Phe Thr Asp Tyr Trp Glu Asp
                340                 345                 350

Ile Gly Thr Ile Arg Ser Phe Phe Asp Ala Asn Met Ala Leu Cys Glu
            355                 360                 365

Gln Pro Pro Lys Phe Glu Phe Tyr Asp Pro Lys Thr Pro Phe Phe Thr
    370                 375                 380

Ser Pro Arg Tyr Leu Pro Pro Thr Lys Ser Asp Lys Cys Arg Ile Lys
385                 390                 395                 400

Glu Ala Ile Ile Ser His Gly Cys Phe Leu Arg Glu Cys Thr Ile Glu
                405                 410                 415

His Ser Ile Ile Gly Val Arg Ser Arg Leu Asn Ser Gly Ser Val Leu
                420                 425                 430

Lys Asn Ala Met Met Met Gly Ala Asp Leu Tyr Glu Thr Glu Asp Glu
            435                 440                 445

Ile Ser Gly Leu Leu Ser Glu Gly Lys Val Pro Ile Gly Val Gly Glu
    450                 455                 460

Asn Ser Lys Leu Ser Asn Cys Ile Ile Asp Met Asn Ala Arg Ile Gly
465                 470                 475                 480

Arg Asp Val Val Ile Ala Asn Ser Glu Gly Val Gln Glu Ala Asp Arg
                485                 490                 495

Pro Glu Glu Gly Tyr Tyr Ile Arg Ser Gly Ile Val Val Ile Leu Lys
                500                 505                 510

Asn Ala Thr Val Lys Asp Gly Thr Val Val
            515                 520

<210> SEQ ID NO 73
<211> LENGTH: 522
<212> TYPE: PRT
<213> ORGANISM: Festuca arundinacea

<400> SEQUENCE: 73

Met Ser Ser Met Gln Phe Ser Ser Val Leu Pro Leu Glu Gly Lys Ala
1               5                   10                  15

Cys Val Cys Pro Val Arg Ser Ala Asn Asn Gly Cys Glu Arg Leu Lys
            20                  25                  30

Val Gly Asp Ser Ser Leu Arg His Glu Met Ala Leu Arg Arg Lys
        35                  40                  45

Cys Asn Gly Ala Arg Gly Gly Ala Ala Asp Gly Ala Gln Cys Val
    50                  55                  60
```

-continued

```
Leu Thr Ser Asp Ala Ser Pro Asp Thr Leu Val Val Arg Ser Ser Phe
 65                  70                  75                  80

Arg Met Asn Tyr Ala Asp Pro Asn Glu Val Ala Val Ile Leu Gly
                 85                  90                  95

Gly Gly Thr Gly Thr Gln Leu Phe Pro Leu Thr Ser Thr Arg Ala Thr
                100                 105                 110

Pro Ala Val Pro Ile Gly Gly Cys Tyr Arg Leu Ile Asp Ile Pro Met
                115                 120                 125

Ser Asn Cys Phe Asn Ser Gly Ile Asn Lys Ile Phe Val Met Thr Gln
130                 135                 140

Phe Asn Ser Ala Ser Leu Asn Arg His Ile His Arg Thr Tyr Leu Gly
145                 150                 155                 160

Gly Gly Ile Asn Phe Thr Asp Gly Ser Val Glu Val Leu Ala Ala Thr
                165                 170                 175

Gln Met Pro Gly Glu Ala Ala Gly Trp Phe Arg Gly Thr Ala Asp Ala
                180                 185                 190

Val Arg Lys Phe Ile Trp Val Leu Glu Asp Tyr Tyr Lys His Lys Ser
                195                 200                 205

Ile Glu His Ile Leu Ile Leu Ser Gly Asp Gln Leu Tyr Arg Met Asp
210                 215                 220

Tyr Met Glu Leu Val Gln Lys His Val Asp Asn Ala Asp Ile Thr
225                 230                 235                 240

Leu Ser Cys Ala Pro Val Gly Glu Ser Arg Ala Ser Glu Tyr Gly Leu
                245                 250                 255

Val Lys Phe Asp Ser Ser Gly Arg Val Ile Gln Phe Ser Glu Lys Pro
                260                 265                 270

Lys Gly Ala Asp Leu Glu Ala Met Lys Val Asp Thr Ser Phe Leu Asn
                275                 280                 285

Phe Ala Ile Asp Asp Pro Ala Lys Asn Pro Tyr Ile Ala Ser Met Gly
                290                 295                 300

Val Tyr Val Phe Lys Arg Glu Val Leu Leu Asn Leu Leu Lys Ser Arg
305                 310                 315                 320

Tyr Thr Glu Leu His Asp Phe Gly Ser Glu Ile Leu Pro Arg Ala Leu
                325                 330                 335

His Asp His Asn Val Gln Ala Tyr Val Phe Thr Asp Tyr Trp Glu Asp
                340                 345                 350

Ile Gly Thr Ile Arg Ser Phe Phe Asp Ala Asn Met Ala Leu Cys Glu
                355                 360                 365

Gln Pro Pro Lys Phe Glu Phe Tyr Asp Pro Lys Thr Pro Phe Phe Thr
                370                 375                 380

Ser Pro Arg Tyr Leu Pro Pro Thr Lys Ser Asp Lys Cys Arg Ile Lys
385                 390                 395                 400

Glu Ala Ile Ile Ser His Gly Cys Phe Leu Arg Glu Cys Thr Ile Glu
                405                 410                 415

His Ser Ile Ile Gly Val Arg Ser Arg Leu Asn Ser Gly Ser Val Leu
                420                 425                 430

Lys Asn Ala Met Met Met Gly Ala Asp Leu Tyr Glu Thr Glu Asp Glu
                435                 440                 445

Ile Ser Gly Leu Leu Ser Glu Gly Lys Val Pro Ile Gly Val Gly Glu
450                 455                 460

Asn Ser Lys Leu Ser Asn Cys Ile Ile Asp Met Asn Ala Arg Ile Gly
465                 470                 475                 480
```

```
Arg Asp Val Val Ile Ala Asn Ser Glu Gly Val Gln Glu Ala Asp Arg
            485                 490                 495

Pro Glu Glu Gly Tyr Tyr Ile Arg Ser Gly Ile Val Val Ile Leu Lys
            500                 505                 510

Asn Ala Thr Val Lys Asp Gly Thr Val Val
            515                 520

<210> SEQ ID NO 74
<211> LENGTH: 525
<212> TYPE: PRT
<213> ORGANISM: Lolium perenne

<400> SEQUENCE: 74

Met Thr Gly Ala Pro Pro Ser Thr Val Met Ala Met Gly Ala Ala Thr
  1               5                  10                  15

Ser Pro Cys Lys Ile Leu Ser Ala Thr Gln Arg Ala Ser Thr Ala Ala
                 20                  25                  30

Ala Ser Ala Ser Thr Ser Arg Glu Ser Val Ser Leu Arg Ala Pro Arg
             35                  40                  45

Gly Arg Arg Gln Arg Pro Arg Pro Arg Gly Leu Ala Leu Ser Leu Ala
 50                  55                  60

Pro Ala Arg Arg Pro Phe Val Phe Ser Pro Arg Ala Val Ser Asp Ser
 65                  70                  75                  80

Lys Ser Ser Gln Thr Cys Leu Asp Pro Asp Ala Ser Thr Ser Val Leu
                 85                  90                  95

Gly Ile Ile Leu Gly Gly Gly Ala Gly Thr Arg Leu Tyr Pro Leu Thr
            100                 105                 110

Lys Lys Arg Ala Lys Pro Ala Val Pro Leu Gly Ala Asn Tyr Arg Leu
            115                 120                 125

Ile Asp Ile Pro Val Ser Asn Cys Leu Asn Ser Asn Ile Ser Lys Ile
130                 135                 140

Tyr Val Leu Thr Gln Phe Asn Ser Ala Ser Leu Asn Arg His Leu Ser
145                 150                 155                 160

Arg Ala Tyr Gly Ser Asn Ile Gly Gly Tyr Lys Asn Glu Gly Phe Val
                165                 170                 175

Glu Val Leu Ala Ala Gln Gln Ser Pro Asp Asn Pro Asn Trp Phe Gln
            180                 185                 190

Gly Thr Ala Asp Ala Val Arg Gln Tyr Leu Trp Leu Phe Glu Glu His
            195                 200                 205

Asn Val Met Glu Tyr Leu Ile Leu Ala Gly Asp His Leu Tyr Arg Met
            210                 215                 220

Asp Tyr Glu Lys Phe Ile Gln Ala His Arg Glu Thr Asp Ala Asp Ile
225                 230                 235                 240

Thr Val Ala Ala Leu Pro Met Asp Glu Glu Arg Ala Thr Ala Phe Gly
                245                 250                 255

Leu Met Lys Ile Asp Glu Glu Gly Arg Ile Val Glu Phe Ala Glu Lys
            260                 265                 270

Pro Lys Gly Glu Gln Leu Lys Ala Met Met Val Asp Thr Thr Ile Leu
            275                 280                 285

Gly Leu Asp Asp Val Arg Ala Lys Glu Met Pro Tyr Ile Ala Ser Met
            290                 295                 300

Gly Ile Tyr Val Ile Ser Lys His Val Met Leu Gln Leu Leu Arg Asp
305                 310                 315                 320

Gln Phe Pro Gly Ala Asn Asp Phe Gly Ser Glu Val Ile Pro Gly Ala
                325                 330                 335
```

-continued

```
Thr Ser Thr Gly Met Arg Val Gln Ala Tyr Leu Tyr Asp Gly Tyr Trp
            340                 345                 350

Glu Asp Ile Gly Thr Ile Glu Ala Phe Tyr Asn Ala Asn Leu Gly Ile
        355                 360                 365

Thr Lys Lys Pro Ile Pro Asp Phe Ser Phe Tyr Asp Arg Ser Ala Pro
    370                 375                 380

Ile Tyr Thr Gln Pro Arg His Leu Pro Pro Ser Lys Val Leu Asp Ala
385                 390                 395                 400

Asp Val Thr Asp Ser Val Ile Gly Glu Gly Cys Val Ile Lys Asn Cys
                405                 410                 415

Lys Ile His His Ser Val Val Gly Leu Arg Ser Cys Ile Ser Glu Gly
            420                 425                 430

Ala Ile Ile Glu Asp Thr Leu Leu Met Gly Ala Asp Tyr Tyr Glu Thr
        435                 440                 445

Glu Ala Asp Lys Lys Leu Leu Ala Asp Lys Gly Ile Pro Ile Gly
    450                 455                 460

Ile Gly Lys Asn Ser His Ile Arg Arg Ala Ile Ile Asp Lys Asn Ala
465                 470                 475                 480

Arg Ile Gly Asp Asn Val Lys Ile Ile Asn Val Asp Asn Val Gln Glu
                485                 490                 495

Ala Ala Arg Glu Thr Asp Gly Tyr Phe Ile Lys Ser Gly Ile Val Thr
            500                 505                 510

Val Ile Lys Asp Ala Leu Leu Pro Ser Gly Thr Val Ile
            515                 520                 525

<210> SEQ ID NO 75
<211> LENGTH: 524
<212> TYPE: PRT
<213> ORGANISM: Festuca arundinacea

<400> SEQUENCE: 75

Met Thr Arg Ala Pro Pro Ser Thr Val Met Ala Met Gly Ala Ala Thr
 1               5                  10                  15

Ser Pro Cys Lys Ile Leu Ser Ala Thr Gln Arg Ala Ser Ala Ala Ala
                20                  25                  30

Pro Ser Ala Ser Thr Ser Arg Glu Ser Val Cys Leu Leu Arg Ala Pro
            35                  40                  45

Arg Gly Arg Arg Gln Arg Pro Arg Gly Leu Ala Leu Ser Leu Ala Pro
        50                  55                  60

Ala Arg Arg Pro Phe Val Phe Ser Pro Arg Ala Val Ser Asp Ser Lys
65                  70                  75                  80

Ser Ser Gln Thr Cys Leu Asp Pro Asp Ala Ser Thr Ser Val Leu Gly
                85                  90                  95

Ile Ile Leu Gly Gly Gly Ala Gly Thr Arg Leu Tyr Pro Leu Thr Lys
            100                 105                 110

Lys Arg Ala Lys Pro Ala Val Pro Leu Gly Ala Asn Tyr Arg Leu Ile
        115                 120                 125

Asp Ile Pro Val Ser Asn Cys Leu Asn Ser Asn Ile Ser Lys Ile Tyr
    130                 135                 140

Val Leu Thr Gln Phe Asn Ser Ala Ser Leu Asn Arg His Leu Ser Arg
145                 150                 155                 160

Ala Tyr Gly Ser Asn Ile Gly Gly Tyr Lys Asn Glu Gly Phe Val Glu
                165                 170                 175

Val Leu Ala Ala Gln Gln Ser Pro Asp Asn Pro Asn Trp Phe Gln Gly
```

```
                    180                 185                 190
Thr Ala Asp Ala Val Arg Gln Tyr Leu Trp Leu Phe Glu Glu His Asn
                195                 200                 205
Val Met Glu Tyr Leu Ile Leu Ala Gly Asp His Leu Tyr Arg Met Asp
            210                 215                 220
Tyr Glu Lys Phe Ile Gln Ala His Arg Glu Thr Asp Ala Asp Ile Thr
225                 230                 235                 240
Val Ala Ala Leu Pro Met Asp Glu Glu Arg Ala Thr Ala Phe Gly Leu
                245                 250                 255
Met Lys Ile Asp Glu Glu Gly Arg Ile Val Glu Phe Ala Glu Lys Pro
            260                 265                 270
Lys Gly Glu Gln Leu Lys Ala Met Met Val Asp Thr Thr Ile Leu Gly
                275                 280                 285
Leu Asp Asp Val Arg Ala Lys Glu Met Pro Tyr Ile Ala Ser Met Gly
            290                 295                 300
Ile Tyr Val Ile Ser Lys His Val Met Leu Gln Leu Leu Arg Asp Gln
305                 310                 315                 320
Phe Pro Gly Ala Asn Asp Phe Gly Ser Glu Val Ile Pro Gly Ala Thr
                325                 330                 335
Ser Thr Gly Met Arg Val Gln Ala Tyr Leu Tyr Asp Gly Tyr Trp Glu
            340                 345                 350
Asp Ile Gly Thr Ile Glu Ala Phe Tyr Asn Ala Asn Leu Gly Ile Thr
            355                 360                 365
Lys Lys Pro Ile Pro Asp Phe Ser Phe Tyr Asp Arg Ser Ala Pro Ile
        370                 375                 380
Tyr Thr Gln Pro Arg His Leu Pro Pro Ser Lys Val Leu Asp Ala Asp
385                 390                 395                 400
Val Thr Asp Ser Val Ile Gly Glu Gly Cys Val Ile Lys Asn Cys Lys
                405                 410                 415
Ile His His Ser Val Val Gly Leu Arg Ser Cys Ile Ser Glu Gly Ala
            420                 425                 430
Ile Ile Glu Asp Thr Leu Leu Met Gly Ala Asp Tyr Tyr Glu Thr Glu
        435                 440                 445
Ala Asp Lys Lys Leu Leu Ala Asp Lys Gly Ile Pro Ile Gly Ile
450                 455                 460
Gly Lys Asn Ser His Ile Arg Arg Ala Ile Ile Asp Lys Asn Ala Arg
465                 470                 475                 480
Ile Gly Asp Asn Val Lys Ile Ile Asn Val Asp Asn Val Gln Glu Ala
                485                 490                 495
Ala Arg Glu Thr Asp Gly Tyr Phe Ile Lys Ser Gly Ile Val Thr Val
            500                 505                 510
Ile Lys Asp Ala Leu Leu Pro Ser Gly Thr Val Ile
        515                 520

<210> SEQ ID NO 76
<211> LENGTH: 398
<212> TYPE: PRT
<213> ORGANISM: Festuca arundinacea

<400> SEQUENCE: 76

Met Ala Ala Thr Met Thr Val Glu Glu Val Arg Lys Ala Gln Arg Ala
  1               5                  10                  15
Glu Gly Pro Ala Thr Val Leu Ala Ile Gly Thr Ala Thr Pro Ala Asn
             20                  25                  30
```

```
Cys Val Tyr Gln Ala Asp Tyr Pro Asp Tyr Tyr Phe Lys Ile Thr Lys
         35                  40                  45

Ser Asp His Leu Ala Asp Leu Lys Glu Lys Phe Lys Arg Met Cys Asp
 50                  55                  60

Lys Ser Gln Ile Arg Lys Arg Tyr Met His Leu Thr Glu Glu Ile Leu
 65                  70                  75                  80

Glu Glu Asn Pro Asn Met Cys Ala Tyr Met Ala Pro Ser Leu Asp Ala
                 85                  90                  95

Arg Gln Asp Ile Val Val Glu Val Pro Lys Leu Gly Lys Ala Ala
                100                 105                 110

Ala Gln Lys Ala Ile Lys Glu Trp Gly Gln Pro Arg Ser Lys Ile Thr
                115                 120                 125

His Leu Val Phe Cys Thr Thr Ser Gly Val Asp Met Pro Gly Ala Asp
                130                 135                 140

Tyr Gln Leu Thr Lys Met Leu Gly Leu Arg Pro Ser Val Lys Arg Leu
145                 150                 155                 160

Met Met Tyr Gln Gln Gly Cys Phe Ala Gly Gly Thr Val Leu Arg Leu
                    165                 170                 175

Ala Lys Asp Leu Ala Glu Asn Asn Arg Gly Ala Arg Val Leu Val Val
                180                 185                 190

Cys Ser Glu Ile Thr Ala Val Thr Phe Arg Gly Pro His Glu Ser His
            195                 200                 205

Leu Asp Ser Leu Val Gly Gln Ala Leu Phe Gly Asp Gly Ala Ala Ala
            210                 215                 220

Val Ile Ile Gly Ala Asp Pro Asp Val Ser Val Glu Arg Pro Leu Phe
225                 230                 235                 240

Gln Leu Val Ser Val Ser Gln Thr Ile Leu Pro Asp Ser Glu Gly Ala
                    245                 250                 255

Ile Asp Gly His Leu Arg Glu Val Gly Leu Thr Phe His Leu Leu Lys
            260                 265                 270

Asp Val Pro Gly Leu Ile Ser Lys Asn Ile Glu Arg Ala Leu Glu Glu
            275                 280                 285

Ala Phe Lys Pro Leu Gly Ile Asp Asp Trp Asn Ser Val Phe Trp Val
            290                 295                 300

Ala His Pro Gly Gly Pro Ala Ile Leu Asp Met Val Glu Ala Lys Val
305                 310                 315                 320

Asn Leu Asn Lys Glu Arg Met Arg Ala Thr Arg His Val Leu Ser Glu
                325                 330                 335

Tyr Gly Asn Met Ser Ser Ala Cys Val Leu Phe Ile Met Asp Glu Met
                340                 345                 350

Arg Lys Arg Ser Ala Glu Asp Gly His Thr Thr Thr Gly Glu Gly Met
            355                 360                 365

Asp Trp Gly Val Leu Phe Gly Phe Gly Pro Gly Leu Thr Val Glu Thr
370                 375                 380

Val Val Leu His Ser Met Pro Ile Ala Ala Asp Ala Thr Ala
385                 390                 395

<210> SEQ ID NO 77
<211> LENGTH: 398
<212> TYPE: PRT
<213> ORGANISM: Festuca arundinacea

<400> SEQUENCE: 77

Met Ala Thr Thr Met Thr Val Glu Glu Val Arg Lys Ala Gln Arg Ala
 1               5                  10                  15
```

Glu Gly Pro Ala Thr Val Leu Ala Ile Gly Thr Ala Thr Pro Ala Asn
                20                  25                  30

Cys Val Tyr Gln Ala Asp Tyr Pro Asp Tyr Tyr Phe Lys Ile Thr Lys
                35                  40                  45

Ser Asp His Leu Ala Asp Leu Lys Glu Lys Phe Lys Arg Met Cys Asp
                50                  55                  60

Lys Ser Gln Ile Arg Lys Arg Tyr Met His Leu Thr Glu Glu Ile Leu
65                  70                  75                  80

Glu Glu Asn Pro Asn Met Cys Ala Tyr Met Ala Pro Ser Leu Asp Ala
                    85                  90                  95

Arg Gln Asp Ile Val Val Glu Val Pro Lys Leu Gly Lys Ala Ala
                   100                 105                 110

Ala Gln Lys Ala Ile Lys Glu Trp Gly Gln Pro Arg Ser Lys Ile Thr
                115                 120                 125

His Leu Val Phe Cys Thr Thr Ser Gly Val Asp Met Pro Gly Ala Asp
                130                 135                 140

Tyr Gln Leu Thr Lys Met Leu Gly Leu Arg Pro Ser Val Lys Arg Leu
145                 150                 155                 160

Met Met Tyr Gln Gln Gly Cys Phe Ala Gly Gly Thr Val Leu Arg Leu
                165                 170                 175

Ala Lys Asp Leu Ala Glu Asn Asn Arg Gly Ala Arg Val Leu Val Val
                180                 185                 190

Cys Ser Glu Ile Thr Ala Val Thr Phe Arg Gly Pro His Glu Ser His
                195                 200                 205

Leu Asp Ser Leu Val Gly Gln Ala Leu Phe Gly Asp Gly Ala Ala Ala
                210                 215                 220

Val Ile Ile Gly Ala Asp Pro Asp Val Ser Val Glu His Pro Leu Phe
225                 230                 235                 240

Gln Leu Val Ser Ala Ser Gln Thr Ile Leu Pro Asp Ser Glu Gly Ala
                245                 250                 255

Ile Asp Gly His Leu Arg Glu Val Gly Leu Thr Phe His Leu Leu Lys
                260                 265                 270

Asp Val Pro Gly Leu Ile Ser Lys Asn Ile Glu Arg Ala Leu Glu Glu
                275                 280                 285

Ala Phe Lys Pro Leu Gly Ile Asp Asp Trp Asn Ser Val Phe Trp Val
                290                 295                 300

Ala His Pro Gly Gly Pro Ala Ile Leu Asp Met Val Glu Ala Lys Val
305                 310                 315                 320

Asn Leu Asn Lys Glu Arg Met Arg Ala Thr Arg His Val Leu Ser Glu
                325                 330                 335

Tyr Gly Asn Met Ser Ser Ala Cys Val Leu Phe Ile Met Asp Glu Met
                340                 345                 350

Arg Lys Arg Ser Ala Glu Asp Gly His Thr Thr Thr Gly Glu Gly Met
                355                 360                 365

Asp Trp Gly Val Leu Phe Gly Phe Gly Pro Gly Leu Thr Val Glu Thr
                370                 375                 380

Val Val Leu His Ser Met Pro Ile Ala Ala Gly Ala Thr Ala
385                 390                 395

<210> SEQ ID NO 78
<211> LENGTH: 277
<212> TYPE: PRT
<213> ORGANISM: Festuca arundinacea

<400> SEQUENCE: 78

```
Arg Ala Asp Leu Glu Glu Glu Gly Ser Phe Asp Asp Ala Val Ala Gly
  1               5                  10                  15

Cys Asp Tyr Ala Phe Leu Val Ala Ala Pro Val Asn Leu Lys Ala Glu
             20                  25                  30

Asn Pro Glu Lys Asp Met Val Glu Pro Ala Val Gly Gly Thr Leu Asn
         35                  40                  45

Ala Met Arg Ser Cys Val Arg Ala Gly Thr Val Lys Arg Val Val Leu
     50                  55                  60

Thr Ser Ser Val Ala Ser Val Ser Ala Arg Pro Leu Leu Gln Gly Asp
 65                  70                  75                  80

Gly His Val Leu Asp Glu Glu Ser Trp Ser Asp Val Asp Phe Leu Arg
                 85                  90                  95

Ala Lys Ala Thr Gly His Trp Gly Tyr Pro Val Ser Lys Val Leu Leu
            100                 105                 110

Glu Lys Ala Ala Cys Ala Phe Ala Gln Ala Ser Gly Ile Ser Leu Val
        115                 120                 125

Thr Val Cys Pro Val Val Val Gly Lys Ala Pro Ala Val Gln Val
130                 135                 140

His Thr Ser Val Pro Asp Val Leu Ser Pro Leu Ser Gly Asp Glu Ala
145                 150                 155                 160

Lys Ile Gln Ile Leu Gln His Ile Glu Arg Ala Ser Gly Ser Ile Ser
                165                 170                 175

Leu Val His Val Asp Asp Leu Cys Arg Ala Glu Val Phe Leu Ala Glu
            180                 185                 190

Glu Glu Ala Val Ala Ser Gly Arg Tyr Ile Cys Cys Ser Leu Ser Thr
        195                 200                 205

Thr Ala Gly Val Leu Ala Arg Phe Leu Ser Val Lys Tyr Pro Gln Tyr
    210                 215                 220

Lys Val Arg Thr Asp Arg Phe Ser Gly Ser Pro Glu Lys Pro Arg Val
225                 230                 235                 240

Cys Met Ser Ser Ala Lys Leu Val Ala Glu Gly Phe Gln Tyr Lys Tyr
                245                 250                 255

Lys Thr Leu Asp Glu Ile Tyr Asp Asp Val Val Glu Tyr Gly Arg Ala
            260                 265                 270

Leu Gly Ile Leu Pro
        275
```

<210> SEQ ID NO 79
<211> LENGTH: 342
<212> TYPE: PRT
<213> ORGANISM: Festuca arundinacea

<400> SEQUENCE: 79

```
Met Ala Ala Ala Gly Asp Gly Ser Arg Arg Lys Thr Ala Cys Val Thr
  1               5                  10                  15

Gly Gly Asn Gly Tyr Ile Ala Ser Ala Leu Val Lys Met Leu Leu Glu
             20                  25                  30

Lys Gly Tyr Ala Val Lys Thr Thr Val Arg Asn Pro Asp Asp Met Glu
         35                  40                  45

Lys Asn Ser His Leu Lys Asp Leu Gln Ala Leu Gly Pro Leu Glu Val
     50                  55                  60

Phe Arg Ala Asp Leu Gln Glu Glu Gly Ser Phe Asp Asp Ala Val Ala
 65                  70                  75                  80
```

Gly Cys Asp Tyr Ala Phe Leu Val Ala Pro Val Asn Leu Lys Ala
                85                  90                  95

Glu Asn Pro Glu Lys Asp Met Val Glu Pro Ala Val Gly Gly Thr Leu
            100                 105                 110

Asn Val Met Arg Ser Cys Val Arg Ala Gly Thr Val Lys Arg Val Val
            115                 120                 125

Leu Thr Ser Ser Val Ala Ser Val Ser Ala Arg Pro Leu Leu Gln Gly
        130                 135                 140

Asp Gly His Val Leu Asp Glu Glu Ser Trp Ser Asp Val Asp Phe Leu
145                 150                 155                 160

Arg Ala Lys Ala Thr Gly His Trp Gly Tyr Pro Val Ser Lys Val Leu
                165                 170                 175

Leu Glu Lys Ala Ala Cys Ala Phe Ala Gln Ala Ser Gly Ile Ser Leu
            180                 185                 190

Val Thr Val Cys Pro Val Val Val Gly Lys Ala Pro Ala Val Gln
            195                 200                 205

Val His Thr Ser Val Pro Asp Val Leu Ser Pro Leu Ser Gly Asp Glu
    210                 215                 220

Ala Lys Ile Gln Ile Leu Gln His Ile Glu Arg Ala Ser Gly Ser Ile
225                 230                 235                 240

Ser Leu Val His Val Asp Asp Leu Cys Arg Ala Glu Val Phe Leu Ala
            245                 250                 255

Glu Glu Glu Ala Val Ala Ser Gly Arg Tyr Ile Cys Cys Ser Leu Ser
            260                 265                 270

Thr Thr Ala Gly Val Leu Ala Arg Phe Leu Ser Val Lys Tyr Pro Gln
        275                 280                 285

Tyr Lys Val Arg Thr Asp Arg Phe Ser Gly Ser Pro Glu Lys Pro Arg
        290                 295                 300

Val Cys Met Ser Ser Ala Lys Leu Val Ala Glu Gly Phe Gln Tyr Lys
305                 310                 315                 320

Tyr Lys Thr Leu Asp Glu Ile Tyr Asp Asp Val Val Glu Tyr Gly Arg
                325                 330                 335

Ala Leu Gly Ile Leu Pro
            340

<210> SEQ ID NO 80
<211> LENGTH: 255
<212> TYPE: PRT
<213> ORGANISM: Lolium perenne

<400> SEQUENCE: 80

Phe Ile Ser Val Thr Val Phe Tyr Val Val Gly Leu Arg Gln Arg Asp
 1               5                  10                  15

Leu Val Gln Ala Gly Val Gln Gly Thr Leu Asn Val Met Arg Ser Cys
            20                  25                  30

Val Lys Ala Gly Thr Val Lys Arg Val Ile Leu Thr Ser Ser Asp Ser
        35                  40                  45

Ala Val Cys Gln Arg Pro Leu Glu Gly Asp Gly His Val Leu Asp Glu
    50                  55                  60

Gly Ser Trp Ser Asp Val Pro Tyr Leu Arg Ala Glu Gln Pro Glu Ala
65                  70                  75                  80

Trp Gly Tyr Ala Val Ser Lys Val Leu Met Glu Glu Ala Ala Gly Lys
                85                  90                  95

Phe Ala Asp Glu Asn Gly Leu Gly Leu Val Ser Val Leu Pro Thr Phe
            100                 105                 110

```
Thr Leu Gly Ala Ala Pro Val Ser Gln Ala Arg Thr Ser Val Pro Val
            115                 120                 125
Val Leu Ser Leu Leu Ser Gly Asp Glu Glu Gln Leu Asn Leu Leu Glu
            130                 135                 140
Ala Met His Leu Ile Thr Glu Ser Val Ser Ile Asn His Ile Asp Asp
145                 150                 155                 160
Leu Cys Arg Ala Gln Val Phe Leu Ala Glu Asn Glu Ala Ser Ser Gly
                165                 170                 175
Arg Tyr Ile Cys Ser Ser His Asp Thr Thr Val Val Gln Leu Ala Arg
                180                 185                 190
Leu Leu Ala Asp Lys Tyr Pro Gln Tyr Asn Val Lys Ser Gln Arg Phe
            195                 200                 205
Asp Gly Ser Pro Glu Lys Pro Arg Val Cys Leu Ser Ser Gln Lys Leu
            210                 215                 220
Ile Gly Glu Gly Phe Val Tyr Lys Tyr Asp Asp Leu Gly Ala Ile Leu
225                 230                 235                 240
Asp Asp Leu Val Glu Tyr Gly Arg Thr Gly Ile Leu Pro Phe
                245                 250                 255

<210> SEQ ID NO 81
<211> LENGTH: 340
<212> TYPE: PRT
<213> ORGANISM: Lolium perenne

<400> SEQUENCE: 81

Met Ala Ser Ala Ala Gly Gly Arg Arg Lys Thr Ala Cys Val Thr Gly
1               5                   10                  15
Gly Ser Gly Tyr Ile Ala Ser Ala Leu Ile Lys Thr Leu Leu Asp His
            20                  25                  30
Gly Tyr Ala Val Lys Thr Thr Val Arg Asn Pro Asp Asp Leu Glu Lys
        35                  40                  45
Thr Ser His Leu Lys Asp Leu Gln Ala Phe Gly Pro Leu Glu Ile Phe
    50                  55                  60
Arg Gly Glu Leu Asp Val Glu Gly Ser Phe Asp Asp Ser Val Ser Gly
65                  70                  75                  80
Cys Asp Tyr Val Phe Leu Val Ala Ala Pro Met Asp Met Gly Ser Leu
                85                  90                  95
Asn Pro Glu Arg Asp Leu Val Gln Ala Gly Val Gln Gly Thr Leu Asn
            100                 105                 110
Val Met Arg Ser Cys Val Lys Ala Gly Thr Val Lys Arg Val Ile Leu
        115                 120                 125
Thr Ser Ser Asp Ser Ala Val Cys Gln Arg Pro Leu Glu Gly Asp Gly
    130                 135                 140
His Val Leu Asp Glu Gly Ser Trp Ser Asp Val Pro Tyr Leu Arg Ala
145                 150                 155                 160
Glu Gln Pro Glu Ala Trp Gly Tyr Ala Val Ser Lys Val Leu Met Glu
                165                 170                 175
Glu Ala Ala Gly Lys Phe Ala Asp Glu Asn Gly Leu Gly Leu Val Ser
            180                 185                 190
Val Leu Pro Thr Phe Thr Leu Gly Ala Ala Pro Val Ser Gln Ala Arg
        195                 200                 205
Thr Ser Val Pro Val Val Leu Ser Leu Leu Ser Gly Asp Glu Glu Gln
    210                 215                 220
Leu Asn Leu Leu Glu Ala Met His Leu Ile Thr Glu Ser Val Ser Ile
```

```
                225                 230                 235                 240
Asn His Ile Asp Asp Leu Cys Arg Ala Gln Val Phe Leu Ala Glu Asn
                    245                 250                 255

Glu Ala Ser Ser Gly Arg Tyr Ile Cys Ser Ser His Asp Thr Thr Val
            260                 265                 270

Val Gln Leu Ala Arg Leu Leu Ala Asp Lys Tyr Pro Gln Tyr Asn Val
        275                 280                 285

Lys Ser Gln Arg Phe Asp Gly Ser Pro Glu Lys Pro Arg Val Cys Leu
    290                 295                 300

Ser Ser Gln Lys Leu Ile Gly Glu Gly Phe Val Tyr Lys Tyr Asp Asp
305                 310                 315                 320

Leu Gly Ala Ile Leu Asp Asp Leu Val Glu Tyr Gly Arg Thr Thr Gly
                325                 330                 335

Ile Leu Pro Phe
            340

<210> SEQ ID NO 82
<211> LENGTH: 508
<212> TYPE: PRT
<213> ORGANISM: Lolium perenne

<400> SEQUENCE: 82

Ala Ala Ala Ser Ile Trp Phe Leu Phe Arg Gly Ser Ser Ser Gly Lys
1               5                   10                  15

Lys Leu Ser Lys Leu Pro Leu Pro Gly Pro Arg Gly Trp Pro Val
            20                  25                  30

Leu Gly Asn Leu Pro Gln Val Gly Ala Lys Pro His His Thr Met Ala
            35                  40                  45

Ala Leu Ser Gln Gln Phe Gly Pro Leu Phe Arg Leu Arg Phe Gly Val
        50                  55                  60

Ala Glu Val Val Ala Ala Ser Ala Lys Val Ala Ser Gln Phe Leu
65                  70                  75                  80

Arg Ala His Asp Ala Asn Phe Ser Asp Arg Pro Pro Asn Ser Gly Ala
                85                  90                  95

Glu His Val Ala Tyr Asn Tyr Gln Asp Leu Val Phe Ala Pro Tyr Gly
            100                 105                 110

Ser Arg Trp Arg Ala Leu Arg Lys Leu Cys Ala Leu His Leu Phe Ser
        115                 120                 125

Ala Lys Ala Leu Asp Ala Leu Arg Ala Val Arg Glu Ala Glu Val Ala
    130                 135                 140

Leu Met Val Lys Gln Leu Lys Glu Ser Ala Pro Ala Gly Val Val Val
145                 150                 155                 160

Gly Gln Glu Ala Asn Val Cys Ala Thr Asn Ala Leu Ala Arg Ala Ala
                165                 170                 175

Val Gly Arg Arg Val Phe Gly Gly Ser Ala Gly Glu Gly Ala Arg Glu
            180                 185                 190

Phe Lys Asp Met Val Val Glu Leu Met Gln Leu Ala Gly Val Phe Asn
        195                 200                 205

Ile Gly Asp Phe Val Pro Ala Leu Arg Trp Leu Asp Pro Gln Gly Val
    210                 215                 220

Val Ala Arg Met Lys Arg Leu His Arg Arg Tyr Asp Ala Met Met Asp
225                 230                 235                 240

Gly Phe Ile Ser Glu Arg Asp Gln Arg His Asn Gln Ala Ala Ala Asp
                245                 250                 255
```

-continued

```
Gly Glu Arg Lys Asp Leu Leu Ser Val Met Leu Gly Tyr Met Arg Pro
                260                 265                 270

Asp Gly Gly Gly Glu Glu Gly Ile Ser Phe Asn His Thr Asp
            275                 280                 285

Ile Lys Ala Leu Leu Asn Leu Phe Thr Ala Gly Thr Asp Thr Thr
    290                 295                 300

Ser Ser Thr Val Glu Trp Ala Leu Ala Glu Leu Ile Arg His Lys Asp
305                 310                 315                 320

Val Leu Thr Gln Ala Gln Arg Glu Leu Asp Asp Ile Val Gly Gln Asp
                325                 330                 335

Arg Leu Val Thr Glu Ser Asp Leu Pro His Leu Thr Phe Leu Thr Ala
                340                 345                 350

Val Ile Lys Glu Thr Phe Arg Leu His Pro Ser Thr Pro Leu Ser Leu
                355                 360                 365

Pro Arg Val Ala Thr Glu Asp Cys Glu Val Glu Gly Tyr Arg Ile Pro
            370                 375                 380

Lys Gly Thr Thr Leu Leu Val Asn Val Trp Ala Ile Ala Arg Asp Pro
385                 390                 395                 400

Ala Ser Trp Gly Pro Asp Ala Leu Glu Phe Arg Pro Ala Arg Phe Leu
                405                 410                 415

Ala Gly Gly Leu His Glu Ser Val Asp Val Lys Gly Ser Asp Tyr Glu
            420                 425                 430

Leu Ile Pro Phe Gly Ala Gly Arg Arg Ile Cys Ala Gly Leu Ser Trp
                435                 440                 445

Gly Leu Arg Met Val Thr Leu Met Thr Ala Thr Leu Val His Ala Phe
            450                 455                 460

Asp Trp Ser Leu Val Asp Gly Leu Thr Pro Glu Lys Leu Asp Met Glu
465                 470                 475                 480

Glu Ala Tyr Gly Leu Thr Leu Gln Arg Ala Ala Pro Leu Met Val Arg
                485                 490                 495

Pro Ile Pro Arg Leu Leu Ser Ser Ala Tyr Thr Val
            500                 505

<210> SEQ ID NO 83
<211> LENGTH: 524
<212> TYPE: PRT
<213> ORGANISM: Lolium perenne

<400> SEQUENCE: 83

Met Asp His Arg Asp Val Leu Val Leu Leu Cys Ser Leu Ala Ala Leu
1               5                   10                  15

Ala Ala Ala Ser Ile Trp Phe Leu Phe Arg Gly Ser Ser Gly Lys
                20                  25                  30

Lys Leu Ser Lys Leu Pro Leu Pro Pro Gly Pro Arg Gly Trp Pro Val
                35                  40                  45

Leu Gly Asn Leu Pro Gln Val Gly Ala Lys Pro His His Thr Met Ala
            50                  55                  60

Ala Leu Ser Gln Gln Phe Gly Pro Leu Phe Arg Leu Arg Phe Gly Val
65                  70                  75                  80

Ala Glu Val Val Val Ala Ala Ser Ala Lys Val Ala Ser Gln Phe Leu
                85                  90                  95

Arg Ala His Asp Ala Asn Phe Ser Asp Arg Pro Pro Asn Ser Gly Ala
            100                 105                 110

Glu His Val Ala Tyr Asn Tyr Gln Asp Leu Val Phe Ala Pro Tyr Gly
        115                 120                 125
```

```
Ser Arg Trp Arg Ala Leu Arg Lys Leu Cys Ala Leu His Leu Phe Ser
    130                 135                 140

Ala Lys Ala Leu Asp Ala Leu Arg Ala Val Arg Glu Ala Glu Val Ala
145                 150                 155                 160

Leu Met Val Lys Gln Leu Lys Glu Ser Ala Pro Ala Gly Val Val Val
                165                 170                 175

Gly Gln Glu Ala Asn Val Cys Ala Thr Asn Ala Leu Ala Arg Ala Ala
            180                 185                 190

Val Gly Arg Arg Val Phe Gly Gly Ser Ala Gly Glu Gly Ala Arg Glu
        195                 200                 205

Phe Lys Asp Met Val Val Glu Leu Met Gln Leu Ala Gly Val Phe Asn
210                 215                 220

Ile Gly Asp Phe Val Pro Ala Leu Arg Trp Leu Asp Pro Gln Gly Val
225                 230                 235                 240

Val Ala Arg Met Lys Arg Leu His Arg Arg Tyr Asp Ala Met Met Asp
                245                 250                 255

Gly Phe Ile Ser Glu Arg Asp Gln Arg His Asn Gln Ala Ala Ala Asp
            260                 265                 270

Gly Glu Arg Lys Asp Leu Leu Ser Val Met Leu Gly Tyr Met Arg Pro
        275                 280                 285

Asp Gly Gly Gly Glu Glu Gly Ile Ser Phe Asn His Thr Asp
290                 295                 300

Ile Lys Ala Leu Leu Leu Asn Leu Phe Thr Ala Gly Thr Asp Thr Thr
305                 310                 315                 320

Ser Ser Thr Val Glu Trp Ala Leu Ala Glu Leu Ile Arg His Lys Asp
                325                 330                 335

Val Leu Thr Gln Ala Gln Arg Glu Leu Asp Asp Ile Val Gly Gln Asp
            340                 345                 350

Arg Leu Val Thr Glu Ser Asp Leu Pro His Leu Thr Phe Leu Thr Ala
        355                 360                 365

Val Ile Lys Glu Thr Phe Arg Leu His Pro Ser Thr Pro Leu Ser Leu
370                 375                 380

Pro Arg Val Ala Thr Glu Asp Cys Glu Val Glu Gly Tyr Arg Ile Pro
385                 390                 395                 400

Lys Gly Thr Thr Leu Leu Val Asn Val Trp Ala Ile Ala Arg Asp Pro
                405                 410                 415

Ala Ser Trp Gly Pro Asp Ala Leu Glu Phe Arg Pro Ala Arg Phe Leu
            420                 425                 430

Ala Gly Gly Leu His Glu Ser Val Asp Val Lys Gly Ser Asp Tyr Glu
        435                 440                 445

Leu Ile Pro Phe Gly Ala Gly Arg Arg Ile Cys Ala Gly Leu Ser Trp
450                 455                 460

Gly Leu Arg Met Val Thr Leu Met Thr Ala Thr Leu Val His Ala Phe
465                 470                 475                 480

Asp Trp Ser Leu Val Asp Gly Leu Thr Pro Glu Lys Leu Asp Met Glu
                485                 490                 495

Glu Ala Tyr Gly Leu Thr Leu Gln Arg Ala Ala Pro Leu Met Val Arg
            500                 505                 510

Pro Ile Pro Arg Leu Leu Ser Ser Ala Tyr Thr Val
        515                 520

<210> SEQ ID NO 84
<211> LENGTH: 525
```

<212> TYPE: PRT
<213> ORGANISM: Festuca arundinacea

<400> SEQUENCE: 84

```
Arg Ser Glu Leu Ala Gly Met Asp Ile Pro Leu Ser Leu Leu Ser
 1               5                  10                  15

Thr Leu Ala Ile Ser Ala Thr Ile Cys Tyr Val Phe Arg Ala Gly
             20                  25                  30

Lys Gly His Arg Ala Pro Leu Pro Leu Pro Gly Pro Arg Gly Trp
         35                  40                  45

Pro Val Leu Gly Asn Leu Pro Gln Leu Gly Gly Lys Thr His Gln Thr
 50                  55                  60

Leu His Glu Met Thr Lys Val Tyr Gly Pro Val Leu Arg Leu Arg Phe
 65                  70                  75                  80

Gly Ser Ser Val Val Val Ala Gly Ser Ala Val Ala Glu Gln
                 85                  90                  95

Phe Leu Arg Thr His Asp Ala Lys Phe Ser Arg Pro Pro Asn Ser
                100                 105                 110

Gly Gly Glu His Met Ala Tyr Asn Tyr Arg Asp Val Val Phe Ala Pro
             115                 120                 125

Tyr Gly Pro Arg Trp Arg Ala Met Arg Lys Val Cys Ala Val Asn Ile
130                 135                 140

Phe Ser Ala Arg Ala Leu Asp Asp Leu Arg Gly Phe Arg Glu Arg Glu
145                 150                 155                 160

Ala Ala Leu Met Val Arg Ser Leu Ala Asp Ala Ala Lys Ala Gly Val
                165                 170                 175

Ala Val Ala Val Gly Lys Ala Ala Asn Val Cys Thr Thr Asn Gly Leu
            180                 185                 190

Ser Arg Ala Ala Val Gly Leu Arg Val Phe Gly Ser Asp Gly Ala Arg
        195                 200                 205

Asp Phe Lys Glu Ile Val Leu Glu Val Met Glu Val Gly Gly Val Leu
    210                 215                 220

Asn Val Gly Asp Phe Val Pro Ala Leu Arg Trp Leu Asp Pro Gln Gly
225                 230                 235                 240

Val Val Ala Arg Leu Lys Lys Leu His Arg Arg Phe Asp Asp Met Met
                245                 250                 255

Asn Gly Ile Ile Ala Glu Arg Arg Thr Gly Thr Lys Thr Ala Val Val
            260                 265                 270

Glu Glu Gly Lys Gly Asp Leu Leu Gly Leu Leu Leu Ala Met Val Gln
        275                 280                 285

Glu Asp Lys Ser Leu Thr Gly Ser Glu Glu Asp Lys Ile Thr Asp Thr
    290                 295                 300

Asp Val Lys Ala Leu Ile Leu Asn Leu Phe Val Ala Gly Thr Glu Thr
305                 310                 315                 320

Thr Ser Ser Ile Val Glu Trp Ala Val Ala Glu Leu Ile Arg His Pro
                325                 330                 335

Asp Ile Leu Lys Gln Ala Gln Glu Glu Leu Asp Ala Val Val Gly Arg
            340                 345                 350

Asp Arg Leu Val Ser Glu Ser Asp Leu Pro Arg Leu Thr Phe Phe Asn
        355                 360                 365

Ala Ile Ile Lys Glu Thr Phe Arg Leu His Pro Ser Thr Pro Leu Ser
    370                 375                 380

Leu Pro Arg Met Ala Ser Glu Glu Cys Glu Val Ala Gly Tyr His Ile
385                 390                 395                 400
```

```
Pro Arg Gly Thr Glu Leu Leu Val Asn Val Trp Gly Ile Ala Arg Asp
                405                 410                 415

Pro Ala Leu Trp Pro Asp Pro Leu Glu Tyr Gln Pro Ala Arg Phe Leu
            420                 425                 430

Pro Gly Gly Ser His Glu Asn Val Asp Leu Lys Gly Asp Phe Gly
            435                 440                 445

Leu Ile Pro Phe Gly Ala Gly Arg Arg Ile Cys Ala Gly Leu Ser Trp
        450                 455                 460

Gly Leu Arg Met Val Thr Ile Thr Thr Ala Thr Leu Val His Ser Phe
465                 470                 475                 480

Asp Trp Glu Leu Pro Ala Gly Gln Thr Pro Asp Lys Leu Asn Met Glu
                485                 490                 495

Glu Ala Phe Ser Leu Leu Gln Arg Ala Val Pro Leu Met Val His
            500                 505                 510

Pro Val Pro Arg Leu Leu Pro Ser Ala Tyr Glu Ile Ser
            515                 520                 525

<210> SEQ ID NO 85
<211> LENGTH: 526
<212> TYPE: PRT
<213> ORGANISM: Festuca arundinacea

<400> SEQUENCE: 85

Met Arg Ser Glu Leu Ala Gly Met Asp Ile Pro Leu Pro Leu Leu Leu
1               5                   10                  15

Ser Thr Leu Ala Ile Ser Ala Thr Ile Cys Tyr Val Phe Phe Arg Ala
                20                  25                  30

Gly Lys Gly His Arg Ala Pro Leu Pro Leu Pro Pro Gly Pro Arg Gly
            35                  40                  45

Trp Pro Val Leu Gly Asn Leu Pro Gln Leu Gly Gly Lys Thr His Gln
        50                  55                  60

Thr Leu His Glu Met Thr Lys Val Tyr Gly Pro Val Leu Arg Leu Arg
65              70                  75                  80

Phe Gly Ser Ser Val Val Val Ala Gly Ser Ala Ala Val Ala Glu
                85                  90                  95

Gln Phe Leu Arg Thr His Asp Ala Lys Phe Ser Ser Arg Pro Pro Asn
            100                 105                 110

Ser Gly Gly Glu His Met Ala Tyr Asn Tyr Arg Asp Val Val Phe Ala
            115                 120                 125

Pro Tyr Gly Pro Arg Trp Arg Ala Met Arg Lys Val Cys Ala Val Asn
        130                 135                 140

Ile Phe Ser Ala Arg Ala Leu Asp Asp Leu Arg Gly Phe Arg Glu Arg
145                 150                 155                 160

Glu Ala Ala Leu Met Val Arg Ser Leu Ala Asp Ala Ala Lys Ala Gly
                165                 170                 175

Val Ala Val Ala Val Gly Lys Ala Ala Asn Val Cys Thr Thr Asn Gly
            180                 185                 190

Leu Ser Arg Ala Ala Val Gly Leu Arg Val Phe Gly Ser Asp Gly Ala
        195                 200                 205

Arg Asp Phe Lys Glu Ile Val Leu Glu Val Met Glu Val Gly Gly Val
        210                 215                 220

Leu Asn Val Gly Asp Phe Val Pro Ala Leu Arg Trp Leu Asp Pro Gln
225                 230                 235                 240

Gly Val Val Ala Arg Leu Lys Lys Leu His Arg Arg Phe Asp Asp Met
```

```
                  245                 250                 255
Met Asn Gly Ile Ile Ala Glu Arg Arg Thr Gly Thr Lys Thr Ala Val
            260                 265                 270

Val Glu Glu Gly Lys Gly Asp Leu Leu Gly Leu Leu Leu Ala Met Val
        275                 280                 285

Gln Glu Asp Lys Ser Leu Thr Gly Ser Glu Glu Asp Lys Ile Thr Asp
    290                 295                 300

Thr Asp Val Lys Ala Leu Ile Leu Asn Leu Phe Val Ala Gly Thr Glu
305                 310                 315                 320

Thr Thr Ser Ser Ile Val Glu Trp Ala Val Ala Glu Leu Ile Arg His
                325                 330                 335

Pro Asp Ile Leu Lys Gln Ala Gln Glu Glu Leu Asp Ala Val Val Gly
            340                 345                 350

Arg Asp Arg Leu Val Ser Glu Ser Asp Leu Pro Arg Leu Thr Phe Phe
        355                 360                 365

Asn Ala Ile Ile Lys Glu Thr Phe Arg Leu His Pro Ser Thr Pro Leu
    370                 375                 380

Ser Leu Pro Arg Met Ala Ser Glu Glu Cys Glu Val Ala Gly Tyr His
385                 390                 395                 400

Ile Pro Arg Gly Thr Glu Leu Leu Val Asn Val Trp Gly Ile Ala Arg
                405                 410                 415

Asp Pro Ala Leu Trp Pro Asp Pro Leu Glu Tyr Gln Pro Ala Arg Phe
            420                 425                 430

Leu Pro Gly Gly Ser His Glu Asn Val Asp Leu Lys Gly Gly Asp Phe
        435                 440                 445

Gly Leu Ile Pro Phe Gly Ala Gly Arg Arg Ile Cys Ala Gly Leu Ser
    450                 455                 460

Trp Gly Leu Arg Met Val Thr Ile Thr Thr Ala Thr Leu Val His Ser
465                 470                 475                 480

Phe Asp Trp Glu Leu Pro Ala Gly Gln Thr Pro Asp Lys Leu Asn Met
                485                 490                 495

Glu Glu Ala Phe Ser Leu Leu Leu Gln Arg Ala Val Pro Leu Met Val
            500                 505                 510

His Pro Val Pro Arg Leu Leu Pro Ser Ala Tyr Glu Ile Ser
        515                 520                 525

<210> SEQ ID NO 86
<211> LENGTH: 491
<212> TYPE: PRT
<213> ORGANISM: Festuca arundinacea

<400> SEQUENCE: 86

Asp Ile Pro Leu Pro Leu Leu Ser Thr Leu Ala Ile Ser Ala Thr
1               5                   10                  15

Ile Cys Tyr Val Phe Phe Arg Ala Gly Lys Thr His Gln Thr Leu His
                20                  25                  30

Glu Met Thr Lys Val Tyr Gly Pro Val Leu Arg Leu Arg Phe Gly Ser
            35                  40                  45

Ser Val Val Val Ala Gly Ser Ala Val Ala Glu Gln Phe Leu
        50                  55                  60

Arg Thr His Asp Ala Lys Phe Ser Ser Arg Pro Asn Ser Gly Gly
65                  70                  75                  80

Glu His Met Ala Tyr Asn Tyr Gln Asp Ile Val Phe Ala Pro Tyr Gly
                85                  90                  95
```

```
Pro Arg Trp Arg Ala Met Arg Lys Val Cys Ala Val Asn Ile Phe Ser
            100                 105                 110
Ala Arg Ala Leu Asp Asp Leu Arg Gly Phe Arg Glu Arg Glu Ala Ala
            115                 120                 125
Leu Met Val Arg Ser Leu Ala Asp Ala Ala Lys Ala Gly Ala Ala Val
        130                 135                 140
Ala Val Gly Lys Ala Ala Asn Val Cys Thr Thr Asn Gly Leu Ser Arg
145                 150                 155                 160
Ala Ala Val Gly Leu Arg Val Phe Gly Ser Asp Gly Thr Arg Asp Phe
                165                 170                 175
Lys Glu Ile Val Leu Glu Val Met Glu Val Gly Val Leu Asn Val
            180                 185                 190
Gly Asp Phe Val Pro Ala Leu Arg Trp Leu Asp Pro Gln Gly Val Val
            195                 200                 205
Ala Arg Met Lys Lys Leu His Arg Arg Phe Asp Asp Ile Met Asn Gly
        210                 215                 220
Ile Ile Ala Glu Arg Arg Thr Gly Ala Lys Thr Ala Val Val Glu Glu
225                 230                 235                 240
Gly Lys Gly Asp Leu Leu Gly Leu Leu Leu Ala Met Val Gln Glu Asp
                245                 250                 255
Lys Ser Leu Thr Gly Ser Glu Glu Asp Lys Ile Thr Asp Thr Asp Val
            260                 265                 270
Lys Ala Leu Ile Leu Asn Leu Phe Val Ala Gly Thr Glu Thr Thr Ser
        275                 280                 285
Ser Ile Val Glu Trp Ala Val Ala Glu Leu Ile Arg His Pro Asp Ile
290                 295                 300
Leu Lys Gln Ala Gln Glu Glu Leu Asp Thr Val Val Gly Arg Asp Arg
        305                 310                 315                 320
Ile Val Ser Glu Ser Asp Leu Pro Arg Leu Thr Phe Asn Ala Ile
                325                 330                 335
Ile Lys Glu Thr Phe Arg Leu His Pro Ser Thr Pro Leu Ser Leu Pro
            340                 345                 350
Arg Met Ala Ser Glu Asp Cys Glu Val Ala Gly Tyr His Ile Pro Arg
        355                 360                 365
Gly Thr Glu Leu Leu Val Asn Val Trp Gly Ile Ala Arg Asp Pro Ser
    370                 375                 380
Leu Trp Pro Asp Pro Leu Glu Tyr Arg Pro Ala Arg Phe Leu Pro Gly
385                 390                 395                 400
Gly Ser His Glu Asn Val Asp Leu Lys Gly Gly Asp Phe Gly Leu Ile
                405                 410                 415
Pro Phe Gly Ala Gly Arg Arg Ile Cys Ala Gly Leu Ser Trp Gly Leu
            420                 425                 430
Arg Met Val Thr Val Thr Thr Ala Thr Leu Val His Ser Phe Asp Trp
        435                 440                 445
Glu Leu Pro Ala Gly Gln Thr Leu Asp Lys Leu Asn Met Glu Glu Ala
    450                 455                 460
Phe Ser Leu Leu Leu Gln Arg Ala Met Pro Leu Met Val His Pro Val
465                 470                 475                 480
Pro Arg Leu Leu Pro Ser Ala Tyr Glu Ile Ser
                485                 490

<210> SEQ ID NO 87
<211> LENGTH: 499
<212> TYPE: PRT
```

<213> ORGANISM: Festuca arundinacea

<400> SEQUENCE: 87

```
Met Arg Asn Glu Leu Ala Gly Met Asp Ile Pro Leu Pro Leu Leu Leu
 1               5                  10                  15

Ser Thr Leu Ala Ile Ser Ala Thr Ile Cys Tyr Val Phe Phe Arg Ala
             20                  25                  30

Gly Lys Thr His Gln Thr Leu His Glu Met Thr Lys Val Tyr Gly Pro
         35                  40                  45

Val Leu Arg Leu Arg Phe Gly Ser Ser Val Val Val Ala Gly Ser
 50                  55                  60

Ala Ala Val Ala Glu Gln Phe Leu Arg Thr His Asp Ala Lys Phe Ser
 65                  70                  75                  80

Ser Arg Pro Pro Asn Ser Gly Gly Glu His Met Ala Tyr Asn Tyr Gln
                 85                  90                  95

Asp Ile Val Phe Ala Pro Tyr Gly Pro Arg Trp Arg Ala Met Arg Lys
            100                 105                 110

Val Cys Ala Val Asn Ile Phe Ser Ala Arg Ala Leu Asp Asp Leu Arg
        115                 120                 125

Gly Phe Arg Glu Arg Glu Ala Ala Leu Met Val Arg Ser Leu Ala Asp
    130                 135                 140

Ala Ala Lys Ala Gly Ala Ala Val Ala Val Gly Lys Ala Ala Asn Val
145                 150                 155                 160

Cys Thr Thr Asn Gly Leu Ser Arg Ala Ala Val Gly Leu Arg Val Phe
                165                 170                 175

Gly Ser Asp Gly Thr Arg Asp Phe Lys Glu Ile Val Leu Glu Val Met
            180                 185                 190

Glu Val Gly Gly Val Leu Asn Val Gly Asp Phe Val Pro Ala Leu Arg
        195                 200                 205

Trp Leu Asp Pro Gln Gly Val Val Ala Arg Met Lys Lys Leu His Arg
    210                 215                 220

Arg Phe Asp Asp Ile Met Asn Gly Ile Ile Ala Glu Arg Arg Thr Gly
225                 230                 235                 240

Ala Lys Thr Ala Val Val Glu Glu Gly Lys Gly Asp Leu Leu Gly Leu
                245                 250                 255

Leu Leu Ala Met Val Gln Glu Asp Lys Ser Leu Thr Gly Ser Glu Glu
            260                 265                 270

Asp Lys Ile Thr Asp Thr Asp Val Lys Ala Leu Ile Leu Asn Leu Phe
        275                 280                 285

Val Ala Gly Thr Glu Thr Thr Ser Ser Ile Val Glu Trp Ala Val Ala
    290                 295                 300

Glu Leu Ile Arg His Pro Asp Ile Leu Lys Gln Ala Gln Glu Glu Leu
305                 310                 315                 320

Asp Thr Val Val Gly Arg Asp Arg Ile Val Ser Glu Ser Asp Leu Pro
                325                 330                 335

Arg Leu Thr Phe Phe Asn Ala Ile Ile Lys Glu Thr Phe Arg Leu His
            340                 345                 350

Pro Ser Thr Pro Leu Ser Leu Pro Arg Met Ala Ser Glu Asp Cys Glu
        355                 360                 365

Val Ala Gly Tyr His Ile Pro Arg Gly Thr Glu Leu Leu Val Asn Val
    370                 375                 380

Trp Gly Ile Ala Arg Asp Pro Ser Leu Trp Pro Asp Pro Leu Glu Tyr
385                 390                 395                 400
```

```
Arg Pro Ala Arg Phe Leu Pro Gly Gly Ser His Glu Asn Val Asp Leu
                405                 410                 415

Lys Gly Gly Asp Phe Gly Leu Ile Pro Phe Gly Ala Gly Arg Arg Ile
            420                 425                 430

Cys Ala Gly Leu Ser Trp Gly Leu Arg Met Val Thr Val Thr Thr Ala
            435                 440                 445

Thr Leu Val His Ser Phe Asp Trp Glu Leu Pro Ala Gly Gln Thr Leu
        450                 455                 460

Asp Lys Leu Asn Met Glu Ala Phe Ser Leu Leu Gln Arg Ala
465                 470                 475                 480

Met Pro Leu Met Val His Pro Val Pro Arg Leu Leu Pro Ser Ala Tyr
                485                 490                 495

Glu Ile Ser

<210> SEQ ID NO 88
<211> LENGTH: 380
<212> TYPE: PRT
<213> ORGANISM: Lolium perenne

<400> SEQUENCE: 88

Met Ala Met Ala Asp Cys Met Gln Glu Trp Pro Glu Pro Val Val Arg
  1               5                  10                  15

Val Gln Ala Val Ala Glu Ser Gly Leu Ala Ala Ile Pro Asp Cys Tyr
             20                  25                  30

Val Lys Pro Pro Arg Asp Arg Pro Ala Ala Gln His Leu Ala Thr Ala
         35                  40                  45

Ala Ser Ala Asp Gly Asp Val Leu His Glu Pro Leu Asp Thr Ser Ile
     50                  55                  60

Pro Val Ile Asp Leu Gly Glu Leu Val Ala Ala Thr Ala Asp Glu Gly
65                  70                  75                  80

Arg Met Arg Gln Ile Met Glu Ala Val Ala Ala Cys Arg Glu Trp
                 85                  90                  95

Gly Phe Phe Gln Val Val Asn His Gly Val Ala Pro Glu Leu Met His
                100                 105                 110

Ala Ala Arg Glu Ala Trp Arg Gly Phe Phe Arg Leu Pro Ile Thr Ala
            115                 120                 125

Lys Gln Gln Tyr Ala Asn Leu Pro Arg Thr Tyr Glu Gly Tyr Gly Ser
        130                 135                 140

Arg Val Gly Val Gln Lys Gly Gly Pro Leu Asp Trp Gly Asp Tyr Tyr
145                 150                 155                 160

Phe Leu His Leu Ala Pro Asp Ala Gly Lys Ser Pro Asp Lys Tyr Trp
                165                 170                 175

Pro Thr Asn Pro Ala Ile Cys Lys Asp Val Ser Glu Glu Tyr Gly Arg
            180                 185                 190

Glu Val Ile Arg Leu Cys Glu Leu Leu Met Lys Val Met Ser Ala Ser
        195                 200                 205

Leu Gly Leu Glu Ala Thr Arg Phe Gln Glu Ala Phe Gly Gly Ser Glu
    210                 215                 220

Cys Gly Val Cys Leu Arg Ala Asn Tyr Tyr Pro Arg Cys Pro Gln Pro
225                 230                 235                 240

Asp Leu Thr Leu Gly Leu Ser Ala His Ser Asp Pro Gly Val Leu Thr
                245                 250                 255

Val Leu Leu Ala Asp Glu His Val Arg Gly Leu Gln Val Arg Arg Ala
            260                 265                 270
```

-continued

```
Asp Gly Glu Trp Val Thr Val Gln Pro Ala Arg His Asp Ala Phe Ile
        275                 280                 285

Val Asn Val Gly Asp Gln Ile Gln Ile Leu Ser Asn Ser Met Tyr Lys
    290                 295                 300

Ser Val Glu His Arg Val Met Val Asn Ala Lys Glu Glu Arg Ile Ser
305                 310                 315                 320

Leu Ala Leu Phe Tyr Asn Pro Arg Gly Asp Val Pro Ile Ala Pro Ala
                325                 330                 335

Pro Glu Thr Val Thr Pro Glu Arg Pro Ala Leu Tyr Pro Ser Met Thr
            340                 345                 350

Phe Asp Glu Tyr Arg Ala Tyr Ile Arg Lys Tyr Gly Pro Arg Gly Lys
        355                 360                 365

Ala Gln Val Glu Gly Ala Lys Gln Gly Gln Gly Ser
    370                 375                 380

<210> SEQ ID NO 89
<211> LENGTH: 20
<212> TYPE: DNA
<213> ORGANISM: Artificial Sequence
<220> FEATURE:
<223> OTHER INFORMATION: Made in the lab

<400> SEQUENCE: 89
gacgcaagga gagatccaga                                               20

<210> SEQ ID NO 90
<211> LENGTH: 20
<212> TYPE: DNA
<213> ORGANISM: Artificial Sequence
<220> FEATURE:
<223> OTHER INFORMATION: Made in the lab

<400> SEQUENCE: 90
agacgaggtg ggtgatcttg                                               20

<210> SEQ ID NO 91
<211> LENGTH: 26
<212> TYPE: DNA
<213> ORGANISM: Artificial Sequence
<220> FEATURE:
<223> OTHER INFORMATION: Made in the lab

<400> SEQUENCE: 91
tacatatgaa gagagtttca tcgcat                                        26

<210> SEQ ID NO 92
<211> LENGTH: 21
<212> TYPE: DNA
<213> ORGANISM: Artificial Sequence
<220> FEATURE:
<223> OTHER INFORMATION: Made in the lab

<400> SEQUENCE: 92
gccgaacaga ccattgaagt a                                             21
```

COMPOSITIONS ISOLATED FROM FORAGE GRASSES AND METHODS FOR THEIR USE

CROSS-REFERENCE TO RELATED APPLICATIONS

This application is a continuation of U.S. patent application Ser. No. 10/431,273, filed May. 6, 2003 now abandoned.

TECHNICAL FIELD OF THE INVENTION

This invention relates to polynucleotides isolated from forage grass tissues, specifically from *Lolium perenne* (perennial ryegrass) and *Festuca arundinacea* (tall fescue), as well as oligonucleotide probes and primers, genetic constructs comprising the polynucleotides, biological materials (including host cells and plants) incorporating the polynucleotides, polypeptides encoded by the polynucleotides, and methods for using the polynucleotides and polypeptides. More particularly, the invention relates to polypeptides involved in the tannin, cellulose and fructan biosynthetic pathways, and to polynucleotides encoding such polypeptides.

BACKGROUND OF THE INVENTION

Over the past 50 years, there have been substantial improvements in the genetic production potential of ruminant animals (sheep, cattle and deer). Levels of meat, milk or fiber production that equal an animal's genetic potential may be attained within controlled feeding systems, where animals are fully fed with energy dense, conserved forages and grains. However, the majority of temperate farming systems worldwide rely on the in situ grazing of pastures. Nutritional constraints associated with temperate pastures can prevent the full expression of an animal's genetic potential. This is illustrated by a comparison between milk production by North American grain-fed dairy cows and New Zealand pasture-fed cattle. North American dairy cattle produce, on average, twice the milk volume of New Zealand cattle, yet the genetic base is similar within both systems (New Zealand Dairy Board and United States Department of Agriculture figures). Significant potential therefore exists to improve the efficiency of conversion of pasture nutrients to animal products through the correction of nutritional constraints associated with pastures.

Carbohydrate Metabolism

Plant carbohydrates can be divided into two groups depending on their function within the plant. Structural carbohydrates, such as cellulose and lignin, are usually part of the extracellular matrix. Non-structural, storage carbohydrates act as either long- or short-term carbohydrate stores. Examples of non-structural carbohydrates include starch, sucrose and fructans.

Fructans are polymers that are stored in the vacuole and that consist of linear and branched chains of fructose units (for review see Vijn and Smeekens *Plant Physiol.* 120:351-359, 199). They play an important role in assimilate partitioning and possibly in stress tolerance in many plant families. Grasses use fructans instead of starch as a water-soluble carbohydrate store (Pollock et al., in "Regulation of primary metabolic pathways in plants", N. J. Kruger et al. (eds), Kluwer Academic Publishers, The Netherlands, pp 195-226, 1999). Increasing the amount of fructans and sucrose in forage crops leads to an increase in the level of water-soluble carbohydrates and thereby enhances the nutritional value of the plants. In addition, increasing the amount of fructans in forage plants decreases methane production in animals fed the plants, thereby leading to lower greenhouse gas emissions, and decreases urea production in animals as less protein is degraded in the rumen (Biggs and Hancock *Trends in Plant Sci.*, 6:8-9, 2001). Fructans have also been implicated in protecting plants against water deficits caused by drought or low temperatures. Introduction of enzymes involved in the fructan biosynthetic pathway into plants that do not naturally synthesize fructans may be employed to confer cold tolerance and drought tolerance (Pilon-Smits, *Plant Physiol.* 107:125-130, 1995).

The number of fructose units within a fructan chain is referred to as the degree of polymerization (DP). In grasses, fructans of DP 6-10 are common. Such fructans of low DP are naturally sweet and are therefore of interest for use as sweeteners in foodstuffs. Long fructan chains form emulsions with a fat-like texture and a neutral taste. The human digestive system is unable to degrade fructans, and fructans of high DP may therefore be used as low-calorie food ingredients. Overexpression of enzymes involved in the fructan biosynthetic pathway may be usefully employed to produce quantities of fructans that can be purified for human consumption.

Five major classes of structurally different fructans have been identified in plants, with each class showing a different linkage of the fructosyl residues. Fructans found in grasses are of the mixed levan class, consisting of both (2-1)- and (2-6)-linked beta-D-fructosyl units (Pollock et al., in "Regulation of primary metabolic pathways in plants", N. J. Kruger et al. (eds), Kluwer Academic Publishers, The Netherlands, pp 195-226, 1999). Fructans are synthesized by the action of fructosyltransferase enzymes on sucrose in the vacuole. These enzymes are closely related to invertases, enzymes that normally hydrolyze sucrose.

Grasses use two fructosyltransferase enzymes to synthesize fructans, namely sucrose:sucrose 1-fructosyltransferase (1-SST) and sucrose:fructan 6-fructosyltransferase (6-SFT) (Pollock et al., in "Regulation of primary metabolic pathways in plants", N. J. Kruger et al. (eds), Kluwer Academic Publishers, The Netherlands, pp 195-226, 1999). 1-SST is a key enzyme in plant fructan biosynthesis, while 6-SFT catalyzes the formation and extension of beta-2,6-linked fructans that is typically found in grasses. Specifically, 1-SST catalyzes the formation of 1-kestose plus glucose from sucrose, while 6-SFT catalyzes the formation of bifurcose plus glucose from sucrose plus 1-kestose and also the formation of 6-kestose plus glucose from sucrose. Both enzymes can modify 1-kestose, 6-kestose and bifurcose further by adding additional fructose molecules. Over-expression of both 1-SST and 6-SFT in the same plant may be employed to produce fructans for use in human foodstuffs (Sevenier et al., *Nature Biotechnology* 16:843-846; Hellewege et al., *Proc. Nat. Acad. Sci., U.S.A.* 97:8699-8704). For a review of the fructan biosynthetic pathway see Vijn I. and Smeekens S. *Plant Physiol.* 120:351-359, 1999.

The synthesis of sucrose from photosynthetic assimilates in plants, and therefore the availability of sucrose for use in fructan formation, is controlled, in part, by the enzymes sucrose phosphate synthase (SPS) and sucrose phosphate phosphatase (SPP). Sucrose plays an important role in plant growth and development, and is a major end product of photosynthesis. It also functions as a primary transport sugar and in some cases as a direct or indirect regulator of gene expression (for review see Smeekens *Curr. Opin. Plant Biol.* 1:230-234, 1998). SPS regulates the synthesis of sucrose by regulating carbon partitioning in the leaves of plants and therefore plays a major role as a limiting factor in the export of photoassimilates out of the leaf. The activity of SPS is regulated by phosphorylation and moderated by concentration of metabolites and light (Huber et al., *Plant Physiol.* 95:291-297, 1991). Specifically, SPS catalyzes the transfer of glucose from UDP-glucose to fructose-6-phosphate, thereby forming sucrose-6-phosphate (Suc-6-P). Suc-6-P is then dephosphorylated by SPP to form sucrose (Lunn et al., *Proc. Nat. Acad. Sci., U.S.A.* 97:12914-12919, 2000). The enzymes SPS and SPP exist as a heterotetramer in the cytoplasm of mesophyll cells in leaves, with SPP functioning to regulate SPS activity. SPS is also important in ripening fruits, sprouting tubers and germinating seeds (Laporte et al. *Planta* 212:817-822, 2001).

Once in the vacuole, sucrose can be converted into fructan by fructosyltransferases as discussed above, or hydrolyzed into glucose and fructose by the hydrolase enzymes known as invertases (Sturm, *Plant Physiol.* 121:1-7, 1999). There are several different types of invertases, namely extracellular (cell wall), vacuolar (soluble acid) and cytoplasmic, with at least two isoforms of each type of invertase normally being found within a plant species. In addition to having different subcellular locations, the different types of invertases have different biochemical properties. For example, soluble and cell wall invertases operate at acidic pH, whereas cytoplasmic invertases work at a more neutral or alkaline pH. Invertases are believed to regulate the entry of sucrose into different utilization pathways (Grof and Campbell *Aust. J. Plant Physiol.* 28:1-12, 2001). Reduced invertase activity may increase the level of water-soluble carbohydrates in plants. Plants contain several isoforms of cell wall invertases (CW-INV), which accumulate as soluble proteins. CWINV plays an important role in phloem unloading and in stress response. *Arabidopsis* contains 9 putative cytoplasmic or neutral invertases that are expressed in all tissues and at all developmental stages implying a more general function than the differentially expressed acid invertases. The neutral invertase cloned from carrot and *Lolium temulentum* show no similarity to acid invertases with the exception of a conserved pentapeptide motif in the grass cDNA (Gallagher *J. Exp. Bot.* 49:789, 1998; Sturm, A. et al., *Physiologia Plantarum*, 107:159-265, 1999).

Another enzyme that acts upon sucrose in plants is soluble sucrose synthase (SUS). Recent results indicate that SUS is localized in the cytosol, associated with the plasma membrane and the actin cytoskeleton. Phosphorylation of SUS is one of the factors controlling localization of the enzyme (Winter and Huber, *Crit. Rev. Biochem. Mol. Biol.* 35:253-89, 2000). It catalyzes the transfer of glucose from sucrose to UDP, yielding UDP-glucose and fructose. Increasing the amount of SUS in a plant increases the amount of cellulose synthesis, whereas decreasing SUS activity should increase fructan levels. Increased SUS concentration may also increase the yield of fruiting bodies. SUS activity is highest in carbon sink tissues in plants and low in photosynthetic source tissues, and studies have indicated that SUS is the main sucrose-cleaving activity in sink tissues. Grasses have two isoforms of SUS that are encoded by separate genes. These genes are differentially expressed in different tissues.

Pyrophosphate-fructose 6-phosphate 1-phosphotransferase (PFP, EC 2.7.1.90) catalyses the reversible conversion of fructose 6-phosphate (Fru-6-P) and pyrophosphate ($Pp_i$) to fructose 1,6-bisphosphate (Fru-1,6-P) and inorganic phosphate ($P_i$). In the plant PFP has important physiological roles in glycosylation, sucrose metabolism, respiratory carbon flow, as well as being a supply of $PP_i$. Along with FBPase and PFK, PFP regulates this step in the pathway of sucrose metabolism. PFP is a cytoplasmic enzyme consisting of a 250 kDa tetramer (two alpha and two beta chains) with the two subunits containing all of the regulatory and catalytical functions, respectively. In the plant cell fructose 2-6-bisphosphate is a potent activator of PFP activity. In sugarcane (a $C_4$ grass), PFP activity is inversely correlated with sucrose content (Whittaker and Botha *Plant Physiol.*, 115, 1651-1659, 1997), indicating that a reduction of PFP enzyme levels will increase the flux of sucrose synthesis. In forage grasses reducing PFP levels in the leaves will increase water-soluble carbohydrate levels in the leaf tissue. The *Arabidopsis* genome contains four closely related PFP genes thought to encode two isoforms of each subunit, however, only 1 cDNA representing each unit of the purified protein has been isolated from Castor Bean, Potato and Spinach (Todd, Blakeley and Dennis *Gene*, 152, 181-186, 1995; Carlisle, Blakeley, Hemmingsen, Trevanion, Hiyoshi, Kruger and Dennis *J. Biol. Chem.*, 265, 18366-18371, 1990).

Sucrose Transporters (SUTs) play a major role in the partitioning of dissacharides (sucrose) across membranes (for a review see Williams et al., *Trends Plant Sci.*, 5:283-290, 2000). In particular SUTs are involved in loading and unloading of sucrose into the phloem and the source-sink relationship within the plant. SUTs are energy dependent and can transport sucrose across large sucrose gradients. In *Arabidopsis* six SUTs have been identified, however in monocots and dicots SUTs form distinct groups. In general, monocots have 2 types of SUTs. For example barley and maize have two SUT proteins, known as SUT1 and SUT2. SUT1 is found in source, not sink, tissues, whereas SUT2 is constitutively expressed at similar levels in all tissues (Hirose, Imaizumi, Scofield, Furbank and Ohsugi *Plant Cell Physiol.* 38:1389-1396; 1997; Weschke, et al., *Plant Journal* 21, 455-457, 2000). Inhibition of SUT1 in potato plants by antisense technology resulted in increased levels of sucrose and starch in the source leaves (Schulz et al. *Planta*, 206, 533-543, 1998). Repressing SUT activity in forage grasses to lower phloem loading in source tissues will increase water soluble carbohydrate content in the leaves.

Cellulose Synthesis

The major source of dietary fibre for grazing animals comes from plant cell walls. Mammals possess no enzymes capable for breaking down the polysaccharides in plant cell walls. Instead animals such as ruminants depend on microbial breakdown of plant cell walls through fermentation in either the rumen or large intestine.

Fibre in plants is measured using the Neutral Detergent Fibre (NDF) technique in which plant samples are boiled in a solution containing sodium lauryl sulfate (van Soest in "Nutritional Ecology of the Ruminant". Cornell University Press, Ithaca, N.Y., 1994). This detergent extracts water-soluble components such as sugars, lipids and organic acids. The remaining insoluble residue (fibre) is termed NDF and consists predominantly of plant cell wall components such as cellulose, hemicellulose, and lignin. The amount of cellulose and lignin in cell walls can be determined using the Acid Detergent Fibre (ADF) method where plant samples are boiled in sulfuric acid and sodium lauryl sulfate. The difference between NDF and ADF for a plant sample is normally considered to be the amount of hemicellulose (van Soest in "Nutritional Ecology of the Ruminant". Cornell University Press, Ithaca, N.Y., 1994).

Stems of most forage species have greater NDF content then leaves. For example, for a temperate $C_3$ grass in mid-flowering such as tall fescue (*Festuca arundinacea*), NDF content of leaves and stems is 50 and 70%, respectively (Buxton & Redfearn *J. Nutrition* 127:S814-S818, 1997). In contrast, for a $C_4$ tropical grass such as switchgrass (*Panicum* virgatum L.) the NDF content of leaves and stems is 70 and 85%, respectively. The digestibility of a forage is determined by cell wall content, so that legumes are more digestible than grasses because they contain less NDF. The NDF of a legume, however, is generally less digestible than that of grasses because a higher proportion of the NDF is made up by lignin. The increase of lignin as a component of NDF is also responsible for the decrease in digestibility of grasses at the time of flowering. In fact, ruminants can digest only 40-50% of NDF in legumes compared to 60-70% for grass NDF (Buxton & Redfearn *J. Nutrition* 127:S814-S818, 1997). Digestibility of cellulose by ruminants is therefore directly related to the extent of lignification. Generally hemicellulose is more digestible than cellulose.

Cellulose is the most abundant carbohydrate in forage making up to 20-40% of dry matter (van Soest in "Nutritional Ecology of the Ruminant". Cornell University Press, Ithaca, N.Y., 1994). The cellulose in forages consists predominantly of β1-4 glucan (85%) and smaller amounts of pentosans (e.g. xylose and arabinose; 15%). There appear to be two pools of cellulose within the plant cell wall, the difference being one is lignified and the other is not (van Soest in "Nutritional Ecology of the Ruminant". Cornell University Press, Ithaca, N.Y., 1994). The lignified cellulose is mostly found in the primary cell wall and in the S1 outer layer of the secondary cell wall. Independent of lignification, it appears that cellulose possesses a variability in nutritive quality (van Soest in "Nutritional Ecology of the Ruminant". Cornell University Press, Ithaca, N.Y., 1994). This indicates that it is possible to alter the rate of cellulose digestibility by modifying the chemical composition of cellulose. This could be achieved through manipulating the actions of the cellulose synthesis and cellulose synthesis-like enzymes found in plant cells. One method to increase digestibility in this way is to increase the activity of the cellulose synthesis and cellulose synthesis-like enzymes responsible for synthesizing hemicellulose or to down regulate the cellulose synthesis and cellulose synthesis-like enzymes making cellulose. Hemicellulose is much more digestible than cellulose and is less likely to become lignified. Another way of manipulating cell wall composition is through modifying the rate and supply of primary components required for cellulose synthesis, i.e. of β1-4 glucan and pentosans such as xylose and arabinose. One way to achieve this is to modify the actions of soluble sucrose synthase and UDP glucose pyrophophorylase (UDP-GP) enzymes that produce the UDP-glucose required for cellulose synthesis. This may be further modified by manipulating the actions of the large and small subunits of ADP-glucose pyrophosphorylase (ADP-GP), the two enzymes that are rate-limiting steps in starch synthesis (Smith, Denyer and Martin *Ann. Rev. Plant Phys. Plant Mol. Biol.* 48:67-87, 1997).

Manipulating expression of the UDPGP and ADP-GP genes would alter the chemical composition of plant cell walls in forage plants. Altering cell wall biosynthesis therefore provides an opportunity to increase digestibility of the plant dry matter. This may be achieved by increasing the amount of carbon in the plant allocated to cellulose biosynthesis at the expense of lignin biosynthesis. Alternatively, decreasing the amount of cellulose biosynthesis and increasing the amount of water-soluble carbohydrates would have a similar effect. Furthermore, specifically increasing hemicellulose levels in the plant cell walls at expense of cellulose would also increase forage digestibility. By utilizing specific promoters in combination with the UDPGP and ADP-GP genes it is possible to increase or decrease the starch, cellulose and/or hemicellulose levels in the leaf or stem.

Tannin Biosynthetic Pathway

Condensed tannins are polymerized flavonoids. More specifically, tannins are composed of catechin 4-ol and catechin monomer units, and are stored in the vacuole. In many temperate forage crops, such as ryegrass and fescue, foliar tissues are tannin-negative. This leads to a high initial rate of fermentation when these crops are consumed by ruminant livestock resulting in both protein degradation and production of ammonia by the livestock. These effects can be reduced by the presence of low to moderate levels of tannin. In certain other plant species, the presence of high levels of tannins reduces palatability and nutritive value. Introduction of genes encoding enzymes involved in the biosynthesis of condensed tannins into a plant may be employed to synthesize flavonoid compounds that are not normally made in the plant. These compounds may then be isolated and used for treating human or animal disorders or as food additives.

Much of the biosynthetic pathway for condensed tannins is shared with that for anthocyanins, which are pigments responsible for flower color. Therefore, modulation of the levels of enzymes involved in the tannin biosynthetic pathway may be employed to alter the color of foliage and the pigments produced in flowers.

Most tannins described to date contain pro-cyanidin units derived from dihydroquercetin and pro-delphinidin units derived from dihydromyricetin. However, some tannins contain pro-pelargonidin units derived from dihydrokaempferol. The initial step in the tannin biosynthetic pathway is the condensation of coumaryl CoA with malonyl CoA to give naringenin-chalcone, which is catalyzed by the enzyme chalcone synthase (CHS). The enzyme chalcone isomerase (CHI) catalyzes the isomerization of naringenin chalcone to naringenin (also known as flavanone), which is then hydroxylated by the action of the enzyme flavonone 3- beta-hydroxylase (F3βH) to give dihydrokaempferol. The enzyme flavonoid 3'-hydroxylase (F3'OH) catalyzes the conversion of dihydrokaempferol to dihydroquercetin, which in turn can be converted into dihydromyricetin by the action of flavonoid 3'5'-hydroxylase (F3'5'OH). F3'OH is a P450 enzyme responsible for the brick red to orange pelargonidin-based pigments, whereas F3'5'OH is responsible for the purple and blue delphinidin-based pigments. The enzyme dihydroflavonol-4-reductase (DFR) catalyzes the last step before dihydrokaempferol, dihydroquercetin and dihydromyricetin are committed for either anthocyanin (flower pigment) or proanthocyanidin (condensed tannin) formation. DFR also converts dihydrokaempferol to afzelchin-4-ol, dihydroquercetin to catechin-4-ol, and dihydromyricetin to gallocatechin-4-ol, probably by the action of more than one isoform. For a review of the tannin biosynthetic pathway, see, Robbins M. P. and Morris P. in Metabolic Engineering of Plant Secondary Metabolism, Verpoorte and Alfermann (eds), Kluwer Academic Publishers, the Netherlands, 2000. The leucoanthocyanidin dioxygenase (LDOX) enzyme belongs to the iron/ascorbate-dependent family of oxidoreductases. In maize the LDOX gene A2 is required for the oxidation of leucoanthocyanidins into anthocyanidins (Menssen, Hoehmann, Martin, Schnable, Peterson, Saedler and Gierl *EMBO J.* 9:3051-3057, 1990).

While polynucleotides encoding some of the enzymes involved in the fructan, cellulose and tannin biosynthetic pathways have been isolated for certain species of plants, genes encoding many of the enzymes in a wide range of plant species have not yet been identified. Thus there remains a need in the art for materials useful in the modification of fructan and tannin content and composition in plants, and for methods for their use.

SUMMARY OF THE INVENTION

The present invention provides enzymes involved in the fructan, cellulose, starch and/or tannin biosynthetic pathways that are encoded by polynucleotides isolated from forage grass tissues. The polynucleotides were isolated from *Lolium perenne* (perennial ryegrass) and *Festuca arundinacea* (tall fescue) tissues taken at different times of the year, specifically in winter and spring, and from different parts of the plants, including: leaf blades, leaf base, pseudostems, roots and stems. Genetic constructs, expression vectors and host cells comprising the inventive polynucleotides are also provided, together with methods for using the inventive polynucleotides and genetic constructs to modulate the biosynthesis of fructans and tannins.

In specific embodiments, the isolated polynucleotides of the present invention comprise a sequence selected from the group consisting of: (a) SEQ ID NO: 1-44; (b) complements of SEQ ID NO: 1-44; (c) reverse complements of SEQ ID NO: 1-44; (d) reverse sequences of SEQ ID NO: 1-44; (e) sequences having a 99% probability of being functionally or evolutionarily related to a sequence of (a)-(d), determined as described below; and (f) sequences having at least 75%, 80%, 90%, 95% or 98% identity to a sequence of (a)-(d), the percentage identity being determined as described below. Polynucleotides comprising at least a specified number of contiguous residues ("x-mers") of any of SEQ ID NO: 1-44, and oligonucleotide probes and primers corresponding to SEQ ID NO: 1-44 are also provided. All of the above polynucleotides are referred to herein as "polynucleotides of the present invention."

In further aspects, the present invention provides isolated polypeptides encoded by the inventive polynucleotides. In specific embodiments, such polypeptides comprise an amino acid sequence of SEQ ID NO: 45-88. The present invention also provides polypeptides comprising a sequence having at least 75%, 80%, 90%, 95% or 98% identity to a sequence of SEQ ID NO: 45-88, wherein the polypeptide possesses the same functional activity as the polypeptide comprising a sequence of SEQ ID NO: 45-88. The present invention also contemplates isolated polypeptides comprising at least a functional portion of an amino acid sequence selected from the group consisting of: (a) SEQ ID NO: 45-88; and (b) sequences having at least 75%, 80%, 90%, 95% or 98% identity to a sequence of SEQ ID NO: 45-88.

In another aspect, the present invention provides genetic constructs, or expression vectors, comprising a polynucleotide of the present invention, either alone, in combination with one or more of the inventive sequences, or in combination with one or more known polynucleotides.

In certain embodiments, the present invention provides genetic constructs comprising, in the 5'-3' direction: a gene promoter sequence; an open reading frame coding for at least a functional portion of a polypeptide of the present invention; and a gene termination sequence. An open reading frame may be orientated in either a sense or anti-sense direction. Genetic constructs comprising a non-coding region of a polynucleotide of the present invention or a polynucleotide complementary to a non-coding region, together with a gene promoter sequence and a gene termination sequence, are also provided. Preferably, the gene promoter and termination sequences are functional in a host cell, such as a plant cell. Most preferably, the gene promoter and termination sequences are those of the original enzyme genes but others generally used in the art, such as the Cauliflower Mosaic Virus (CMV) promoter, with or without enhancers, such as the Kozak sequence or Omega enhancer, and the *Agrobacterium tumefaciens* nopalin synthase terminator may be usefully employed in the present invention. Tissue-specific promoters may be employed in order to target expression to one or more desired tissues. The construct may further include a marker for the identification of transformed cells.

In a further aspect, transgenic cells, such as transgenic plant cells, comprising the genetic constructs of the present invention are provided, together with tissues and plants comprising such transgenic cells, and fruits, seeds and other products, derivatives, or progeny of such plants.

In yet another aspect, the present invention provides methods for modulating the fructan, cellulose, starch and/or tannin content and composition of a target organism, such as a plant, by modulating the amount and/or activity of an inventive polynucleotide or polypeptide in the organism. In certain embodiments, such methods include stably incorporating into the genome of the target plant a genetic construct of the present invention. In a preferred embodiment, the target plant is a forage grass, preferably selected from the group consisting of *Lolium* and *Festuca* species, and most preferably from the group consisting of *Lolium perenne* and *Festuca arundinacea*.

In a related aspect, methods for producing a plant having altered fructan or tannin composition is provided. Such methods comprise modulating the amount and/or activity of an inventive polynucleotide or polypeptide in a plant cell by, for example, transforming a plant cell with a genetic construct of the present invention to provide a transgenic cell, and cultivating the transgenic cell under conditions conducive to regeneration and mature plant growth.

In yet a further aspect, the present invention provides methods for modifying the activity of an enzyme in a target organism, such as a plant, comprising modulating the amount and/or activity of an inventive polynucleotide or polypeptide in the target organism by, for example stably incorporating into the genome of the target organism a genetic construct of the present invention. In a preferred embodiment, the target plant is a forage grass, preferably selected from the group consisting of *Lolium* and *Festuca* species, and most preferably from the group consisting of *Lolium perenne* and *Festuca arundinacea*.

BRIEF DESCRIPTION OF THE FIGURES

FIG. 3 shows the amino acid sequence of SEQ ID NO: 45. The conserved UTP-glucose-1-phosphate uridylyltransferase domain is underlined.

FIG. 4 shows the amino acid sequence of SEQ ID NO: 46. The conserved UTP-glucose-1-phosphate uridylyltransferase domain is underlined.

FIG. 5 shows the amino acid sequence of SEQ ID NO: 47. The conserved glycoside hydrolase, family 32 domain is underlined.

FIG. 6 shows the amino acid sequence of SEQ ID NO: 48. A transmembrane domain is underlined.

FIG. 7 shows the amino acid sequence of SEQ ID NO: 53. The signal peptide is in bold/italics.

FIG. 8 shows the amino acid sequence of SEQ ID NO: 54. The signal peptide is in bold/italics and two conserved Antifreeze protein, type I domains are underlined.

FIG. 9 shows the amino acid sequence of SEQ ID NO: 55. The signal peptide is in bold/italics.

FIG. 10 shows the amino acid sequence of SEQ ID NO: 56. Two transmembrane domains are double underlined.

FIG. 11 shows the amino acid sequence of SEQ ID NO: 57. Two transmembrane domains are double underlined.

FIG. 12 shows the amino acid sequence of SEQ ID NO: 58. Two transmembrane domains are double underlined.

FIG. 13 shows the amino acid sequence of SEQ ID NO: 59. The conserved phosphofructokinase domain is underlined and a transmembrane domain is double underlined.

FIG. 14 shows the amino acid sequence of SEQ ID NO: 60. The conserved phosphofructokinase domain is underlined and a transmembrane domain is double underlined.

FIG. 15 shows the amino acid sequence of SEQ ID NO: 61. The conserved phosphofructokinase is underlined.

FIG. 16 shows the amino acid sequence of SEQ ID NO: 62. The conserved phosphofructokinase domain is underlined.

FIG. 17 shows the amino acid sequence of SEQ ID NO: 63. The conserved phosphofructokinase domain is underlined.

FIG. 18 shows the amino acid sequence of SEQ ID NO: 64. The conserved glycosyl transferase, group 1 domain is underlined and two transmembrane domains are double underlined.

FIG. 19 shows the amino acid sequence of SEQ ID NO: 65. The conserved glycosyl transferase, group 1 domain is underlined and two transmembrane domains are double underlined.

FIG. 20 shows the amino acid sequence of SEQ ID NO: 66. The conserved substrate transporter domain is in bold and eleven transmembrane domains are double underlined.

FIG. 21 shows the amino acid sequence of SEQ ID NO: 67. Nine transmembrane domains are double underlined.

FIG. 22 shows the amino acid sequence of SEQ ID NO: 68. The conserved substrate transporter domain is in bold and eleven transmembrane domains are double underlined.

FIG. 23 shows the amino acid sequence of SEQ ID NO: 69. The conserved substrate transporter domain is in bold and eleven transmembrane domains are double underlined.

FIG. 24 shows the amino acid sequence of SEQ ID NO: 70. The conserved substrate transporter domain is in bold and eleven transmembrane domains are double underlined.

FIG. 25 shows the amino acid sequence of SEQ ID NO: 71.

FIG. 26 shows the amino acid sequence of SEQ ID NO: 72. The conserved nucleotidyl transferase domain is in bold and three ADP-glucose pyrophosphorylase are boxed. Nine transmembrane domains are double underlined.

FIG. 27 shows the amino acid sequence of SEQ ID NO: 73. The conserved nucleotidyl transferase domain is in bold and three ADP-glucose pyrophosphorylase domains are boxed. A transmembrane domain is double underlined.

FIG. 28 shows the amino acid sequence of SEQ ID NO: 74. The conserved nucleotidyl transferase domain is in bold and three ADP-glucose pyrophosphorylase domains are boxed. A transmembrane domain is double underlined.

FIG. 29 shows the amino acid sequence of SEQ ID NO: 75. The conserved nucleotidyl transferase domain is in bold and three ADP-glucose pyrophosphorylase domains are boxed. The signal peptide is in bold/italics and a transmembrane domain is double underlined.

FIG. 30 shows the amino acid sequence of SEQ ID NO: 76. The conserved naringenin-chalcone synthase domain is underlined. The signal peptide is in bold/italics and a transmembrane domain is double underlined.

FIG. 31 shows the amino acid sequence of SEQ ID NO: 77. The conserved naringenin-chalcone synthase domain is underlined and two transmembrane domains are double underlined.

FIG. 32 shows the amino acid sequence of SEQ ID NO: 78. The conserved naringenin-chalcone synthase domain is underlined and two transmembrane domains are double underlined.

FIG. 33 shows the amino acid sequence of SEQ ID NO: 79. A transmembrane domain is double underlined.

FIG. 34 shows the amino acid sequence of SEQ ID NO: 80. A transmembrane domain is double underlined.

FIG. 35 shows the amino acid sequence of SEQ ID NO: 81. A transmembrane domain is double underlined.

FIG. 36 shows the amino acid sequence of SEQ ID NO: 82. The conserved Cytochrome P450 domain is underlined and three transmembrane domains are double underlined.

FIG. 37 shows the amino acid sequence of SEQ ID NO: 83. The conserved Cytochrome P450 domain is boxed, the signal peptide is in bold and a transmembrane domain is double underlined.

FIG. 38 shows the amino acid sequence of SEQ ID NO: 84. The conserved Cytochrome P450 domain is boxed and three transmembrane domains are double underlined.

FIG. 39 shows the amino acid sequence of SEQ ID NO: 85. The conserved Cytochrome P450 domain is boxed, the signal peptide is in bold/italics and three transmembrane domains are double underlined.

FIG. 40 shows the amino acid sequence of SEQ ID NO: 86. The conserved Cytochrome P450 domain is boxed and three transmembrane domains are double underlined.

FIG. 41 shows the amino acid sequence of SEQ ID NO: 87. The conserved Cytochrome P450 domain is boxed, the signal peptide is in bold/italics and three transmembrane domains are double underlined.

FIG. 42 shows the amino acid sequence of SEQ ID NO: 88. The conserved 2OG-Fe(II) oxygenase superfamily domain is underlined.

DETAILED DESCRIPTION OF THE INVENTION

Figure 1:
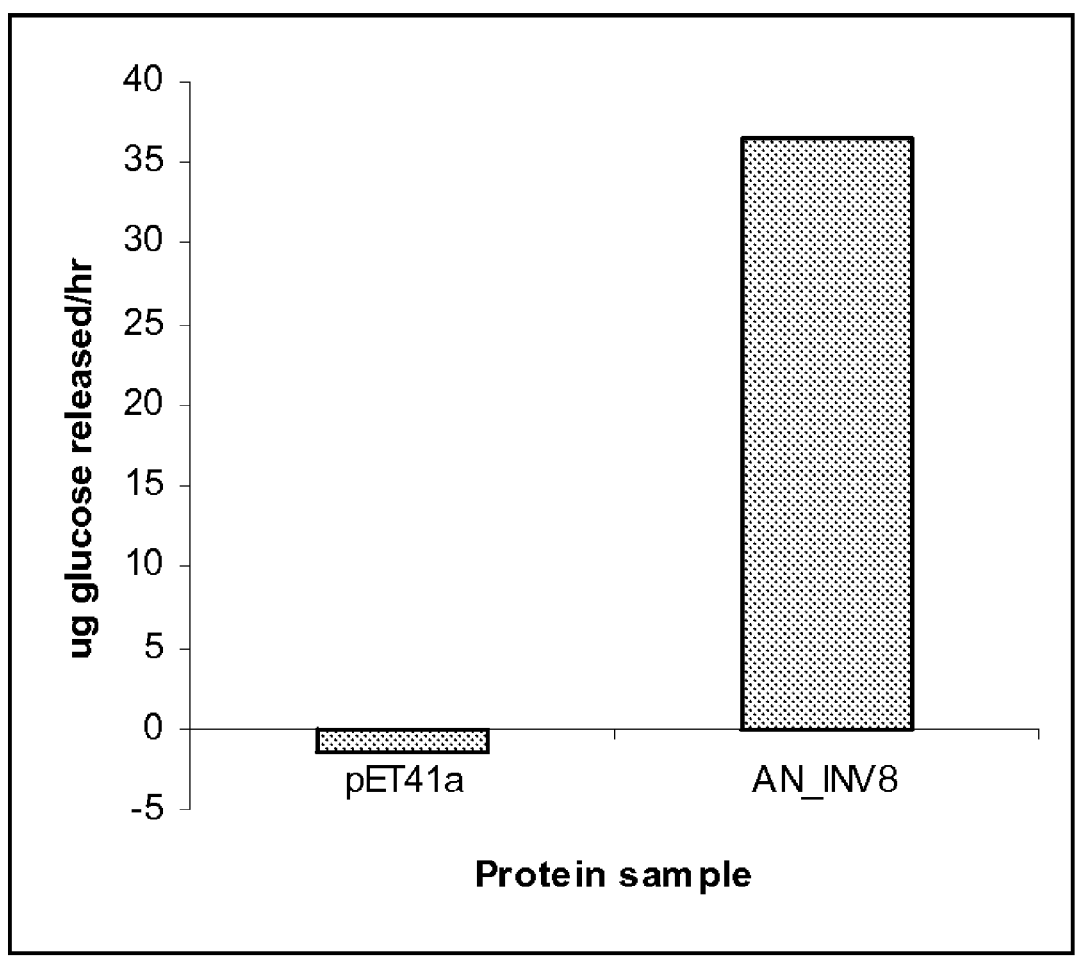
FIG. 1 shows the neutral invertase activity of the recombinant grass alkaline/neutral invertase protein AN_INV8 from *L. perenne* (amino acid sequence provided in SEQ ID NO: 56; cDNA sequence provided in SEQ ID NO: 12). Activity was measured as the µg of glucose release from cleavage of sucrose per hour at pH 7. Also shown is an empty vector negative control (pET41a).

The polypeptides of the present invention, and the polynucleotides encoding such polypeptides, have activity in fructan, cellulose, starch and/or tannin biosynthetic pathways in plants. Using the methods and materials of the present invention, the fructan, cellulose, starch and/or tannin content of a plant may be modulated by modulating expression of polynucleotides of the present invention, or by modifying the activity of the polynucleotides or polypeptides encoded by the polynucleotides. The isolated polynucleotides and polypeptides of the present invention may thus be usefully employed in the correction of nutritional imbalances associated with temperate pastures and to increase the yield of animal products from pastures.

The fructan, cellulose, starch and/or tannin content of a target organism, such as a plant, may be modified, for example, by incorporating additional copies of genes encoding enzymes involved in the fructan, cellulose, starch and/or tannin biosynthetic pathways into the genome of the target plant. Similarly, a modified fructan, cellulose, starch and/or tannin content can be obtained by transforming the target plant with anti-sense copies of such genes. In addition, the number of copies of genes encoding for different enzymes in the fructan, cellulose, starch and tannin biosynthetic pathways can be manipulated to modify the relative amount of each monomer unit synthesized, thereby leading to the formation of fructans, cellulose, starch or tannins having altered composition.

The present invention thus provides methods for modulating the polynucleotide and/or polypeptide content and composition of an organism. In certain embodiments, such methods involve stably incorporating into the genome of the organism a genetic construct comprising one or more polynucleotides of the present invention. In one embodiment, the target organism is a plant species, preferably a forage plant, more preferably a grass of the *Lolium* or *Festuca* species, and most preferably *Lolium perenne* or *Festuca arundinacea*. In related aspects, methods for producing a plant having an altered genotype or phenotype is provided, such methods comprising transforming a plant cell with a genetic construct of the present invention to provide a transgenic cell, and cultivating the transgenic cell under conditions conducive to regeneration and mature plant growth. Plants having an altered genotype or phenotype as a consequence of modulation of the level or content of a polynucleotide or polypeptide of the present invention compared to a wild-type organism, as well as components (seeds, etc.) of such plants, and the progeny of such plants, are contemplated by and encompassed within the present invention.

The isolated polynucleotides of the present invention additionally have utility in genome mapping, in physical mapping, and in positional cloning of genes. The polynucleotide sequences identified as SEQ ID NOS: 1-44 and their variants, may also be used to design oligonucleotide probes and primers. Oligonucleotide probes and primers have sequences that are substantially complementary to the polynucleotide of interest over a certain portion of the polynucleotide, preferably over substantially the entire length of the polynucleotides. Oligonucleotide probes designed using the inventive polynucleotides may be employed to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the inventive polynucleotides may also be used in connection with various microarray technologies, including the microarray technology of Affymetrix (Santa Clara, Calif.).

In a first aspect, the present invention provides isolated polynucleotide sequences identified in the attached Sequence Listing as SEQ ID NOS: 1-44, and polypeptide sequences identified in the attached Sequence Listing as SEQ ID NO: 45-88. The polynucleotides and polypeptides of the present invention have demonstrated similarity to the following polypeptides that are known to be involved in fructan, cellulose, starch and/or tannin biosynthetic processes:

TABLE 1

| SEQ ID NO: DNA | SEQ ID NO: polypeptide | Category | Description |
| --- | --- | --- | --- |
| 1, 2 | 45, 46 | Carbohydrate metabolism | Homolog of UDP-glucose pyrophosphorylase (EC 2.7.7.9) (UDPGP or UGPASE) which is one of the key enzymes of the carbohydrate metabolic pathway. It plays a central role as glucosyl donor in cellular metabolic pathways. UDP-glucose pyrophosphorylase catalyzes the reversible uridylyl transfer from UDP-glucose to MgPPi, forming glucose 1-phosphate and MgUTP. |
| 3, 4 | 47, 48 | Fructan metabolism | Homolog of Sucrose (Suc): Suc 1-fructosyl-transferase (1-SST) isolated from *L. perenne*. 1-SST is the key enzyme in plant fructan biosynthesis and catalyzes the de novo fructan synthesis from sucrose. Fructans play an important role in assimilation partitioning and in stress tolerance in many plants. It contains a typical signature of the glycosyl hydrolases family 32 (amino acid residues 126 to 139). The glycosyl hydrolases family 32 domain signature has a consensus of HYQPxxH/NxxNDPNG, where D is the active site residue (Henrissat, Biochem. J. 280: 309-316, 1991). |
| 5-14 | 49-58 | Fructan metabolism | Homolog of alkaline/neutral invertase (AN-INV) that is involved in catalyzing sucrose into hexoses for utilization as a source of carbon and energy. AN-INV belongs to the family 32 of glycosyl hydrolases. Neutral invertase is an octamer of 456 kDa with subunits of 57 kDa, whereas alkaline invertase is a 504 kDa tetramer with subunits of 126 kDa. Neutral invertase also hydrolyzes raffinose and stachyose and, therefore, is a beta-fructo-furanosidase. In contrast, alkaline invertase is |

TABLE 1-continued

| SEQ ID NO: DNA | SEQ ID NO: polypeptide | Category | Description |
|---|---|---|---|
| | | | highly specific for sucrose (Lee and Sturm, Plant Physiol. 112: 1513-1522, 1996). |
| 15, 16 | 59, 60 | Fructan metabolism | Homologue of the alpha subunit of Pyro-phosphate-dependent 6-phosphofructo-1-phosphotransferase (PFPA) that plays a role in carbohydrate metabolism. PFP is involved in the first step of glycolysis in the phosphorylation of fructose 6-phosphate (Fru 6-P). PFPA acts as a regulatory protein in regulating both the catalytic activity and the Fru-2,6-P2-binding affinity of the beta subunit (Siebers et al., *J. Bacteriol.* 180: 2137-2143, 1998). |
| 17-19 | 61-63 | Fructan metabolism | Homolog of the beta subunit of Pyrophosphate-dependent 6-phosphofructo-1-phospho-transferase (PFPB) which plays a role in carbohydrate metabolism. PFP is involved in the first step of glycolysis in the phosphorylation of fructose 6-phosphate (Fru-6-P). The catalytic activity of the PFP enzyme is associated with the beta subunit PFPB while PFPA acts as a regulatory protein in regulating both the catalytic activity and the Fru-2,6-P2-binding affinity of the beta subunit (Carlisle et al., *J. Biol. Chem.* 265: 18366-18371, 1990; Siebers etat., *J. Bacteriol.* 180: 2137-2143, 1998). |
| 20, 21 | 64, 65 | Fructan metabolism | Homologue of sucrose phosphate synthase which is involved in the sucrose synthesis pathway. Sucrose plays an important role in plant growth and development and is a major end product of photosynthesis. It also functions as a primary transport sugar and in some cases as a direct or indirect regulator of gene expression. SPS-1 regulates the synthesis of sucrose by regulating carbon partitioning in the leaves of plants and therefore plays a major role as a limiting factor in the export of photoassimilates out of the leaf. The activity of SPS is regulated by phosphorylation and moderated by concentration of metabolites and light. |
| 22-24 | 66-68 | Fructan metabolism | Homologue of the sugar transporter SUT1, a member of the SUT family of low- and high-affinity sucrose transporters that is involved in transport of sucrose from mature leaves via the phloem. Expression of SUT1 has also been observed in other tissues (stems and parts of flower) suggesting that SUT1 may also have other functions, such as sucrose retrieval and phloem unloading (Burkle et al., Plant Physiol. 118: 59-68, 1998). |
| 25, 26 | 69, 70 | Fructan metabolism | Homologue of sugar transporter SUT2, a member of the SUT family of low- and high-affinity sucrose transporters. SUT2 is more highly expressed in sink than in source leaves, is inducible by sucrose and regulates the relative activity of low- and high-affinity sucrose transport into sieve elements (Barker et al., Plant Cell 12: 1153-1164, 2000). |
| 27 | 71 | Fructan metabolism | Homologue of a sugar transporter, a member of the SUT family of low- and high-affinity sucrose transporters that is involved in transport of sucrose from mature leaves via the phloem. |
| 28, 29 | 72, 73 | Fructan metabolism | Homolog of the large subunit (LSU) of ADP-glucose pyrophosphorylase (AGPase), which plays a role in starch biosynthesis. It catalyzes the synthesis of the activated glycosyl donor, ADP-glucose from glucose-1-phosphate and |

TABLE 1-continued

| SEQ ID NO: DNA | SEQ ID NO: polypeptide | Category | Description |
|---|---|---|---|
| | | | ATP. The enzyme is found in chloroplasts of leaves and amyloplasts of developing endosperm. AGPase belongs to the glucose-1-phosphate adenylyltransferase family. |
| 30, 31 | 74, 75 | Carbohydrate metabolism | Homolog of the small subunit (SSU) of ADP-glucose pyrophosphorylase (AGPase), which plays a role in starch biosynthesis. It catalyzes the synthesis of the activated glycosyl donor, ADP-glucose from glucose-1-phosphate and ATP. The enzyme is found in chloroplasts of leaves and amyloplasts of developing endosperm. AGPase belongs to the glucose-1-phosphate adenylyltransferase family. |
| 32, 33 | 76, 77 | Tannin biosynthesis | Homolog of Chalcone Synthase (CHS) which is an important enzyme in flavonoid synthesis. The molecule contains a conserved chalcone synthase active site (Lanz et al., J. Biol. Chem. 266: 9971-9976, 1991) at amino acid residues 166 to 176, with the conserved Cys residue at position 167. |
| 34-37 | 78-81 | Tannin metabolism | Homologue of dihydroflavonal-4-reductase (DFR) that belongs to the dihydroflavonol-4-reductases family and is involved in the flavonoid synthesis and anthocyanidins biosynthesis. Flavonoids are secondary metabolites derived from phenylalanine and acetate metabolism that perform a variety of essential functions in higher plants. |
| 38-43 | 82-87 | Tannin metabolism | Homologue of flavonoid 3'-hydroxylase (F3'H) which is a key enzyme in the flavonoid pathway leading to the production of the colored anthocyanins where it is involved in determination of flower coloring. Anthocyanins synthesized in plants are controlled by flavonoid 3'-hydroxylase and flavonoid 3',5'-hydroxylase which are members of the cytochrome P450 family, a large group of membrane-bound heme-containing enzymes that are involved in a range of NADPH- and O2-dependent hydroxylation reactions. Plants have evolved a large number of different P450 enzymes for the synthesis of secondary metabolites. The F3 'H transcript is most abundant in petals from flowers at an early stage of development and levels decline as the flower matures. Transcripts are also detected in the ovaries, sepals, peduncles, stems and anthers of the petunia plant (Brugliera et al., Plant J. 19: 441-45 1, 1999 |
| 44 | 88 | Tannin biosynthesis | Homologue of leucoanthocyanidin dioxygenase (LDOX) which is an enzyme in the flavonoid biosynthesis pathway. LDOX is expressed as a late gene in the flavonoid biosynthesis pathway. |

All the polynucleotides and polypeptides provided by the present invention are isolated and purified, as those terms are commonly used in the art. Preferably, the polypeptides and polynucleotides are at least about 80% pure, more preferably at least about 90% pure, and most preferably at least about 99% pure.

The word "polynucleotide(s)," as used herein, means a polymeric collection of nucleotides, and includes DNA and corresponding RNA molecules and both single and double stranded molecules, including HnRNA and mRNA molecules, sense and anti-sense strands of DNA and RNA molecules, and comprehends cDNA, genomic DNA, and wholly or partially synthesized polynucleotides. A polynucleotide of the present invention may be an entire gene, or any portion thereof. As used herein, a "gene" is a DNA sequence which codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al., Methods in Enzymol. 254(23): 363-375, 1995 and Kawasaki et al., Artific. Organs 20(8): 836-848, 1996.

In specific embodiments, the present invention provides isolated polynucleotides comprising a sequence of SEQ ID NO: 1-44; polynucleotides comprising variants of SEQ ID NO: 1-44; polynucleotides comprising extended sequences of SEQ ID NO: 1-44 and their variants, oligonucleotide primers and probes corresponding to the sequences set out in SEQ ID NO: 1-44 and their variants, polynucleotides comprising at least a specified number of contiguous residues of any of SEQ ID NO: 1-44 (x-mers), and polynucleotides comprising extended sequences which include portions of the sequences set out in SEQ ID NO: 1-44, all of which are referred to herein, collectively, as "polynucleotides of the present invention." Polynucleotides that comprise complements of such polynucleotide sequences, reverse complements of such polynucleotide sequences, or reverse sequences of such polynucleotide sequences, together with variants of such sequences, are also provided.

The definition of the terms "complement(s)," "reverse complement(s)," and "reverse sequence(s)," as used herein, is best illustrated by the following example. For the sequence 5' AGGACC 3', the complement, reverse complement, and reverse sequence are as follows:

| | |
|---|---|
| complement | 3' TCCTGG 5' |
| reverse complement | 3' GGTCCT 5' |
| reverse sequence | 5' CCAGGA 3'. |

Preferably, sequences that are complements of a specifically recited polynucleotide sequence are complementary over the entire length of the specific polynucleotide sequence.

As used herein, the term "x-mer," with reference to a specific value of "x," refers to a polynucleotide comprising at least a specified number ("x") of contiguous residues of: any of the polynucleotides provided in SEQ ID NO: 1-44. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NO: 1-44, or their variants. Similarly, polypeptides of the present invention comprehend polypeptides comprising at least a specified number of contiguous residues (x-mers) of any of the polypeptides identified as SEQ ID NO: 45-88. According to preferred embodiments, the value of x is at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer, a 250-mer; or a 300-mer, 400-mer, 500-mer or 600-mer of a polynucleotide provided in SEQ ID NO: 1-44, or a variant of one of the polynucleotides corresponding to the polynucleotides provided in SEQ ID NO: 1-44. Polypeptides of the present invention include polypeptides comprising a 20-mer, a 40- mer, a 60-mer, an 80-mer, a 100-mer, a 120-mer, a 150-mer, a 180-mer, a 220-mer, a 250-mer; or a 300-mer, 400-mer, 500-mer or 600-mer of a polypeptide provided in SEQ ID NO: 45-88, or a variant thereof.

The polynucleotides of the present invention were isolated by high throughput sequencing of cDNA libraries prepared from forage grass tissue collected from *Lolium perenne* and *Festuca arundinacea*. Some of the polynucleotides of the present invention may be "partial" sequences, in that they do not represent a full-length gene encoding a full-length polypeptide. Such partial sequences may be extended by analyzing and sequencing various DNA libraries using primers and/or probes and well known hybridization and/or PCR techniques. Partial sequences may be extended until an open reading frame encoding a polypeptide, a full-length polynucleotide and/or gene capable of expressing a polypeptide, or another useful portion of the genome is identified. Such extended sequences, including full-length polynucleotides and genes, are described as "corresponding to" a sequence identified as one of the sequences of SEQ ID NO: 1-44 or a variant thereof, or a portion of one of the sequences of SEQ ID NO: 1-44 or a variant thereof, when the extended polynucleotide comprises an identified sequence or its variant, or an identified contiguous portion (x-mer) of one of the sequences of SEQ ID NO: 1-44 or a variant thereof. Similarly, RNA sequences, reverse sequences, complementary sequences, anti-sense sequences and the like, corresponding to the polynucleotides of the present invention, may be routinely ascertained and obtained using the cDNA sequences identified as SEQ ID NO: 1-44.

The polynucleotides identified as SEQ ID NOS: 1-44 contain open reading frames ("ORFs") encoding polypeptides and functional portions of polypeptides. Open reading frames may be identified using techniques that are well known in the art. These techniques include, for example, analysis for the location of known start and stop codons, most likely reading frame identification based on codon frequencies, etc. Suitable tools and software for ORF analysis are well known in the art and include, for example, GeneWise, available from The Sanger Center, Wellcome Trust Genome Campus, Hinxton, Cambridge, CB10 1SA, United Kingdom; Diogenes, available from Computational Biology Centers, University of Minnesota, Academic Health Center, UMHG Box 43 Minneapolis Minn. 55455; and GRAIL, available from the Informatics Group, Oak Ridge National Laboratories, Oak Ridge, Tennessee, Tenn. Once a partial open reading frame is identified, the polynucleotide may be extended in the area of the partial open reading frame using techniques that are well known in the art until the polynucleotide for the full open reading frame is identified.

The location of ORFs (by nucleotide position) contained within SEQ ID NO: 1-44, and the corresponding amino acid sequences are provided in Table 2 below.

TABLE 2

| SEQ ID NO: Polynucleotide | ORF | SEQ ID NO: Polypeptide |
|---|---|---|
| 1 | 72-1493 | 45 |
| 2 | 66-1481 | 46 |
| 3 | 0-1607 | 47 |
| 4 | 1-1914 | 48 |
| 5 | 123-1934 | 49 |
| 6 | 0-1671 | 50 |
| 7 | 114-1979 | 51 |
| 8 | 0-737 | 52 |
| 9 | 47-1783 | 53 |
| 10 | 170-2029 | 54 |
| 11 | 113-1849 | 55 |
| 12 | 154-1818 | 56 |
| 13 | 211-1866 | 57 |

TABLE 2-continued

| SEQ ID NO: Polynucleotide | ORF | SEQ ID NO: Polypeptide |
|---|---|---|
| 14 | 79-1767 | 58 |
| 15 | 76-1926 | 59 |
| 16 | 80-1930 | 60 |
| 17 | 91-1782 | 61 |
| 18 | 91-1782 | 62 |
| 19 | 84-1775 | 63 |
| 20 | 97-2994 | 64 |
| 21 | 112-3065 | 65 |
| 22 | 226-1794 | 66 |
| 23 | 0-1226 | 67 |
| 24 | 243-1811 | 68 |
| 25 | 207-1727 | 69 |
| 26 | 101-1615 | 70 |
| 27 | 108-1634 | 71 |
| 28 | 150-1718 | 72 |
| 29 | 169-1737 | 73 |
| 30 | 12-1589 | 74 |
| 31 | 5-1579 | 75 |
| 32 | 136-1332 | 76 |
| 33 | 136-1332 | 77 |
| 34 | 95-836 | 78 |
| 35 | 95-1123 | 79 |
| 36 | 82-847 | 80 |
| 37 | 82-1104 | 81 |
| 38 | 0-1532 | 82 |
| 39 | 58-1632 | 83 |
| 40 | 0-1580 | 84 |
| 41 | 16-1596 | 85 |
| 42 | 0-1478 | 86 |
| 43 | 20-1519 | 87 |
| 44 | 117-1259 | 88 |

Once open reading frames are identified, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

The polynucleotides of the present invention may be isolated by high throughput sequencing of cDNA libraries prepared from forage grass tissue, as described below in Example 1. Alternatively, oligonucleotide probes and primers based on the sequences provided in SEQ ID NO: 1-44 can be synthesized as detailed below, and used to identify positive clones in either cDNA or genomic DNA libraries from forage grass tissue cells by means of hybridization or polymerase chain reaction (PCR) techniques. Hybridization and PCR techniques suitable for use with such oligonucleotide probes are well known in the art (see, for example, Mullis et al., *Cold Spring Harbor Symp. Quant. Biol.*, 51:263, 1987; Erlich, ed., PCR technology, Stockton Press: NY, 1989; and Sambrook et al., eds., *Molecular cloning: a laboratory manual*, 2nd ed., CSHL Press: Cold Spring Harbor, N.Y., 1989). In addition to DNA-DNA hybridization, DNA-RNA or RNA-RNA hybridization assays are also possible. In the first case, the mRNA from expressed genes would then be detected instead of genomic DNA or cDNA derived from mRNA of the sample. In the second case, RNA probes could be used. Artificial analogs of DNA hybridizing specifically to target sequences could also be employed. Positive clones may be analyzed by restriction enzyme digestion, DNA sequencing or the like.

The polynucleotides of the present invention may also, or alternatively, be synthesized using techniques that are well known in the art. The polynucleotides may be synthesized, for example, using automated oligonucleotide synthesizers (e.g., Beckman Oligo 1000M DNA Synthesizer; Beckman Coulter Ltd., Fullerton, Calif.) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

Oligonucleotide probes and primers complementary to and/or corresponding to SEQ ID NO: 1-44 and variants of those sequences, are also comprehended by the present invention. Such oligonucleotide probes and primers are substantially complementary to the polynucleotide of interest over a certain portion of the polynucleotide. An oligonucleotide probe or primer is described as "corresponding to" a polynucleotide of the present invention, including one of the sequences set out as SEQ ID NO: 1-44 or a variant thereof, if the oligonucleotide probe or primer, or its complement, is contained within one of the sequences set out as SEQ ID NOS: 1-44 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions.

In specific embodiments, the inventive oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length, preferably from about 10 to 50 base pairs in length, and more preferably from about 15 to 40 base pairs in length. The probes can be easily selected using procedures well known in the art, taking into account DNA-DNA hybridization stringencies, annealing and melting temperatures, potential for formation of loops, and other factors which are well known in the art. Preferred techniques for designing PCR primers are disclosed in Dieffenbach and Dyksler, *PCR Primer: a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

The isolated polynucleotides of the present invention also have utility in genome mapping, in physical mapping, and in positional cloning of genes.

The polynucleotides identified as SEQ ID NO: 1-44 were isolated from cDNA clones and represent sequences that are expressed in the tissue from which the cDNA was prepared. RNA sequences, reverse sequences, complementary sequences, anti-sense sequences, and the like, corresponding to the polynucleotides of the present invention, may be routinely ascertained and obtained using the cDNA sequences identified as SEQ ID NO: 1-44.

Identification of genomic DNA and heterologous species DNA can be accomplished by standard DNA/DNA hybridization techniques, under appropriately stringent conditions, using all or part of a polynucleotide sequence as a probe to screen an appropriate library. Alternatively, PCR techniques using oligonucleotide primers that are designed based on known genomic DNA, cDNA and protein sequences can be used to amplify and identify genomic and cDNA sequences.

In another aspect, the present invention provides isolated polypeptides encoded by the above polynucleotides. As used herein, the term "polypeptide" encompasses amino acid chains of any length, including full-length proteins, wherein the amino acid residues are linked by covalent peptide bonds. The term "polypeptide encoded by a polynucleotide" as used herein, includes polypeptides encoded by a polynucleotide that comprises a partial isolated polynucleotide sequence provided herein. In specific embodiments, the inventive polypeptides comprise an amino acid sequence selected from the group consisting of SEQ ID NO: 45-88, as well as variants of such sequences.

As noted above, polypeptides of the present invention may be produced recombinantly by inserting a polynucleotide sequence encoding the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a polynucleotide molecule that encodes a recombinant polypeptide. Suitable host cells include prokaryotes, yeast, and higher eukaryotic cells. Preferably, the host cells employed are plant, *E. coli*, insect, yeast, or a mammalian cell line such as COS or CHO. The polynucleotide sequences expressed in this manner may encode naturally occurring polypeptides, portions of naturally occurring polypeptides, or other variants thereof. The expressed polypeptides may be used in various assays known in the art to determine their biological activity. Such polypeptides may also be used to raise antibodies, to isolate corresponding interacting proteins or other compounds, and to quantitatively determine levels of interacting proteins or other compounds.

In a related aspect, polypeptides are provided that comprise at least a functional portion of a polypeptide having an amino acid sequence selected from the group consisting of sequences provided in SEQ ID NO: 45-88 and variants thereof. As used herein, the "functional portion" of a polypeptide is that portion which contains an active site essential for affecting the function of the polypeptide, for example, a portion of the molecule that is capable of binding one or more reactants. The active site may be made up of separate portions present on one or more polypeptide chains and will generally exhibit high binding affinity. Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using methods well known to those of skill in the art, including the representative assays described below.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85: 2149-2146, 1963. Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagenesis (Kunkel, *Proc. Natl. Acad. Sci. USA* 82: 488-492, 1985). Sections of DNA sequences may also be removed using standard techniques to permit preparation of truncated polypeptides.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 75%, more preferably at least 80%, more preferably at least 90%, more preferably yet at least 95%, and most preferably at least 98% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotides and polypeptides having a specified percentage identity to a polynucleotide or polypeptide identified in one of SEQ ID NO: 1-88 thus share a high degree of similarity in their primary structure. In addition to a specified percentage identity to a polynucleotide of the present invention, variant polynucleotides and polypeptides preferably have additional structural and/or functional features in common with a polynucleotide of the present invention. Polynucleotides having a specified degree of identity to, or capable of hybridizing to, a polynucleotide of the present invention preferably additionally have at least one of the following features: (1) they contain an open reading frame, or partial open reading frame, encoding a polypeptide, or a functional portion of a polypeptide, having substantially the same functional properties as the polypeptide, or functional portion thereof, encoded by a polynucleotide in a recited SEQ ID NO:; or (2) they contain identifiable domains in common.

Polynucleotide or polypeptide sequences may be aligned, and percentages of identical nucleotides or amino acids in a specified region may be determined against another polynucleotide or polypeptide, using computer algorithms that are publicly available. For example, the BLASTN and FASTA algorithms, set to the default parameters described in the documentation and distributed with the algorithm, may be used for aligning and identifying the similarity of polynucleotide sequences. The alignment and similarity of polypeptide sequences may be examined using the BLASTP algorithm. BLASTX and FASTX algorithms compare nucleotide query sequences translated in all reading frames against polypeptide sequences. The FASTA and FASTX algorithms are described in Pearson and Lipman, *Proc. Natl. Acad. Sci. USA* 85:2444-2448, 1988; and in Pearson, *Methods in Enzymol.* 183:63-98, 1990. The FASTA software package is available from the University of Virginia by contacting the Assistant Provost for Research, University of Virginia, PO Box 9025, Charlottesville, Va. 22906-9025. The BLASTN software is available from the National Center for Biotechnology Information (NCBI), National Library of Medicine, Building 38A, Room 8N805, Bethesda, Md. 20894. The BLASTN algorithm Version 2.0.11 [Jan. 20, 2000] set to the default parameters described in the documentation and distributed with the algorithm, is preferred for use in the determination of polynucleotide variants according to the present invention. The use of the BLAST family of algorithms, including BLASTN, BLASTP and BLASTX, is described in the publication of Altschul et al., "Gapped BLAST and PSI-BLAST: a new generation of protein database search programs," *Nucleic Acids Res.* 25:3389-3402, 1997.

The following running parameters are preferred for determination of alignments and similarities using BLASTN that contribute to the percentage identity and E values for polynucleotides: Unix running command with the following default parameters: blastall -p blastn -d embldb -e 10 -G 0 -E 0 -r 1 -v 30 -b 30 -i queryseq -o results; and parameters are: -p Program Name [String]; -d Database [String]; -e Expectation value (E) [Real]; -G Cost to open a gap (zero invokes default behavior) [Integer]; -FF low complexity filter; -E Cost to extend a gap (zero invokes default behavior) [Integer]; -r Reward for a nucleotide match (BLASTN only) [Integer]; -v Number of one-line descriptions (V) [Integer]; -b Number of alignments to show (B) [Integer]; -i Query File [File In]; -o BLAST report Output File [File Out] Optional.

The following running parameters are preferred for determination of alignments and similarities using BLASTP that contribute to the percentage identity and E values of polypeptide sequences: blastall -p blastp -d swissprotdb -e 10 -G 0 -E 0 -v 30 -b 30 -i queryseq -o results; the parameters are: -p Program Name [String]; -d Database [String]; -e Expectation value (E) [Real]; -G Cost to open a gap (zero invokes default behavior) [Integer]; -FF low complexity filter; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, BLASTP, FASTA or a similar algorithm, align and identify similar portions of sequences. The hits are arranged in order of the degree of similarity and the length of sequence overlap. Hits to a database sequence generally represent an overlap over only a fraction of the sequence length of the queried sequence.

As noted above, the percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity. By way of example, a queried polynucleotide having 220 nucleic acids has a hit to a polynucleotide sequence in the EMBL database having 520 nucleic acids over a stretch of 23 nucleotides in the alignment produced by the BLASTN algorithm using the default parameters. The 23-nucleotide hit includes 21 identical nucleotides, one gap and one different nucleotide. The percentage identity of the queried polynucleotide to the hit in the EMBL database is thus 21/220 times 100, or 9.5%. The percentage identity of polypeptide sequences may be determined in a similar fashion.

The BLASTN and BLASTX algorithms also produce "Expect" values for polynucleotide and polypeptide alignments. The Expect value (E) indicates the number of hits one can "expect" to see over a certain number of contiguous sequences by chance when searching a database of a certain size. The Expect value is used as a significance threshold for determining whether the hit to a database indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being related. For sequences having an E value of 0.01 or less over aligned and matched portions, the probability of finding a match by chance in the EMBL database is 1% or less using the BLASTN algorithm. E values for polypeptide sequences may be determined in a similar fashion using various polypeptide databases, such as the SwissProt database.

According to one embodiment, "variant" polynucleotides and polypeptides, with reference to each of the polynucleotides and polypeptides of the present invention, preferably comprise sequences having the same number or fewer nucleotides or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being related to the polynucleotide or polypeptide of the present invention, measured as having an E value of 0.01 or less using the BLASTN or BLASTX algorithms set at the default parameters. According to a preferred embodiment, a variant polynucleotide is a sequence having the same number or fewer nucleic acids than a polynucleotide of the present invention that has at least a 99% probability of being related to the polynucleotide of the present invention, measured as having an E value of 0.01 or less using the BLASTN algorithm set at the default parameters. Similarly, according to a preferred embodiment, a variant polypeptide is a sequence having the same number or fewer amino acids than a polypeptide of the present invention that has at least a 99% probability of being related as the polypeptide of the present invention, measured as having an E value of 0.01 or less using the BLASTP algorithm set at the default parameters.

In an alternative embodiment, variant polynucleotides are sequences that hybridize to a polynucleotide of the present invention under stringent conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents, and extent of base mismatching, the combination of parameters is more important than the absolute measure of any one alone. An example of "stringent conditions" is prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity to a polypeptide encoded by a polynucleotide of the present invention. Thus, polynucleotides comprising sequences that differ from the polynucleotide sequences recited in SEQ ID NO: 1-44, or complements, reverse sequences, or reverse complements of those sequences, as a result of conservative substitutions are contemplated by and encompassed within the present invention. Additionally, polynucleotides comprising sequences that differ from the polynucleotide sequences recited in SEQ ID NO: 1-44, or complements, reverse complements or reverse sequences thereof, as a result of deletions and/or insertions totaling less than 10% of the total sequence length are also contemplated by and encompassed within the present invention. Similarly, polypeptides comprising sequences that differ from the polypeptide sequences recited in SEQ ID NO: 45-88 as a result of amino acid substitutions, insertions, and/or deletions totaling less than 10% of the total sequence length are contemplated by and encompassed within the present invention, provided the variant polypeptide has activity in a fructan, cellulose, starch and/or tannin biosynthetic pathway.

In another aspect, the present invention provides genetic constructs comprising, in the 5'-3' direction, a gene promoter sequence; an open reading frame coding for at least a functional portion of a polypeptide of the present invention; and a gene termination sequence. The open reading frame may be orientated in either a sense or anti-sense direction. For applications where amplification of fructan, cellulose, starch or tannin synthesis is desired, the open reading frame may be inserted in the construct in a sense orientation, such that transformation of a target organism with the construct will lead to an increase in the number of copies of the gene and therefore an increase in the amount of enzyme. When downregulation of fructan, cellulose, starch or tannin synthesis is desired, the open reading frame may be inserted in the construct in an anti-sense orientation, such that the RNA produced by transcription of the polynucleotide is complementary to the endogenous mRNA sequence. This, in turn, will result in a decrease in the number of copies of the gene and therefore a decrease in the amount of enzyme. Alternatively, regulation may be achieved by inserting appropriate sequences or subsequences (e.g., DNA or RNA) in ribozyme constructs.

Genetic constructs comprising a non-coding region of a gene coding for a polypeptide of the present invention, or a nucleotide sequence complementary to a non-coding region, together with a gene promoter sequence and a gene termination sequence, are also provided. As used herein the term "non-coding region" includes both transcribed sequences which are not translated, and non-transcribed sequences within about 2000 base pairs 5' or 3' of the translated sequences or open reading frames. Examples of non-coding regions which may be usefully employed in the inventive constructs include introns and 5'-non-coding leader sequences. Transformation of a target plant with such a genetic construct may lead to a reduction in the amount of fructan, cellulose, starch or tannin synthesized by the plant by the process of cosuppression, in a manner similar to that discussed, for example, by Napoli et al., *Plant Cell* 2:279-290, 1990; and de Carvalho Niebel et al., *Plant Cell* 7:347-358, 1995.

The genetic constructs of the present invention further comprise a gene promoter sequence and a gene termination sequence, operably linked to the polynucleotide to be transcribed, which control expression of the gene. The gene promoter sequence is generally positioned at the 5' end of the polynucleotide to be transcribed, and is employed to initiate transcription of the polynucleotide. Gene promoter sequences are generally found in the 5' non-coding region of a gene but they may exist in introns (Luehrsen, *Mol. Gen. Genet.* 225:81-93, 1991) or in the coding region, as for example in PAL of tomato (Bloksberg, *Studies on the Biology of Phenylalanine Ammonia Lyase and Plant Pathogen Interaction*, Ph.D. Thesis, University of California, Davis, 1991, University Microfilms International Order No. 9217564). When the construct includes an open reading frame in a sense orientation, the gene promoter sequence also initiates translation of the open reading frame. For genetic constructs comprising either an open reading frame in an anti-sense orientation or a non-coding region, the gene promoter sequence consists only of a transcription initiation site having a RNA polymerase binding site.

A variety of gene promoter sequences which may be usefully employed in the genetic constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter or the superubiquitin promoter (PCT International Patent Publication WO 00/58474), will affect the activity of the enzyme in all parts of the plant. Use of a tissue specific promoter will result in production of the desired sense or anti-sense RNA only in the tissue of interest. With DNA constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as *Lolium* or *Festuca*, are used. Grass promoters different from the original gene may also be usefully employed in the inventive genetic constructs in order to prevent feedback inhibition. For example, the fructosyltransferase gene will be regulated by sucrose sensing systems; therefore removing the gene from under control of its normal promoter allows the gene to be active all the time. Other examples of gene promoters which may be usefully employed in the present invention include, mannopine synthase (mas), octopine synthase (ocs) and those reviewed by Chua et al., *Science* 244:174-181, 1989.

The gene termination sequence, which is located 3' to the polynucleotide to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original enzyme gene or from the target species to be transformed.

The genetic constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds., *Methods for Plant Molecular Biology*, Academic Press Inc.: San Diego, Calif., 1988). Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Sambrook et al., (*Molecular cloning: a laboratory manual*, CSHL Press: Cold Spring Harbor, N.Y., 1989). The genetic construct of the present invention may be linked to a vector having at least one replication system, for example, *E. coli*, whereby after each manipulation, the resulting construct can be cloned and sequenced, and the correctness of the manipulation determined.

The genetic constructs of the present invention may be used to transform a variety of plants, both monocotyledonous (e.g., grasses, maize/corn, grains, oats, rice, sorghum, millet, rye, sugar cane, wheat and barley), dicotyledonous (e.g., Arabidopsis, tobacco, legumes, alfalfa, oaks, eucalyptus, maple), and gymnosperms. In a preferred embodiment, the inventive genetic constructs are employed to transform grasses. Preferably the target plant is selected from the group consisting of *Lolium* and *Festuca* species, most preferably from the group consisting of *Lolium perenne* and *Festuca arundinacea*. Plants that may be usefully transformed with the inventive genetic constructs include other species of ryegrass and fescue, including, but not limited to *Lolium multiflorum* (Italian ryegrass), *Lolium hybridum* (hybrid ryegrass), *Lolium rigidum* (Wimerra grass), *Lolium temulentum* (darnel), *Festuca rubra* (red fescue) and *Festuca pratensis* (meadow fescue). As discussed above, transformation of a plant with a genetic construct of the present invention will produce a modified fructan, cellulose, starch or tannin content in the plant.

The production of RNA in target cells may be controlled by choice of the promoter sequence, or by selecting the number of functional copies or the site of integration of the polynucleotides incorporated into the genome of the target organism. A target plant may be transformed with more than one construct of the present invention, thereby modulating the fructan, cellulose, starch and/or tannin biosynthetic pathways by affecting the activity of more than one enzyme, affecting enzyme activity in more than one tissue, or affecting enzyme activity at more than one expression time. Similarly, a construct may be assembled containing more than one open reading frame coding for an enzyme encoded by a polynucleotide of the present invention or more than one non-coding region of a gene coding for such an enzyme. The polynucleotides of the present invention may also be employed in combination with other known sequences encoding enzymes involved in the lignin, fructan and/or tannin biosynthetic pathways. In this manner, more than one biosynthetic pathway may be modulated, or a fructan, cellulose, starch or tannin biosynthetic pathway may be added to a plant to produce a plant having an altered phenotype.

Techniques for stably incorporating genetic constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants, and certain monocots and gymnosperms may be transformed by *Agrobacterium* Ti plasmid technology, as described, for example by Bevan, *Nucleic Acid Res.* 12:8711-8721, 1984. Targets for the introduction of the genetic constructs of the present invention include tissues, such as leaf tissue, disseminated cells, protoplasts, seeds, embryos, meristematic regions; cotyledons, hypocotyls, and the like. Transformation techniques which may be usefully employed in the inventive methods include those taught by Ellis et al., *Plant Cell Reports*, 8:16-20, 1989; Wilson et al., *Plant Cell Reports* 7:704-707, 1989; and Tautorus et al., *Theor. Appl. Genet.* 78:531-536, 1989.

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. The resulting transformed plants may be reproduced sexually or asexually, using methods well known in the art, to give successive generations of transgenic plants.

Polynucleotides of the present invention may also be used to specifically suppress gene expression by methods that operate post-transcriptionally to block the synthesis of products of targeted genes, such as RNA interference (RNAi), and quelling. Briefly, traditional methods of gene suppression, employing anti-sense RNA or DNA, operate by binding to the reverse sequence of a gene of interest such that binding interferes with subsequent cellular processes and therefore blocks synthesis of the corresponding protein. RNAi also operates on a post-translational level and is sequence specific, but suppresses gene expression far more efficiently. Exemplary methods for controlling or modifying gene expression using RNAi are provided in U.S. Pat. No. 6,506,559 and PCT International Publications WO 99/49029 and WO 99/53050. In these methods, post-transcriptional gene silencing is brought about by a sequence-specific RNA degradation process which results in the rapid degradation of transcripts of sequence-related genes. Studies have shown that double-stranded RNA may act as a mediator of sequence-specific gene silencing (see, for example, Montgomery and Fire, *Trends in Genetics*, 14:255-258, 1998). Gene constructs that produce transcripts with self-complementary regions are particularly efficient at gene silencing. A unique feature of this post-transcriptional gene silencing pathway is that silencing is not limited to the cells where it is initiated. The gene-silencing effects may be disseminated to other parts of an organism and even transmitted through the germ line to several generations.

The polynucleotides of the present invention may thus be employed to generate gene silencing constructs and/or gene-specific self-complementary RNA sequences that can be delivered by conventional art-known methods to plant tissues, such as forage grass tissues. Within genetic constructs, sense and antisense sequences can be placed in regions flanking an intron sequence in proper splicing orientation with donor and acceptor splicing sites, such that intron sequences are removed during processing of the transcript, and sense and antisense sequences, as well as splice junction sequences, bind together to form double-stranded RNA. Alternatively, spacer sequences of various lengths may be employed to separate self-complementary regions of sequence in the construct. During processing of the gene construct transcript, intron sequences are spliced-out, allowing sense and anti-sense sequences, as well as splice junction sequences, to bind forming double-stranded RNA. Select ribonucleases then bind to and cleave the double-stranded RNA, thereby initiating the cascade of events leading to degradation of specific mRNA gene sequences, and silencing specific genes. Alternatively, rather than using a gene construct to express the self-complementary RNA sequences, the gene-specific double-stranded RNA segments are delivered to one or more targeted areas to be internalized into the cell cytoplasm to exert a gene silencing effect. The double-stranded RNA must have sufficient homology to the targeted gene to mediate RNAi and is preferably at least 25 nucleotides in length. Preferably, the double-stranded RNA corresponds specifically to a polynucleotide of the present invention. Gene silencing RNA sequences comprising the polynucleotides of the present invention are useful for creating genetically modified plants with desired phenotypes as well as for characterizing genes (for example, in high-throughput screening of sequences), and studying their functions in intact organisms.

EXAMPLE 1

Isolation of cDNA Sequences From *L. Perenne* and *F. Arundinacea* cDNA Libraries

*L. perenne* and *F. arundinacea* cDNA expression libraries were constructed and screened as follows. Tissue was collected from *L. perenne* and *F. arundinacea* during winter and spring, and snap-frozen in liquid nitrogen. The tissues collected included those obtained from leaves, pseudostem, roots, inflorescence (day 0), stem bases from day 7 emerged inflorescence, basal leaf day 3 and day 6, floral stem and vegetative stem. Total RNA was isolated from each tissue type using TRIzol Reagent (BRL Life Technologies, Gaithersburg, Md.). mRNA from each tissue type was obtained using a Poly(A) Quik mRNA isolation kit (Stratagene, La Jolla, Calif.), according to the manufacturer's specifications.

cDNA expression libraries were constructed from the purified mRNA by reverse transcriptase synthesis followed by insertion of the resulting cDNA in Lambda ZAP using a ZAP Express cDNA Synthesis Kit (Stratagene), according to the manufacturer's protocol. The resulting cDNA clones were packaged using a Gigapack II Packaging Extract (Stratagene) employing 1 µl of sample DNA from the 5 µl ligation mix. Mass excision of the libraries was performed using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing 5-bromo-4-chloro-3-indolyl-beta-D-galactosidase (X-gal) and isopropylthio-beta-galactoside (IPTG).

Of the colonies plated and picked for DNA preparations, the large majority contained an insert suitable for sequencing. Positive colonies were cultured in NZY broth with kanamycin and DNA was purified following standard protocols. Agarose gel at 1% was used to screen sequencing templates for chromosomal contamination. Dye terminator sequences were prepared using a Biomek 2000 robot (Beckman Coulter Inc., Fullerton, Calif.) for liquid handling and DNA amplification using a 9700 PCR machine (Perkin Elmer/Applied Biosystems, Foster City, Calif.) according to the manufacturer's protocol.

The DNA sequences for positive clones were obtained using a Perkin Elmer/Applied Biosystems Division Prism 377 sequencer. cDNA clones were sequenced from the 5' end. The polynucleotide sequences identified as SEQ ID NO: 1, 3-5, 8-15, 17, 18, 20, 25, 27, 28, 30, 36-39 and 44 were identified from *Lolium perenne* cDNA expression libraries, with the polynucleotides of SEQ ID NO: 2, 6, 7, 16, 19, 21-24, 26, 29, 31-35 and 40-43 being identified from *Festuca arundinacea* cDNA expression libraries.

BLASTN Polynucleotide Analysis

The isolated cDNA sequences were compared to sequences in the EMBL DNA database using the computer algorithm BLASTN. Comparisons of DNA sequences provided in SEQ ID NO: 1-44 to sequences in the EMBL DNA database were made as of Apr. 28, 2003, using BLASTN algorithm Version 2.0.11 [Jan. 20, 2000], and the following Unix running command: blastall -p blastn -d embldb -e 10 -FF -G0 -E0 -r 1 -v 30 -b 30 -i queryseq -o.

The sequences of SEQ ID NO: 6-9, 11-19, 21, 25-27 and 34-44 were determined to have less than 50% identity, determined as described above using the computer algorithm BLASTN, to sequences in the EMBL database. The sequence of SEQ ID NO: 3, 4, 10, 20, 22-24, 28, 29 and 31-33 was determined to have less than 75% identity, determined as described above, to sequences in the EMBL database. The sequences of SEQ ID NO: 1, 2 and 30 were determined to have less than 90% identity to sequences in the EMBL database using the computer algorithm BLASTN, as described above. Finally, the sequence of SEQ ID NO: 5 were determined to have less than 98% identity to sequences in the SwissProt database using the computer algorithm BLASTP, as described above.

BLASTP Polypeptide Analysis

The isolated sequences were compared to sequences in the SwissProt protein database using the computer algorithm BLASTP. Specifically, comparisons of polypeptide sequences provided in SEQ ID NO: 45-88 to sequences in the SwissProt protein database were made as of Apr. 28, 2003, using BLASTP algorithm Version 2.0.11 [Jan. 20, 2000], and the following Unix running command: blastall -p blastn -d embldb -e 10 -FF -G0 -E0 -v 30 -b 30 -i queryseq -o.

The sequences of SEQ ID NO: 78-81 were determined to have less than 50% identity to sequences in the SwissProt database using the computer algorithm BLASTP as described above. The sequences of SEQ ID NO: 51, 53, 55, 56, 71, 83 and 88 were determined to have less than 75% identity to sequences in the SwissProt database using the computer algorithm BLASTP, as described above. The sequences of SEQ ID NO: 50, 52, 54, 57-68, 82 and 84-87 were determined to have less than 90% identity to sequences in the SwissProt database using the computer algorithm BLASTP, as described above. Finally, the sequences of SEQ ID NO: 45-49, 69, 70 and 72-77 were determined to have less than 98% identity to sequences in the SwissProt database using the computer algorithm BLASTP, as described above.

BLASTX Polynucleotide Analysis

The isolated cDNA sequences were compared to sequences in the SwissProt protein DNA database using the computer algorithm BLASTX. Comparisons of DNA sequences provided in SEQ ID NOS: 1-44, to sequences in the SwissProt DNA database (using BLASTX) were made as of Apr. 28, 2003, using BLAST algorithm Version 2.0.11 [Jan. 20. 2000], and the following Unix running command: blastall -p blastn -d embldb -e 10 -FF -G0 -E0 -r 1 -v 30 -b 30 -i queryseq-o.

The sequences of SEQ ID NO: 27 and 34-37 were determined to have less than 50% identity, determined as described above, to sequences in the SwissProt database using the computer algorithm BLASTX, as described above. The sequences of SEQ ID NO: 3, 4, 6-19, 21-26, 28, 29, 33 and 38-44 were determined to have less than 75% identity, determined as described above, to sequences in the SwissProt database using the computer algorithm BLASTX, as described above. Finally, the sequences of SEQ ID NO: 1, 2, 5, 20 and 30-32 were determined to have less than 90% identity, determined as described above, to sequences in the SwissProt database using the computer algorithm BLASTX, as described above.

FIGS. 3-41 show the positions of domains within the amino acid sequences of SEQ ID NO: 45-48, 53-70 and 72-88, respectively. These domains were determined with InterProScan software Release v3.1, Nov. 6, 2001. The InterPro database integrates PROSITE, PRINTS, Pfam, ProDom, SMART and TIGRFAMs databases, and the addition of others is scheduled. InterPro data is distributed in XML format and it is freely available under the InterPro Consortium copyright. The European Bioinformatics Institute (EBI) is a non-profit academic organization that forms part of the European Molecular Biology Laboratory (EMBL): Wellcome Trust Genome Campus, Hinxton, Cambridge, CB10 1SD UK.

EXAMPLE 2

Use of Chalcone Synthase Genes to Modify Tannin Biosynthesis

Certain *Arabidopsis* mutants of the transparent testa (tt) phenotype do not make the anthocyanin pigment cyanidin and therefore have no seed coat color. The genes responsible for many of these mutants have now been identified as shown in Table 3.

TABLE 3

| Enzyme | Abbreviation | Locus | Chromosome |
|---|---|---|---|
| Dihydroflavanol-4-reductase | DFR | tt3 | 5 |
| Chalcone synthase | CHS | tt4 | 5 |

TABLE 3-continued

| Enzyme | Abbreviation | Locus | Chromosome |
|---|---|---|---|
| Chalcone isomerase | CHI | tt5 | 3 |
| Flavanone 3-β-hydroxylase | F3βH | tt6 | 3 |

Over-expression of the maize gene for CHS has been shown to complement the *Arabidopsis* tt4 mutant, thereby restoring cyanidin synthesis and seed coat color (Dong et al., *Plant Physiol.* 127:46-57, 2001). Complementation of these *Arabidopsis* mutants may therefore be employed to demonstrate the function of the inventive polynucleotides encoding enzymes involved in the tannin biosynthetic pathway.

Two chalcone synthase genes were identified from *F. arundinacea* (SEQ ID NO: 32 and 33). Sense constructs containing a polynucleotide including the coding region of one chalcone synthase gene, FaCHS2, (SEQ ID NO: 33) under the control of the CaMV 35S promoter were inserted into a binary vector and used to transform *Agrobacterium tumefaciens* LBA4404 using published methods (see, An G, Ebert PR, Mitra A, Ha SB, "Binary Vectors," in Gelvin SB, Schilperoort R A, eds., *Plant Molecular Biology Manual*, Kluwer Academic Publishers: Dordrecht, 1988). The presence and integrity of the binary vector in *A. tumefaciens* was verified by polymerase chain reaction (PCR) using the forward primer provided in SEQ ID NO: 89 and reverse primer provided in SEQ ID: 90.

The *A. tumefaciens* containing the sense gene construct were used to transform *Arabidopsis* tt4 mutants by floral dipping (Clough and Bent, *Plant J.* 16:735-743, 1998) and several independent transformed plant lines were established for the sense. Transformed plants containing the appropriate tannin gene construct were verified using PCR.

The presence of cyanidin in the transformed plants is demonstrated by a phenotypic change in plant seedling color and by analyzing cyanidin extracts made from transgenic plants grown under stressed conditions (Dong et al., *Plant Physiol.* 127:46-57, 2001). Briefly, cyanidins are extracted from plant tissue with an acid/alcohol solution (HCl/methanol) and water. Chlorophyll is removed by freezing the extracts followed by centrifugation at 4° C. at 20,000×g for 20 min. Any remaining chlorophyll is removed through a chloroform extraction. The absorbance at 530 nm is measured for each of the cyanidin extracts. Non-transgenic wild type and control *Arabidopsis* plants are used as controls.

EXAMPLE 3

Use of Sucrose Transporters to Complement a Yeast Strain Unable to Grow on Sucrose Two *Lolium perenne* genes, LpSUT2 (SEQ ID: 25) and LpSUT-like (SEQ ID: 27), and two *Festuca arundinacea* genes, FaSUT1 (SEQ ID NO: 22) and FaSUT2 (SEQ ID NO: 26) share amino acid sequence identity with sucrose transporter (SUT1 and SUT2) genes from other plant species (Barker et al., *Plant Cell* 12:1153-1164, 2000; Weise et al., *Plant Cell* 12:1345-55, 2000; Lemoine R., *Biochim Biophys Acta* 1465:246-62, 2000). The first plant gene encoding a sucrose carrier protein, from spinach, was isolated by functional expression in a yeast strain, SUSY7 (Riesmeier et al., *EMBO J.* 11:4705-4713).

The gene of SEQ ID NO: 27 was digested and cloned into the yeast expression vector pYEP 112 A1 NE for functional complementation using this yeast system. Plasmid DNA was verified by sequencing and transformed into S. cerevisiae strain SUSY7, which had been engineered to express cytosolic sucrose synthase enabling it to metabolize sucrose entering the cell. Constitutive expression of the grass sucrose transporters within this yeast strain facilitated transport of sucrose in to the cell and its growth on sucrose minimal media. Growth rates of recombinant and wild type yeast strains in both sucrose and glucose minimal media were measured.

Results showed that the yeast strain containing the gene of SEQ ID NO: 27 was able to grow on sucrose minimal medium because the constitutive expression of the SUT-like gene within this yeast strain facilitated transport of sucrose into the cell.

EXAMPLE 4

Use of Alkaline/Neutral Invertases to Cleave Sucrose

A number of Lolium perenne and Festuca arundinacea genes (SEQ ID NO: 5, 7 and 9-14) were identified that share amino acid sequence identity with alkaline/neutral invertase genes from other plant species (Sturm et al., *Physiol. Planta* 107:159-165, 1999; Gallagher and Pollock, *J. Exp. Bot.* 49:789-795, 1998).

L. perenne gene AN_INV8 (SEQ ID NO: 12) was amplified by PCR from the start methionine using forward (SEQ ID NO: 91) and reverse (SEQ ID NO: 92) primers, then cloned into the pET41a expression plasmid. The resulting plasmid was transformed into E. coli BL21 cells using standard protocols, and protein expression induced using IPTG. The soluble recombinant protein was assayed for its ability to cleave sucrose. Cells were lysed in citrate buffer and the soluble protein incubated with 50 mM sucrose in citrate buffer pH7. Reactions were terminated by boiling. Cleavage of the sucrose by neutral invertase activity was determined by the formation of glucose in this reaction. Levels of glucose were determined with a Glucose HK assay kit GAHK-20 (Sigma, St Louis Mo.) utilizing hexokinase coupled to glucose-6-phosphate dehydrogenase, and reduction of NAD measured by absorbance at 340 nm.

FIG. 1 shows the invertase activity of recombinant AN_INV8 protein, measured as the amount (in μg) of glucose release from cleavage of sucrose per hour at pH7, and that of an empty vector (pET41a) control sample. The results showed that the purified protein released 35 μg of glucose per hour through the invertase cleavage of sucrose. No release was measured with the empty vector control.

EXAMPLE 5

Use of Pyrophosphate-Dependent Phosphofructokinase to Phosphorylate Fructose-6-Phosphate Two Lolium perenne genes, LpPFPA (SEQ ID: 15) and LpPFPB (SEQ ID NO: 18), and two Festuca arundinacea genes, FaPFPA (SEQ ID NO: 16) and FaPFPB (SEQ ID NO: 19) share amino acid sequence identity with the A and B subunits of pyrophosphate-dependent phosphofructoskinase genes (PFP) from other plant species (Todd et al., *Gene* 152: 181-6, 1995; Carlisle et al., *J. Biol. Chem.* 265:18366-71, 1990).

The entire coding regions were cloned into expression vector pBK-CMV, under the control of the CMV promoter for expression of recombinant protein in mammalian cells. The PFPA and PFPB genes from Lolium perenne or Festuca arundinacea were co-transfected in to mammalian HEK293T cells and protein extracted 48 hours later. Protein was also extracted from cells transfected with a negative control vector containing the β-galactosidase gene. Purified potato PFP (Sigma, St. Louis Mo.) was used as positive control. Activity of the PFP enzyme was measured spectrophotometrically by a decrease NADH and absorbance at 340 nm in a coupled reaction as described previously (Theodorou and Kruger, *Planta* 213:147-157, 2001). Briefly, the conversion of fructose-6-phosphate to fructose-1,6-diphosphate in the presence of activator, fructose-2,6-diphosphate was initiated by the addition of pyrophosphate and measured in a coupled reaction with aldolase, triose phosphate isomerase and glycerophosphate dehydrogenase.

Figure 2:
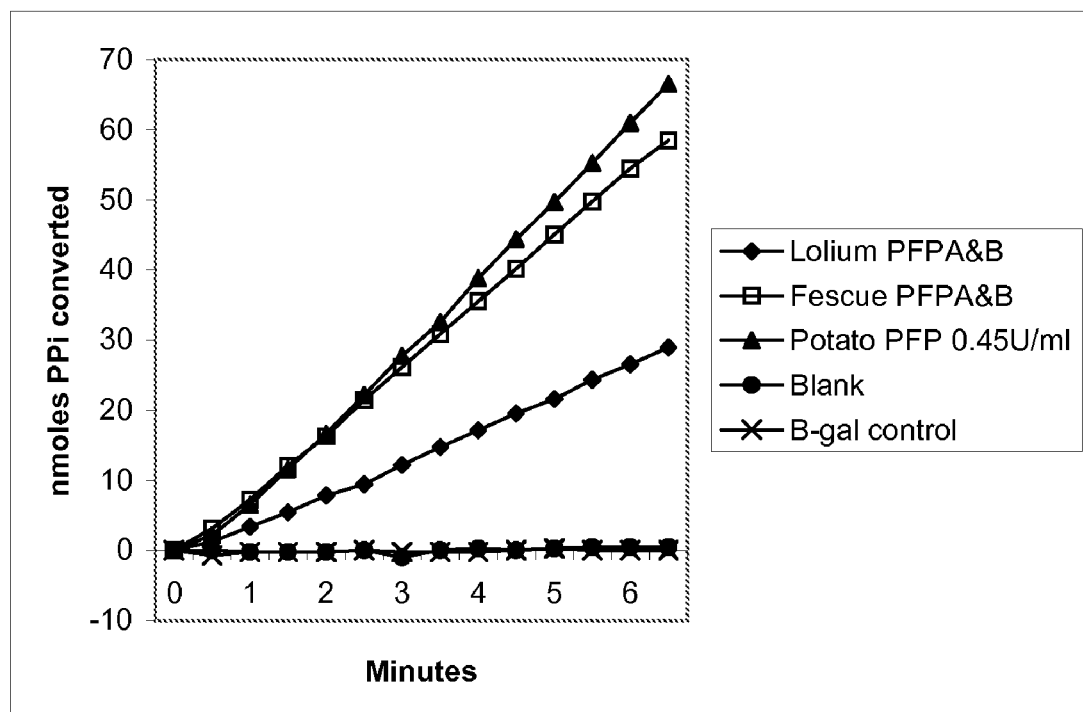
FIG. 2 shows the PFP activity of *L. perenne* and *F. arundinacea* PFPA and PFPB subunits in coupled reactions. Amino acid sequences for *L. perenne* PFPA and PFPB are given in SEQ ID NO: 59 and 62, respectively (corresponding cDNA sequences are SEQ ID NO: 15 and 18), and amino acid sequences for *F. arundinacea* PFPA and PFPB are given in SEQ ID NO: 60 and 63, respectively (corresponding cDNA sequences are SEQ ID NO: 16 and 19). Oxidation of NADH was measured as nmoles PPi converted.

FIG. 2 shows the PFP activity of the purified protein (conversion of fructose-6-phosphate to fructose-1-6-diphosphate) measured as conversion of PPi to inorganic phosphate. No conversion was obtained with the β-galactosidase negative control.

EXAMPLE 6

Use of Sucrose Phosphate Synthase Enzymes to Synthesize Sucrose

A Lolium perenne polynucleotide sequence (SEQ ID NO: 20) and a F. arundinacea polynucleotide sequence (SEQ ID NO: 21) have been identified that share identity with sucrose phosphate synthase (SPS) from other plant species. These genes are expressed in E. coli or Pichia using standard protocols, and the resulting purified protein assayed for its ability to synthesize sucrose from fructose-6-phosphate and uridine 5'-diphosphoglucose. Sucrose is detected by adding NAD and UDP-Glucose dehydrogenase, followed by the addition of anthrone reagent and then measuring the change in absorbance at 620 nm (Botha and Black, Aust. *J. Plant Physiol.* 27:81-85, 2000).

SEQ ID NOS: 1-88 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

We claim:

1. An isolated polynucleotide comprising SEQ ID NO: 4.

2. An isolated polynucleotide comprising a sequence selected from the group consisting of:
   (a) complements of SEQ ID NO: 4;
   (b) reverse complements of SEQ ID NO: 4; and
   (c) reverse sequences of SEQ ID NO: 4

3. An isolated polynucleotide comprising a sequence selected from the group consisting of:
   (a) sequences having at least 95% identity to a sequence of SEQ ED NO: 4;
   (b) sequences having at least 98% identity to a sequence of SEQ ID NO: 4; and
   (c) sequences that hybridize to a sequence of SEQ ID NO: 4 in 0.2×SSC, 0.1% SDS at 65° C,
   wherein the polynueleotide encodes a polypeptide having substantially the same functional activity as a polypeptide encoded by a polynucleotide of SEQ ID NO: 4.

4. An isolated polynucleotide that encodes the polypeptide of SEQ ID NO: 48.

5. A genetic construct comprising a polynucleotide of any one of claims 1-3.

6. A transgenic cell comprising a genetic construct according to claim 5.

7. A genetic construct comprising, in the 5'-3' direction:
   (a) a gene promoter sequence;
   (b) a polynucleotide sequence comprising at least one of the following: (1) a polynucleotide coding for at least a functional portion of SEQ ID NO: 48; and (2) a polynucleotide comprising a non-coding region of a polynucleotide of any one of claims 1-3; and
   (c) a gene termination sequence.

8. The genetic construct of claim 7, wherein the pollynucleotide sequence is in a sense orientation.

9. A transgenic plant cell comprising a genetic construct of claim 7.

10. A plant comprising a transgenic plant cell, or fruit or seeds or progeny thereof, wherein the plant cell, fruit, seeds or progeny comprise the genetic construct of claim 7.

11. The plant of claim 10, wherein the plant is selected from the group consisting of *Festuca arundinacea* and *Lolium perenne* species.

12. A method for modulating the fructan composition of a plant, comprising stably incorporating into the genome of the plant a polynucleotide of any one of claims 1-3.

13. A method for modulating the fructan composition of a plant, comprising stably incorporating into the genome of the plant a genetic construct of claim 7.

14. A method for producing a plant having altered fructan composition comprising:
   (a) transforming a plant cell with a genetic construct of claim 7 to provide a transgenic cell; and
   (b) cultivating the transgenic cell under conditions conducive to regeneration and mature plant growth.

15. A method for modifying the activity of a polypeptide involved in a fructan biosynthetic pathway in a plant, comprising stably incorporating into the genome of the plant a genetic construct of claim 7.

* * * * *